(12) United States Patent
Fremaux et al.

(10) Patent No.: US 11,530,405 B2
(45) Date of Patent: Dec. 20, 2022

(54) ANTI-CRISPR GENES AND PROTEINS AND METHODS OF USE

(71) Applicants: DUPONT NUTRITION BIOSCIENCES APS, Copenhagen (DK); UNIVERSITE LAVAL (CANADA), Québec (CA)

(72) Inventors: Christophe Fremaux, Poitiers (FR); Philippe Horvath, Châtellerault (FR); Dennis A. Romero, Oregon, WI (US); Sylvain Moineau, Quebec (CA); Alexander Hynes, Québec (CA); Geneviève Rousseau, Québec (CA)

(73) Assignees: DUPONT NUTRITION BIOSCIENCES APS, Kongens Lyngby (DK); UNIVERSITE LAVAL (CANADA), Quebec (CA)

( * ) Notice: Subject to any disclaimer, the term of this patent is extended or adjusted under 35 U.S.C. 154(b) by 550 days.

(21) Appl. No.: 16/607,200

(22) PCT Filed: Apr. 24, 2018

(86) PCT No.: PCT/EP2018/060481
§ 371 (c)(1),
(2) Date: Oct. 22, 2019

(87) PCT Pub. No.: WO2018/197495
PCT Pub. Date: Nov. 1, 2018

(65) Prior Publication Data
US 2020/0040328 A1 Feb. 6, 2020

Related U.S. Application Data

(60) Provisional application No. 62/510,896, filed on May 25, 2017, provisional application No. 62/488,969, filed on Apr. 24, 2017.

(51) Int. Cl.
| | | |
|---|---|---|
| *C12N 15/10* | (2006.01) | |
| *C07K 14/005* | (2006.01) | |
| *C07K 14/315* | (2006.01) | |
| *C12N 1/36* | (2006.01) | |
| *C12N 15/74* | (2006.01) | |

(52) U.S. Cl.
CPC ........ *C12N 15/1079* (2013.01); *C07K 14/005* (2013.01); *C07K 14/315* (2013.01); *C12N 1/36* (2013.01); *C12N 15/746* (2013.01); *C12N 2795/10022* (2013.01); *C12N 2795/10322* (2013.01)

(58) Field of Classification Search
None
See application file for complete search history.

(56) References Cited

FOREIGN PATENT DOCUMENTS

| | | |
|---|---|---|
| WO | 2015124718 A1 | 8/2015 |
| WO | 2016012552 A1 | 1/2016 |

OTHER PUBLICATIONS

Barrangou et al., CRISPR Provides Acquired Resistance Against Viruses in Prokaryotes, Science, vol. 315, Mar. 2007, 1709-1712.
Bondy-Denomy et al., Bacteriophage genes that inactivate the CRISPR/Cas bacterial immune system, Nature, vol. 493, Jan. 2013, 429-432.
Bondy-Denomy et al., Multiple mechanisms for CRISPR-Cas inhibition by anti-CRISPR proteins, Nature, vol. 526, Oct. 2015, 136-150.
Chowdhury et al., Structure reveals mechanisms of viral suppressors that intercept a CRISPR RNA-guided surveillance complex, Cell, 169(1), Mar. 2017, 47-57.
Chylinksi et al., Classification and evolution of type II CRISPR-Cas systems, Nucleic Acids Research, Apr. 2014, vol. 42, No. 10, 6091-6105.
Dayhoff et al., A Model of Evolutionary Change in Proteins, Chapter 22, Atlas of Protein Sequence and Structure (Natl. Biomed. Res. Found., Washington, D.C.), 1978, 345-352.
Dupuis et al., CRISPR-Cas and restriction-modification systems are compatible and increase phage resistance, Nature Communications, Jul. 2013, 1-8.
Jiang et al., CRISPR-assisted editing of bacterial genomes, Nat Biotechnol. Mar. 2013, 31(3), 233-239, and Supplement (21 pgs).
Jinek et al., A programmable dual RNA-guided DNA endonuclease in adaptive bacterial immunity, Science, Aug. 2012, 17, 337(6096), 816-821.
Labrie et al., Bacteriophage resistance mechanisms, Nature Reviews, vol. 8, May 2010, 317-327.
Lemay et al., Genome Engineering of Virulent Lactococcal Phages Using CRISPRCas9, ACS Synth. Biol., Mar. 2017, 6, 1351-1358, and supplement (6 pgs.).
Makarova et al., An updated evolutionary classification of CRISPR-Cas systems, Nature Reviews, vol. 13, Nov. 2015, 722-736.
Makarova et al., Snapshot: Class 2 CRISPR-Cas Systems, Cell 168, Jan. 2017, 328-328.e1.
Maxwell et al., The Solution Structure of an anti-CRISPR protein, Nature Communications 7:13134, Oct. 2016, 1-5.
McDonnell et al., Generation of Bacteriophage-Insensitive Mutants of *Streptococcus thermophilus* via an Antisense RNA CRISPR-Cas Silencing Approach, Appl. Environ. Microbiol., 84(4), Feb. 2018, 1-14.
O'Sullivan et al., High- and low-copy number Lactococcus shuttle cloning vectors with features for clone screening, Gene, 137, Dec. 1993, 227-231.

(Continued)

*Primary Examiner* — Oluwatosin A Ogunbiyi

(57) ABSTRACT

The invention relates to anti-CRISPR genes and anti-CRISPR proteins, and their uses in various biotechnology applications.

14 Claims, 4 Drawing Sheets

Specification includes a Sequence Listing.

(56) References Cited

OTHER PUBLICATIONS

Pawluk et al., A New Group of Phage Anti-CRISPR Genes Inhibits the Type I-E CRISPR-Cas System of Pseudomonas aeruginosa, mBio, vol. 5(2), Mar./Apr. 2014, 1-7.
Pawluk et al., Inactivation of CRISPR-Cas systems by anti-CRISPR proteins in diverse bacterial species, Nature Microbiology, 1, Aug. 2016, 1-6.
Pawluk et al., Naturally Occurring Off-Switches for CRISPR-Cas9, Cell 167, Dec. 2016, 1829-1838.
Rauch et al., Inhibition of CRISPR-Cas9 with Bacteriophage Proteins, Cell 168, Jan. 2017, 150-158.
Samson et al., Revenge of the phages: defeating bacterial defences, Nature Reviews, vol. 11, Oct. 2013, 375-687.
Shmakov et al., Diversity and evolution of class 2 CRISPR-Cas systems, Nat Rev Microbiol. Mar. 2017, 15(3): 169-182.
Hynes et al., An anti-CRISPR from a virulent streptococcal phage inhibits *Streptococcus pyogenes* Cas9, Nature Microbiology, vol. 2, Oct. 2017, 1374-1380.
International Search Report and Written Opinion issued in PCT/EP2018/060481 dated Sep. 19, 2018, 20 pgs.

SEQUENCE LISTING

<160> NUMBER OF SEQ ID NOS: 552

<210> SEQ ID NO 1
<211> LENGTH: 327
<212> TYPE: DNA
<213> ORGANISM: Bacteriophage O1205

<400> SEQUENCE: 1

```
atggcatacg gaaaaagcag atacaactca tataggaaac gcagtttcaa tagaagcgat      60
aagcaacgta gagaatacgc acaagaaatg gatagattag aacaaacatt tgaaaaactt     120
gatggttggt atctatctag catgaaagat agtgcgtata aagatttcgg aaaatacgaa     180
attcgcttat caaatcattc agcagacaac aaatatcatg acctagaaaa tggtcgttta     240
attgttaatg tcaaagcaag taaattgaaa ttcgttgata tcaaatgtta ctataaggga     300
tttaagacaa agaaggatgt aatctaa                                          327
```

<210> SEQ ID NO 2
<211> LENGTH: 108
<212> TYPE: PRT
<213> ORGANISM: Bacteriophage O1205

<400> SEQUENCE: 2

```
Met Ala Tyr Gly Lys Ser Arg Tyr Asn Ser Tyr Arg Lys Arg Ser Phe
1               5                   10                  15

Asn Arg Ser Asp Lys Gln Arg Arg Glu Tyr Ala Gln Glu Met Asp Arg
            20                  25                  30

Leu Glu Gln Thr Phe Glu Lys Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Val Lys Ala Ser Lys Leu Lys Phe Val Asp Ile Lys Cys
                85                  90                  95

Tyr Tyr Lys Gly Phe Lys Thr Lys Lys Asp Val Ile
            100                 105
```

<210> SEQ ID NO 3
<211> LENGTH: 423
<212> TYPE: DNA
<213> ORGANISM: Bacteriophage Sfi21

<400> SEQUENCE: 3

```
atggcatacg gaaaaagtag atataactca tatagaaagc gcagttttaa cagaagtaat      60
aagcaacgta gagaatacgc acaagaaatg gatagattag agaaagcttt cgaaaatctt     120
gacggatggt atctatctag catgaaagat agtgcgtaca aagatttcgg aaaatacgaa     180
attcgcttat caaatcattc agcagacaac aaatatcatg acctagaaaa tggtcgttta     240
```

```
attgttaatg tcaaagcaag taaattgaac ttcgttgata tcatcgagaa caaacttgat    300
aaaatcattg agaagattga tactcttgat ttagataagt acagattcat taatgctact    360
aaattggaac gtgatatcaa atgctactat aaaggctata agacaaagaa ggatgtaatc    420
taa                                                                  423
```

<210> SEQ ID NO 4
<211> LENGTH: 140
<212> TYPE: PRT
<213> ORGANISM: Bacteriophage Sfi21

<400> SEQUENCE: 4

```
Met Ala Tyr Gly Lys Ser Arg Tyr Asn Ser Tyr Arg Lys Arg Ser Phe
1               5                   10                  15

Asn Arg Ser Asn Lys Gln Arg Arg Glu Tyr Ala Gln Glu Met Asp Arg
            20                  25                  30

Leu Glu Lys Ala Phe Glu Asn Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Asp Lys Ile Ile Glu Lys Ile Asp Thr Leu Asp Leu Asp
            100                 105                 110

Lys Tyr Arg Phe Ile Asn Ala Thr Lys Leu Glu Arg Asp Ile Lys Cys
        115                 120                 125

Tyr Tyr Lys Gly Tyr Lys Thr Lys Lys Asp Val Ile
    130                 135                 140
```

<210> SEQ ID NO 5
<211> LENGTH: 423
<212> TYPE: DNA
<213> ORGANISM: Bacteriophage TP-778L

<400> SEQUENCE: 5

```
atggcatacg gaaaaagcag atacaactca tatagaaaac gtagtttcaa cataagtgac     60
acaaagcgta gggaatatgc aaaagaaatg gagaaattag aacaagcatt tgaaaagcta    120
gatggttggt atctatctag catgaaggat agtgcataca aggattttgg aaaatacgaa    180
atccgcttat caaatcattc agcagacaat aaatatcatg acctagaaaa tggtcgttta    240
attgttaatg ttaaagcaag taaattgaac ttcgttgata tcatcgaaaa caaacttgat    300
aaaatcatcg agaagattga taagcttgat ttagataagt acagatttat taacgctact    360
agaatggagc atgacattaa atgctactat aaaggattta agacaaagaa agatgtaatc    420
taa                                                                  423
```

<210> SEQ ID NO 6
<211> LENGTH: 140
<212> TYPE: PRT
<213> ORGANISM: Bacteriophage TP-778L

<400> SEQUENCE: 6

```
Met Ala Tyr Gly Lys Ser Arg Tyr Asn Ser Tyr Arg Lys Arg Ser Phe
1               5                   10                  15
```

Asn Ile Ser Asp Thr Lys Arg Arg Glu Tyr Ala Lys Glu Met Glu Lys
            20                  25                  30

Leu Glu Gln Ala Phe Glu Lys Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Arg Met Glu His Asp Ile Lys Cys
        115                 120                 125

Tyr Tyr Lys Gly Phe Lys Thr Lys Lys Asp Val Ile
            130                 135                 140

<210> SEQ ID NO 7
<211> LENGTH: 423
<212> TYPE: DNA
<213> ORGANISM: Streptococcus sp.

<400> SEQUENCE: 7
atggcatttg gcaagaacag atacaatcca tacaggaaac gtagttttaa tcgtagtgat     60
aaacaatgtc gagagtatgc tcaggcaatg gacgaactag aacaagcctt tgaggaactt    120
gatggatggc acttatctag tatgatggat agtgcttata gaattttga aaagtaccag     180 gttcgcctat caaatcattc agcagacaac caatatcatg acttagaaaa tggttacttg    240
attgtcaatg ttaaagcaag taaattgaac tttgtcgata ttatcgaaaa taaattggat    300
aagattttag agaaagtaga caagcttgat cttgataagt ataggtttat caatgcgacc    360
aatctggaac atgatattaa atgttatctc aaaggctata agacgaaaaa agacgtgatt    420
taa                                                                  423

<210> SEQ ID NO 8
<211> LENGTH: 140
<212> TYPE: PRT
<213> ORGANISM: Streptococcus sp.

<400> SEQUENCE: 8

Met Ala Phe Gly Lys Asn Arg Tyr Asn Pro Tyr Arg Lys Arg Ser Phe
1               5                   10                  15

Asn Arg Ser Asp Lys Gln Cys Arg Glu Tyr Ala Gln Ala Met Asp Glu
            20                  25                  30

Leu Glu Gln Ala Phe Glu Glu Leu Asp Gly Trp His Leu Ser Ser Met
        35                  40                  45

Met Asp Ser Ala Tyr Lys Asn Phe Glu Lys Tyr Gln Val Arg Leu Ser
    50                  55                  60

Asn His Ser Ala Asp Asn Gln Tyr His Asp Leu Glu Asn Gly Tyr Leu
65                  70                  75                  80

Ile Val Asn Val Lys Ala Ser Lys Leu Asn Phe Val Asp Ile Ile Glu
                85                  90                  95

Asn Lys Leu Asp Lys Ile Leu Glu Lys Val Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Leu Lys Gly Tyr Lys Thr Lys Lys Asp Val Ile
    130             135             140

<210> SEQ ID NO 9
<211> LENGTH: 423
<212> TYPE: DNA
<213> ORGANISM: Bacteriophage D4276

<400> SEQUENCE: 9
atggcatacg gaaaaagtag atataactca tatagaaagc gcagttttaa cagaagtaat      60
aagcaacgta gagaatacgc acaagaaatg gatagattag agaaagcttt cgaaaatctt     120
gacggatggt atctatctag catgaaagac agtgcttaca aggattttgg gaaatacgaa     180
attcgcttat caaatcattc ggcagacaac aaatatcacg acttagaaaa cggtcgttta     240
attgttaata ttaaagctag taaattgaat ttcgttgata tcatcgagaa taagcttgat     300
aaaataatcg agaagattga taagcttgat ttagataagt accgattcat caatgcgacc     360
aacctagagc atgatatcaa atgctattac aaggggttta aacgaaaaa ggaggtaatc      420 taa                                                                  423

<210> SEQ ID NO 10
<211> LENGTH: 140
<212> TYPE: PRT
<213> ORGANISM: Bacteriophage D4276

<400> SEQUENCE: 10

Met Ala Tyr Gly Lys Ser Arg Tyr Asn Ser Tyr Arg Lys Arg Ser Phe
1               5                   10                  15

Asn Arg Ser Asn Lys Gln Arg Arg Glu Tyr Ala Gln Glu Met Asp Arg
            20                  25                  30

Leu Glu Lys Ala Phe Glu Asn Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Ile Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Tyr Lys Gly Phe Lys Thr Lys Lys Glu Val Ile
    130             135             140

<210> SEQ ID NO 11
<211> LENGTH: 423
<212> TYPE: DNA
<213> ORGANISM: Bacteriophage D1126

<400> SEQUENCE: 11
atggcatacg gaaaaagcag atacaattca tataggaagc gaaacttctc tataagcgac      60
aatcagcgta gggaatatgc taaaaaaatg aaggagttag aacaagcgtt tgaaaacctt     120
gacggatggt atctatctag catgaaagat agtgcgtaca agatttcgg aaatacgaa       180 attcgcttat caaatcattc agcagacaat agatatcatg acctagaaaa tggtcgctta     240

```
atcgttaatg ttaaagctag taaattgaac ttcgttgata tcatcgagaa taaacttggt    300
aaaatcattg agaagattga tactcttgat ttagataagt acagattcat taatgctact    360
aaattggaac gtgatatcaa atgctactat aaaggctata agacaaagaa ggatgtaatc    420
taa                                                                 423
```

<210> SEQ ID NO 12
<211> LENGTH: 140
<212> TYPE: PRT
<213> ORGANISM: Bacteriophage D1126

<400> SEQUENCE: 12

```
Met Ala Tyr Gly Lys Ser Arg Tyr Asn Ser Tyr Arg Lys Arg Asn Phe
1               5                   10                  15

Ser Ile Ser Asp Asn Gln Arg Arg Glu Tyr Ala Lys Lys Met Lys Glu
            20                  25                  30

Leu Glu Gln Ala Phe Glu Asn Leu Asp Gly Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Arg Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Gly Lys Ile Ile Glu Lys Ile Asp Thr Leu Asp Leu Asp
            100                 105                 110

Lys Tyr Arg Phe Ile Asn Ala Thr Lys Leu Glu Arg Asp Ile Lys Cys
        115                 120                 125

Tyr Tyr Lys Gly Tyr Lys Thr Lys Lys Asp Val Ile
    130                 135                 140
```

<210> SEQ ID NO 13
<211> LENGTH: 423
<212> TYPE: DNA
<213> ORGANISM: Bacteriophage D4250

<400> SEQUENCE: 13

```
atggcatacg gaaaaagtag atataactca tatagaaaac gcagtttcaa cagaagcgat     60
aaacagcgta gagaatacgc acaagcaatg gaagaattag agcaagcatt tgaaaacttt    120
gatgattggt atctatcaag catgaaagac agtgcttaca aggatttttgg gaaatacgaa   180 attcgcttat caaatcattc ggcagacaac aaatatcacg acttagaaaa cggtcgttta    240
attgttaata ttaaagctag taaattgaat ttcgttgata tcatcgagaa taagcttgat    300
aaaataatcg agaagattga taagcttgat ttagataagt accgattcat caatgcgacc    360
aacctagagc atgatatcaa atgctattac aagggggttta aaacgaaaaa ggaggtaatc    420
taa                                                                 423
```

<210> SEQ ID NO 14
<211> LENGTH: 140
<212> TYPE: PRT
<213> ORGANISM: Bacteriophage D4250

<400> SEQUENCE: 14

```
Met Ala Tyr Gly Lys Ser Arg Tyr Asn Ser Tyr Arg Lys Arg Ser Phe
1               5                   10                  15

Asn Arg Ser Asp Lys Gln Arg Arg Glu Tyr Ala Gln Ala Met Glu Glu
```

```
                    20                  25                  30
Leu Glu Gln Ala Phe Glu Asn Phe Asp Asp Trp Tyr Leu Ser Ser Met
            35                  40                  45

Lys Asp Ser Ala Tyr Lys Asp Phe Gly Lys Tyr Glu Ile Arg Leu Ser
        50                  55                  60

Asn His Ser Ala Asp Asn Lys Tyr His Asp Leu Glu Asn Gly Arg Leu
65                  70                  75                  80

Ile Val Asn Ile Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Tyr Lys Gly Phe Lys Thr Lys Lys Glu Val Ile
    130                 135                 140

<210> SEQ ID NO 15
<211> LENGTH: 423
<212> TYPE: DNA
<213> ORGANISM: Bacteriophage D4252

<400> SEQUENCE: 15
atggcatacg gaaaaagcag atacaactca tatagaaagc gcagttttaa cagaagtgat      60
aagcaacgta gagaatacgc taaaaaaatg aaggagttag aacaagcgtt tgaaaacctt    120
gatggttggt atctatcgag catgaatgac agtgcttata aaatttttgg caaatatgaa    180
gttcgattgt caaatcattc ggcagataat aaatatcacg acatagaaaa cggtcgttta    240
attgttaatg ttaaagctag taaattgaat ttcgttgata tcatcgagaa caagcttgat    300
aaaataatcg agaagattga taagcttgat ttagataagt accgattcat caacgctacc    360
aatctagagc ataatattaa atgctattac aagggattta agacaagaa ggatgtaata     420 taa                                                                  423

<210> SEQ ID NO 16
<211> LENGTH: 140
<212> TYPE: PRT
<213> ORGANISM: Bacteriophage D4252

<400> SEQUENCE: 16

Met Ala Tyr Gly Lys Ser Arg Tyr Asn Ser Tyr Arg Lys Arg Ser Phe
1               5                   10                  15

Asn Arg Ser Asp Lys Gln Arg Arg Glu Tyr Ala Lys Lys Met Lys Glu
            20                  25                  30

Leu Glu Gln Ala Phe Glu Asn Leu Asp Gly Trp Tyr Leu Ser Ser Met
        35                  40                  45

Asn Asp Ser Ala Tyr Lys Asn Phe Gly Lys Tyr Glu Val Arg Leu Ser
    50                  55                  60

Asn His Ser Ala Asp Asn Lys Tyr His Asp Ile Glu Asn Gly Arg Leu
65                  70                  75                  80

Ile Val Asn Val Lys Ala Ser Lys Leu Asn Phe Val Asp Ile Ile Glu
                85                  90                  95

Asn Lys Leu Asp Lys Ile Ile Glu Lys Ile Asp Lys Leu Asp Leu Asp
            100                 105                 110

Lys Tyr Arg Phe Ile Asn Ala Thr Asn Leu Glu His Asn Ile Lys Cys
        115                 120                 125
```

Tyr Tyr Lys Gly Phe Lys Thr Lys Lys Asp Val Ile
            130                 135                 140

<210> SEQ ID NO 17
<211> LENGTH: 423
<212> TYPE: DNA
<213> ORGANISM: Bacteriophage D4598

<400> SEQUENCE: 17
atggcatacg gaaaaagtag atataactca tatagaaaac gcagtttcaa cagaagcgat      60
aaacagcgtg gagaatacgc acaagcaatg gaagaattag agcaagcatt tgaaaacttt     120
gatgattggt atctatcaag catgaaagac agtgcttaca aggattttgg gaaatacgaa     180
attcgcttat caaatcattc ggcagacaat aaatatcatg acctagaaaa tggtcgctta     240
atcgttaatg ttaaagctag taaattgaac ttcgtcgata tcatcgagaa taaaatcgat     300
aaaatcattg agaagattga taagcttgat ttagataagt accgattcat caacgctacc     360
aacctagagc atgatatcaa atgttattac aagggattta agacaaaaaa ggatgtaatc     420
taa                                                                  423

<210> SEQ ID NO 18
<211> LENGTH: 140
<212> TYPE: PRT
<213> ORGANISM: Bacteriophage D4598

<400> SEQUENCE: 18

Met Ala Tyr Gly Lys Ser Arg Tyr Asn Ser Tyr Arg Lys Arg Ser Phe
1               5                   10                  15

Asn Arg Ser Asp Lys Gln Arg Gly Glu Tyr Ala Gln Ala Met Glu Glu
            20                  25                  30

Leu Glu Gln Ala Phe Glu Asn Phe Asp Asp Trp Tyr Leu Ser Ser Met
        35                  40                  45

Lys Asp Ser Ala Tyr Lys Asp Phe Gly Lys Tyr Glu Ile Arg Leu Ser
    50                  55                  60

Asn His Ser Ala Asp Asn Lys Tyr His Asp Leu Glu Asn Gly Arg Leu
65                  70                  75                  80

Ile Val Asn Val Lys Ala Ser Lys Leu Asn Phe Val Asp Ile Ile Glu
                85                  90                  95

Asn Lys Ile Asp Lys Ile Glu Lys Ile Asp Lys Leu Asp Leu Asp
            100                 105                 110

Lys Tyr Arg Phe Ile Asn Ala Thr Asn Leu Glu His Asp Ile Lys Cys
        115                 120                 125

Tyr Tyr Lys Gly Phe Lys Thr Lys Lys Asp Val Ile
            130                 135                 140

<210> SEQ ID NO 19
<211> LENGTH: 423
<212> TYPE: DNA
<213> ORGANISM: Streptococcus mutans

<400> SEQUENCE: 19
atggcatttg aaaaagaag atataactcg tatcgtaaac gcagttttaa tagaagtgat      60
aagcaacgtc gagaatatgc acaagcaatg gaagaacttg aacaaacatt tgaaaatctt    120
gaaggttgga atttatcaag catgaaagat agtgcttata agattatgga taaatatgaa    180
gttcgacttt caaatcattc agctgataat caatatcata acttacaaga tggtaaatta    240
atcatcaata tcaaagctag taaatgaat tttgtttgga ttatagaaaa taaacttgat     300

```
gcaattcttg aaaaagtaaa taagttagac cttagcaaat acagatttat taatgctaca      360
agtttagatc atgatatcaa atgttattac aaaaattata aaacaaagaa agatgtaatt      420
taa                                                                    423
```

<210> SEQ ID NO 20
<211> LENGTH: 140
<212> TYPE: PRT
<213> ORGANISM: Streptococcus mutans

<400> SEQUENCE: 20

```
Met Ala Phe Gly Lys Arg Arg Tyr Asn Ser Tyr Arg Lys Arg Ser Phe
1               5                   10                  15

Asn Arg Ser Asp Lys Gln Arg Arg Glu Tyr Ala Gln Ala Met Glu Glu
            20                  25                  30

Leu Glu Gln Thr Phe Glu Asn Leu Glu Gly Trp Asn Leu Ser Ser Met
        35                  40                  45

Lys Asp Ser Ala Tyr Lys Asp Tyr Asp Lys Tyr Glu Val Arg Leu Ser
    50                  55                  60

Asn His Ser Ala Asp Asn Gln Tyr His Asn Leu Gln Asp Gly Lys Leu
65                  70                  75                  80

Ile Ile Asn Ile Lys Ala Ser Lys Met Asn Phe Val Trp Ile Ile Glu
                85                  90                  95

Asn Lys Leu Asp Ala Ile Leu Glu Lys Val Asn Lys Leu Asp Leu Ser
            100                 105                 110

Lys Tyr Arg Phe Ile Asn Ala Thr Ser Leu Asp His Asp Ile Lys Cys
        115                 120                 125

Tyr Tyr Lys Asn Tyr Lys Thr Lys Lys Asp Val Ile
    130                 135                 140
```

<210> SEQ ID NO 21
<211> LENGTH: 423
<212> TYPE: DNA
<213> ORGANISM: Streptococcus mutans

<400> SEQUENCE: 21

```
atggcatttg gaacaagaag atataattca tatcgtaaac gcagttttaa tagaagtgat       60
aagcaacgtc gagaatatgc acaagcaatg gaagaacttg aacaaacatt tgaaaatctt      120
gaagattgga atttgtcgag catgaaagat agtgcttata aagattatga taaatatgaa      180
gttcgacttt caaatcattc agctgataat caatatcata acttacaaga tggtaaatta      240
atcatcaata tcaaagctag taaatgaat tttgtttgga ttatagaaaa taaacttgat      300
gcaattcttg aaaaagtaaa taagttagac cttagcagat acagatttat taatgctaca      360
aatttagaac atgatatcaa atgttattac aaaaattata aaacaaagaa agatgtaatt      420
taa                                                                    423
```

<210> SEQ ID NO 22
<211> LENGTH: 140
<212> TYPE: PRT
<213> ORGANISM: Streptococcus mutans

<400> SEQUENCE: 22

```
Met Ala Phe Gly Thr Arg Arg Tyr Asn Ser Tyr Arg Lys Arg Ser Phe
1               5                   10                  15

Asn Arg Ser Asp Lys Gln Arg Arg Glu Tyr Ala Gln Ala Met Glu Glu
            20                  25                  30
```

Leu Gln Thr Phe Glu Asn Leu Glu Asp Trp Asn Leu Ser Ser Met
    35                  40                  45

Lys Asp Ser Ala Tyr Lys Asp Tyr Asp Lys Tyr Glu Val Arg Leu Ser
 50                  55                  60

Asn His Ser Ala Asp Asn Gln Tyr His Asn Leu Gln Asp Gly Lys Leu
 65                  70                  75                  80

Ile Ile Asn Ile Lys Ala Ser Lys Met Asn Phe Val Trp Ile Ile Glu
                 85                  90                  95

Asn Lys Leu Asp Ala Ile Leu Glu Lys Val Asn Lys Leu Asp Leu Ser
                100                 105                 110

Arg Tyr Arg Phe Ile Asn Ala Thr Asn Leu Glu His Asp Ile Lys Cys
                115                 120                 125

Tyr Tyr Lys Asn Tyr Lys Thr Lys Lys Asp Val Ile
                130                 135                 140

<210> SEQ ID NO 23
<211> LENGTH: 423
<212> TYPE: DNA
<213> ORGANISM: Streptococcus mutans

<400> SEQUENCE: 23
atggcatttg gaacaagaag atataattca tatcgtaaac gcagttttaa tagaagtgat      60
aagcaacgtc gagaatatgc acaagcaatg gaagaacttg aacaaacatt tgaaaatctt     120
gaagattgga atttgtcgag catgaaagat agtgcttata agattatga taaatatgaa     180 gttagacttt caaatcattc agctgataat caatatcata acttacaaga tggtaaatta     240
atcatcaata tcaaagctag taaatgaat tttgtttgga ttatagaaaa taaacttgat     300
gtaattcttg aaaaagtaaa taagttagac cttagcaaat acagatttat taatgctaca     360
agtttagatc atgatatcaa atgttattac aaaaattata aaacaaagaa agatgtaatc     420
taa                                                                    423

<210> SEQ ID NO 24
<211> LENGTH: 140
<212> TYPE: PRT
<213> ORGANISM: Streptococcus mutans

<400> SEQUENCE: 24

Met Ala Phe Gly Thr Arg Arg Tyr Asn Ser Tyr Arg Lys Arg Ser Phe
 1               5                  10                  15

Asn Arg Ser Asp Lys Gln Arg Arg Glu Tyr Ala Gln Ala Met Glu Glu
                 20                  25                  30

Leu Glu Gln Thr Phe Glu Asn Leu Glu Asp Trp Asn Leu Ser Ser Met
            35                  40                  45

Lys Asp Ser Ala Tyr Lys Asp Tyr Asp Lys Tyr Glu Val Arg Leu Ser
 50                  55                  60

Asn His Ser Ala Asp Asn Gln Tyr His Asn Leu Gln Asp Gly Lys Leu
 65                  70                  75                  80

Ile Ile Asn Ile Lys Ala Ser Lys Met Asn Phe Val Trp Ile Ile Glu
                 85                  90                  95

Asn Lys Leu Asp Val Ile Leu Glu Lys Val Asn Lys Leu Asp Leu Ser
                100                 105                 110

Lys Tyr Arg Phe Ile Asn Ala Thr Ser Leu Asp His Asp Ile Lys Cys
                115                 120                 125

Tyr Tyr Lys Asn Tyr Lys Thr Lys Lys Asp Val Ile

<210> SEQ ID NO 25
<211> LENGTH: 423
<212> TYPE: DNA
<213> ORGANISM: Streptococcus mutans

<400> SEQUENCE: 25

```
atggcatttg gaacaagaag atataattca tatcgtaaac gcaattttaa tagaagtgat      60
aaacaacgtc gagaatatgc acaagcaatg gaagaacttg aacaaacatt tgaaaatctt    120
gaagattgga atttgtcgag catgaaagat agtgcttata agattatga taaatttgaa     180
gttcgacttt caaatcattc agctgataat caatatcata acttacaaga tggtaaatta    240
atcatcaata tcaaagctag taaatgaat tttgtttgga ttatagaaaa taaacttgat     300
gcaattcttg aaaaggtaaa taagttagac cttagcaaat acagatttat taatgctaca    360
agtttagatc atgatatcaa atgttattac aaaaattata aaacaaaaaa agatgtaatt    420
taa                                                                  423
```

<210> SEQ ID NO 26
<211> LENGTH: 140
<212> TYPE: PRT
<213> ORGANISM: Streptococcus mutans

<400> SEQUENCE: 26

```
Met Ala Phe Gly Thr Arg Arg Tyr Asn Ser Tyr Arg Lys Arg Asn Phe
1               5                   10                  15
Asn Arg Ser Asp Lys Gln Arg Arg Glu Tyr Ala Gln Ala Met Glu Glu
            20                  25                  30
Leu Glu Gln Thr Phe Glu Asn Leu Glu Asp Trp Asn Leu Ser Ser Met
        35                  40                  45
Lys Asp Ser Ala Tyr Lys Asp Tyr Asp Lys Phe Glu Val Arg Leu Ser
    50                  55                  60
Asn His Ser Ala Asp Asn Gln Tyr His Asn Leu Gln Asp Gly Lys Leu
65                  70                  75                  80
Ile Ile Asn Ile Lys Ala Ser Lys Met Asn Phe Val Trp Ile Ile Glu
                85                  90                  95
Asn Lys Leu Asp Ala Ile Leu Glu Lys Val Asn Lys Leu Asp Leu Ser
            100                 105                 110
Lys Tyr Arg Phe Ile Asn Ala Thr Ser Leu Asp His Asp Ile Lys Cys
        115                 120                 125
Tyr Tyr Lys Asn Tyr Lys Thr Lys Lys Asp Val Ile
    130                 135                 140
```

<210> SEQ ID NO 27
<211> LENGTH: 552
<212> TYPE: DNA
<213> ORGANISM: Bacteriophage D1811

<400> SEQUENCE: 27

```
atgaaaataa atgacgacat caaagagtta atttagaat atatgagccg ttacttcaaa      60
ttcgagaacg acttttataa actgccaggc atcaagttca ctgatgcaaa ttggcagaag    120
ttcaaaaatg gaggcactga cattgagaag atggggggcgg cacgagtaaa cgccatgctc    180
gactgcctat tcgacgattt cgagcttgct atgattggca aggctcaaac taattattac    240
aatgataatt cactaaagat gaacatgcca ttttacactt actatgacat gttcaaaaag    300
```

```
cagcaacttc taaaatggct taaaaataac cgtgatgatg tcatcggcgg aactggtagg    360
atgtacacag caagtggtaa ttacattgct aacgcttatt tagaggtggc attagaatcg    420
agctcgcttg gtagtggctc ttacatgctt caaatgaggt ttaaagacta ttcaaaaggt    480
caagaaccta ttccgtcagg tcgtcagaat cgacttgaat ggattgaaaa caatctcgaa    540
aacattcgat aa                                                        552
```

<210> SEQ ID NO 28
<211> LENGTH: 183
<212> TYPE: PRT
<213> ORGANISM: Bacteriophage D1811

<400> SEQUENCE: 28

```
Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Gly Thr Asp Ile
        35                  40                  45

Glu Lys Met Gly Ala Ala Arg Val Asn Ala Met Leu Asp Cys Leu Phe
    50                  55                  60

Asp Asp Phe Glu Leu Ala Met Ile Gly Lys Ala Gln Thr Asn Tyr Tyr
65                  70                  75                  80

Asn Asp Asn Ser Leu Lys Met Asn Met Pro Phe Tyr Thr Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180
```

<210> SEQ ID NO 29
<211> LENGTH: 552
<212> TYPE: DNA
<213> ORGANISM: Bacteriophage D1024

<400> SEQUENCE: 29

```
atgaaaataa atgacgacat caaagagtta attttagaat atatgagccg ttacttcaaa     60
ttcgagaacg acttttataa actgccaggc atcaagttca ctgatgcaaa ttggcagaag    120
ttcaaaaatg gaggcactga cattgagaag atggggggcgg cacgagtaaa tgccatgctt    180
tcctgcctat tcgaggattt tgagcttgca atgattggca aggctcaaac taattattac    240
attgataact cacttaaatt gaacatgcca ttttacgctt actatgacat gttcaaaaag    300
caacttctta taaattggct taaaaataac cgtgatgatg tcatctgcgg aactggtagg    360
atgtacacag caagtggtaa ttacattgct aacgcttatt tagaggtggc attagaatct    420
agccgtctgg gtggtggtga gtacatgttg caaatgcgtt ttaaaaatta ttcaagaagt    480
caagaaccta ttccgtctgg tcgtcagaat cgacttgaat ggattgaaaa caatcttgaa    540
```
aacattcgat aa                                                                552

<210> SEQ ID NO 30
<211> LENGTH: 183
<212> TYPE: PRT
<213> ORGANISM: Bacteriophage D1024

<400> SEQUENCE: 30

Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Gly Thr Asp Ile
        35                  40                  45

Glu Lys Met Gly Ala Ala Arg Val Asn Ala Met Leu Ser Cys Leu Phe
50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ala Tyr Leu Glu Val Ala Leu Glu Ser Ser Arg Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 31
<211> LENGTH: 552
<212> TYPE: DNA
<213> ORGANISM: Bacteriophage D4530

<400> SEQUENCE: 31
atgaaaatca ataatgacat caaagagcta attttggaat atgtaagtcg ctattttaaa     60
tttgaaaacg acttctacaa attgccaggc atcaaattca ctgatgcaaa ttggcaaaaa    120
ttcaagaatg gagatacttc catcgagaag atgggggcag cacgagtaaa tgccatgctt    180
gactgcctgt tcgaagattt tgagcttgca atgattggca aggctcaaac taattattac    240
aatgataatt cactaaagat gaacatgcca ttttacactt actatgacat gttcaaaaag    300
cagcaacttc taaatggct taaaaataac cgtgatgatg tcatctgcgg aactggtagg    360
atgtacacag caagtggtaa ttacattgct aacgcttatt tagaaattgc gttagaatct    420
agccgtctgg gtagtggctc ttacatgctt caaatgagat tcaaagacta ttcaagaagt    480
caagaaccta ttccgtctgg tcgccaaaat agactagaat ggattgagag caacttggaa    540
aacattcgat aa                                                        552

<210> SEQ ID NO 32
<211> LENGTH: 183
<212> TYPE: PRT

<213> ORGANISM: Bacteriophage D4530

<400> SEQUENCE: 32

```
Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Asn Asp Asn Ser Leu Lys Met Asn Met Pro Phe Tyr Thr Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ala Tyr Leu Glu Ile Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180
```

<210> SEQ ID NO 33
<211> LENGTH: 552
<212> TYPE: DNA
<213> ORGANISM: Bacteriophage D2759

<400> SEQUENCE: 33

```
atgaaaatca ataatgacat caaagagcta atttttggaat atgtaagtcg ctattttaaa    60
tttgaaaacg acttctacaa attgccaggc atcaaattca ctgatgcaaa ttggcaaaaa   120
ttcaagaatg gagatacttc catcgagaag atggggcag cacgagtaaa tgccatgctt    180
gactgcctat tcgacgattt tgagcttgct ttgattggca aggctcaaac taattattac    240
attgataact cacttaaatt gaacatgcca ttttacgctt actatgacat gttcaaaaag   300
cagcaacttc taaaatggct taaaaataac cgtgatgatg tcatctgcgg aactggtagg   360
atgtacacag caagtggtaa ttacattgct aactcttatt tagaggtagc gttagaatct   420
agccgtctgg gtagtggctc ttacatgctt caaatgagat tcaaagacta ttcaagaagt   480
caagaaccta ttccatctgg tcgccaaaat agactagaat ggattgagag caacttggaa   540
aacattcgat aa                                                       552
```

<210> SEQ ID NO 34
<211> LENGTH: 183
<212> TYPE: PRT
<213> ORGANISM: Bacteriophage D2759

<400> SEQUENCE: 34

```
Met Lys Ile Asn Asn Asp Ile Lys Glu Leu Ile Leu Glu Tyr Val Ser
1               5                   10                  15
```

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Asp Asp Phe Glu Leu Ala Leu Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
            115                 120                 125

Ile Ala Asn Ser Tyr Leu Glu Val Ala Leu Glu Ser Ser Arg Leu Gly
        130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 35
<211> LENGTH: 552
<212> TYPE: DNA
<213> ORGANISM: Bacteriophage D1297

<400> SEQUENCE: 35
atgaaaatca ataatgacat caaagagcta attttggaat atgtaagtcg ctattttaaa      60
tttgaaaacg acttctacaa attgcaaggc atcaaattca ctgatgcaaa ttggcaaaaa     120
ttcaagaatg gagatacttc catcgagaag atgggggcag cacgagtaaa tgccatgctt     180
gactgcctat tcgacgattt tgagcttgct ttgattggca aggctcaaca agaatactat     240
tcggataatt ccttgaaatt gaacatgcca ttttacgctt actatgacat gttcaaaaag     300
cagcaacttc taaaatggct aaaaaataac cgtgatgatg tcatctgcgg aactggtagg     360
atgtacacag caagtggtaa ttacattgct aactcttatt tagaggtagc gttagaatct     420
agccgtctgg gtagtggctc ttacatgctt caaatgagat tcaaagacta ttcaagaagt     480
caagaaccta ttccgtcagg tcgcaaaaac cgacttgagt ggattgaaaa caatctggaa     540
aatattcgat aa                                                         552

<210> SEQ ID NO 36
<211> LENGTH: 183
<212> TYPE: PRT
<213> ORGANISM: Bacteriophage D1297

<400> SEQUENCE: 36

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Gln Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe

```
                   50                  55                  60

Asp Asp Phe Glu Leu Ala Leu Ile Gly Lys Ala Gln Gln Glu Tyr Tyr
 65                  70                  75                  80

Ser Asp Asn Ser Leu Lys Leu Asn Met Pro Phe Tyr Ala Tyr Tyr Asp
                     85                  90                  95

Met Phe Lys Lys Gln Gln Leu Leu Lys Trp Leu Lys Asn Asn Arg Asp
                100                 105                 110

Asp Val Ile Cys Gly Thr Gly Arg Met Tyr Thr Ala Ser Gly Asn Tyr
                115                 120                 125

Ile Ala Asn Ser Tyr Leu Glu Val Ala Leu Glu Ser Ser Arg Leu Gly
                130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
                180
```

<210> SEQ ID NO 37
<211> LENGTH: 552
<212> TYPE: DNA
<213> ORGANISM: Bacteriophage M5728

<400> SEQUENCE: 37

```
atgaaaatca ataatgacat caaagagcta attttggaat atgtaagtcg ctattttaaa      60
tttgaaaacg acttctacaa attgccaggc atcaaattca ctgatgcaaa ttggcaaaaa     120
ttcaagaatg gagatacttc catcgagaag atgggggcag cacgagtaaa tgccatgctt     180
gactgcctat tcgacgattt tgagcttgct tttattggca aggctcaaca agaatactat     240
tcggataatt ccttgaaatt gaacatgcca ttttacgctt actatgacat gttcaaaaag     300
cagcaacttc taaaatggct aaaaataac cgtgatgatg tcatctgcgg aactggtagg      360
atgtacacag caagtggtaa ttacattgct aactcttatt tagaggtagc gttagaatct     420
agccgtctgg gtagtggctc ttacatgctt caaatgagat tcaaagacta ttcaagaagt     480
caagaaccta ttccatctgg tcgccaaaat agactagaat ggattgaaaa caatcttgag     540
aatattcgat aa                                                         552
```

<210> SEQ ID NO 38
<211> LENGTH: 183
<212> TYPE: PRT
<213> ORGANISM: Bacteriophage M5728

<400> SEQUENCE: 38

```
Met Lys Ile Asn Asn Asp Ile Lys Glu Leu Ile Leu Glu Tyr Val Ser
 1               5                  10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
        50                  55                  60

Asp Asp Phe Glu Leu Ala Phe Ile Gly Lys Ala Gln Gln Glu Tyr Tyr
 65                  70                  75                  80

Ser Asp Asn Ser Leu Lys Leu Asn Met Pro Phe Tyr Ala Tyr Tyr Asp
                 85                  90                  95
```

```
Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
            115                 120                 125

Ile Ala Asn Ser Tyr Leu Glu Val Ala Leu Glu Ser Ser Arg Leu Gly
            130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 39
<211> LENGTH: 552
<212> TYPE: DNA
<213> ORGANISM: Bacteriophage D4419

<400> SEQUENCE: 39
atgaaaatca ataatgacat caaagagcta attttggaat atgtaagtcg ctattttaaa     60
tttgaaaacg acttctacaa attgccaggc atcaaattca ctgatgcaaa ttggcaaaaa    120
ttcaagaatg agatacttc catcgagaag atggggcag cacgagtaaa tgccatgctt      180
gactgcctat tcgacgattt tgagcttgct ttgattggca aggctcaaca agaatactat    240
tcggataatt ccttgaaatt gaacatgcca ttttacgctt actatgacat gttcaaaaag    300
cagcaacttc taaaatggct taaaaataac cgtgatgatg tcatctgcgg aactggtagg    360
atgtacacag caagtggtaa ttacattgct aactcttatt tagaggtagc gttagaatct    420
agccgtctgg gtagtggctc ttacatgctt caaatgagat tcaaagacta ttcaagaagt    480
caagaaccta ttccatctgg tcgccaaaat agactagaat ggattgagag caacttggaa    540
aacattcgat aa                                                        552

<210> SEQ ID NO 40
<211> LENGTH: 183
<212> TYPE: PRT
<213> ORGANISM: Bacteriophage D4419

<400> SEQUENCE: 40

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Asp Asp Phe Glu Leu Ala Leu Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
            115                 120                 125
```

```
Ile Ala Asn Ser Tyr Leu Glu Val Ala Leu Glu Ser Ser Arg Leu Gly
        130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
            165                 170                 175

Ser Asn Leu Glu Asn Ile Arg
            180

<210> SEQ ID NO 41
<211> LENGTH: 552
<212> TYPE: DNA
<213> ORGANISM: Bacteriophage D5891

<400> SEQUENCE: 41
atgaaaatca ataatgacat caaagagcta attttggaat atgtaagtcg ctattttaaa      60
tttgaaaacg acttctacaa attgccaggc atcaaattca ctgatgcaaa ttggcaaaaa     120
ttcaagaatg gagatacttc catcgagaag atggggggcag cacgagtaaa tgccatgctt    180
gactgcctat tcgacgattt tgagcttgct tttattggca aggctcaaca agaatactat     240
tcggataatt ccttgaaatt gaacatgcca ttttacgctt actatgacat gttcaaaaag     300
cagcaacttc taaaatggct taaaaataac cgtgatgatg tcatctgcgg aactggtagg     360
atgtacacag caagtggtaa ttacattgct aactcttatt tagaggtagc gttagaatct     420
agccgtctgg gtagtggctc ttacatgctt caaatgagat tcaaagacta ttcaagaagt     480
caagaaccta ttccatctgg tcgccaaaat agactagaat ggattgagag caacttggaa     540
aacattcgat aa                                                         552

<210> SEQ ID NO 42
<211> LENGTH: 183
<212> TYPE: PRT
<213> ORGANISM: Bacteriophage D5891

<400> SEQUENCE: 42

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Asp Asp Phe Glu Leu Ala Phe Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
            85                  90                  95

Met Phe Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
        130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
```

Ser Asn Leu Glu Asn Ile Arg
            180

<210> SEQ ID NO 43
<211> LENGTH: 552
<212> TYPE: DNA
<213> ORGANISM: Bacteriophage ALQ13.2

<400> SEQUENCE: 43

| | | | | | |
|---|---|---|---|---|---|
| atgaaaatca | ataatgacat | caaagagcta | attttggaat | atgtaagtcg | ctattttaaa | 60 |
| tttgaaaacg | acttctacaa | attgccaggc | atcaaattca | ctgatgcaaa | ttggcaaaaa | 120 |
| ttcaagaacg | gagatacttc | catcgagaag | atggggcag | cacgagtaaa | tgccatgctt | 180 |
| gactgcctat | tcgacgattt | tgagcttgct | ttgattggca | aggctcaaca | agaatactat | 240 |
| tcggataatt | ccttgaaatt | gaacatgcca | ttttacgctt | actatgacat | gttaaaaaag | 300 |
| cagcaacttc | taaaatggct | taaaaataac | cgtgatgatg | tcatctgcgg | aactggtagg | 360 |
| atgtacacag | caagtggtaa | ttacattgct | aactcttatt | tagaggtagc | gttagaatct | 420 |
| agccgtctgg | gtagtggctc | ttacatgctt | caaatgagat | tcaaagacta | ttcaagaagt | 480 |
| caagaaccta | ttccatctgg | tcgccaaaat | agactagaat | ggattgagag | caacttggaa | 540 |
| aacattcgat | ga | | | | | 552 |

<210> SEQ ID NO 44
<211> LENGTH: 183
<212> TYPE: PRT
<213> ORGANISM: Bacteriophage ALQ13.2

<400> SEQUENCE: 44

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Asp Asp Phe Glu Leu Ala Leu Ile Gly Lys Ala Gln Gln Glu Tyr Tyr
65                  70                  75                  80

Ser Asp Asn Ser Leu Lys Leu Asn Met Pro Phe Tyr Ala Tyr Tyr Asp
                85                  90                  95

Met Leu Lys Lys Gln Gln Leu Leu Lys Trp Leu Lys Asn Asn Arg Asp
            100                 105                 110

Asp Val Ile Cys Gly Thr Gly Arg Met Tyr Thr Ala Ser Gly Asn Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 45

<211> LENGTH: 552
<212> TYPE: DNA
<213> ORGANISM: Bacteriophage D802

<400> SEQUENCE: 45

```
atgaaaatca ataatgacat caaagagcta attttggaat atgtaagtcg ctattttaaa      60
ttcgagaacg acttttacag attgcctggc atcaaattca ctgatgccaa ctggcaaaaa     120
ttcaagaatg gaggcactgc cattgagaag atgggagcag cacgagttaa tgccatgctt     180
tcctgcctat tcgaggattt tgagcttgca atgattggca aggctcaata tgaatactat     240
tcggataatt ccttgaaatt gaacatgcca ttttacgctt actatgacat gttcaaaaag     300
cagcaacttc taaaatggct taaaaataac cgtgatgatg tcatcggcgg aactggtaga     360
atgtacacgt caagcggtag ttacattgct aacgcttatt tagaaattgc gttagaatct     420
agccgtctgg gtagtggctc ttacatgctt caaatgagat tcaaagacta ttcaagaagt     480
caagaaccta ttccgtctgg tcgccaaaat agacttgaat ggattgagag caacttggaa     540
aacattcgat aa                                                         552
```

<210> SEQ ID NO 46
<211> LENGTH: 183
<212> TYPE: PRT
<213> ORGANISM: Bacteriophage D802

<400> SEQUENCE: 46

```
Met Lys Ile Asn Asn Asp Ile Lys Glu Leu Ile Leu Glu Tyr Val Ser
1               5                   10                  15
Arg Tyr Phe Lys Phe Glu Asn Asp Phe Tyr Arg Leu Pro Gly Ile Lys
            20                  25                  30
Phe Thr Asp Ala Asn Trp Gln Lys Phe Lys Asn Gly Gly Thr Ala Ile
        35                  40                  45
Glu Lys Met Gly Ala Ala Arg Val Asn Ala Met Leu Ser Cys Leu Phe
    50                  55                  60
Glu Asp Phe Glu Leu Ala Met Ile Gly Lys Ala Gln Tyr Glu Tyr Tyr
65                  70                  75                  80
Ser Asp Asn Ser Leu Lys Leu Asn Met Pro Phe Tyr Ala Tyr Tyr Asp
                85                  90                  95
Met Phe Lys Lys Gln Gln Leu Leu Lys Trp Leu Lys Asn Asn Arg Asp
            100                 105                 110
Asp Val Ile Gly Gly Thr Gly Arg Met Tyr Thr Ser Ser Gly Ser Tyr
        115                 120                 125
Ile Ala Asn Ala Tyr Leu Glu Ile Ala Leu Glu Ser Ser Arg Leu Gly
    130                 135                 140
Ser Gly Ser Tyr Met Leu Gln Met Arg Phe Lys Asp Tyr Ser Arg Ser
145                 150                 155                 160
Gln Glu Pro Ile Pro Ser Gly Arg Gln Asn Arg Leu Glu Trp Ile Glu
                165                 170                 175
Ser Asn Leu Glu Asn Ile Arg
            180
```

<210> SEQ ID NO 47
<211> LENGTH: 552
<212> TYPE: DNA
<213> ORGANISM: Bacteriophage 73

<400> SEQUENCE: 47

```
atgaaaatca ataatgacat caaagagcta attttggaat atgtaagtcg ctattttaaa      60
```

```
tttgaaaacg acttctacaa attacctggc atcaaattca ctgatgccaa ctggcaaaaa    120
ttcaagaatg gagatacttc catcgagaag atggggggcag cacgagtaaa tgccatgctt    180
gactgcctat tcgaggattt tgagcttgca atgattggca aggctcaaac taattattac    240
attgataact cacttaaatt gaacatgcca ttttacgctt actatgacat gttcaaaaag    300
cagcaacttc taaaatggct taaaaataac cgtgatgatg tcatcggcgg aactggtagg    360
atgtacacag caagtggtaa ttacattgct aacgcttatt tagaggtggc attagaatcg    420
agctcgcttg gtagtggctc ttacatgctt caaatgaggt ttaaagacta ttcaaaaggt    480
caagaaccta ttccgtcagg tcgtcagaat cgacttgaat ggattgaaaa caatctcgaa    540
aacattcgat aa                                                         552
```

```
<210> SEQ ID NO 48
<211> LENGTH: 183
<212> TYPE: PRT
<213> ORGANISM: Bacteriophage 73

<400> SEQUENCE: 48

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180
```

```
<210> SEQ ID NO 49
<211> LENGTH: 552
<212> TYPE: DNA
<213> ORGANISM: Bacteriophage DT1

<400> SEQUENCE: 49
atgaaaatca ataatgacat caaagagcta attttggaat atgtaagtcg ctattttaaa    60
tttgaaaacg acttctacaa attacctggc atcaaattca ctgatgccaa ctggcaaaaa    120
ttcaagaatg gagaaacttc aatcgaaaaa atgggagcag cacgagttaa tgccatgctt    180
tcatgcctat tcgaggattt tgagcttgca atgattggca aggctcaaac taattattac    240
```

```
attgataact cacttaaatt gaacatgcca ttttacgctt actatgacat gttcaaaaag    300
caacttctta taaattggct taaaaataac cgtgatgatg tcatcggcgg aactggtagg    360
atgtacacag caagtggtaa ttacattgct aacgcttatt tagaggtggc attagaatca    420
agctcgcttg gtagtggctc ttacatgatc caaatgaggt ttaaagacta ttcaaaaggt    480
caagaaccta ttccgtcagg tcgcaaaaac cgacttgagt ggattgaaaa caatctggaa    540
aatattcgat aa                                                        552
```

```
<210> SEQ ID NO 50
<211> LENGTH: 183
<212> TYPE: PRT
<213> ORGANISM: Bacteriophage DT1

<400> SEQUENCE: 50

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Glu Thr Ser Ile
            35                  40                  45

Glu Lys Met Gly Ala Ala Arg Val Asn Ala Met Leu Ser Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180
```

```
<210> SEQ ID NO 51
<211> LENGTH: 552
<212> TYPE: DNA
<213> ORGANISM: Bacteriophage D1427

<400> SEQUENCE: 51
atgaaaatca ataatgacat caaagagcta attttggaat atgtaagtcg ctattttaaa     60
tttgaaaacg acttctacaa attacctggc atcaaattca ctgatgccaa ctggcaaaaa    120
ttcaagaatg gagaaacttc aatcgaaaaa atgggagcag cacgagttaa tgccatgctt    180
tcatgcctat tcgaggattt tgagcttgca atgattggca aggctcaaac taattattac    240
attgataact cacttaaatt gaacatgcca ttttacgctt actatgacat gttcaaaaag    300
caacttctta taaattggct taaaaataac cgtgatgatg tcatcggcgg aactggtagg    360
atgtacacag caagtggtaa ttacattgct aacgcttatt tagaggtggc attagaatca    420
agctcgcttg gtagtggctc ttacatgatc caaatgaggt ttaaagacta ttcaaaaggt    480
```

```
caagaaccta ttccgtcagg tcgccaaaat agactagaat ggattgagag caacttggaa      540
aacattcgat aa                                                          552

<210> SEQ ID NO 52
<211> LENGTH: 183
<212> TYPE: PRT
<213> ORGANISM: Bacteriophage D1427

<400> SEQUENCE: 52

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Ser Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Leu Leu Ile Asn Trp Leu Lys Asn Asn Arg Asp
            100                 105                 110

Asp Val Ile Gly Gly Thr Gly Arg Met Tyr Thr Ala Ser Gly Asn Tyr
        115                 120                 125

Ile Ala Asn Ala Tyr Leu Glu Val Ala Leu Glu Ser Ser Leu Gly
    130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 53
<211> LENGTH: 552
<212> TYPE: DNA
<213> ORGANISM: Bacteriophage N1162

<400> SEQUENCE: 53
atgaaaatca ataatgacat caaagagcta attttggaat atgtaagtcg ctattttaaa       60
tttgaaaacg acttctacaa attacctggc atcaaattca ctgatgccaa ctggcaaaaa      120
ttcaagaatg gagatacttc catcgagaag atggggggcag cacgagtaaa tgccatgctt      180
gactgcctat tcgaggattt tgagcttgca atgattggca aggctcaaac taattattac      240
attgataact cacttaaatt gaacatgcca ttttacgctt actatgacat gttcaaaaag      300
cagcaacttc taaaatggct taaaaataac cgtgatgatg tcatcggcgg aactggtagg      360
atgtacacat caaccggtaa ttacattgct aacgcttatt tagaaattgc gttagaatct      420
agccgtctgg gtagtggctc ttacatgatc caaatgaggt ttaaagacta ttcaaaaggt      480
caagaaccta ttccgtctgg tcgtcagaat cgacttgaat ggattgaaaa caatctggaa      540
aatattcgat aa                                                          552

<210> SEQ ID NO 54
```

```
<211> LENGTH: 183
<212> TYPE: PRT
<213> ORGANISM: Bacteriophage N1162

<400> SEQUENCE: 54

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
            100                 105                 110

Asp Val Ile Gly Gly Thr Gly Arg Met Tyr Thr Ser Thr Gly Asn Tyr
        115                 120                 125

Ile Ala Asn Ala Tyr Leu Glu Ile Ala Leu Glu Ser Ser Arg Leu Gly
130                 135                 140

Ser Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 55
<211> LENGTH: 552
<212> TYPE: DNA
<213> ORGANISM: Bacteriophage D1018

<400> SEQUENCE: 55
atgaaaatca ataatgatat caaagagcta attttggaat atgtaagtcg ctattttaaa      60
tttgaaaacg acttctacaa attgccagac atcaagttca cagatgctaa ttggcaaaaa     120
tttaagaatg gagaaacttc aatcgaaaaa atgggagcag cacgagtaaa tgccatgctt     180
gactgcctat tcgaggattt tgagcttgca atgattggca aggctcaaac taattattac     240
attgataact cacttaaatt gaacatgcca ttttacgctt actatgacat gttcaaaaag     300
cagcaacttc taaaatggct aaaaataac cgtgatgatg tcatcggcgg aactggtagg     360
atgtacacat caaccggtaa ttacattgct aacgcttatt tagaaattgc gttagaatct     420
agccgtctgg gtagtggctc ttacatgatc caaatgaggt ttaaagacta ttcaaaaggt     480
caagaaccta ttccgtctgg tcgtcagaat cgacttgaat ggattgaaaa caatctggaa     540
aatattcgat aa                                                          552

<210> SEQ ID NO 56
<211> LENGTH: 183
<212> TYPE: PRT
<213> ORGANISM: Bacteriophage D1018

<400> SEQUENCE: 56

Met Lys Ile Asn Asn Asp Ile Lys Glu Leu Ile Leu Glu Tyr Val Ser
```

```
               1               5                  10                 15
Arg Tyr Phe Lys Phe Glu Asn Asp Phe Tyr Lys Leu Pro Asp Ile Lys
                20                  25                 30

Phe Thr Asp Ala Asn Trp Gln Lys Phe Lys Asn Gly Glu Thr Ser Ile
                35                  40                 45

Glu Lys Met Gly Ala Ala Arg Val Asn Ala Met Leu Asp Cys Leu Phe
        50                  55                 60

Glu Asp Phe Glu Leu Ala Met Ile Gly Lys Ala Gln Thr Asn Tyr Tyr
65                  70                  75                 80

Ile Asp Asn Ser Leu Lys Leu Asn Met Pro Phe Tyr Ala Tyr Tyr Asp
                85                  90                 95

Met Phe Lys Lys Gln Gln Leu Leu Lys Trp Leu Lys Asn Asn Arg Asp
                100                 105                110

Asp Val Ile Gly Gly Thr Gly Arg Met Tyr Thr Ser Thr Gly Asn Tyr
                115                 120                125

Ile Ala Asn Ala Tyr Leu Glu Ile Ala Leu Glu Ser Ser Arg Leu Gly
        130                 135                 140

Ser Gly Ser Tyr Met Ile Gln Met Arg Phe Lys Asp Tyr Ser Lys Gly
145                 150                 155                160

Gln Glu Pro Ile Pro Ser Gly Arg Gln Asn Arg Leu Glu Trp Ile Glu
                165                 170                175

Asn Asn Leu Glu Asn Ile Arg
                180
```

<210> SEQ ID NO 57
<211> LENGTH: 552
<212> TYPE: DNA
<213> ORGANISM: Bacteriophage D3577

<400> SEQUENCE: 57

```
atgaaaataa acaacgatat caaagagcta attttggaat acgctaaacg ttatttcaag      60
tttgaaaacg acttctacaa actgccagac atcaaattca ctgatgccaa ctggcaaaaa     120
tttaagaatg gagaaacttc catcgaaaaa atgggagcag cacgagttaa tgccatgctt     180
tcctgcctgt tcgacgattt tgagcttgct atgattggca aggctcaaac taattattac     240
aatgataact cacttaaatt gaacatgcca ttttacgctt actatgacat gttcaaaaag     300
cagcaacttc taaaatggct taaaaataac cgtgatgata tcatctgcgg aactggtaga     360
atgtacactt caagaggtag ttacattgct aacgcttatt tagaggtagc gttagaatca     420
agcttgcttg gtagtggctc ttacatgctt caaatgaggt tcaaagacta ttcaaaaagt     480
caagaaccta ttccatctgg tcgtcagaat cgacttgaat ggattgagag caacttggaa     540
aatattcgat aa                                                         552
```

<210> SEQ ID NO 58
<211> LENGTH: 183
<212> TYPE: PRT
<213> ORGANISM: Bacteriophage D3577

<400> SEQUENCE: 58

```
Met Lys Ile Asn Asn Asp Ile Lys Glu Leu Ile Leu Glu Tyr Ala Lys
1               5                   10                  15

Arg Tyr Phe Lys Phe Glu Asn Asp Phe Tyr Lys Leu Pro Asp Ile Lys
                20                  25                  30

Phe Thr Asp Ala Asn Trp Gln Lys Phe Lys Asn Gly Glu Thr Ser Ile
            35                  40                  45
```

Glu Lys Met Gly Ala Ala Arg Val Asn Ala Met Leu Ser Cys Leu Phe
        50                  55                  60

Asp Asp Phe Glu Leu Ala Met Ile Gly Lys Ala Gln Thr Asn Tyr Tyr
65                  70                  75                  80

Asn Asp Asn Ser Leu Lys Leu Asn Met Pro Phe Tyr Ala Tyr Tyr Asp
                85                  90                  95

Met Phe Lys Lys Gln Gln Leu Leu Lys Trp Leu Lys Asn Asn Arg Asp
                100                 105                 110

Asp Ile Ile Cys Gly Thr Gly Arg Met Tyr Thr Ser Arg Gly Ser Tyr
                115                 120                 125

Ile Ala Asn Ala Tyr Leu Glu Val Ala Leu Gly Ser Ser Leu Leu Gly
            130                 135                 140

Ser Gly Ser Tyr Met Leu Gln Met Arg Phe Lys Asp Tyr Ser Lys Ser
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180

<210> SEQ ID NO 59
<211> LENGTH: 552
<212> TYPE: DNA
<213> ORGANISM: Bacteriophage CHPC577

<400> SEQUENCE: 59
atgaaaataa acaacgatat caaagagcta attttggaat atggaagtcg ctattttaaa      60
tttgaaaacg acttctacaa actgcctggc atcaagttca ctgatgctaa ttggcaaaaa     120
ttcaaaaatg gtgatacttt aatcgaaaaa atggggggcag cacgagtaaa tgccatgctt     180
gactgcctgt tcgacgattt tgagcttgct atgattggca aggctcaaac taattattac     240
aatgataatt ccttgaaatt gaacatgcca ttttacgctt actatgacat gttcaaaaag     300
caacagctta acattggct caaaacaac cgtgatgaca tcgtaggcgg aactggtaga     360
ctgtacactt caagcggtag ttacattgct aacgcttatt tagaaattgc attagaatcg     420
agctcgcttg gtagtggctc ttacatgctt caaatgagat tcaaaaacta ttcaaaaagt     480
caagaaccta ttccatctgg tcgccagaat cgacttgaat ggattgaaaa caatcttgag     540
aatattcgat aa                                                         552

<210> SEQ ID NO 60
<211> LENGTH: 183
<212> TYPE: PRT
<213> ORGANISM: Bacteriophage CHPC577

<400> SEQUENCE: 60

Met Lys Ile Asn Asn Asp Ile Lys Glu Leu Ile Leu Glu Tyr Gly Ser
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Leu Ile
            35                  40                  45

Glu Lys Met Gly Ala Ala Arg Val Asn Ala Met Leu Asp Cys Leu Phe
        50                  55                  60

Asp Asp Phe Glu Leu Ala Met Ile Gly Lys Ala Gln Thr Asn Tyr Tyr
65                  70                  75                  80

```
Asn Asp Asn Ser Leu Lys Leu Asn Met Pro Phe Tyr Ala Tyr Tyr Asp
                85                  90                  95

Met Phe Lys Lys Gln Gln Leu Ile His Trp Leu Lys Asn Asn Arg Asp
            100                 105                 110

Asp Ile Val Gly Gly Thr Gly Arg Leu Tyr Thr Ser Ser Gly Ser Tyr
            115                 120                 125

Ile Ala Asn Ala Tyr Leu Glu Ile Ala Leu Glu Ser Ser Ser Leu Gly
130                 135                 140

Ser Gly Ser Tyr Met Leu Gln Met Arg Phe Lys Asn Tyr Ser Lys Ser
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180
```

<210> SEQ ID NO 61
<211> LENGTH: 552
<212> TYPE: DNA
<213> ORGANISM: Bacteriophage D4237

<400> SEQUENCE: 61

```
atgaaaataa ataacgacat caaagaatta attttagaat atatgagccg ttacttcaaa      60
ttcgaaaacg acttctacaa attgccagac atcaagttca cagatgctaa ttggcaaaaa     120
tttaagaatg agaaacttca atcgaaaaa atgggagcag cacgagttaa tgccatgctc      180
aactgcctat tcgaagattt tgagcttgct atgattggca aggctcaaat taattattac     240
aatgataact cacttaaaat gaacatgcca ttttacgctt actatgatat gttcaaaaaa     300
caacagcttc taaatggct aaagatcac catgatgaca tcatcggagg agctggcaga      360
atgtacacat caaccggtag ttacattgct aatgcttatt tagaggtagc gttagaatca     420
agctcgcttg gtgatggtga gtacatgttg caaatgcgtt ttaaaaatta ttcacgaagt     480
caagaaccta ttccgtcagg tcgcaaaaac cgacttgagt ggattgaaaa caatctggaa     540
aatattcgat aa                                                         552
```

<210> SEQ ID NO 62
<211> LENGTH: 183
<212> TYPE: PRT
<213> ORGANISM: Bacteriophage D4237

<400> SEQUENCE: 62

```
Met Lys Ile Asn Asn Asp Ile Lys Glu Leu Ile Leu Glu Tyr Met Ser
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Glu Thr Ser Ile
        35                  40                  45

Glu Lys Met Gly Ala Ala Arg Val Asn Ala Met Leu Asn Cys Leu Phe
50                  55                  60

Glu Asp Phe Glu Leu Ala Met Ile Gly Lys Ala Gln Ile Asn Tyr Tyr
65                  70                  75                  80

Asn Asp Asn Ser Leu Lys Met Asn Met Pro Phe Tyr Ala Tyr Tyr Asp
                85                  90                  95

Met Phe Lys Lys Gln Gln Leu Leu Lys Trp Leu Lys Asp His His Asp
            100                 105                 110

Asp Ile Ile Gly Gly Ala Gly Arg Met Tyr Thr Ser Thr Gly Ser Tyr
```

```
            115                 120                 125
Ile Ala Asn Ala Tyr Leu Glu Val Ala Leu Glu Ser Ser Leu Gly
        130                 135                 140

Asp Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 63
<211> LENGTH: 552
<212> TYPE: DNA
<213> ORGANISM: Bacteriophage 9874

<400> SEQUENCE: 63
atgaaaataa atgacgacat caaagaatta attttagaat atatgagccg ttacttcaaa      60
ttcgagaacg acttctacaa attgcctgac atcaaattca ctgatgccaa ctggcaaaaa     120
ttcaaaaatg gagatacttc catcgagaag atgggggcag cacgagtaaa tgccatgctt     180
gactgcctat tcgaagattt cgaacttgcc atgattggca aggctcaaca agaatactat     240
ttggataatt cactaaagat gaacatgcca ttttacgctt attatgatat gttcaagaaa     300
aaacagctcg tcaatggct taaagatcac catgatgaca tcctaggcgg aactggtagg     360
atgtacactt cagacggtag ttacattgct aactcttatt tagaggtagc gttagaatct     420
agccgtctgg gtagtggctc ttacatgctt caaatgagat tcaaagacta ttcaagaagt     480
caagaaccca ttccgtcagg tcgcaaaaac cgacttgagt ggattgaaaa caatctggaa     540
aatattcgat aa                                                         552

<210> SEQ ID NO 64
<211> LENGTH: 183
<212> TYPE: PRT
<213> ORGANISM: Bacteriophage 9874

<400> SEQUENCE: 64

Met Lys Ile Asn Asp Asp Ile Lys Glu Leu Ile Leu Glu Tyr Met Ser
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Gln Glu Tyr Tyr
65                  70                  75                  80

Leu Asp Asn Ser Leu Lys Met Asn Met Pro Phe Tyr Ala Tyr Tyr Asp
                85                  90                  95

Met Phe Lys Lys Gln Leu Val Lys Trp Leu Lys Asp His His Asp
            100                 105                 110

Asp Ile Leu Gly Gly Thr Gly Arg Met Tyr Thr Ser Asp Gly Ser Tyr
        115                 120                 125

Ile Ala Asn Ser Tyr Leu Glu Val Ala Leu Glu Ser Ser Arg Leu Gly
    130                 135                 140

Ser Gly Ser Tyr Met Leu Gln Met Arg Phe Lys Asp Tyr Ser Arg Ser
145                 150                 155                 160
```

Gln Glu Pro Ile Pro Ser Gly Arg Lys Asn Arg Leu Glu Trp Ile Glu
            165                 170                 175

Asn Asn Leu Glu Asn Ile Arg
            180

<210> SEQ ID NO 65
<211> LENGTH: 552
<212> TYPE: DNA
<213> ORGANISM: Bacteriophage 5093

<400> SEQUENCE: 65
atggaaatca acaacgatat caaagagtta attttggaat acgtgaaaag atacttcaag      60
ttcgagaacg acttctacaa attgcctgac atcaaattca ctgatgccaa ctggcagaag     120
ttcaaaaatg gcgaaacagc cattgagaag atggggggcag cacgagtaaa cgcaatgctc    180
gactgcctat tcgaagattt tgagcttgcc atgattggca aggctcaaac taattattat     240
attgataact cgcttaaatt aaacatgcca ttttatgctt actatgatat gtttaagaaa     300
caacagctcg tcaaatggct tgaaactagt cgtgaagaca tcatcggagg ggctggcaga     360
atgtacactt cagacggtag ttacattgct aacgcttatt tagaagtagc gttagaatca     420
agctcgcttg gtgatagtga atacatgttg caaatgcgtt ttaaaaatta ttcaaaaagt     480
caagaaccta ttccgtctgg tcgtcaaaat agactggaat ggattgaaaa caatcttaaa     540
aacattcgat aa                                                          552

<210> SEQ ID NO 66
<211> LENGTH: 183
<212> TYPE: PRT
<213> ORGANISM: Bacteriophage 5093

<400> SEQUENCE: 66

Met Glu Ile Asn Asn Asp Ile Lys Glu Leu Ile Leu Glu Tyr Val Lys
1               5                   10                  15

Arg Tyr Phe Lys Phe Glu Asn Asp Phe Tyr Lys Leu Pro Asp Ile Lys
            20                  25                  30

Phe Thr Asp Ala Asn Trp Gln Lys Phe Lys Asn Gly Glu Thr Ala Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Val Lys Trp Leu Glu Thr Ser Arg Glu
            100                 105                 110

Asp Ile Ile Gly Gly Ala Gly Arg Met Tyr Thr Ser Asp Gly Ser Tyr
        115                 120                 125

Ile Ala Asn Ala Tyr Leu Glu Val Ala Leu Glu Ser Ser Ser Leu Gly
    130                 135                 140

Asp Ser Glu Tyr Met Leu Gln Met Arg Phe Lys Asn Tyr Ser Lys Ser
145                 150                 155                 160

Gln Glu Pro Ile Pro Ser Gly Arg Gln Asn Arg Leu Glu Trp Ile Glu
                165                 170                 175

Asn Asn Leu Lys Asn Ile Arg
            180

<210> SEQ ID NO 67
<211> LENGTH: 552
<212> TYPE: DNA
<213> ORGANISM: Bacteriophage D4154

<400> SEQUENCE: 67

| | | | | | |
|---|---|---|---|---|---|
| atgctaataa | ataacgacat | caaagagttg | attttggaat | acgtcaaacg | ctattttaaa | 60 |
| tatgaaaatg | acttctacag | attgccgggc | atcaagttta | ccgatgcaaa | ttggcagaag | 120 |
| tttaaaaatg | gcgacacttc | catcgagaag | atggggggcag | cacgagtaaa | cgccatgctc | 180 |
| gactgcctat | tcgaagattt | tgagcttgcc | atgattggta | aggctcaaac | caattattat | 240 |
| atcaataatt | cattgaaaat | gaatatgccg | ttttacgctt | actatgatat | gttcaagaag | 300 |
| gaacagctta | tgaaatggct | tgaaaccagc | cgtgaagaca | tcataggcgg | aactggcagg | 360 |
| atgtacactt | cagacggtag | ttacattgct | aacgcttatt | tggaaattgc | attagaatcg | 420 |
| agctcgcttg | gtagtggctc | ttacatgctt | caaatgcgtt | ttaaagatta | ttcaaaaggt | 480 |
| caagagccta | tcccgtctgg | tcgtcaaaac | cgacttgagt | ggattgaaaa | caatcttgaa | 540 |
| aacattcgat | aa | | | | | 552 |

<210> SEQ ID NO 68
<211> LENGTH: 183
<212> TYPE: PRT
<213> ORGANISM: Bacteriophage D4154

<400> SEQUENCE: 68

Met Leu Ile Asn Asn Asp Ile Lys Glu Leu Ile Leu Glu Tyr Val Lys
1               5                   10                  15

Arg Tyr Phe Lys Tyr Glu Asn Asp Phe Tyr Arg Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asn Asn Ser Leu Lys Met Asn Met Pro Phe Tyr Ala Tyr Tyr Asp
                85                  90                  95

Met Phe Lys Lys Glu Gln Leu Met Lys Trp Leu Glu Thr Ser Arg Glu
            100                 105                 110

Asp Ile Ile Gly Gly Thr Gly Arg Met Tyr Thr Ser Asp Gly Ser Tyr
        115                 120                 125

Ile Ala Asn Ala Tyr Leu Glu Ile Ala Leu Glu Ser Ser Leu Gly
    130                 135                 140

Ser Gly Ser Tyr Met Leu Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Asn Asn Leu Glu Asn Ile Arg
            180

<210> SEQ ID NO 69
<211> LENGTH: 552
<212> TYPE: DNA
<213> ORGANISM: Streptococcus thermophilus

<400> SEQUENCE: 69

```
atgctaataa ataacgacat caaagagttg attttggaat acgtcaaacg ctattttaaa      60
tttgaaaatg acttctacag attgccgggc atcaagtttta ccgatgcaaa ttggcagaag    120
tttaaaaatg gcgacactgc cattgagaag atgggggcat cacgagtaaa ctctatgctt    180
gactgcctgt tcgaagattt tgagcttgct atgattggca aggctcaaga tgaatactat    240
ttggataatt cactaaagat gaacatgcca ttttacgctt attatgatat gttcaagaaa    300
aaacagctcg tcaaatggct taaagatcac catgatgaca tcctaggcgg aactggtagg    360
atgtatactt caagcggcaa ttacattgct aacgcttatt tagaggtagc gttagaatca    420
agctcgcttg gtagtggctc ttacatgatt caaatgcgtt ttaaaaatta ttcaaaaggt    480
caagagccta tcccgtctgg tcgtcaaaac cgacttgagt ggattgaaaa aaacttggag    540
aacattcgat aa                                                         552

<210> SEQ ID NO 70
<211> LENGTH: 183
<212> TYPE: PRT
<213> ORGANISM: Streptococcus thermophilus

<400> SEQUENCE: 70

Met Leu Ile Asn Asn Asp Ile Lys Glu Leu Ile Leu Glu Tyr Val Lys
1               5                   10                  15

Arg Tyr Phe Lys Phe Glu Asn Asp Phe Tyr Arg Leu Pro Gly Ile Lys
            20                  25                  30

Phe Thr Asp Ala Asn Trp Gln Lys Phe Lys Asn Gly Asp Thr Ala Ile
        35                  40                  45

Glu Lys Met Gly Ala Ser Arg Val Asn Ser Met Leu Asp Cys Leu Phe
    50                  55                  60

Glu Asp Phe Glu Leu Ala Met Ile Gly Lys Ala Gln Asp Glu Tyr Tyr
65                  70                  75                  80

Leu Asp Asn Ser Leu Lys Met Asn Met Pro Phe Tyr Ala Tyr Tyr Asp
                85                  90                  95

Met Phe Lys Lys Lys Gln Leu Val Lys Trp Leu Lys Asp His His Asp
            100                 105                 110

Asp Ile Leu Gly Gly Thr Gly Arg Met Tyr Thr Ser Ser Gly Asn Tyr
        115                 120                 125

Ile Ala Asn Ala Tyr Leu Glu Val Ala Leu Glu Ser Ser Ser Leu Gly
    130                 135                 140

Ser Gly Ser Tyr Met Ile Gln Met Arg Phe Lys Asn Tyr Ser Lys Gly
145                 150                 155                 160

Gln Glu Pro Ile Pro Ser Gly Arg Gln Asn Arg Leu Glu Trp Ile Glu
                165                 170                 175

Lys Asn Leu Glu Asn Ile Arg
            180

<210> SEQ ID NO 71
<211> LENGTH: 552
<212> TYPE: DNA
<213> ORGANISM: Streptococcus thermophilus

<400> SEQUENCE: 71
atggaaatca acaacgatat taaacaactg atcttggaat acgctaaacg ttatttcaag     60
tttgagaacg acttttataa actgccaggc atcaagttca ctgatgcaaa ttggcagaag    120
ttcaaaaatg gaggcactgc cattgagaag atgggggcag cacgagtaaa cgccatgctc    180
```

```
gactgcctat tcgaagattt cgagcttgca atgattggca aggctcaaca agaatactat    240
tcggataatt ccttgaaagt aaatatggca ttctatgctt attacgatca attcaaaaaa    300
caacagctta tgaaatggct aaagataat cacgatgaca tcataggagg gactggtaga     360
atgtacacgt caagcggtag ttacattgct aacgcttatt tagaaattgc gttagaatct    420
agccgtctgg gtggtggttc ttacatgatc caaatgaggt ttaaagacta ttcaaaaggt    480
caagaaccta ttccgtctgg tcgtcagaat cgacttgaat ggattgagag caacttggaa    540
aacattcgat aa                                                        552
```

<210> SEQ ID NO 72
<211> LENGTH: 183
<212> TYPE: PRT
<213> ORGANISM: Streptococcus thermophilus

<400> SEQUENCE: 72

```
Met Glu Ile Asn Asn Asp Ile Lys Gln Leu Ile Leu Glu Tyr Ala Lys
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Gly Thr Ala Ile
            35                  40                  45

Glu Lys Met Gly Ala Ala Arg Val Asn Ala Met Leu Asp Cys Leu Phe
        50                  55                  60

Glu Asp Phe Glu Leu Ala Met Ile Gly Lys Ala Gln Gln Glu Tyr Tyr
65                  70                  75                  80

Ser Asp Asn Ser Leu Lys Val Asn Met Ala Phe Tyr Ala Tyr Tyr Asp
                85                  90                  95

Gln Phe Lys Lys Gln Gln Leu Met Lys Trp Leu Lys Asp Asn His Asp
            100                 105                 110

Asp Ile Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Arg Leu Gly
    130                 135                 140

Gly Gly Ser Tyr Met Ile Gln Met Arg Phe Lys Asp Tyr Ser Lys Gly
145                 150                 155                 160

Gln Glu Pro Ile Pro Ser Gly Arg Gln Asn Arg Leu Glu Trp Ile Glu
                165                 170                 175

Ser Asn Leu Glu Asn Ile Arg
            180
```

<210> SEQ ID NO 73
<211> LENGTH: 552
<212> TYPE: DNA
<213> ORGANISM: Bacteriophage Sfi19

<400> SEQUENCE: 73

```
atggaaatca acaacgacat taaacaactg atcttggaat acgtgggacg ctattttaaa     60
tttgaaaatg acttctacaa attgcccggc atcaaattca ctgatgccaa ttggcagaag    120
ttcaaaaatg gcgatacttc catcgaaaag atgggagcag cacgagtaaa cgcaatgctt    180
gactgcctgt tcgaagattt cgaacttgcc atgattggca aggctcaaac taattattat    240
attgataatt cccttaaatt aaacatgcca ttttacgctt attatgatat gttcaagaag    300
gaacagctta tgaaatggct aaagatcac catgatgaca tcataggcgg aactggtagg    360
atgtacattt caagcggtag ctacattgct aacgcttatt tggaaattgc actagaatca    420
```

```
agtacgcttg gtggtggtga gtacatgttg caaatgcgct ttaaaaatta ttcacgaagc      480
caagaaccta ttccatcagg tcgcaaaaat agacttgaat ggattgaaaa caatcttgaa      540
aacattcgat aa                                                          552
```

```
<210> SEQ ID NO 74
<211> LENGTH: 183
<212> TYPE: PRT
<213> ORGANISM: Bacteriophage Sfi19

<400> SEQUENCE: 74
```

```
Met Glu Ile Asn Asn Asp Ile Lys Gln Leu Ile Leu Glu Tyr Val Gly
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Glu Gln Leu Met Lys Trp Leu Lys Asp His His Asp
            100                 105                 110

Asp Ile Ile Gly Gly Thr Gly Arg Met Tyr Ile Ser Ser Gly Ser Tyr
        115                 120                 125

Ile Ala Asn Ala Tyr Leu Glu Ile Ala Leu Glu Ser Ser Thr Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180
```

```
<210> SEQ ID NO 75
<211> LENGTH: 552
<212> TYPE: DNA
<213> ORGANISM: Bacteriophage Sfi11

<400> SEQUENCE: 75
```

```
atggaaatca caacgacat taaacaactg atcttggaat acgtgggacg ctattttaaa       60
tttgaaaatg acttctacaa attgcccggc atcaaattca ctgatgccaa ttggcagaag      120
ttcaaaaatg gcgatacttc catcgaaaag atgggagcag cacgagtaaa cgcaatgctt      180
gactgcctgt tcgaagattt cgaacttgcc atgattggca aggctcaaac taattattat      240
attgataatt cccttaaatt aaacatgcca ttttacgctt attatgatat gttcaagaag      300
gaacagctta tgaaatggct taaagatcac catgatgaca tcataggcgg aactggtagg      360
atgtacactt caagcggtag ctacattgct aacgcttatt tggaaattgc actagaatca      420
agtacgcttg gtggtggtga gtacatgttg caaatgcgct ttaaaaatta ttcacgaagc      480
caagaaccta ttccatcagg tcgcaaaaat agacttgaat ggattgaaaa caatcttgaa      540
aacattcgat aa                                                          552
```

<210> SEQ ID NO 76
<211> LENGTH: 183
<212> TYPE: PRT
<213> ORGANISM: Bacteriophage Sfi11

<400> SEQUENCE: 76

Met Glu Ile Asn Asn Asp Ile Lys Gln Leu Ile Glu Tyr Val Gly
1               5                   10                  15

Arg Tyr Phe Lys Phe Glu Asn Asp Phe Tyr Lys Leu Pro Gly Ile Lys
            20                  25                  30

Phe Thr Asp Ala Asn Trp Gln Lys Phe Lys Asn Gly Asp Thr Ser Ile
        35                  40                  45

Glu Lys Met Gly Ala Ala Arg Val Asn Ala Met Leu Asp Cys Leu Phe
50                  55                  60

Glu Asp Phe Glu Leu Ala Met Ile Gly Lys Ala Gln Thr Asn Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Glu Gln Leu Met Lys Trp Leu Lys Asp His His Asp
            100                 105                 110

Asp Ile Ile Gly Gly Thr Gly Arg Met Tyr Thr Ser Ser Gly Ser Tyr
        115                 120                 125

Ile Ala Asn Ala Tyr Leu Glu Ile Ala Leu Glu Ser Ser Thr Leu Gly
    130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 77
<211> LENGTH: 552
<212> TYPE: DNA
<213> ORGANISM: Streptococcus thermophilus

<400> SEQUENCE: 77
atggaaatca acaaagacat caaagagttg attttggaat acgtcaaacg ctatttaaa      60 tttgaaaatg atttctacag attgccgggc atcaagttta ccgatgccaa ctggcaaaaa    120
ttcaagaatg gagatacttc catcgagaag atggggcag cacgagtaaa cgccatgctt      180
gactgcctgt tcgaagattt cgaacttgct atgattggca aggctcaaga tgaatactat    240
ttggataatt cacttaagtt taatatggca ttccatactt attacgatca atttaaaaaa    300
caacagctta tgaaatggct tgaaactagc ctcgaagaca tcataggcgg aactggtagg    360
atgtacactt caagcggtag ttacattgct aacgcttatt tggaaattgc actagaatca    420
agctcgcttg gtggtggtga gtacatgttg caaatgcgtt ttaaaaatta ttcacgaagc    480
caagaaccta ttccgtcagg tcgcaaaaac cgacttgagt ggattgaaaa caatctggaa    540
aatatccgat aa                                                        552

<210> SEQ ID NO 78
<211> LENGTH: 183
<212> TYPE: PRT
<213> ORGANISM: Streptococcus thermophilus

<400> SEQUENCE: 78

```
Met Glu Ile Asn Lys Asp Ile Lys Glu Leu Ile Leu Glu Tyr Val Lys
1               5                   10                  15

Arg Tyr Phe Lys Phe Glu Asn Asp Phe Tyr Arg Leu Pro Gly Ile Lys
            20                  25                  30

Phe Thr Asp Ala Asn Trp Gln Lys Phe Asn Gly Asp Thr Ser Ile
        35                  40                  45

Glu Lys Met Gly Ala Ala Arg Val Asn Ala Met Leu Asp Cys Leu Phe
    50                  55                  60

Glu Asp Phe Glu Leu Ala Met Ile Gly Lys Ala Gln Asp Glu Tyr Tyr
65                  70                  75                  80

Leu Asp Asn Ser Leu Lys Phe Asn Met Ala Phe His Thr Tyr Tyr Asp
                85                  90                  95

Gln Phe Lys Lys Gln Gln Leu Met Lys Trp Leu Glu Thr Ser Leu Glu
                100                 105                 110

Asp Ile Ile Gly Gly Thr Gly Arg Met Tyr Thr Ser Ser Gly Ser Tyr
            115                 120                 125

Ile Ala Asn Ala Tyr Leu Glu Ile Ala Leu Glu Ser Ser Leu Gly
        130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 79
<211> LENGTH: 552
<212> TYPE: DNA
<213> ORGANISM: Bacteriophage D4769

<400> SEQUENCE: 79
atgaaaatca ataatgacat caaagagcta attttggaat atgtaagtcg ctattttaaa      60
tttgaaaacg acttctacaa attacctggc atcaaattca ctgatgccaa ctggcaaaaa     120
ttcaagaatg gagatacttc catcgagaag atgggggcag cacgagtaaa cgccatgctt     180
gactgcctgt tcgaagattt cgaacttgct atgattggca aggctcaaga tgaatactat     240
ttggataatt cacttaagtt taatatggca ttccatactt attacgatca atttaaaaaa     300
caacagctta tgaaatggct tgaaactagc ctcgaagaca tcataggcgg aactggtagg     360
atgtacactt caagcggtag ttacattgct aacgcttatt tggaaattgc actagaatca     420
agctcgcttg gtggtggtga gtacatgttg caaatgcgtt ttaaaaatta ttcacgaagc     480
caagaaccta ttccgtcagg tcgcaaaaac cgacttgagt ggattgaaaa caatctggaa     540
aatatccgat aa                                                         552

<210> SEQ ID NO 80
<211> LENGTH: 183
<212> TYPE: PRT
<213> ORGANISM: Bacteriophage D4769

<400> SEQUENCE: 80

Met Lys Ile Asn Asn Asp Ile Lys Glu Leu Ile Leu Glu Tyr Val Ser
1               5                   10                  15

Arg Tyr Phe Lys Phe Glu Asn Asp Phe Tyr Lys Leu Pro Gly Ile Lys
            20                  25                  30
```

```
Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
 50                  55                  60

Glu Asp Phe Glu Leu Ala Met Ile Gly Lys Ala Gln Asp Glu Tyr Tyr
 65                  70                  75                  80

Leu Asp Asn Ser Leu Lys Phe Asn Met Ala Phe His Thr Tyr Tyr Asp
                 85                  90                  95

Gln Phe Lys Lys Gln Gln Leu Met Lys Trp Leu Glu Thr Ser Leu Glu
            100                 105                 110

Asp Ile Ile Gly Gly Thr Gly Arg Met Tyr Thr Ser Ser Gly Ser Tyr
            115                 120                 125

Ile Ala Asn Ala Tyr Leu Glu Ile Ala Leu Glu Ser Ser Ser Leu Gly
            130                 135                 140

Gly Gly Glu Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Asn Asn Leu Glu Asn Ile Arg
            180

<210> SEQ ID NO 81
<211> LENGTH: 552
<212> TYPE: DNA
<213> ORGANISM: Bacteriophage D5691

<400> SEQUENCE: 81
atgattataa atattgatat caaggaattg attttagagt atatgagtag atacttcaaa      60
tttgaaaatg atttctacaa actccccggc atcaaattca ctgatgccaa ttggcaaaaa     120
tttaagaatg gtgacacttc catcgaaaag atgggagcgg ctcgagtaaa tgccatgctc     180
gactgtctat tcgatgactt tgaacttgct atgattggca aggctcaaat taattattac     240
atagacaatt cccttaaatt gaacatgcca ttctatgctt attatgacat gttcaaaaaa     300
caacaactga tcaaatggat tgaaaccagc cgtgatgatg tcatcggagg aactggcagg     360
atgtatacag caagcggaag ctacatagct aacgcttatc tagaaatagc actagaatct     420
agctctctgg gtggtggctc ttatatgctt caaatgagat tcaaaaacta ctcacgaagc     480
caagagccaa taccatctgg tcggaaaaac cgacttgagt ggattgagag caacttggaa     540
aacattagat aa                                                         552

<210> SEQ ID NO 82
<211> LENGTH: 183
<212> TYPE: PRT
<213> ORGANISM: Bacteriophage D5691

<400> SEQUENCE: 82

Met Ile Ile Asn Ile Asp Ile Lys Glu Leu Ile Leu Glu Tyr Met Ser
  1               5                  10                  15

Arg Tyr Phe Lys Phe Glu Asn Asp Phe Tyr Lys Leu Pro Gly Ile Lys
             20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
 50                  55                  60

Asp Asp Phe Glu Leu Ala Met Ile Gly Lys Ala Gln Ile Asn Tyr Tyr
```

```
                65                  70                  75                  80
Ile Asp Asn Ser Leu Lys Leu Asn Met Pro Phe Tyr Ala Tyr Tyr Asp
                    85                  90                  95

Met Phe Lys Lys Gln Gln Leu Ile Lys Trp Ile Glu Thr Ser Arg Asp
                100                 105                 110

Asp Val Ile Gly Gly Thr Gly Arg Met Tyr Thr Ala Ser Gly Ser Tyr
                115                 120                 125

Ile Ala Asn Ala Tyr Leu Glu Ile Ala Leu Glu Ser Ser Ser Leu Gly
            130                 135                 140

Gly Gly Ser Tyr Met Leu Gln Met Arg Phe Lys Asn Tyr Ser Arg Ser
145                 150                 155                 160

Gln Glu Pro Ile Pro Ser Gly Arg Lys Asn Arg Leu Glu Trp Ile Glu
                165                 170                 175

Ser Asn Leu Glu Asn Ile Arg
            180

<210> SEQ ID NO 83
<211> LENGTH: 552
<212> TYPE: DNA
<213> ORGANISM: Streptococcus sp.

<400> SEQUENCE: 83
atggaaatca acaatgacat caaagagtta atcttggaat acgtgggacg ctatttcaag      60
tttgaaaatg attttacaa attgccgggc atcaaattta ccgatgcaaa ttggcaaaaa     120
ttcaaaaacg gtgatacatc catcgagaaa atgggggcgg cacgagtaaa cgcaatgctc     180
gactgcctat tcgatgattt cgagcttgct atgattggca aggctcaaac tgattattac     240
attgataact cacttaaatt gaacatgcca ttttatgctt attatgacat gttcaaaaaa     300
caacagcttc taaaatggat tgagaatagt cgtgaagaca tcatcggagg ggctggcaga     360
atgtacacag cggcgggtaa ttggatttct agcgcttatt tagagatcgc attagaatct     420
agttccatcg gtggcggtgg ctatatgctt caaatgcggt tcaaaaacta ctcaagagac     480
cctagaccga ttccagcagg ccaccaaaat cgtctcgaat ggattgaaaa caacttggag     540
aatatccgat aa                                                         552

<210> SEQ ID NO 84
<211> LENGTH: 183
<212> TYPE: PRT
<213> ORGANISM: Streptococcus sp.

<400> SEQUENCE: 84

Met Glu Ile Asn Asn Asp Ile Lys Glu Leu Ile Leu Glu Tyr Val Gly
1               5                   10                  15

Arg Tyr Phe Lys Phe Glu Asn Asp Phe Tyr Lys Leu Pro Gly Ile Lys
                20                  25                  30

Phe Thr Asp Ala Asn Trp Gln Lys Phe Lys Asn Gly Asp Thr Ser Ile
            35                  40                  45

Glu Lys Met Gly Ala Ala Arg Val Asn Ala Met Leu Asp Cys Leu Phe
        50                  55                  60

Asp Asp Phe Glu Leu Ala Met Ile Gly Lys Ala Gln Thr Asp Tyr Tyr
65                  70                  75                  80

Ile Asp Asn Ser Leu Lys Leu Asn Met Pro Phe Tyr Ala Tyr Tyr Asp
                85                  90                  95

Met Phe Lys Lys Gln Gln Leu Leu Lys Trp Ile Glu Asn Ser Arg Glu
                100                 105                 110
```

Asp Ile Ile Gly Gly Ala Gly Arg Met Tyr Thr Ala Gly Gly Asn Trp
        115                 120                 125

Ile Ser Ser Ala Tyr Leu Glu Ile Ala Leu Glu Ser Ser Ile Gly
    130                 135                 140

Gly Gly Gly Tyr Met Leu Gln Met Arg Phe Lys Asn Tyr Ser Arg Asp
145                 150                 155                 160

Pro Arg Pro Ile Pro Ala Gly His Gln Asn Arg Leu Glu Trp Ile Glu
                165                 170                 175

Asn Asn Leu Glu Asn Ile Arg
            180

<210> SEQ ID NO 85
<211> LENGTH: 552
<212> TYPE: DNA
<213> ORGANISM: Streptococcus sp.

<400> SEQUENCE: 85

```
atggaaatca acaatgacat caaggaccta attttagaat acgtaggacg atattttcga      60
tttgaaaacg acttctacaa acttcccaga atcaagttta ccgattccaa ttggcaaaaa     120
ttcaagaacg gtgacacttc catcgaaaaa atgggagctg gcagagtgaa cgcaatgctc     180
gattgtctat ttgatgattt tgagcttgct atgattggta aggctcaaac cgattactac     240
atggacaatt ctttaaagat gaatatgcca ttttatgcct attatgacca atttaagaaa     300
cagcaactat tgaaatggat cgagaatagt agagaggata tcataggcgg tgctggcaga     360
atgtacacag ctagtgggaa ttggatttct agtgcctatt tagaaattgc attggaatcc     420
agctcgttag gtggtggtga gtacatgttg caaatgcgtt tcaaagacta ctcacgaagc     480
caagagccga taccagcagg ccgccagaat cgacttgagt ggattgagaa taatttggag     540
aatattcgat aa                                                        552
```

<210> SEQ ID NO 86
<211> LENGTH: 183
<212> TYPE: PRT
<213> ORGANISM: Streptococcus sp.

<400> SEQUENCE: 86

Met Glu Ile Asn Asn Asp Ile Lys Asp Leu Ile Leu Glu Tyr Val Gly
1               5                   10                  15

Arg Tyr Phe Arg Phe Glu Asn Asp Phe Tyr Lys Leu Pro Arg Ile Lys
                20                  25                  30

Phe Thr Asp Ser Asn Trp Gln Lys Phe Lys Asn Gly Asp Thr Ser Ile
            35                  40                  45

Glu Lys Met Gly Ala Gly Arg Val Asn Ala Met Leu Asp Cys Leu Phe
    50                  55                  60

Asp Asp Phe Glu Leu Ala Met Ile Gly Lys Ala Gln Thr Asp Tyr Tyr
65                  70                  75                  80

Met Asp Asn Ser Leu Lys Met Asn Met Pro Phe Tyr Ala Tyr Tyr Asp
                85                  90                  95

Gln Phe Lys Lys Gln Gln Leu Leu Lys Trp Ile Glu Asn Ser Arg Glu
                100                 105                 110

Asp Ile Ile Gly Gly Ala Gly Arg Met Tyr Thr Ala Ser Gly Asn Trp
        115                 120                 125

Ile Ser Ser Ala Tyr Leu Glu Ile Ala Leu Glu Ser Ser Leu Gly
    130                 135                 140

Gly Gly Glu Tyr Met Leu Gln Met Arg Phe Lys Asp Tyr Ser Arg Ser
145                 150                 155                 160

Gln Glu Pro Ile Pro Ala Gly Arg Gln Asn Arg Leu Glu Trp Ile Glu
            165                 170                 175

Asn Asn Leu Glu Asn Ile Arg
            180

<210> SEQ ID NO 87
<211> LENGTH: 315
<212> TYPE: DNA
<213> ORGANISM: Bacteriophage D4252

<400> SEQUENCE: 87
atgaaaaaag ctaaacaact actcaaagaa attaaaacca ataatgtatc atacgcaatt      60
atggacgagg ataatgaaat ttattgcaac aaggaaacta acaacatcat ggatatttat     120
gaatatgata atgaaaatgg ccatttctat ggtgtttata gtgacgttgt tggtggtaaa     180
gttgatagta gatacttatc tgacgaatat attttgaaag ctatcgataa attgctaaat     240
ttaggcgatc ccgtgaaacg cactgaacta cctgcggacg ctgatttcaa acgcacattc     300 tttttgaag aataa                                                       315

<210> SEQ ID NO 88
<211> LENGTH: 104
<212> TYPE: PRT
<213> ORGANISM: Bacteriophage D4252

<400> SEQUENCE: 88

Met Lys Lys Ala Lys Gln Leu Leu Lys Glu Ile Lys Thr Asn Asn Val
1               5                   10                  15

Ser Tyr Ala Ile Met Asp Glu Asp Asn Glu Ile Tyr Cys Asn Lys Glu
            20                  25                  30

Thr Asn Asn Ile Met Asp Ile Tyr Glu Tyr Asp Asn Glu Asn Gly His
        35                  40                  45

Phe Tyr Gly Val Tyr Ser Asp Val Val Gly Gly Lys Val Asp Ser Arg
    50                  55                  60

Tyr Leu Ser Asp Glu Tyr Ile Leu Lys Ala Ile Asp Lys Leu Leu Asn
65                  70                  75                  80

Leu Gly Asp Pro Val Lys Arg Thr Glu Leu Pro Ala Asp Ala Asp Phe
                85                  90                  95

Lys Arg Thr Phe Phe Phe Glu Glu
            100

<210> SEQ ID NO 89
<211> LENGTH: 315
<212> TYPE: DNA
<213> ORGANISM: Bacteriophage D802

<400> SEQUENCE: 89
atgaaaaaag ctcaacaact gctcaaagaa attaaaaaca ctaatgtatc atacgcaatt      60
atggacgagg ataatgaaat ttattgcaac aaggaaacta acaacatcat ggatatttat     120
ggatatgata atgaaaatgg ccatttctat ggtgtttata gtgacgttgt tggtggtaaa     180
gttgatagta gatacttatc tgacgaatat attttgaaag ctatcgataa attgctattc     240
ctaggcgacc ctataaaacg aacagatcta ccttcggacg ctgatttcaa acgcacattc     300 tttttgaag aataa                                                       315

-continued

```
<210> SEQ ID NO 90
<211> LENGTH: 104
<212> TYPE: PRT
<213> ORGANISM: Bacteriophage D802

<400> SEQUENCE: 90
```

Met Lys Lys Ala Gln Gln Leu Leu Lys Glu Ile Lys Asn Thr Asn Val
1               5                   10                  15

Ser Tyr Ala Ile Met Asp Glu Asp Asn Glu Ile Tyr Cys Asn Lys Glu
            20                  25                  30

Thr Asn Asn Ile Met Asp Ile Tyr Gly Tyr Asp Asn Glu Asn Gly His
        35                  40                  45

Phe Tyr Gly Val Tyr Ser Asp Val Val Gly Gly Lys Val Asp Ser Arg
    50                  55                  60

Tyr Leu Ser Asp Glu Tyr Ile Leu Lys Ala Ile Asp Lys Leu Leu Phe
65                  70                  75                  80

Leu Gly Asp Pro Ile Lys Arg Thr Asp Leu Pro Ser Asp Ala Asp Phe
                85                  90                  95

Lys Arg Thr Phe Phe Glu Glu
            100

```
<210> SEQ ID NO 91
<211> LENGTH: 291
<212> TYPE: DNA
<213> ORGANISM: Bacteriophage P9874

<400> SEQUENCE: 91
atgaaaaaca gacttttggg ttctcgatat actgacgcga tcaaaaacga ttgcggaaca      60
gccaataaaa tgtcgaatat ttacaataaa ttgaacaaag atagtttgcg agaaatccat     120
agtgcactat atggcctatt aacagctgga tacgacatta gtaacatgcg aaacatcgaa     180
gatttagaaa atatgtgaa tttaaaaaaa tcacgtggcc aactattaaa tgtttcgagc      240
gatgatatta agctatacca taaattattt gtcatcagat ttgaaaaata g              291
```

```
<210> SEQ ID NO 92
<211> LENGTH: 96
<212> TYPE: PRT
<213> ORGANISM: Bacteriophage P9874

<400> SEQUENCE: 92
```

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
            20                  25                  30

Lys Asp Ser Leu Arg Glu Ile His Ser Ala Leu Tyr Gly Leu Leu Thr
        35                  40                  45

Ala Gly Tyr Asp Ile Ser Asn Met Arg Asn Ile Glu Asp Leu Glu Lys
    50                  55                  60

Tyr Val Asn Leu Lys Lys Ser Arg Gly Gln Leu Leu Asn Val Ser Ser
65                  70                  75                  80

Asp Asp Ile Lys Leu Tyr His Lys Leu Phe Val Ile Arg Phe Glu Lys
                85                  90                  95

```
<210> SEQ ID NO 93
<211> LENGTH: 279
<212> TYPE: DNA
<213> ORGANISM: Bacteriophage CHPC577

<400> SEQUENCE: 93
```

```
atgaaaaaca aactttatac tgacgcaatc aaaaacgatt ccagaacagc cagtaaaatg    60
gcgaacattt acaataaatt ggaaagcgat actatgcgag aaatccatag tgcactatct   120
ggcctattaa cggctggata cgacattagt aacatgcgaa acatcgaaga gttagaaaaa   180
tatgtgactt taaaaaaatc acgtggccaa ctattaaatg tctctagcga agacattaaa   240
ttgtaccata aattatttgt catcaggttt ggcaaatag                          279
```

```
<210> SEQ ID NO 94
<211> LENGTH: 92
<212> TYPE: PRT
<213> ORGANISM: Bacteriophage CHPC577

<400> SEQUENCE: 94

Met Lys Asn Lys Leu Tyr Thr Asp Ala Ile Lys Asn Asp Ser Arg Thr
1               5                   10                  15

Ala Ser Lys Met Ala Asn Ile Tyr Asn Lys Leu Glu Ser Asp Thr Met
            20                  25                  30

Arg Glu Ile His Ser Ala Leu Ser Gly Leu Leu Thr Ala Gly Tyr Asp
        35                  40                  45

Ile Ser Asn Met Arg Asn Ile Glu Glu Leu Glu Lys Tyr Val Thr Leu
    50                  55                  60

Lys Lys Ser Arg Gly Gln Leu Leu Asn Val Ser Ser Glu Asp Ile Lys
65                  70                  75                  80

Leu Tyr His Lys Leu Phe Val Ile Arg Phe Gly Lys
                85                  90
```

```
<210> SEQ ID NO 95
<211> LENGTH: 297
<212> TYPE: DNA
<213> ORGANISM: Bacteriophage D1297

<400> SEQUENCE: 95
atgaaaaaca gacttttggg ttctcgatat actgacgcga tcaaaaacga ttgcggaaca    60
gccaataaaa tgtcgaatat ttacaataaa ttgaacaaag atagtttgcg agaaattcat   120
agtgcactat atggcctatt aacagctggt tacgacatta gtaacatgcg aaaaatagaa   180
gagttagaaa aatatgtgaa tttaaaaaaa tcacgtggcc aactattaaa tgtttctagc   240
aacgatatta agctatacca taaattattt gtcatcagat ttggaaaaga gaggtaa     297
```

```
<210> SEQ ID NO 96
<211> LENGTH: 98
<212> TYPE: PRT
<213> ORGANISM: Bacteriophage D1297

<400> SEQUENCE: 96

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
            20                  25                  30

Lys Asp Ser Leu Arg Glu Ile His Ser Ala Leu Tyr Gly Leu Leu Thr
        35                  40                  45

Ala Gly Tyr Asp Ile Ser Asn Met Arg Lys Ile Glu Glu Leu Glu Lys
    50                  55                  60

Tyr Val Asn Leu Lys Lys Ser Arg Gly Gln Leu Leu Asn Val Ser Ser
65                  70                  75                  80

Asn Asp Ile Lys Leu Tyr His Lys Leu Phe Val Ile Arg Phe Gly Lys
```

-continued

```
                        85                  90                  95

Glu Arg

<210> SEQ ID NO 97
<211> LENGTH: 285
<212> TYPE: DNA
<213> ORGANISM: Bacteriophage D2759

<400> SEQUENCE: 97
atgaaaaaca gactatatac tgacgcgatc aaaaacgatt gcggaacagc caataaaatg       60
tcgaatattt acaataaatt gaacaaagat agtttgcgag aaattcatag tgcactatat      120
ggcctattaa cagctggtta cgacattagt aacatgcgaa aaatagaaga gttagaaaaa      180
tatgtgaatt taaaaaaatc acgtggccaa ctattaaatg tttctagcaa cgatattaag      240
ctataccata aattatttgt catcagattt ggaaaagaga ggtaa                      285

<210> SEQ ID NO 98
<211> LENGTH: 94
<212> TYPE: PRT
<213> ORGANISM: Bacteriophage D2759

<400> SEQUENCE: 98

Met Lys Asn Arg Leu Tyr Thr Asp Ala Ile Lys Asn Asp Cys Gly Thr
1               5                   10                  15

Ala Asn Lys Met Ser Asn Ile Tyr Asn Lys Leu Asn Lys Asp Ser Leu
            20                  25                  30

Arg Glu Ile His Ser Ala Leu Tyr Gly Leu Leu Thr Ala Gly Tyr Asp
        35                  40                  45

Ile Ser Asn Met Arg Lys Ile Glu Glu Leu Glu Lys Tyr Val Asn Leu
    50                  55                  60

Lys Lys Ser Arg Gly Gln Leu Leu Asn Val Ser Ser Asn Asp Ile Lys
65                  70                  75                  80

Leu Tyr His Lys Leu Phe Val Ile Arg Phe Gly Lys Glu Arg
                85                  90

<210> SEQ ID NO 99
<211> LENGTH: 279
<212> TYPE: DNA
<213> ORGANISM: Bacteriophage D3577

<400> SEQUENCE: 99
atgaaaaaca aactttatac tgacgcaatc aaaaacgatt ccgcaacagc caataaaatg       60
gcgaatattt atagcaagct aaacaaagat agtttgcgag aaatccatag tgcactatct      120
ggcctattaa cggctggata cgacattagt aacatgcaaa acatcgcaga gttacaaaaa      180
tatgtgattt taaaaaaatc acggggggcaa ctattaaatg tctctagcaa agacattgaa      240
ctgtatcata aattatttgt catcagattt ggaaaataa                             279

<210> SEQ ID NO 100
<211> LENGTH: 92
<212> TYPE: PRT
<213> ORGANISM: Bacteriophage D3577

<400> SEQUENCE: 100

Met Lys Asn Lys Leu Tyr Thr Asp Ala Ile Lys Asn Asp Ser Ala Thr
1               5                   10                  15

Ala Asn Lys Met Ala Asn Ile Tyr Ser Lys Leu Asn Lys Asp Ser Leu
            20                  25                  30
```

```
Arg Glu Ile His Ser Ala Leu Ser Gly Leu Leu Thr Ala Gly Tyr Asp
        35                  40                  45

Ile Ser Asn Met Gln Asn Ile Ala Glu Leu Gln Lys Tyr Val Ile Leu
    50                  55                  60

Lys Lys Ser Arg Gly Gln Leu Leu Asn Val Ser Ser Lys Asp Ile Glu
65                  70                  75                  80

Leu Tyr His Lys Leu Phe Val Ile Arg Phe Gly Lys
                85                  90

<210> SEQ ID NO 101
<211> LENGTH: 291
<212> TYPE: DNA
<213> ORGANISM: Bacteriophage D4741

<400> SEQUENCE: 101
atgaaaaaca gacttttggg ttctcgatat actgacgcga tcaaaaacga ttgcggaaca    60
gccaataaaa tgtcgaatat ttacaataaa ttgaacaaag atagtttgcg agaaattcat   120
agtgcactat atggcctatt aacagctggt tacgacatta gtaacatgcg aaaaatagaa   180
gagttagaaa atatgtgaa tttaaaaaaa tcacgtggcc aactattaaa tgtttctagc    240
aacgatatta agctatacca taaattattt gtcatcagat ttggaaaata g            291

<210> SEQ ID NO 102
<211> LENGTH: 96
<212> TYPE: PRT
<213> ORGANISM: Bacteriophage D4741

<400> SEQUENCE: 102

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
            20                  25                  30

Lys Asp Ser Leu Arg Glu Ile His Ser Ala Leu Tyr Gly Leu Leu Thr
        35                  40                  45

Ala Gly Tyr Asp Ile Ser Asn Met Arg Lys Ile Glu Glu Leu Glu Lys
    50                  55                  60

Tyr Val Asn Leu Lys Lys Ser Arg Gly Gln Leu Leu Asn Val Ser Ser
65                  70                  75                  80

Asn Asp Ile Lys Leu Tyr His Lys Leu Phe Val Ile Arg Phe Gly Lys
                85                  90                  95

<210> SEQ ID NO 103
<211> LENGTH: 285
<212> TYPE: DNA
<213> ORGANISM: Bacteriophage D4419

<400> SEQUENCE: 103
atgaaaaaca gacttttggg ttctcgatat actgacgcga tcaaaaacga ttgcggaaca    60
gccaataaaa tgtcgaatat ttacaataaa ttgaacaaag atagtttgcg agaaattcat   120
agtgcactat atggcctatt aacagctggt tacgacatta gtaacatgcg aaaaatagaa   180
gagttagaaa atatgtgaa tttatcacgt ggccaactat taaatgtttc tagcaacgat   240
attaagctat atcataaatt atttgtcatc agatttggaa aatag                   285

<210> SEQ ID NO 104
<211> LENGTH: 94
<212> TYPE: PRT
```

<213> ORGANISM: Bacteriophage D4419

<400> SEQUENCE: 104

```
Met Lys Asn Arg Leu Leu Gly Ser Arg Tyr Thr Asp Ala Ile Lys Asn
1               5                   10                  15
Asp Cys Gly Thr Ala Asn Lys Met Ser Asn Ile Tyr Asn Lys Leu Asn
            20                  25                  30
Lys Asp Ser Leu Arg Glu Ile His Ser Ala Leu Tyr Gly Leu Leu Thr
        35                  40                  45
Ala Gly Tyr Asp Ile Ser Asn Met Arg Lys Ile Glu Glu Leu Glu Lys
    50                  55                  60
Tyr Val Asn Leu Ser Arg Gly Gln Leu Leu Asn Val Ser Ser Asn Asp
65                  70                  75                  80
Ile Lys Leu Tyr His Lys Leu Phe Val Ile Arg Phe Gly Lys
                85                  90
```

<210> SEQ ID NO 105
<211> LENGTH: 303
<212> TYPE: DNA
<213> ORGANISM: Bacteriophage D5861

<400> SEQUENCE: 105

```
atgaaaaaca gacttttggg ttctcgatat actgacgcaa tcaaaaacga ttccggaaca    60
gccaataaaa tgtctaatat ttacaattca gtcataaaca aggagggggtt gcgaggaatc   120
catagtgcac tatatggcct attaacagct ggatacgaca ttagtaacat gcgaaaaata   180
gaagagttag aaaaatatgt gaatttaaaa aaatcacgtg ccaactatt aaatgtttct    240
agcagcgata ttaagctata ccataaatta tttgtcatca gatttggaaa aagttaaaa    300
taa                                                                 303
```

<210> SEQ ID NO 106
<211> LENGTH: 100
<212> TYPE: PRT
<213> ORGANISM: Bacteriophage D5861

<400> SEQUENCE: 106

```
Met Lys Asn Arg Leu Leu Gly Ser Arg Tyr Thr Asp Ala Ile Lys Asn
1               5                   10                  15
Asp Ser Gly Thr Ala Asn Lys Met Ser Asn Ile Tyr Asn Ser Val Ile
            20                  25                  30
Asn Lys Glu Gly Leu Arg Gly Ile His Ser Ala Leu Tyr Gly Leu Leu
        35                  40                  45
Thr Ala Gly Tyr Asp Ile Ser Asn Met Arg Lys Ile Glu Glu Leu Glu
    50                  55                  60
Lys Tyr Val Asn Leu Lys Lys Ser Arg Gly Gln Leu Leu Asn Val Ser
65                  70                  75                  80
Ser Ser Asp Ile Lys Leu Tyr His Lys Leu Phe Val Ile Arg Phe Gly
                85                  90                  95
Lys Lys Leu Lys
            100
```

<210> SEQ ID NO 107
<211> LENGTH: 297
<212> TYPE: DNA
<213> ORGANISM: Bacteriophage D6252

<400> SEQUENCE: 107

```
atgaaaaatg gtaacaaaat tttaggttat cgatacactg atgagattaa aaacgattct    60
gcaacagaga ataaaatgtc taatctttat aacaaattgg acaaagatag tttacgagag   120
atccatagtg cattatacgg tctattaaca gctggatatg atatcagcaa catgcgaaat   180
gtcgaagaac ttgaaaaata cgtgaacgtt aaaaaatctc atggaaaatt attagatgtt   240
actaatagtg acattcagtt atatcataaa ttatttgttg ttcgatttgg gaagtag     297
```

<210> SEQ ID NO 108
<211> LENGTH: 98
<212> TYPE: PRT
<213> ORGANISM: Bacteriophage D6252

<400> SEQUENCE: 108

```
Met Lys Asn Gly Asn Lys Ile Leu Gly Tyr Arg Tyr Thr Asp Glu Ile
1               5                   10                  15

Lys Asn Asp Ser Ala Thr Glu Asn Lys Met Ser Asn Leu Tyr Asn Lys
                20                  25                  30

Leu Asp Lys Asp Ser Leu Arg Glu Ile His Ser Ala Leu Tyr Gly Leu
            35                  40                  45

Leu Thr Ala Gly Tyr Asp Ile Ser Asn Met Arg Asn Val Glu Glu Leu
        50                  55                  60

Glu Lys Tyr Val Asn Val Lys Ser His Gly Lys Leu Leu Asp Val
65                  70                  75                  80

Thr Asn Ser Asp Ile Gln Leu Tyr His Lys Leu Phe Val Val Arg Phe
                85                  90                  95

Gly Lys
```

<210> SEQ ID NO 109
<211> LENGTH: 291
<212> TYPE: DNA
<213> ORGANISM: Bacteriophage D7130

<400> SEQUENCE: 109

```
atgaaaaaca gactttgggg ttctcgatat actgacgcga tcaaaaacga ttgcggaaca    60
gccaataaaa tgtcgaatat ttacaataaa ttgaacaaag atagtttgcg agaaatccat   120
agtgcactat atggcctatt aacagctgga tacgacatta gtaacatgcg aaacatcgaa   180
gagttagaaa atatgtgaa tttaaaaaaa tcacgtggcc aactattaaa tgtttctagc   240
agcgatatta gctatacca taaattattt gtcatcagat ttggaaaata g            291
```

<210> SEQ ID NO 110
<211> LENGTH: 96
<212> TYPE: PRT
<213> ORGANISM: Bacteriophage D7130

<400> SEQUENCE: 110

```
Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
                20                  25                  30

Lys Asp Ser Leu Arg Glu Ile His Ser Ala Leu Tyr Gly Leu Leu Thr
            35                  40                  45

Ala Gly Tyr Asp Ile Ser Asn Met Arg Asn Ile Glu Glu Leu Glu Lys
        50                  55                  60

Tyr Val Asn Leu Lys Lys Ser Arg Gly Gln Leu Leu Asn Val Ser Ser
65                  70                  75                  80
```

```
Ser Asp Ile Lys Leu Tyr His Lys Leu Phe Val Ile Arg Phe Gly Lys
            85                  90                  95
```

<210> SEQ ID NO 111
<211> LENGTH: 294
<212> TYPE: DNA
<213> ORGANISM: Bacteriophage N1062

<400> SEQUENCE: 111

```
atgaaaaaca gacttttggg ttctcgatat actgacgcaa tcaaaaacga ttccggaaca      60
gccaataaaa tgtctaatat ttacaattca gtcataaaca aggagggtt gcgaggaatc     120 catagtgcac tatatggcct attaacagct ggatacgaca ttagtaacat gcgaaaaata    180
gaagagttag aaaaatatgt gaatttaaaa aaatcacgtg ccaactatt aatgttttct    240 agcagcgata ttaagctata ccataaatta tttgtcatca gatttggaaa atag          294
```

<210> SEQ ID NO 112
<211> LENGTH: 97
<212> TYPE: PRT
<213> ORGANISM: Bacteriophage N1062

<400> SEQUENCE: 112

```
Met Lys Asn Arg Leu Leu Gly Ser Arg Tyr Thr Asp Ala Ile Lys Asn
1               5                   10                  15

Asp Ser Gly Thr Ala Asn Lys Met Ser Asn Ile Tyr Asn Ser Val Ile
            20                  25                  30

Asn Lys Glu Gly Leu Arg Gly Ile His Ser Ala Leu Tyr Gly Leu Leu
        35                  40                  45

Thr Ala Gly Tyr Asp Ile Ser Asn Met Arg Lys Ile Glu Glu Leu Glu
    50                  55                  60

Lys Tyr Val Asn Leu Lys Lys Ser Arg Gly Gln Leu Leu Asn Val Ser
65                  70                  75                  80

Ser Ser Asp Ile Lys Leu Tyr His Lys Leu Phe Val Ile Arg Phe Gly
            85                  90                  95

Lys
```

<210> SEQ ID NO 113
<211> LENGTH: 294
<212> TYPE: DNA
<213> ORGANISM: Bacteriophage N488

<400> SEQUENCE: 113

```
atgaaaaaca gacttttggg ttctcgatat actgacgcaa tcaaaaacga ttccggaaca      60
gccaataaaa tgtctaatat ttacaattca gtcataaaca aggagggtt gcgagaaatc     120 catagtgcac tatatggcct attaacagct ggttacgaca ttagtaacat gcgaaaaata    180
gaagagttag aaaaatatgt gaatttaaaa aaatcacgtg ccaactatt aatgtgtct    240 agcaatgata ttaagctata ccataaatta tttgtcacca gatttggaaa ataa          294
```

<210> SEQ ID NO 114
<211> LENGTH: 97
<212> TYPE: PRT
<213> ORGANISM: Bacteriophage N488

<400> SEQUENCE: 114

```
Met Lys Asn Arg Leu Leu Gly Ser Arg Tyr Thr Asp Ala Ile Lys Asn
1               5                   10                  15

Asp Ser Gly Thr Ala Asn Lys Met Ser Asn Ile Tyr Asn Ser Val Ile
```

20                  25                  30

Asn Lys Glu Gly Leu Arg Glu Ile His Ser Ala Leu Tyr Gly Leu Leu
             35                  40                  45

Thr Ala Gly Tyr Asp Ile Ser Asn Met Arg Lys Ile Glu Glu Leu Glu
         50                  55                  60

Lys Tyr Val Asn Leu Lys Ser Arg Gly Gln Leu Leu Asn Val Ser
 65                  70                  75                  80

Ser Asn Asp Ile Lys Leu Tyr His Lys Leu Phe Val Thr Arg Phe Gly
                 85                  90                  95

Lys

<210> SEQ ID NO 115
<211> LENGTH: 291
<212> TYPE: DNA
<213> ORGANISM: Bacteriophage P5641

<400> SEQUENCE: 115
atgaaaaaca gacttttggg ttctcgatat actgacgcaa tcaaaaacga ttccggaaca    60
gccaataaaa tgtcgaatat ttacaataaa ttgaacaaag atagtttgcg agaaattcat   120
agtgcactat atggcctatt aacagctggt tacgacatta gtaacatgcg aaacatcgaa   180
gagttagaaa atatgtgaa tttaaaaaaa tcacgtggcc aactattaaa tgttactagc   240
aatgatatta agctatacca taaattattt gtcatcagat ttggaaaata g           291

<210> SEQ ID NO 116
<211> LENGTH: 96
<212> TYPE: PRT
<213> ORGANISM: Bacteriophage P5641

<400> SEQUENCE: 116

Met Lys Asn Arg Leu Leu Gly Ser Arg Tyr Thr Asp Ala Ile Lys Asn
 1               5                  10                  15

Asp Ser Gly Thr Ala Asn Lys Met Ser Asn Ile Tyr Asn Lys Leu Asn
             20                  25                  30

Lys Asp Ser Leu Arg Glu Ile His Ser Ala Leu Tyr Gly Leu Leu Thr
         35                  40                  45

Ala Gly Tyr Asp Ile Ser Asn Met Arg Asn Ile Glu Glu Leu Glu Lys
     50                  55                  60

Tyr Val Asn Leu Lys Lys Ser Arg Gly Gln Leu Leu Asn Val Thr Ser
 65                  70                  75                  80

Asn Asp Ile Lys Leu Tyr His Lys Leu Phe Val Ile Arg Phe Gly Lys
                 85                  90                  95

<210> SEQ ID NO 117
<211> LENGTH: 291
<212> TYPE: DNA
<213> ORGANISM: Bacteriophage P7602

<400> SEQUENCE: 117
atgaaaaaca gacttttggg ttctcgatat actgacgcga tcaaaaacga ttgcggaaca    60
gccaataaaa tgtcgaatat ttacaataaa ttgaacaaag atagtttgcg agagatccat   120
agtgcactat atggcctatt aacagctgga tacgacatta gtaacatgcg aaacatcgaa   180
gagttagaaa atatgtgaa tttaaaaaaa tcacgtggcc aactattaaa tgtttcgagc   240
gatgatatta agctatacca taaattattt gtcatcagat ttggaaaata g           291

```
<210> SEQ ID NO 118
<211> LENGTH: 96
<212> TYPE: PRT
<213> ORGANISM: Bacteriophage P7602

<400> SEQUENCE: 118

Met Lys Asn Arg Leu Leu Gly Ser Arg Tyr Thr Asp Ala Ile Lys Asn
1               5                   10                  15

Asp Cys Gly Thr Ala Asn Lys Met Ser Asn Ile Tyr Asn Lys Leu Asn
            20                  25                  30

Lys Asp Ser Leu Arg Glu Ile His Ser Ala Leu Tyr Gly Leu Leu Thr
        35                  40                  45

Ala Gly Tyr Asp Ile Ser Asn Met Arg Asn Ile Glu Glu Leu Glu Lys
    50                  55                  60

Tyr Val Asn Leu Lys Lys Ser Arg Gly Gln Leu Leu Asn Val Ser Ser
65                  70                  75                  80

Asp Asp Ile Lys Leu Tyr His Lys Leu Phe Val Ile Arg Phe Gly Lys
                85                  90                  95

<210> SEQ ID NO 119
<211> LENGTH: 297
<212> TYPE: DNA
<213> ORGANISM: Bacteriophage V442

<400> SEQUENCE: 119
atgaaaaatg gtaacaaaat tttaggttat cgatacactg atgagattaa aaacgattct      60
gcaacagaga ataaaatgtc taatctttat aacaaattgg acaaagatag tttacgagag     120
atccatagtg cattatacgg tctattaaca gctggatatg atatcagcaa catgcgaaat     180
gtcgaagaac ttgaaaaata cgtgaacgtt aaaaaatctc atggaaaatt attagatgtt     240
actaatagtg acattcagtt atatcataaa ttatttgttg ttcgatttgg gaggtaa       297

<210> SEQ ID NO 120
<211> LENGTH: 98
<212> TYPE: PRT
<213> ORGANISM: Bacteriophage V442

<400> SEQUENCE: 120

Met Lys Asn Gly Asn Lys Ile Leu Gly Tyr Arg Tyr Thr Asp Glu Ile
1               5                   10                  15

Lys Asn Asp Ser Ala Thr Glu Asn Lys Met Ser Asn Leu Tyr Asn Lys
            20                  25                  30

Leu Asp Lys Asp Ser Leu Arg Glu Ile His Ser Ala Leu Tyr Gly Leu
        35                  40                  45

Leu Thr Ala Gly Tyr Asp Ile Ser Asn Met Arg Asn Val Glu Glu Leu
    50                  55                  60

Glu Lys Tyr Val Asn Val Lys Lys Ser His Gly Lys Leu Leu Asp Val
65                  70                  75                  80

Thr Asn Ser Asp Ile Gln Leu Tyr His Lys Leu Phe Val Val Arg Phe
                85                  90                  95

Gly Arg

<210> SEQ ID NO 121
<211> LENGTH: 387
<212> TYPE: DNA
<213> ORGANISM: Bacteriophage D4090

<400> SEQUENCE: 121
```

```
atgacagaat ggaaaacaat aaactttaat gcacaaaaca ttgaatacga ggcggcaaaa    60
gcaatcctca ttaagatgcc aaacaattct gaatggcacg gttacacttt ctggcatccg   120
tcaaaatgtg tgcgtacatt aagcaagggt aatggttatt tcaaaacttt cagctataca   180
gaaaattggg agtttaccat tttcaaatca aataaaaaag gggaaagaac cattgaacaa   240
gtacttacgg caagagatat ggaaaaagca tttagtgtgg tgaatgaaca aattgcaagt   300
aatgcttcaa cagaaagtta ccttgaaatt gaagaaccta aaaaggttga taaaacagtt   360
agtattaaca atgagttaaa acgttaa                                       387
```

<210> SEQ ID NO 122
<211> LENGTH: 128
<212> TYPE: PRT
<213> ORGANISM: Bacteriophage D4090

<400> SEQUENCE: 122

```
Met Thr Glu Trp Lys Thr Ile Asn Phe Asn Ala Gln Asn Ile Glu Tyr
1               5                   10                  15

Glu Ala Ala Lys Ala Ile Leu Ile Lys Met Pro Asn Asn Ser Glu Trp
            20                  25                  30

His Gly Tyr Thr Phe Trp His Pro Ser Lys Cys Val Arg Thr Leu Ser
        35                  40                  45

Lys Gly Asn Gly Tyr Phe Lys Thr Phe Ser Tyr Thr Glu Asn Trp Glu
    50                  55                  60

Phe Thr Ile Phe Lys Ser Asn Lys Lys Gly Glu Arg Thr Ile Glu Gln
65                  70                  75                  80

Val Leu Thr Ala Arg Asp Met Glu Lys Ala Phe Ser Val Val Asn Glu
                85                  90                  95

Gln Ile Ala Ser Asn Ala Ser Thr Glu Ser Tyr Leu Glu Ile Glu Glu
            100                 105                 110

Pro Lys Lys Val Asp Lys Thr Val Ser Ile Asn Asn Glu Leu Lys Arg
        115                 120                 125
```

<210> SEQ ID NO 123
<211> LENGTH: 387
<212> TYPE: DNA
<213> ORGANISM: Bacteriophage D4254

<400> SEQUENCE: 123

```
atgacagaat ggaaaacgat taattttaat aaacaaaaca ttgaacatga acagcgaaa     60 gctgttctca ttaagatgcc aaataattct gaatggtacg gctataaatt ctggcatccg   120
tcaaaatgtg tgcgtacatt aagcaagggc aatggttatt tcaaaacttt cagctataca   180
gaaaattggg agtttaccat tttcaaatca aataaaaagg gggaaagaac cgctgaacaa   240
atacttacag cagaggatat ggaaatagct tttgatgttg ttaacgaaca aattagcgcg   300
aacgcttcaa cagaaagtta tcttgaaatt gaagaaccta aaaaggttga taaaacagtt   360
agtattaaca atgagttaaa acgttaa                                       387
```

<210> SEQ ID NO 124
<211> LENGTH: 128
<212> TYPE: PRT
<213> ORGANISM: Bacteriophage D4254

<400> SEQUENCE: 124

```
Met Thr Glu Trp Lys Thr Ile Asn Phe Asn Lys Gln Asn Ile Glu His
1               5                   10                  15
```

```
Glu Thr Ala Lys Ala Val Leu Ile Lys Met Pro Asn Asn Ser Glu Trp
            20                  25                  30

Tyr Gly Tyr Lys Phe Trp His Pro Ser Lys Cys Val Arg Thr Leu Ser
        35                  40                  45

Lys Gly Asn Gly Tyr Phe Lys Thr Phe Ser Tyr Thr Glu Asn Trp Glu
    50                  55                  60

Phe Thr Ile Phe Lys Ser Asn Lys Lys Gly Glu Arg Thr Ala Glu Gln
65                  70                  75                  80

Ile Leu Thr Ala Glu Asp Met Glu Ile Ala Phe Asp Val Val Asn Glu
                85                  90                  95

Gln Ile Ser Ala Asn Ala Ser Thr Glu Ser Tyr Leu Glu Ile Glu Glu
                100                 105                 110

Pro Lys Lys Val Asp Lys Thr Val Ser Ile Asn Asn Glu Leu Lys Arg
            115                 120                 125

<210> SEQ ID NO 125
<211> LENGTH: 387
<212> TYPE: DNA
<213> ORGANISM: Bacteriophage D4368

<400> SEQUENCE: 125
atgacagaat ggaaaacaat aaactttaat gcacaaaaca ttgaatacga ggcggcaaaa      60
gcaatcctca ttaagatgcc aaacaattct gaatggcacg gttacacttt ctggcatccg     120
tcaaatgtgt gcgtacatt aagcaagggt aatggttatt caaaactttt cagctataca     180
gaaaattggg agtttaccat tttcaaatca aataaaaagg gggaagaac cgctgaacaa     240 atacttacag cagaggatat ggaaatagct tttgatgttg ttaacgaaca aatcagtgta     300
gacgcttcga cagaaagtta ccttgaaatc gaagagccta aaaaggttga taaaacagtt     360
agtattaaca atgaattaaa acgttaa                                         387

<210> SEQ ID NO 126
<211> LENGTH: 128
<212> TYPE: PRT
<213> ORGANISM: Bacteriophage D4368

<400> SEQUENCE: 126

Met Thr Glu Trp Lys Thr Ile Asn Phe Asn Ala Gln Asn Ile Glu Tyr
1               5                   10                  15

Glu Ala Ala Lys Ala Ile Leu Ile Lys Met Pro Asn Asn Ser Glu Trp
            20                  25                  30

His Gly Tyr Thr Phe Trp His Pro Ser Lys Cys Val Arg Thr Leu Ser
        35                  40                  45

Lys Gly Asn Gly Tyr Phe Lys Thr Phe Ser Tyr Thr Glu Asn Trp Glu
    50                  55                  60

Phe Thr Ile Phe Lys Ser Asn Lys Lys Gly Glu Arg Thr Ala Glu Gln
65                  70                  75                  80

Ile Leu Thr Ala Glu Asp Met Glu Ile Ala Phe Asp Val Val Asn Glu
                85                  90                  95

Gln Ile Ser Val Asp Ala Ser Thr Glu Ser Tyr Leu Glu Ile Glu Glu
                100                 105                 110

Pro Lys Lys Val Asp Lys Thr Val Ser Ile Asn Asn Glu Leu Lys Arg
            115                 120                 125

<210> SEQ ID NO 127
<211> LENGTH: 381
<212> TYPE: DNA
```

<213> ORGANISM: Bacteriophage D4598

<400> SEQUENCE: 127

```
atgtggaaat caatcaattt taacgcacaa aacatcgaac acgagacagc gaaagctgtt      60
ctcattaaga tgccaaataa ttctgaatgg agtggttata aattttggca cccatctaaa     120
tgcgtccgta ctctaagcaa gggcaaaggc tatttcaaaa ttttcagcta tacagaaaat     180
tgggagttta ccattttcaa atcaaataaa aaggggggaaa gaaccgctga acaaatactt    240
acagcagagg atatggaaat agcttttgat gttgttaacg aacaaattag cgcgaacgct     300
tcaacagaaa gttatcttga aattgaagaa cctaaaaagg ttgataaaac agttagtatt     360
aacaatgagt taaaacgtta a                                               381
```

<210> SEQ ID NO 128
<211> LENGTH: 126
<212> TYPE: PRT
<213> ORGANISM: Bacteriophage D4598

<400> SEQUENCE: 128

```
Met Trp Lys Ser Ile Asn Phe Asn Ala Gln Asn Ile Glu His Glu Thr
1               5                   10                  15
Ala Lys Ala Val Leu Ile Lys Met Pro Asn Asn Ser Glu Trp Ser Gly
            20                  25                  30
Tyr Lys Phe Trp His Pro Ser Lys Cys Val Arg Thr Leu Ser Lys Gly
        35                  40                  45
Lys Gly Tyr Phe Lys Ile Phe Ser Tyr Thr Glu Asn Trp Glu Phe Thr
    50                  55                  60
Ile Phe Lys Ser Asn Lys Lys Gly Glu Arg Thr Ala Glu Gln Ile Leu
65                  70                  75                  80
Thr Ala Glu Asp Met Glu Ile Ala Phe Asp Val Val Asn Glu Gln Ile
                85                  90                  95
Ser Ala Asn Ala Ser Thr Glu Ser Tyr Leu Glu Ile Glu Glu Pro Lys
            100                 105                 110
Lys Val Asp Lys Thr Val Ser Ile Asn Asn Glu Leu Lys Arg
        115                 120                 125
```

<210> SEQ ID NO 129
<211> LENGTH: 381
<212> TYPE: DNA
<213> ORGANISM: Bacteriophage D5693

<400> SEQUENCE: 129

```
atgtggaaat caatcaattt taacgcacaa aacatcgaac acgagacagc gaaagctgtt      60
ctcattaaga tgccaaataa ttctgaatgg agtggttata aattttggca cccatctaaa     120
ttcgtccgta ctctaagcaa gggcaaaggc tatttcaaaa ttttcagcta tacagaaaat     180
tgggagttta ccattttcaa atcaaataaa aaggggggaaa gaaccgctga acaaatactt    240
acagcagagg atatggaaat agcttttgat gttgttaacg aacaaattag cgcgaacgct     300
tcaacagaaa gttatcttga aattgaagaa cctaaaaagg ttgataaaac agttagtatt     360
aacaatgagt taaaacgtta a                                               381
```

<210> SEQ ID NO 130
<211> LENGTH: 126
<212> TYPE: PRT
<213> ORGANISM: Bacteriophage D5693

<400> SEQUENCE: 130

```
Met Trp Lys Ser Ile Asn Phe Asn Ala Gln Asn Ile Glu His Glu Thr
1               5                   10                  15

Ala Lys Ala Val Leu Ile Lys Met Pro Asn Asn Ser Glu Trp Ser Gly
                20                  25                  30

Tyr Lys Phe Trp His Pro Ser Lys Phe Val Arg Thr Leu Ser Lys Gly
            35                  40                  45

Lys Gly Tyr Phe Lys Ile Phe Ser Tyr Thr Glu Asn Trp Glu Phe Thr
        50                  55                  60

Ile Phe Lys Ser Asn Lys Lys Gly Glu Arg Thr Ala Glu Gln Ile Leu
65                  70                  75                  80

Thr Ala Glu Asp Met Glu Ile Ala Phe Asp Val Val Asn Glu Gln Ile
                85                  90                  95

Ser Ala Asn Ala Ser Thr Glu Ser Tyr Leu Glu Ile Glu Glu Pro Lys
                100                 105                 110

Lys Val Asp Lys Thr Val Ser Ile Asn Asn Glu Leu Lys Arg
            115                 120                 125

<210> SEQ ID NO 131
<211> LENGTH: 381
<212> TYPE: DNA
<213> ORGANISM: Bacteriophage D6961

<400> SEQUENCE: 131
atgtggaaat caatcaattt taacgcacaa aacatcgaac acgagacagc gaaagctgtt        60
ctcattaaga tgccaaataa ttctgaatgg agtggttata aattttggca ctcatctaaa       120
tgcgtccgta ctctaagcaa gggcaaaggc tatttccaaa gtttcagcta tacagaaaat       180
tgggagttta ccattttcaa atcaaataaa aaggggaaa gaaccgctga acaaatactt        240
acagcagagg atatggaaat agcttttgat gttgttaacg aacaaattag cgcgaacgct       300
tcaacagaaa gttatcttga aattgaagaa cctaaaaagg ttgataaaac agttagtatt       360
aacaatgagt taaaacgtta a                                                 381

<210> SEQ ID NO 132
<211> LENGTH: 126
<212> TYPE: PRT
<213> ORGANISM: Bacteriophage D6961

<400> SEQUENCE: 132

Met Trp Lys Ser Ile Asn Phe Asn Ala Gln Asn Ile Glu His Glu Thr
1               5                   10                  15

Ala Lys Ala Val Leu Ile Lys Met Pro Asn Asn Ser Glu Trp Ser Gly
                20                  25                  30

Tyr Lys Phe Trp His Ser Ser Lys Cys Val Arg Thr Leu Ser Lys Gly
            35                  40                  45

Lys Gly Tyr Phe Gln Ser Phe Ser Tyr Thr Glu Asn Trp Glu Phe Thr
        50                  55                  60

Ile Phe Lys Ser Asn Lys Lys Gly Glu Arg Thr Ala Glu Gln Ile Leu
65                  70                  75                  80

Thr Ala Glu Asp Met Glu Ile Ala Phe Asp Val Val Asn Glu Gln Ile
                85                  90                  95

Ser Ala Asn Ala Ser Thr Glu Ser Tyr Leu Glu Ile Glu Glu Pro Lys
                100                 105                 110

Lys Val Asp Lys Thr Val Ser Ile Asn Asn Glu Leu Lys Arg
            115                 120                 125
```

<210> SEQ ID NO 133
<211> LENGTH: 387
<212> TYPE: DNA
<213> ORGANISM: Bacteriophage D7059

<400> SEQUENCE: 133

```
atgacagaat ggaaaacgat taattttaat aaacaaaaca ttgaacatga acagtgaaa      60
gctgttctca ttaagatgcc aaataattct gaatggtacg gctataaatt ctggcatccg    120
tcaaaatgtg tgcgtacatt aagcaagggc aatggttatt tcaaaacttt cagctataca    180
gaaaattggg agtttaccat tttcaaatca aataaaaagg gggaaagaac cgctgaacaa    240
atacttacag cagaggatat ggaaatagct tttgatgttg ttaacgaaca aattagcgcg    300
aacgcttcaa cagaaagtta tcttgaaatt gaagaaccta aaaaggttga taaaacagtt    360
agtattaaca atgagttaaa acgttaa                                        387
```

<210> SEQ ID NO 134
<211> LENGTH: 128
<212> TYPE: PRT
<213> ORGANISM: Bacteriophage D7059

<400> SEQUENCE: 134

```
Met Thr Glu Trp Lys Thr Ile Asn Phe Asn Lys Gln Asn Ile Glu His
1               5                   10                  15
Glu Thr Val Lys Ala Val Leu Ile Lys Met Pro Asn Asn Ser Glu Trp
            20                  25                  30
Tyr Gly Tyr Lys Phe Trp His Pro Ser Lys Cys Val Arg Thr Leu Ser
        35                  40                  45
Lys Gly Asn Gly Tyr Phe Lys Thr Phe Ser Tyr Thr Glu Asn Trp Glu
    50                  55                  60
Phe Thr Ile Phe Lys Ser Asn Lys Lys Gly Glu Arg Thr Ala Glu Gln
65                  70                  75                  80
Ile Leu Thr Ala Glu Asp Met Glu Ile Ala Phe Asp Val Val Asn Glu
                85                  90                  95
Gln Ile Ser Ala Asn Ala Ser Thr Glu Ser Tyr Leu Glu Ile Glu Glu
            100                 105                 110
Pro Lys Lys Val Asp Lys Thr Val Ser Ile Asn Asn Glu Leu Lys Arg
        115                 120                 125
```

<210> SEQ ID NO 135
<211> LENGTH: 372
<212> TYPE: DNA
<213> ORGANISM: Bacteriophage D4250

<400> SEQUENCE: 135

```
atgtggaaat caatcaaatt taacgcacag aacataaaat ttgagactgc gaaagcagta      60
ttgattaaaa tgccgaataa gtctaggtat gctggatata tgttctggca tccttttaaa    120
cttgtccgtg ttgaaggcgg aaaaggctac tttatgagtt ttagctatac agatgatttt    180
gagtttaagg tttttaaaca aggtaaaaat cgtcaaatca ccgctgaatc aatattatca    240
cacgaagaaa ttgaggaagc ttttgaaatt gtgaatgaac aattatctta tatggatgaa    300
tgctatctag aggttacaga acctactaaa attgataaag aggtagaggt caaagaagaa    360
ttgagaaagt aa                                                        372
```

<210> SEQ ID NO 136
<211> LENGTH: 123

<212> TYPE: PRT
<213> ORGANISM: Bacteriophage D4250

<400> SEQUENCE: 136

Met Trp Lys Ser Ile Lys Phe Asn Ala Gln Asn Ile Lys Phe Glu Thr
1               5                   10                  15

Ala Lys Ala Val Leu Ile Lys Met Pro Asn Lys Ser Arg Tyr Ala Gly
                20                  25                  30

Tyr Met Phe Trp His Pro Leu Lys Leu Val Arg Val Glu Gly Gly Lys
            35                  40                  45

Gly Tyr Phe Met Ser Phe Ser Tyr Thr Asp Asp Phe Glu Phe Lys Val
        50                  55                  60

Phe Lys Gln Gly Lys Asn Arg Gln Ile Thr Ala Glu Ser Ile Leu Ser
65                  70                  75                  80

His Glu Glu Ile Glu Glu Ala Phe Glu Ile Val Asn Glu Gln Leu Ser
                85                  90                  95

Tyr Met Asp Glu Cys Tyr Leu Glu Val Thr Glu Pro Thr Lys Ile Asp
            100                 105                 110

Lys Glu Val Glu Val Lys Glu Glu Leu Arg Lys
        115                 120

<210> SEQ ID NO 137
<211> LENGTH: 372
<212> TYPE: DNA
<213> ORGANISM: Bacteriophage D4252

<400> SEQUENCE: 137
atgtggaaat caatcaaatt taatgcacaa acatcaaat tcgagacagc aaaagcagtc      60
ttgattaaaa tgcccaataa atctaggtat gctgggtata tgttctggca tcctgcaaaa    120
ctagtccgag tggtaggtgg aaaaggttac tttatgagtt ttagctatac tgatgaattt    180
gagtttaaga tatttaaaca aggaaaaaat cgtcaaatta ctgttgaaaa aatcttatca    240
cccgaagaaa tagaagacgc ttttgaagtt gtgaacgaac aattatctga tatcgatgaa    300
tgctatttag aagtgacaga accaactaaa attaatgata aggtagaaat cagagcagaa    360
ttaagaaaat aa                                                        372

<210> SEQ ID NO 138
<211> LENGTH: 123
<212> TYPE: PRT
<213> ORGANISM: Bacteriophage D4252

<400> SEQUENCE: 138

Met Trp Lys Ser Ile Lys Phe Asn Ala Gln Asn Ile Lys Phe Glu Thr
1               5                   10                  15

Ala Lys Ala Val Leu Ile Lys Met Pro Asn Lys Ser Arg Tyr Ala Gly
                20                  25                  30

Tyr Met Phe Trp His Pro Ala Lys Leu Val Arg Val Val Gly Gly Lys
            35                  40                  45

Gly Tyr Phe Met Ser Phe Ser Tyr Thr Asp Glu Phe Glu Phe Lys Ile
        50                  55                  60

Phe Lys Gln Gly Lys Asn Arg Gln Ile Thr Val Glu Lys Ile Leu Ser
65                  70                  75                  80

Pro Glu Glu Ile Glu Asp Ala Phe Glu Val Val Asn Glu Gln Leu Ser
                85                  90                  95

Asp Ile Asp Glu Cys Tyr Leu Glu Val Thr Glu Pro Thr Lys Ile Asn
            100                 105                 110

```
<210> SEQ ID NO 139
<211> LENGTH: 372
<212> TYPE: DNA
<213> ORGANISM: Bacteriophage D4276

<400> SEQUENCE: 139
atgtggaaat caatcaaatt taacgcacag aacataaaat tcgagactgc gaaagcagta      60
ttaattaaaa tgccaaataa atctaggtat gctggatata tgttctggca tccttcaaaa     120
cttgtccgtg ttgaaggcgg aaaaggctac tttatgagtt ttagctatac agatgatttt     180
gagtttaagg tttttaaaca aggtaaaaat cgtcaaatca ccgctgaatc aatattatca     240
cacgaagaaa ttgaggaagc ttttgaaatt gtgaatgaac aattatctta tatggatgaa     300
tgctatctag aggttacaga acctactaaa attgataaag aggtagaggt caaagaagaa     360
ttgagaaagt aa                                                         372

<210> SEQ ID NO 140
<211> LENGTH: 123
<212> TYPE: PRT
<213> ORGANISM: Bacteriophage D4276

<400> SEQUENCE: 140
```

Met Trp Lys Ser Ile Lys Phe Asn Ala Gln Asn Ile Lys Phe Glu Thr
1               5                   10                  15

Ala Lys Ala Val Leu Ile Lys Met Pro Asn Lys Ser Arg Tyr Ala Gly
            20                  25                  30

Tyr Met Phe Trp His Pro Ser Lys Leu Val Arg Val Glu Gly Gly Lys
        35                  40                  45

Gly Tyr Phe Met Ser Phe Ser Tyr Thr Asp Asp Phe Glu Phe Lys Val
    50                  55                  60

Phe Lys Gln Gly Lys Asn Arg Gln Ile Thr Ala Glu Ser Ile Leu Ser
65                  70                  75                  80

His Glu Glu Ile Glu Glu Ala Phe Glu Ile Val Asn Glu Gln Leu Ser
                85                  90                  95

Tyr Met Asp Glu Cys Tyr Leu Glu Val Thr Glu Pro Thr Lys Ile Asp
            100                 105                 110

Lys Glu Val Glu Val Lys Glu Glu Leu Arg Lys
        115                 120

```
<210> SEQ ID NO 141
<211> LENGTH: 372
<212> TYPE: DNA
<213> ORGANISM: Bacteriophage D6938

<400> SEQUENCE: 141
atgtggaaat caataaaatt taatgcacaa aacgtaaaat tcgagactgc gaattcagtt      60
ttgattaaaa tgccgaataa atctagctat gctggatata tgttctggca ccctgcgaaa     120
ctagttcgtg tgttaggtgg caaaggttac ttttgagtt ttagctatac agatgaattt      180
gagtttaagg tttttaagca aggaaaaaat cgtcaaatca ccgctgaagc aatcttatca     240
cacgaagaaa tggaagacgc gtttgaaatt gtgaatgagc atttgtccta tacagatgaa     300
tgctatctag aagttgcaga acctactaaa atcgataaag aggtagagat cagagaagaa     360
ttgagaaagt aa                                                         372
```

<210> SEQ ID NO 142
<211> LENGTH: 123
<212> TYPE: PRT
<213> ORGANISM: Bacteriophage D6938

<400> SEQUENCE: 142

```
Met Trp Lys Ser Ile Lys Phe Asn Ala Gln Asn Val Lys Phe Glu Thr
1               5                   10                  15

Ala Asn Ser Val Leu Ile Lys Met Pro Asn Lys Ser Ser Tyr Ala Gly
            20                  25                  30

Tyr Met Phe Trp His Pro Ala Lys Leu Val Arg Val Leu Gly Gly Lys
        35                  40                  45

Gly Tyr Phe Leu Ser Phe Ser Tyr Thr Asp Glu Phe Glu Phe Lys Val
    50                  55                  60

Phe Lys Gln Gly Lys Asn Arg Gln Ile Thr Ala Glu Ala Ile Leu Ser
65                  70                  75                  80

His Glu Glu Met Glu Asp Ala Phe Glu Ile Val Asn Glu His Leu Ser
                85                  90                  95

Tyr Thr Asp Glu Cys Tyr Leu Glu Val Ala Glu Pro Thr Lys Ile Asp
            100                 105                 110

Lys Glu Val Glu Ile Arg Glu Glu Leu Arg Lys
        115                 120
```

<210> SEQ ID NO 143
<211> LENGTH: 180
<212> TYPE: DNA
<213> ORGANISM: Bacteriophage D1422

<400> SEQUENCE: 143

```
atgaaagttt attataatct agcagatagc ggactcttca agaaatcaa gaaacaacta      60 gctctggacg atgcggaaaa cggcgattta attcatacaa cagaagacaa cgaggcttca     120
gatgggacaa aaatcgtcgc aatctggaac gcaaacagac aaaactattt tataaagtaa    180
```

<210> SEQ ID NO 144
<211> LENGTH: 59
<212> TYPE: PRT
<213> ORGANISM: Bacteriophage D1422

<400> SEQUENCE: 144

```
Met Lys Val Tyr Tyr Asn Leu Ala Asp Ser Gly Leu Phe Lys Glu Ile
1               5                   10                  15

Lys Lys Gln Leu Ala Leu Asp Asp Ala Glu Asn Gly Asp Leu Ile His
            20                  25                  30

Thr Thr Glu Asp Asn Glu Ala Ser Asp Gly Thr Lys Ile Val Ala Ile
        35                  40                  45

Trp Asn Ala Asn Arg Gln Asn Tyr Phe Ile Lys
    50                  55
```

<210> SEQ ID NO 145
<211> LENGTH: 438
<212> TYPE: DNA
<213> ORGANISM: Bacteriophage D1765

<400> SEQUENCE: 145

```
atgagaaacg atttttattaa taaagtttat gatgaattaa atcagattat taatcattgg      60
gctaaacaaa aatatttaag tgataagatt tttgaatata ctaatacttt tagtattaag    120
```

```
aaggtttatg gactttattg ggaagttaag attttatgta agaatgatta tcgaattttg      180
ttgagatttt ataaaaatta tgagtggtat aacgattcta atattttaaa tgtatctgta      240
ttagcacctg cggtggaaag agttaaaaat gaagatggaa gcgttgatgt ttatccaagt      300
aaaataatta agataaaat tgaatttatt gaaggtgatt ttgatattga tggagatgat       360
tgggtagatg aagtgttgga atatataaat aaatgggtaa ataagataaa agctgatgtg      420
gaggtattag ataaatga                                                    438
```

<210> SEQ ID NO 146
<211> LENGTH: 145
<212> TYPE: PRT
<213> ORGANISM: Bacteriophage D1765

<400> SEQUENCE: 146

```
Met Arg Asn Asp Phe Ile Asn Lys Val Tyr Asp Glu Leu Asn Gln Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Leu Arg Phe Tyr
    50                  55                  60

Lys Asn Tyr Glu Trp Tyr Asn Asp Ser Asn Ile Leu Asn Val Ser Val
65                  70                  75                  80

Leu Ala Pro Ala Val Glu Arg Val Lys Asn Glu Asp Gly Ser Val Asp
                85                  90                  95

Val Tyr Pro Ser Lys Ile Ile Lys Asp Lys Ile Glu Phe Ile Glu Gly
            100                 105                 110

Asp Phe Asp Ile Asp Gly Asp Asp Trp Val Asp Glu Val Leu Glu Tyr
        115                 120                 125

Ile Asn Lys Trp Val Asn Lys Asp Lys Ala Asp Val Glu Val Leu Asp
    130                 135                 140

Lys
145
```

<210> SEQ ID NO 147
<211> LENGTH: 438
<212> TYPE: DNA
<213> ORGANISM: Bacteriophage D4212

<400> SEQUENCE: 147

```
atgagaaacg attttattaa taaagtttat gatgaattaa atcagattat taatcattgg      60
gctaaacaaa aatatttaag tgataagatt tttgaatata ctaatacttt tagtattaag      120
aaggtttatg gactttattg ggaagttaag attttatgta agaatgatta tcgaattttg      180
ttgagatttt ataaaaatta tgagtggtat aacgattcta atattttaaa tgtatctgta      240
ttagcacctg cggtggaaag agttaaaaat gaagatggaa gcgttgatgt ttatccaagt      300
aaaaaaatta agataaaat tgaatttatt gaaggtgatt ttgatattga tggagatgat       360
tgggtagatg aagtgttgga atatataaat aaatgggtaa ataagataaa agctgatgtg      420
gaggtattag ataaatga                                                    438
```

<210> SEQ ID NO 148
<211> LENGTH: 145
<212> TYPE: PRT
<213> ORGANISM: Bacteriophage D4212

<400> SEQUENCE: 148

```
Met Arg Asn Asp Phe Ile Asn Lys Val Tyr Asp Glu Leu Asn Gln Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Arg Phe Tyr
    50                  55                  60

Lys Asn Tyr Glu Trp Tyr Asn Asp Ser Asn Ile Leu Asn Val Ser Val
65              70                  75                  80

Leu Ala Pro Ala Val Glu Arg Val Lys Asn Glu Asp Gly Ser Val Asp
                85                  90                  95

Val Tyr Pro Ser Lys Lys Ile Lys Asp Lys Ile Glu Phe Ile Glu Gly
                100                 105                 110

Asp Phe Asp Ile Asp Gly Asp Asp Trp Val Asp Val Leu Glu Tyr
            115                 120                 125

Ile Asn Lys Trp Val Asn Lys Asp Lys Ala Asp Val Glu Val Leu Asp
    130                 135                 140

Lys
145
```

<210> SEQ ID NO 149
<211> LENGTH: 438
<212> TYPE: DNA
<213> ORGANISM: Bacteriophage D4250

<400> SEQUENCE: 149

```
atgagaaacg attttattaa taaagtttat gatgaattaa atcagattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatta tgagtggtat aacgattcta atattttaaa tgtatctgta     240
ttagcacctg cggtggaaag agttaaaaat gaagatggaa gcgttgatgt ttatccaagt     300
aaaaaaatta agataaaaat tgaatttatt gaaggtaatt ttgatattga tggagatgat     360
tgggtagatg aagtgttgga atatataaat aaatgggtaa ataagataaa agctgatgtg     420
gaggtattag ataaatga                                                    438
```

<210> SEQ ID NO 150
<211> LENGTH: 145
<212> TYPE: PRT
<213> ORGANISM: Bacteriophage D4250

<400> SEQUENCE: 150

```
Met Arg Asn Asp Phe Ile Asn Lys Val Tyr Asp Glu Leu Asn Gln Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Arg Phe Tyr
    50                  55                  60

Lys Asn Tyr Glu Trp Tyr Asn Asp Ser Asn Ile Leu Asn Val Ser Val
65              70                  75                  80
```

Leu Ala Pro Ala Val Glu Arg Val Lys Asn Glu Asp Gly Ser Val Asp
                85                  90                  95

Val Tyr Pro Ser Lys Lys Ile Lys Asp Lys Ile Glu Phe Ile Glu Gly
            100                 105                 110

Asn Phe Asp Ile Asp Gly Asp Asp Trp Val Asp Glu Val Leu Glu Tyr
        115                 120                 125

Ile Asn Lys Trp Val Asn Lys Asp Lys Ala Asp Val Glu Val Leu Asp
    130                 135                 140

Lys
145

<210> SEQ ID NO 151
<211> LENGTH: 366
<212> TYPE: DNA
<213> ORGANISM: Bacteriophage D4287

<400> SEQUENCE: 151
atgagaaacg attttattaa taaagtttat gatgaattaa atcagattat taatcattgg      60
gctaaacaaa aatatttaag tgataagatt tttgaatata ctaatacttt tagtattaag     120
aaggtttatg gactttattg ggaagttaag attttatgta agaatgatta tcgaattttg     180
ttgagatttt ataaaaatta tgagtggtat aacgattcta atattttaaa tgtatctgta     240
ttagcacctg cggtggaaag agttaaaaat gaagatggaa gcgttgatgt ttatccaagt     300
aaaaaattaa agataaaaatt gaatttattg aaggtgattt tgatattgat ggagatgatt     360
gggtag                                                                 366

<210> SEQ ID NO 152
<211> LENGTH: 121
<212> TYPE: PRT
<213> ORGANISM: Bacteriophage D4287

<400> SEQUENCE: 152

Met Arg Asn Asp Phe Ile Asn Lys Val Tyr Asp Glu Leu Asn Gln Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Leu Arg Phe Tyr
    50                  55                  60

Lys Asn Tyr Glu Trp Tyr Asn Asp Ser Asn Ile Leu Asn Val Ser Val
65                  70                  75                  80

Leu Ala Pro Ala Val Glu Arg Val Lys Asn Glu Asp Gly Ser Val Asp
                85                  90                  95

Val Tyr Pro Ser Lys Lys Leu Lys Ile Lys Leu Asn Leu Leu Lys Val
            100                 105                 110

Ile Leu Ile Leu Met Glu Met Ile Gly
        115                 120

<210> SEQ ID NO 153
<211> LENGTH: 438
<212> TYPE: DNA
<213> ORGANISM: Bacteriophage D6252

<400> SEQUENCE: 153
atgagaaacg attttattaa taaagtttat gatgaattaa atcagattat taatcattgg      60

```
gctaaacaaa aatatttaag tgataagatt tttgaatata ctaatacttt tagtattaag    120
aaggtttatg gactttattg ggaagttaag attttatgta agaatgatta tcgaattttg    180
ttgagatttt ataaaaatta tgagtggtat aacgattcta atattttaaa tgtatctgta    240
ttagcacctg cggtggaaag agttgaaaat gaagatggaa gcgttgatgt ttatccaagt    300
aaaataatta agataaaat tgaatttatt gaaggtgatt ttgatatcga tggagatgat    360
tgggtagatg aagtgttgga atatataaat aaatgggtaa ataagataaa agctgatgtg    420
gaggtattag ataaatga                                                   438
```

<210> SEQ ID NO 154
<211> LENGTH: 145
<212> TYPE: PRT
<213> ORGANISM: Bacteriophage D6252

<400> SEQUENCE: 154

```
Met Arg Asn Asp Phe Ile Asn Lys Val Tyr Asp Glu Leu Asn Gln Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Leu Arg Phe Tyr
    50                  55                  60

Lys Asn Tyr Glu Trp Tyr Asn Asp Ser Asn Ile Leu Asn Val Ser Val
65                  70                  75                  80

Leu Ala Pro Ala Val Glu Arg Val Glu Asn Glu Asp Gly Ser Val Asp
                85                  90                  95

Val Tyr Pro Ser Lys Ile Ile Lys Asp Lys Ile Glu Phe Ile Glu Gly
            100                 105                 110

Asp Phe Asp Ile Asp Gly Asp Asp Trp Val Asp Glu Val Leu Glu Tyr
        115                 120                 125

Ile Asn Lys Trp Val Asn Lys Asp Lys Ala Asp Val Glu Val Leu Asp
    130                 135                 140

Lys
145
```

<210> SEQ ID NO 155
<211> LENGTH: 438
<212> TYPE: DNA
<213> ORGANISM: Bacteriophage D6312

<400> SEQUENCE: 155

```
atgagaaacg attttattaa taaagtttat gatgaattaa atccgattat taatcattgg     60
gctaaacaaa aatatttaag tgataagatt tttgaatata ctaatacttt tagtattaag    120
aaggtttatg gactttattg ggaagttaag attttatgta agaatgatta tcgaattttg    180
ttgagatttt ataaaaatca tgagtggtat aatgattcta atattttaaa tgtatctgta    240
ttagcacctg cggtggaaag agttaaacat gaagatggaa gcgttgatgt ttatccaagt    300
aaaataatta agataaaat tgaatttatt gaaggtgatt ttgatattga tggatatgat    360
tgggtagatg aagtgttgga atatataaat aaatgggtaa ataagataaa agatgatgtg    420
gaggtattag ataagtga                                                   438
```

<210> SEQ ID NO 156

```
<211> LENGTH: 145
<212> TYPE: PRT
<213> ORGANISM: Bacteriophage D6312

<400> SEQUENCE: 156

Met Arg Asn Asp Phe Ile Asn Lys Val Tyr Asp Glu Leu Asn Pro Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Val Tyr Gly Leu Tyr Trp Glu
        35                  40                  45

Val Lys Ile Leu Cys Lys Asn Asp Tyr Arg Ile Leu Leu Arg Phe Tyr
    50                  55                  60

Lys Asn His Glu Trp Tyr Asn Asp Ser Asn Ile Leu Asn Val Ser Val
65                  70                  75                  80

Leu Ala Pro Ala Val Glu Arg Val Lys His Glu Asp Gly Ser Val Asp
                85                  90                  95

Val Tyr Pro Ser Lys Ile Ile Lys Asp Lys Ile Glu Phe Ile Glu Gly
            100                 105                 110

Asp Phe Asp Ile Asp Gly Tyr Asp Trp Val Asp Glu Val Leu Glu Tyr
        115                 120                 125

Ile Asn Lys Trp Val Asn Lys Asp Lys Asp Asp Val Glu Val Leu Asp
    130                 135                 140

Lys
145

<210> SEQ ID NO 157
<211> LENGTH: 438
<212> TYPE: DNA
<213> ORGANISM: Bacteriophage O1205

<400> SEQUENCE: 157
atgagaaacg attttattaa taaagtctat gatgaattaa atcagattat taatcattgg    60
gctaaacaaa aatatttaag tgataagatt tttgaatata ctaatacttt tagtattaag    120
aaggtttatg gactctattg gaagttaag atttttatgta agaatgatta tcgaattttg    180
ttgagatttt ataaaaatta tgagtggtat aatgattcta atattttaaa tgtatctgta    240
ttagcacctg cggtggaaag agttaaaaat gaagatggaa gcgttgatgt ttatccaagt    300
aaaataatta agataaaat tgaatttatt gaaggtaatt ttgatattga tggagatgat    360
tgggtagatg aagtgttgga atatataaat aaatgggtaa ataaagataa agctgatgtg    420
gaggtattag ataaatga                                                  438

<210> SEQ ID NO 158
<211> LENGTH: 145
<212> TYPE: PRT
<213> ORGANISM: Bacteriophage O1205

<400> SEQUENCE: 158

Met Arg Asn Asp Phe Ile Asn Lys Val Tyr Asp Glu Leu Asn Gln Ile
1               5                   10                  15

Ile Asn His Trp Ala Lys Gln Lys Tyr Leu Ser Asp Lys Ile Phe Glu
            20                  25                  30

Tyr Thr Asn Thr Phe Ser Ile Lys Lys Val Tyr Gly Leu Tyr Trp Glu
        35                  40                  45

Val Lys Ile Leu Cys Lys Asn Asp Tyr Arg Ile Leu Leu Arg Phe Tyr
    50                  55                  60
```

```
Lys Asn Tyr Glu Trp Tyr Asn Asp Ser Asn Ile Leu Asn Val Ser Val
 65                  70                  75                  80

Leu Ala Pro Ala Val Glu Arg Val Lys Asn Glu Asp Gly Ser Val Asp
                 85                  90                  95

Val Tyr Pro Ser Lys Ile Ile Lys Asp Lys Ile Glu Phe Ile Glu Gly
            100                 105                 110

Asn Phe Asp Ile Asp Gly Asp Asp Trp Val Asp Glu Val Leu Glu Tyr
        115                 120                 125

Ile Asn Lys Trp Val Asn Lys Asp Lys Ala Asp Val Glu Val Leu Asp
    130                 135                 140

Lys
145

<210> SEQ ID NO 159
<211> LENGTH: 318
<212> TYPE: DNA
<213> ORGANISM: Bacteriophage D4769

<400> SEQUENCE: 159
atgaaaaatt tcaaaataag ctctacttat agagctgcac gaaaacagca gaaaactgct    60
aatcgtaaat cgttttataa cgatgagggc tacatgatca gcccaagtga atgggctgat   120
ggagtcatta aggggcttat aaaccctaaa aactcttggt caaatgacca tgtgaaaggg   180
taccctccct agagtttcccc acgtagccat ggacaaaga atggttatag ggagtacctt   240
ggtattggta atcaaggga tatccctgaa aaagagcctg aagttatcga tgatggat     300 ctcgagttag ttccttaa                                                 318

<210> SEQ ID NO 160
<211> LENGTH: 105
<212> TYPE: PRT
<213> ORGANISM: Bacteriophage D4769

<400> SEQUENCE: 160

Met Lys Asn Phe Lys Ile Ser Ser Thr Tyr Arg Ala Ala Arg Lys Gln
  1               5                  10                  15

Gln Lys Thr Ala Asn Arg Lys Ser Phe Tyr Asn Asp Glu Gly Tyr Met
             20                  25                  30

Ile Ser Pro Ser Glu Trp Ala Asp Gly Val Ile Lys Gly Leu Ile Asn
         35                  40                  45

Pro Lys Asn Ser Trp Ser Asn Asp His Val Lys Gly Tyr Leu Pro Arg
     50                  55                  60

Val Ser Pro Arg Ser His Trp Thr Lys Asn Gly Tyr Arg Glu Tyr Leu
 65                  70                  75                  80

Gly Ile Gly Lys Ser Arg Asp Ile Pro Glu Lys Glu Pro Glu Val Ile
                 85                  90                  95

Glu Met Met Asp Leu Glu Leu Val Pro
            100                 105

<210> SEQ ID NO 161
<211> LENGTH: 318
<212> TYPE: DNA
<213> ORGANISM: Bacteriophage P7633

<400> SEQUENCE: 161
atgaaaaatt tcaaaataag ctctacttat agagctgcac gaaaacagca gaaaactgct    60
aatcgtaaat cgttttataa cgatgagggc tacatgatca gcccaagtga atgggttgat   120
```

```
ggagtcatta aggggcttat aaaccctaaa aactcttggt caaatgacca tgtgaaaggg    180
tacctcccta gagtttcccc acgtagccat tggacaaaga atggttatag ggagtacctt    240
ggtattggta aatcaaggga tatccctgaa aaagagcctg aagttatcga gatgatggat    300
ctcgagttag ttccttaa                                                  318
```

```
<210> SEQ ID NO 162
<211> LENGTH: 105
<212> TYPE: PRT
<213> ORGANISM: Bacteriophage P7633

<400> SEQUENCE: 162
```

```
Met Lys Asn Phe Lys Ile Ser Ser Thr Tyr Arg Ala Ala Arg Lys Gln
1               5                   10                  15

Gln Lys Thr Ala Asn Arg Lys Ser Phe Tyr Asn Asp Glu Gly Tyr Met
            20                  25                  30

Ile Ser Pro Ser Glu Trp Val Asp Gly Val Ile Lys Gly Leu Ile Asn
        35                  40                  45

Pro Lys Asn Ser Trp Ser Asn Asp His Val Lys Gly Tyr Leu Pro Arg
    50                  55                  60

Val Ser Pro Arg Ser His Trp Thr Lys Asn Gly Tyr Arg Glu Tyr Leu
65                  70                  75                  80

Gly Ile Gly Lys Ser Arg Asp Ile Pro Glu Lys Glu Pro Glu Val Ile
                85                  90                  95

Glu Met Met Asp Leu Glu Leu Val Pro
            100                 105
```

```
<210> SEQ ID NO 163
<211> LENGTH: 318
<212> TYPE: DNA
<213> ORGANISM: Bacteriophage Proph1

<400> SEQUENCE: 163
```

```
atgaaaaatt tcaaataag ctctacttat agagctgcac gaaaacagca gaaaactgct     60
aatcgtaaat cgttttataa cgatgagggc tacatgatca gcccaagtga atgggctgat    120
ggagtcatta aggggcttat aaaccctaaa aactcttggt caaatgacca tgtgaaaggg    180
tacctcccta gagtttcccc acgtagccat tggacaaaga atggttatag ggagtacctt    240
ggtattggta aatcaaggga tatccctaaa aaagagcctg aagttatcga gatgatggat    300
ctcgagttag ttccttaa                                                  318
```

```
<210> SEQ ID NO 164
<211> LENGTH: 105
<212> TYPE: PRT
<213> ORGANISM: Bacteriophage Proph1

<400> SEQUENCE: 164
```

```
Met Lys Asn Phe Lys Ile Ser Ser Thr Tyr Arg Ala Ala Arg Lys Gln
1               5                   10                  15

Gln Lys Thr Ala Asn Arg Lys Ser Phe Tyr Asn Asp Glu Gly Tyr Met
            20                  25                  30

Ile Ser Pro Ser Glu Trp Ala Asp Gly Val Ile Lys Gly Leu Ile Asn
        35                  40                  45

Pro Lys Asn Ser Trp Ser Asn Asp His Val Lys Gly Tyr Leu Pro Arg
    50                  55                  60

Val Ser Pro Arg Ser His Trp Thr Lys Asn Gly Tyr Arg Glu Tyr Leu
```

```
                65                  70                  75                  80
Gly Ile Gly Lys Ser Arg Asp Ile Pro Lys Lys Glu Pro Glu Val Ile
                    85                  90                  95

Glu Met Met Asp Leu Glu Leu Val Pro
            100                 105

<210> SEQ ID NO 165
<211> LENGTH: 387
<212> TYPE: DNA
<213> ORGANISM: Bacteriophage D5691

<400> SEQUENCE: 165
atgaaatatg ataagtcagg aatcatgaaa gaagcttgga acttatttaa taatgatgac      60 atcactttg cagactttga atatctcact cgtgaagaac gccaaggtaa aaaaacattt      120
actctttgct tgaaagaagc ttgggcacac gaaaagaaa ttgttgacag catcaaaaaa      180
gaccacgctg atgctgaaca ttcagtggaa gcaaaagctt gggattgggc ttgtaaaaaa      240
ttaggtgtct ctattgaaat ggatgcttac acaaaattcg ttaacgttaa cgatatgaaa      300
aaagaagcat ggcctggaac aagcgtttgg tcattggcta tgcgtgcggt taaactacat      360
atcaaacttt ttggtcaagt agcttaa                                          387

<210> SEQ ID NO 166
<211> LENGTH: 128
<212> TYPE: PRT
<213> ORGANISM: Bacteriophage D5691

<400> SEQUENCE: 166

Met Lys Tyr Asp Lys Ser Gly Ile Met Lys Glu Ala Trp Asn Leu Phe
1               5                   10                  15

Asn Asn Asp Asp Ile Thr Phe Ala Asp Phe Glu Tyr Leu Thr Arg Glu
                20                  25                  30

Glu Arg Gln Gly Lys Lys Thr Phe Thr Leu Cys Leu Lys Glu Ala Trp
            35                  40                  45

Ala His Glu Lys Glu Ile Val Asp Ser Ile Lys Lys Asp His Ala Asp
        50                  55                  60

Ala Glu His Ser Val Glu Ala Lys Ala Trp Asp Trp Ala Cys Lys Lys
65                  70                  75                  80

Leu Gly Val Ser Ile Glu Met Asp Ala Tyr Thr Lys Phe Val Asn Val
                85                  90                  95

Asn Asp Met Lys Lys Glu Ala Trp Pro Gly Thr Ser Val Trp Ser Leu
            100                 105                 110

Ala Met Arg Ala Val Lys Leu His Ile Lys Leu Phe Gly Gln Val Ala
        115                 120                 125

<210> SEQ ID NO 167
<211> LENGTH: 522
<212> TYPE: DNA
<213> ORGANISM: Bacteriophage D6252

<400> SEQUENCE: 167
ttgaatggat taaaaacaat cttgaaaaca ttcgataaaa acatatattt tttaaccaaa      60
agtgttgaca tacgtcaaca taggagatat aatatatatg taagttaag agaggaagta      120 aatgacatga aaaatcaac atacgacaaa tcaggaatta tgaaagaagc ttggaattta      180
tttaataacg atgacatcac tactgcagat tttgaatatc tcactcgtgg agaattgcaa      240
gaaggaaaaa catttgctat tgcttaaaaa gaagcttggg ctcacgaaaa agacattgtt      300
```

```
gaaagtttaa acgaagatta tgaaaatgct gaacattcag tacaagctaa agcttgggac    360
tgggcttgta aaaaattagg tgtctctatt gaagtagatg cttacacaaa attggttaac    420
gtcaacgaca tgcaaaaaga atcatggcct ggaacaagcg catggtcttt ggctatgcgt    480
gcagttaaac tacatatcaa acttttcggt caagcggctt aa                      522
```

<210> SEQ ID NO 168
<211> LENGTH: 173
<212> TYPE: PRT
<213> ORGANISM: Bacteriophage D6252

<400> SEQUENCE: 168

```
Met Asn Gly Leu Lys Thr Ile Leu Lys Thr Phe Asp Lys Asn Ile Tyr
1               5                   10                  15

Phe Leu Thr Lys Ser Val Asp Ile Arg Gln His Arg Arg Tyr Asn Ile
            20                  25                  30

Tyr Val Lys Leu Arg Glu Glu Val Asn Asp Met Lys Lys Ser Thr Tyr
        35                  40                  45

Asp Lys Ser Gly Ile Met Lys Glu Ala Trp Asn Leu Phe Asn Asn Asp
    50                  55                  60

Asp Ile Thr Thr Ala Asp Phe Glu Tyr Leu Thr Arg Gly Glu Leu Gln
65                  70                  75                  80

Glu Gly Lys Thr Phe Ala Ile Cys Leu Lys Glu Ala Trp Ala His Glu
                85                  90                  95

Lys Asp Ile Val Glu Ser Leu Asn Glu Asp Tyr Glu Asn Ala Glu His
            100                 105                 110

Ser Val Gln Ala Lys Ala Trp Asp Trp Ala Cys Lys Lys Leu Gly Val
        115                 120                 125

Ser Ile Glu Val Asp Ala Tyr Thr Lys Leu Val Asn Val Asn Asp Met
    130                 135                 140

Gln Lys Glu Ser Trp Pro Gly Thr Ser Ala Trp Ser Leu Ala Met Arg
145                 150                 155                 160

Ala Val Lys Leu His Ile Lys Leu Phe Gly Gln Ala Ala
                165                 170
```

<210> SEQ ID NO 169
<211> LENGTH: 522
<212> TYPE: DNA
<213> ORGANISM: Bacteriophage D7163

<400> SEQUENCE: 169

```
ttgaatggat taaaaacaat cttgaaaaca ttcgataaaa acatatattt tttaaccaaa     60
agtgttgaca tacgtcaaca caggagatat aatatatatg taaagttaag agaggaagta   120
aatgacatga aaaaatcaac atacgacaaa tcaggaatta tgaaagaagc ttggaattta   180
tttaataacg atgacatcac tactgcagat tttgaatatc ttactcgtgg agaattgcaa   240
gaaggaaaaa catttgctat tgcttaaaa gaagcttggg ctcacgaaaa agacattgtt   300
gaaagtttaa acgaagatta tgaaaatgct gaacattcag tacaagctaa agcttgggac   360
tgggcttgta aaaaattagg tgtctctatt gaagtagatg cttacacaaa attggttaac   420
gtcaacgaca tgcaaaaaga atcatggcct ggaacaagcg catggtcttt ggctatgcgt   480
gcagttaaac tacatatcaa acttttcggt caagcggctt aa                      522
```

<210> SEQ ID NO 170
<211> LENGTH: 173

```
<212> TYPE: PRT
<213> ORGANISM: Bacteriophage D7163

<400> SEQUENCE: 170

Met Asn Gly Leu Lys Thr Ile Leu Lys Thr Phe Asp Lys Asn Ile Tyr
1               5                   10                  15

Phe Leu Thr Lys Ser Val Asp Ile Arg Gln His Arg Arg Tyr Asn Ile
            20                  25                  30

Tyr Val Lys Leu Arg Glu Glu Val Asn Asp Met Lys Lys Ser Thr Tyr
        35                  40                  45

Asp Lys Ser Gly Ile Met Lys Glu Ala Trp Asn Leu Phe Asn Asn Asp
    50                  55                  60

Asp Ile Thr Thr Ala Asp Phe Glu Tyr Leu Thr Arg Gly Glu Leu Gln
65                  70                  75                  80

Glu Gly Lys Thr Phe Ala Ile Cys Leu Lys Glu Ala Trp Ala His Glu
                85                  90                  95

Lys Asp Ile Val Glu Ser Leu Asn Glu Asp Tyr Glu Asn Ala Glu His
            100                 105                 110

Ser Val Gln Ala Lys Ala Trp Asp Trp Ala Cys Lys Lys Leu Gly Val
        115                 120                 125

Ser Ile Glu Val Asp Ala Tyr Thr Lys Leu Val Asn Val Asn Asp Met
    130                 135                 140

Gln Lys Glu Ser Trp Pro Gly Thr Ser Ala Trp Ser Leu Ala Met Arg
145                 150                 155                 160

Ala Val Lys Leu His Ile Lys Leu Phe Gly Gln Ala Ala
                165                 170

<210> SEQ ID NO 171
<211> LENGTH: 336
<212> TYPE: DNA
<213> ORGANISM: Bacteriophage 5093

<400> SEQUENCE: 171
atgaaaaaag aagttatgac aaacgcatgg aaaatcgcta agaagcagt taagaaattc     60 ggcggcaaag ctatcgaata catcgcagaa gcattgaaaa tggcttgggc tgccgcaaaa    120
ggcggaaacg ctagcctagc taaatttcaa gcagtagaat ctaaaatgcg taaagctggt    180
aaatactcaa tgattcaagt tttaaatttc gctaaggaag tgaaatttaa cgaagttatg    240
cacaaagttg gtgcttacta cggtatcgaa gtagtagctg acggagacag cattggtact    300
tactacatcg ctgaaaaagt ttgggatgca gcttaa                              336

<210> SEQ ID NO 172
<211> LENGTH: 111
<212> TYPE: PRT
<213> ORGANISM: Bacteriophage 5093

<400> SEQUENCE: 172

Met Lys Lys Glu Val Met Thr Asn Ala Trp Lys Ile Ala Lys Glu Ala
1               5                   10                  15

Val Lys Lys Phe Gly Gly Lys Ala Ile Glu Tyr Ile Ala Glu Ala Leu
            20                  25                  30

Lys Met Ala Trp Ala Ala Ala Lys Gly Gly Asn Ala Ser Leu Ala Lys
        35                  40                  45

Phe Gln Ala Val Glu Ser Lys Met Arg Lys Ala Gly Lys Tyr Ser Met
    50                  55                  60

Ile Gln Val Leu Asn Phe Ala Lys Glu Val Lys Phe Asn Glu Val Met
```

His Lys Val Gly Ala Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

<210> SEQ ID NO 173
<211> LENGTH: 336
<212> TYPE: DNA
<213> ORGANISM: Bacteriophage P9874

<400> SEQUENCE: 173
atgaaaaaag aaattatgac aaaagcatgg aaaatcgcta agaagcagt taaaactttt      60 ggtgggaaag ctatcgaata catcgctggg gctatgaaaa tggcttgggc tgctatcaaa    120
gataacggaa ctagccttgc taaattccaa gctgttgaag caaaaatgcg taaagctggt    180
aaatactcaa tgatccaagt tcttgatttt gctaaagaag tacgtttcaa tgaagtaatg    240
cacaaagttg gcgcttatta cggaatcgaa gtaattgctg atggtgatag cattggtact    300
tactacatcg ctgagaatgt ttggaacgca gcataa                              336

<210> SEQ ID NO 174
<211> LENGTH: 111
<212> TYPE: PRT
<213> ORGANISM: Bacteriophage P9874

<400> SEQUENCE: 174

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Gly Ala Met
            20                  25                  30

Lys Met Ala Trp Ala Ala Ile Lys Asp Asn Gly Thr Ser Leu Ala Lys
        35                  40                  45

Phe Gln Ala Val Glu Ala Lys Met Arg Lys Ala Gly Lys Tyr Ser Met
    50                  55                  60

Ile Gln Val Leu Asp Phe Ala Lys Glu Val Arg Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Tyr Ile Ala Glu Asn Val Trp Asn Ala Ala
            100                 105                 110

<210> SEQ ID NO 175
<211> LENGTH: 336
<212> TYPE: DNA
<213> ORGANISM: Bacteriophage CHPC577

<400> SEQUENCE: 175
atgaaaaaag aaattatgac aaaagcatgg aaaatcgcta aaaacgcaag tacaaaattc      60
ggtggcaaag ctatcgaata cattgctgga gctatgaaaa tggcttgggc tgctatcaaa    120
gaaaacggaa ctagccttgc taaattccaa gcagttgaag ctaaaatgcg caaagctggc    180
aaacactcaa tggtccaagt ttttaaattttt gctaaggaag tgaaatttaa cgaagttatg    240
cataaagttg gtgcttacta cggaattgaa gtaattgctg atggtgatag cattggtact    300
tactacatcg ctgaaaaagt ttggaacgca gcataa                              336

<210> SEQ ID NO 176

```
<211> LENGTH: 111
<212> TYPE: PRT
<213> ORGANISM: Bacteriophage CHPC577

<400> SEQUENCE: 176

Met Lys Lys Glu Ile Met Thr Lys Ala Trp Lys Ile Ala Lys Asn Ala
1               5                   10                  15

Ser Thr Lys Phe Gly Gly Lys Ala Ile Glu Tyr Ile Ala Gly Ala Met
                20                  25                  30

Lys Met Ala Trp Ala Ala Ile Lys Glu Asn Gly Thr Ser Leu Ala Lys
            35                  40                  45

Phe Gln Ala Val Glu Ala Lys Met Arg Lys Ala Gly Lys His Ser Met
50                  55                  60

Val Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Tyr Ile Ala Glu Lys Val Trp Asn Ala Ala
                100                 105                 110

<210> SEQ ID NO 177
<211> LENGTH: 336
<212> TYPE: DNA
<213> ORGANISM: Bacteriophage D1024

<400> SEQUENCE: 177
atgaaaaaag aaattatgac aaaagcatgg aaaatcgcta agaagcagt tgaaaaattc      60 ggtggcaaag ctatcgaata catcgctgga gctatgaaaa tggcttgggc tgctgctaaa    120
gctggaaaca ctagcgtcgc taaatttcaa gctgttgaag ataaaatgcg caaagctggt    180
aaatactcaa tgattcaagt tttaaatttc gctaatgaag tgaaatttaa cgaagttatg    240
cacaaagctg gtgcgtacta cggcatcgaa gtaattgctg atggtgatag cattggtact    300
tactacatcg ctgaaaaagt ttgggaagta gcataa                              336

<210> SEQ ID NO 178
<211> LENGTH: 111
<212> TYPE: PRT
<213> ORGANISM: Bacteriophage D1024

<400> SEQUENCE: 178

Met Lys Lys Glu Ile Met Thr Lys Ala Trp Lys Ile Ala Lys Glu Ala
1               5                   10                  15

Val Glu Lys Phe Gly Gly Lys Ala Ile Glu Tyr Ile Ala Gly Ala Met
                20                  25                  30

Lys Met Ala Trp Ala Ala Ala Lys Ala Gly Asn Thr Ser Val Ala Lys
            35                  40                  45

Phe Gln Ala Val Glu Asp Lys Met Arg Lys Ala Gly Lys Tyr Ser Met
50                  55                  60

Ile Gln Val Leu Asn Phe Ala Asn Glu Val Lys Phe Asn Glu Val Met
65                  70                  75                  80

His Lys Ala Gly Ala Tyr Tyr Gly Ile Glu Val Ile Ala Asp Gly Asp
                85                  90                  95

Ser Ile Gly Thr Tyr Tyr Ile Ala Glu Lys Val Trp Glu Val Ala
                100                 105                 110

<210> SEQ ID NO 179
<211> LENGTH: 327
```

```
<212> TYPE: DNA
<213> ORGANISM: Bacteriophage D1126

<400> SEQUENCE: 179
atgaaaaaag aagttatgac aaacgcgtgg gaaattgcta aaacgcttc taaaaaattc      60
ggtggtaaag ctatcgaata catcgctgga gctatgaaaa tggcttgggc tgctgcaaaa     120
ggcggcttag ctaaattcca agcagtagaa tctaaaatgc gtaaagctgg aaaacattca     180
atggtgcaag tgttgaattt cgctaaggaa gtgaaattta cgaagttat gcacaaagct      240
ggtgcttact acggtatcga agtaatcgct gatggtgata gcattggtac ttactacatt     300
tctgaaaaag tttgggaagt agcttaa                                          327

<210> SEQ ID NO 180
<211> LENGTH: 108
<212> TYPE: PRT
<213> ORGANISM: Bacteriophage D1126

<400> SEQUENCE: 180

Met Lys Lys Glu Val Met Thr Asn Ala Trp Glu Ile Ala Lys Asn Ala
1               5                   10                  15

Ser Lys Lys Phe Gly Gly Lys Ala Ile Glu Tyr Ile Ala Gly Ala Met
            20                  25                  30

Lys Met Ala Trp Ala Ala Ala Lys Gly Gly Leu Ala Lys Phe Gln Ala
        35                  40                  45

Val Glu Ser Lys Met Arg Lys Ala Gly Lys His Ser Met Val Gln Val
    50                  55                  60

Leu Asn Phe Ala Lys Glu Val Lys Phe Asn Glu Val Met His Lys Ala
65                  70                  75                  80

Gly Ala Tyr Tyr Gly Ile Glu Val Ile Ala Asp Gly Asp Ser Ile Gly
                85                  90                  95

Thr Tyr Tyr Ile Ser Glu Lys Val Trp Glu Val Ala
            100                 105

<210> SEQ ID NO 181
<211> LENGTH: 336
<212> TYPE: DNA
<213> ORGANISM: Bacteriophage D1297

<400> SEQUENCE: 181
atgaaaaaag aaattatgac aaaagcatgg aaaatcgcta agaagcagt taaaactttc      60
ggtggtaaag ctatcgaata cattgctgga gctatgaaaa tggcttgggc tgctgctaaa     120
gctggaaaca ctagcttagc taaattccaa gcagtagaat ctaaaatgcg taaagctggt     180
aaatactcaa tgattcaagt tttaaatttc gctaaggaag tgaaatttaa cgaagttatg     240
cacaaagttg gcgcttatta cggtatcgaa gtaattgctg atggtgatag cattggtact     300
tactacatcg ctgaaagcgt ttgggaagta gcataa                              336

<210> SEQ ID NO 182
<211> LENGTH: 111
<212> TYPE: PRT
<213> ORGANISM: Bacteriophage D1297

<400> SEQUENCE: 182

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Gly Ala Met
            20                  25                  30
```

```
Lys Met Ala Trp Ala Ala Lys Ala Gly Asn Thr Ser Leu Ala Lys
        35                  40                  45

Phe Gln Ala Val Glu Ser Lys Met Arg Lys Ala Gly Lys Tyr Ser Met
 50                  55                  60

Ile Gln Val Leu Asn Phe Ala Lys Glu Val Lys Phe Asn Glu Val Met
 65                  70                  75                  80

His Lys Val Gly Ala Tyr Tyr Gly Ile Glu Val Ile Ala Asp Gly Asp
                 85                  90                  95

Ser Ile Gly Thr Tyr Tyr Ile Ala Glu Ser Val Trp Glu Val Ala
                100                 105                 110

<210> SEQ ID NO 183
<211> LENGTH: 336
<212> TYPE: DNA
<213> ORGANISM: Bacteriophage D1422

<400> SEQUENCE: 183
atgaaaaaag aaattatgac aaaagcatgg aaaatcgcta agaagcagt tgaaaaattc      60 ggtggcaaag ctatcgaata catcgctgga gctatgaaaa tggcttgggc tgctgctaaa    120
gctgaaaaca ctagcgtcgc taaatttcaa gctgttgaag ataaaatgcg caaagctggt    180
aaatactcaa tgattcaagt tttaaatttc gctaatgaag tgaaatttaa cgaagttatg    240
cacaaagctg gtgcgtacta cggaatcgaa gtaattgctg atggtgatag cattggtact    300
tactacatcg ctgaaaaagt ttgggaagta gcataa                              336

<210> SEQ ID NO 184
<211> LENGTH: 111
<212> TYPE: PRT
<213> ORGANISM: Bacteriophage D1422

<400> SEQUENCE: 184

Met Lys Lys Glu Ile Met Thr Lys Ala Trp Lys Ile Ala Lys Glu Ala
 1               5                  10                  15

Val Glu Lys Phe Gly Gly Lys Ala Ile Glu Tyr Ile Ala Gly Ala Met
                 20                  25                  30

Lys Met Ala Trp Ala Ala Ala Lys Ala Gly Asn Thr Ser Val Ala Lys
        35                  40                  45

Phe Gln Ala Val Glu Asp Lys Met Arg Lys Ala Gly Lys Tyr Ser Met
 50                  55                  60

Ile Gln Val Leu Asn Phe Ala Asn Glu Val Lys Phe Asn Glu Val Met
 65                  70                  75                  80

His Lys Ala Gly Ala Tyr Tyr Gly Ile Glu Val Ile Ala Asp Gly Asp
                 85                  90                  95

Ser Ile Gly Thr Tyr Tyr Ile Ala Glu Lys Val Trp Glu Val Ala
                100                 105                 110

<210> SEQ ID NO 185
<211> LENGTH: 318
<212> TYPE: DNA
<213> ORGANISM: Bacteriophage D2759

<400> SEQUENCE: 185
atgaaaaaag aaattatgac aaaagcatgg aaaatcgcta agaagcagt taaaactttc      60 ggtggaaaag ctatcgaata cattgcggaa gcatgaaaaa tggcttgggc tgctgctaaa    120
ggcggcttag ctaaattcca agcagtagaa tctaaaatgc gtaaagctgg aatgattcaa    180
```

```
gttttaaatt tcgctaagga agtgaaattt aacgaagtta tgcacaaagt tggcgcttat    240
tacggtatcg aagtaattgc tgatggtgat agcattggta cttactacat cgctgaaagc    300
gtttgggaag tagcataa                                                  318
```

<210> SEQ ID NO 186
<211> LENGTH: 105
<212> TYPE: PRT
<213> ORGANISM: Bacteriophage D2759

<400> SEQUENCE: 186

```
Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Met
            20                  25                  30

Lys Met Ala Trp Ala Ala Ala Lys Gly Gly Leu Ala Lys Phe Gln Ala
        35                  40                  45

Val Glu Ser Lys Met Arg Lys Ala Gly Met Ile Gln Val Leu Asn Phe
    50                  55                  60

Ala Lys Glu Val Lys Phe Asn Glu Val Met His Lys Val Gly Ala Tyr
65                  70                  75                  80

Tyr Gly Ile Glu Val Ile Ala Asp Gly Asp Ser Ile Gly Thr Tyr Tyr
                85                  90                  95

Ile Ala Glu Ser Val Trp Glu Val Ala
            100                 105
```

<210> SEQ ID NO 187
<211> LENGTH: 336
<212> TYPE: DNA
<213> ORGANISM: Bacteriophage D3577

<400> SEQUENCE: 187

```
atgaaatcac aagtaatgag cctagcatgg aaaatcgcta aaaacgcaag tacaaaattc     60
ggtggcaaag ctatcgaata cattgctaga gctatgaaaa tggcttggtc tgctatcaaa    120
gaaaacggaa ctagccttgc taaatttcaa gcaattgaag ctaaaattcg caaagctgga    180
aaacactcaa tggtccaagt tttaaaattc gctaaggaag tgaaatttaa cgaagttatg    240
cataaagttg gtgcttacta cggaattgaa gtaattgctg atggtgatag cattggtact    300
tactacatcg ctgaaaaagt ttgggatgca gcgtaa                              336
```

<210> SEQ ID NO 188
<211> LENGTH: 111
<212> TYPE: PRT
<213> ORGANISM: Bacteriophage D3577

<400> SEQUENCE: 188

```
Met Lys Ser Gln Val Met Ser Leu Ala Trp Lys Ile Ala Lys Asn Ala
1               5                   10                  15

Ser Thr Lys Phe Gly Gly Lys Ala Ile Glu Tyr Ile Ala Arg Ala Met
            20                  25                  30

Lys Met Ala Trp Ser Ala Ile Lys Glu Asn Gly Thr Ser Leu Ala Lys
        35                  40                  45

Phe Gln Ala Ile Glu Ala Lys Ile Arg Lys Ala Gly Lys His Ser Met
    50                  55                  60

Val Gln Val Leu Lys Phe Ala Lys Glu Val Lys Phe Asn Glu Val Met
65                  70                  75                  80

His Lys Val Gly Ala Tyr Tyr Gly Ile Glu Val Ile Ala Asp Gly Asp
```

85                  90                  95
Ser Ile Gly Thr Tyr Tyr Ile Ala Glu Lys Val Trp Asp Ala Ala
            100                 105                 110

<210> SEQ ID NO 189
<211> LENGTH: 336
<212> TYPE: DNA
<213> ORGANISM: Bacteriophage D4154

<400> SEQUENCE: 189
atgaaaaaag aaattatgaa aaaagcatgg aaaatcgcta agaagcagt taagaaattc      60 ggtggtaaag ctatcgaata catcgcagaa gcattgaaaa tggcttgggc tgatgctaaa    120
ggtggtaaca ctagcttggc taaattccaa gctgttgagg aaaagatgcg taaagctggc    180
aaatactcaa tgattcaagt gctcaacttt gctaaagaag tgaaattcaa cgaagtaatg    240
cataaagttg gtgcttacta cggaattgaa gttattgctg acggagacaa aatcggtact    300
tactttatcg ctgaaaaagt ttgggatgca gcttaa                              336

<210> SEQ ID NO 190
<211> LENGTH: 111
<212> TYPE: PRT
<213> ORGANISM: Bacteriophage D4154

<400> SEQUENCE: 190

Met Lys Lys Glu Ile Met Lys Lys Ala Trp Lys Ile Ala Lys Glu Ala
1               5                   10                  15

Val Lys Lys Phe Gly Gly Lys Ala Ile Glu Tyr Ile Ala Glu Ala Leu
            20                  25                  30

Lys Met Ala Trp Ala Asp Ala Lys Gly Gly Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Lys Ile Gly Thr Tyr Phe Ile Ala Glu Lys Val Trp Asp Ala Ala
            100                 105                 110

<210> SEQ ID NO 191
<211> LENGTH: 336
<212> TYPE: DNA
<213> ORGANISM: Bacteriophage D4160

<400> SEQUENCE: 191
atgaaaaaag aacttatgaa agacgcttgg gaaattgcta aaaacgcttc taaaaaattc      60
ggtggtaaag ctatcgaata cattgctgga gctatgaaaa tggcttgggc tgctgctaaa    120
gctggaaaca ctagcgtcgc taaattccaa gcggtagaag ctaaaatgcg caaagctggc    180
aaacactcaa tgattcaagt tctcgatttc gctaaagaag ttaagttcaa cgaagtgatg    240
cacaaagttg gtgcgtacta cggcatcgaa gtagtcgctg acggcgatag cattggtact    300
tactacatcg ctgaaaaagt ttgggatgta gcttaa                              336

<210> SEQ ID NO 192
<211> LENGTH: 111
<212> TYPE: PRT
<213> ORGANISM: Bacteriophage D4160

<400> SEQUENCE: 192

Met Lys Lys Glu Leu Met Lys Asp Ala Trp Glu Ile Ala Lys Asn Ala
1               5                   10                  15

Ser Lys Lys Phe Gly Gly Lys Ala Ile Glu Tyr Ile Ala Gly Ala Met
            20                  25                  30

Lys Met Ala Trp Ala Ala Ala Lys Ala Gly Asn Thr Ser Val Ala Lys
        35                  40                  45

Phe Gln Ala Val Glu Ala Lys Met Arg Lys Ala Gly Lys His Ser Met
    50                  55                  60

Ile Gln Val Leu Asp Phe Ala Lys Glu Val Lys Phe Asn Glu Val Met
65                  70                  75                  80

His Lys Val Gly Ala Tyr Tyr Gly Ile Glu Val Val Ala Asp Gly Asp
                85                  90                  95

Ser Ile Gly Thr Tyr Tyr Ile Ala Glu Lys Val Trp Asp Val Ala
                100                 105                 110

<210> SEQ ID NO 193
<211> LENGTH: 336
<212> TYPE: DNA
<213> ORGANISM: Bacteriophage D4212

<400> SEQUENCE: 193
atgaaaaaag aagttatgac aaacgcatgg aaaatcgcta aagaagcagt taagaaattc      60
ggtggtaaag ctatcgaata catctctgaa gctatgaaaa tggcttgggc tgctgccaag    120
ggtgaaaaca ctagcttagc taaattccaa gctgttgagg aaaagatgcg taaagctggc    180
aaatactcaa tgattcaagt tcttgacttt gctaagaag ttaaattcaa cgaagtaatg     240
cataaagttg gtgcttacta cggaattgaa gttattgctg acggagacaa cattggtact    300
tactacattg ctgaaaaagt ttgggaagta gcataa                              336

<210> SEQ ID NO 194
<211> LENGTH: 111
<212> TYPE: PRT
<213> ORGANISM: Bacteriophage D4212

<400> SEQUENCE: 194

Met Lys Lys Glu Val Met Thr Asn Ala Trp Lys Ile Ala Lys Glu Ala
1               5                   10                  15

Val Lys Lys Phe Gly Gly Lys Ala Ile Glu Tyr Ile Ser Glu Ala Met
            20                  25                  30

Lys Met Ala Trp Ala Ala Ala Lys Gly Glu Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Asn Ile Gly Thr Tyr Tyr Ile Ala Glu Lys Val Trp Glu Val Ala
                100                 105                 110

<210> SEQ ID NO 195
<211> LENGTH: 321
<212> TYPE: DNA
<213> ORGANISM: Bacteriophage D4276

```
<400> SEQUENCE: 195
atgacaaacg catggaaaat cgctaaagaa gcagttaaga aattcggtgg taaagctatc      60
gaatacatct ctgaagctat gaaaattgct tgggctgacg ctaaagaagg aaacactagc     120
gtagctaaat ccaagctgt agaagctaaa atgcgtaaag ctggaaaaca ttcaatggtg     180
caagtgttga atttcgctaa agaagtgaaa ttcaacgaag taatgcacaa agttggtgct     240
tactacggta tcgaagtaat cgctgatggt gatagcattg gtacttacta catttctgaa     300
aaagtttggg aagtagctta a                                               321

<210> SEQ ID NO 196
<211> LENGTH: 106
<212> TYPE: PRT
<213> ORGANISM: Bacteriophage D4276

<400> SEQUENCE: 196

Met Thr Asn Ala Trp Lys Ile Ala Lys Glu Ala Val Lys Lys Phe Gly
1               5                   10                  15

Gly Lys Ala Ile Glu Tyr Ile Ser Glu Ala Met Lys Ile Ala Trp Ala
            20                  25                  30

Asp Ala Lys Glu Gly Asn Thr Ser Val Ala Lys Phe Gln Ala Val Glu
        35                  40                  45

Ala Lys Met Arg Lys Ala Gly Lys His Ser Met Val Gln Val Leu Asn
    50                  55                  60

Phe Ala Lys Glu Val Lys Phe Asn Glu Val Met His Lys Val Gly Ala
65                  70                  75                  80

Tyr Tyr Gly Ile Glu Val Ile Ala Asp Gly Asp Ser Ile Gly Thr Tyr
                85                  90                  95

Tyr Ile Ser Glu Lys Val Trp Glu Val Ala
            100                 105

<210> SEQ ID NO 197
<211> LENGTH: 336
<212> TYPE: DNA
<213> ORGANISM: Bacteriophage D4419

<400> SEQUENCE: 197
atgaaaaaag aaattatgac aaaagcatgg aaaatcgcta agaagcagt taaaactttc      60 ggtggaaaag ctatcgaata cattgcggaa gcaatgaaaa tggcttgggc tgctgctaaa     120
ggcggaaacg ctagcttagc taaattccaa gcagtagaat ctaaaatgcg taaagctggt     180
aaatactcaa tgattcaagt tttaaatttc gctaaggaag tgaaatttaa cgaagttatg     240
cacaaagttg gcgcttatta cggtattgaa gtaattgctg atggtgatag cattggtact     300
tactacatcg ctgaaagcgt ttgggaagta gcataa                               336

<210> SEQ ID NO 198
<211> LENGTH: 111
<212> TYPE: PRT
<213> ORGANISM: Bacteriophage D4419

<400> SEQUENCE: 198

Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Met
            20                  25                  30

Lys Met Ala Trp Ala Ala Ala Lys Gly Gly Asn Ala Ser Leu Ala Lys
        35                  40                  45
```

```
Phe Gln Ala Val Glu Ser Lys Met Arg Lys Ala Gly Lys Tyr Ser Met
            50                  55                  60

Ile Gln Val Leu Asn Phe Ala Lys Glu Val Lys Phe Asn Glu Val Met
 65                  70                  75                  80

His Lys Val Gly Ala Tyr Tyr Gly Ile Glu Val Ile Ala Asp Gly Asp
                 85                  90                  95

Ser Ile Gly Thr Tyr Tyr Ile Ala Glu Ser Val Trp Glu Val Ala
             100                 105                 110

<210> SEQ ID NO 199
<211> LENGTH: 327
<212> TYPE: DNA
<213> ORGANISM: Bacteriophage D4741

<400> SEQUENCE: 199
atgaaaaaag aaattatgac aaaagcatgg aaaatcgcta agaagcagt taaaactttc      60 ggtggaaaag ctatcgaata cattgcggaa gcaatgaaaa tggcttgggc tgctgctaaa    120
ggcggcttag ctaaattcca agcagtagaa tctaaaatgc gtaaagctgg taatactca    180 atgattcaag tttttaaattt cgctaaggaa gtgaaattta cgaagttat gcacaaagtt    240 ggcgcttatt acggtatcga gtaattgct gatggtgata gcattggtac ttactacatc    300
gctgaaagcg tttgggaagt agcataa                                        327

<210> SEQ ID NO 200
<211> LENGTH: 108
<212> TYPE: PRT
<213> ORGANISM: Bacteriophage D4741

<400> SEQUENCE: 200

Met Lys Lys Glu Ile Met Thr Lys Ala Trp Lys Ile Ala Lys Glu Ala
  1               5                  10                  15

Val Lys Thr Phe Gly Gly Lys Ala Ile Glu Tyr Ile Ala Glu Ala Met
             20                  25                  30

Lys Met Ala Trp Ala Ala Ala Lys Gly Gly Leu Ala Lys Phe Gln Ala
         35                  40                  45

Val Glu Ser Lys Met Arg Lys Ala Gly Lys Tyr Ser Met Ile Gln Val
     50                  55                  60

Leu Asn Phe Ala Lys Glu Val Lys Phe Asn Glu Val Met His Lys Val
 65                  70                  75                  80

Gly Ala Tyr Tyr Gly Ile Glu Val Ile Ala Asp Gly Asp Ser Ile Gly
                 85                  90                  95

Thr Tyr Tyr Ile Ala Glu Ser Val Trp Glu Val Ala
            100                 105

<210> SEQ ID NO 201
<211> LENGTH: 336
<212> TYPE: DNA
<213> ORGANISM: Bacteriophage D5839

<400> SEQUENCE: 201
atgaagaaag agattatgaa aaaagcgtgg gaaatcgcta agaagcagt taaaaaattc      60 ggtggcaaag ctatcgaata catcgcagaa gcattgaaaa tggcttggtc tgatgcaaag   120
ggtagtaata ctagcttagc taaattccaa gctgttgagg aaaagatgcg taaagctggc   180
aaatactcaa tgattcaagt tcttgacttt gctaagaag ttaaattcaa tgaagtaatg    240
cacaaagaag gtgcttacta tggtatcgaa gtggtagctg acggagacag cattggtact   300
```

```
tattacattg ctgaaaaagt ttgggaagta gcataa                                   336
```

<210> SEQ ID NO 202
<211> LENGTH: 111
<212> TYPE: PRT
<213> ORGANISM: Bacteriophage D5839

<400> SEQUENCE: 202

Met Lys Lys Glu Ile Met Lys Lys Ala Trp Glu Ile Ala Lys Glu Ala
1               5                   10                  15

Val Lys Lys Phe Gly Gly Lys Ala Ile Glu Tyr Ile Ala Glu Ala Leu
            20                  25                  30

Lys Met Ala Trp Ser Asp Ala Lys Gly Ser Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Phe Asn Glu Val Met
65                  70                  75                  80

His Lys Glu Gly Ala Tyr Tyr Gly Ile Glu Val Val Ala Asp Gly Asp
                85                  90                  95

Ser Ile Gly Thr Tyr Tyr Ile Ala Glu Lys Val Trp Glu Val Ala
            100                 105                 110

<210> SEQ ID NO 203
<211> LENGTH: 336
<212> TYPE: DNA
<213> ORGANISM: Bacteriophage D5861

<400> SEQUENCE: 203

```
atgaaaaaag aaattatgac aaaagcatgg gaaattgcta aaaacgcttc taaaaaattc      60
ggtggtaaag ctatcgaata catcgctgga gctatgaaaa tggcttgggc tgctgctaaa     120
gctggaaaca ctagcgtcgc taaattccaa gcggtagaag ctaaaatgcg caaagctgga     180
aaacattcaa tggtccaagt tttgaatttt gcaaagaag ttaagttcaa cgaagtaatg     240
cacaaagttg gcacttatta cggcatcgaa gtagtagctg acggcgatag cattggtact     300
tactacatcg ctgaaaaagt tgggatgca gcataa                               336
```

<210> SEQ ID NO 204
<211> LENGTH: 111
<212> TYPE: PRT
<213> ORGANISM: Bacteriophage D5861

<400> SEQUENCE: 204

Met Lys Lys Glu Ile Met Thr Lys Ala Trp Glu Ile Ala Lys Asn Ala
1               5                   10                  15

Ser Lys Lys Phe Gly Gly Lys Ala Ile Glu Tyr Ile Ala Gly Ala Met
            20                  25                  30

Lys Met Ala Trp Ala Ala Ala Lys Ala Gly Asn Thr Ser Val Ala Lys
        35                  40                  45

Phe Gln Ala Val Glu Ala Lys Met Arg Lys Ala Gly Lys His Ser Met
    50                  55                  60

Val Gln Val Leu Asn Phe Ala Lys Glu Val Lys Phe Asn Glu Val Met
65                  70                  75                  80

His Lys Val Gly Thr Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

```
                    100                 105                 110
```

<210> SEQ ID NO 205
<211> LENGTH: 336
<212> TYPE: DNA
<213> ORGANISM: Bacteriophage D6252

<400> SEQUENCE: 205

```
atgaaaaaag aaattatgac aaaagcttgg gaaattgcta aaaacgcttc taaaaaattc      60
ggtggtaaag ctatcgaata catcgctgga gctatgaaaa tggcttgggc tgctgctaaa     120
gctggaaaaa ctagcgtcgc taaattccaa gcggtagaag ctaaaatgcg caaagctgga     180
aaacattcaa tggtccaagt tttgaatttt gctaaagaag tacgtttcaa cgaagtaatg     240
cacaaagctg gcgcttatta cggtatcgaa gtaattgctg atggtgatag cattggtact     300
tacttcattg ctgagaatgt ttggaacgca gcataa                               336
```

<210> SEQ ID NO 206
<211> LENGTH: 111
<212> TYPE: PRT
<213> ORGANISM: Bacteriophage D6252

<400> SEQUENCE: 206

```
Met Lys Lys Glu Ile Met Thr Lys Ala Trp Glu Ile Ala Lys Asn Ala
1               5                   10                  15

Ser Lys Lys Phe Gly Gly Lys Ala Ile Glu Tyr Ile Ala Gly Ala Met
            20                  25                  30

Lys Met Ala Trp Ala Ala Ala Lys Ala Gly Lys Thr Ser Val Ala Lys
        35                  40                  45

Phe Gln Ala Val Glu Ala Lys Met Arg Lys Ala Gly Lys His Ser Met
    50                  55                  60

Val Gln Val Leu Asn Phe Ala Lys Glu Val Arg Phe Asn Glu Val Met
65                  70                  75                  80

His Lys Ala Gly Ala Tyr Tyr Gly Ile Glu Val Ile Ala Asp Gly Asp
                85                  90                  95

Ser Ile Gly Thr Tyr Phe Ile Ala Glu Asn Val Trp Asn Ala Ala
            100                 105                 110
```

<210> SEQ ID NO 207
<211> LENGTH: 336
<212> TYPE: DNA
<213> ORGANISM: Bacteriophage D6312

<400> SEQUENCE: 207

```
atgaaaaaag aaattatgac aaaagcatgg aaaatcgcta agaagcagt taaaactttc       60 ggtggtaaag ctatcgaata catcgcagaa gcattgaaaa tggcttgggc tgctgccaag    120
ggtgaaaaca ctagcttagc taaaattcaa gctgttgagg aaaagatgcg taaatctggt    180
aaatactcaa tgatccaagt tcttgatttt gctaaagaag tgaaatttaa cgaagtaatg    240
cacaaagctg gtgcttacta cggtatcgaa gttattgctg atggcgatag cattggtact    300
tattacattg ctgaaaaagt ttgggaagta gcttaa                              336
```

<210> SEQ ID NO 208
<211> LENGTH: 111
<212> TYPE: PRT
<213> ORGANISM: Bacteriophage D6312

<400> SEQUENCE: 208

```
Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Leu
                20                  25                  30

Lys Met Ala Trp Ala Ala Ala Lys Gly Glu Asn Thr Ser Leu Ala Lys
            35                  40                  45

Ile Gln Ala Val Glu Glu Lys Met Arg Lys Ser Gly Lys Tyr Ser Met
        50                  55                  60

Ile Gln Val Leu Asp Phe Ala Lys Glu Val Lys Phe Asn Glu Val Met
65                  70                  75                  80

His Lys Ala Gly Ala Tyr Tyr Gly Ile Glu Val Ile Ala Asp Gly Asp
                85                  90                  95

Ser Ile Gly Thr Tyr Tyr Ile Ala Glu Lys Val Trp Glu Val Ala
                100                 105                 110
```

<210> SEQ ID NO 209
<211> LENGTH: 336
<212> TYPE: DNA
<213> ORGANISM: Bacteriophage D7130

<400> SEQUENCE: 209

```
atgaaaaaag aaattatgac aaaagcatgg aaaatcgcta agaagcagt taaaactttc      60 ggtggaaaag ctatcgaata cattgcggaa gcatgaaaaa tggcttgggc tgctgctaaa    120
ggcggaaacg ctagcttagc taaattccaa gcagtagaat ctaaaatgcg taaagctggt    180
aaatactcaa tgattcaagt tttaaatttc gctaaggaag tgaaatttaa cgaagttatg    240
cacaaagttg gcgcttatta cggtatcgaa gtaattgctg atggtgatag cattggtact    300
tactacatcg ctgaaaacgt ttggaacgca gcataa                              336
```

<210> SEQ ID NO 210
<211> LENGTH: 111
<212> TYPE: PRT
<213> ORGANISM: Bacteriophage D7130

<400> SEQUENCE: 210

```
Met Lys Lys Glu Ile Met Thr Lys Ala Trp Lys Ile Ala Lys Glu Ala
1               5                   10                  15

Val Lys Thr Phe Gly Gly Lys Ala Ile Glu Tyr Ile Ala Glu Ala Met
                20                  25                  30

Lys Met Ala Trp Ala Ala Ala Lys Gly Gly Asn Ala Ser Leu Ala Lys
            35                  40                  45

Phe Gln Ala Val Glu Ser Lys Met Arg Lys Ala Gly Lys Tyr Ser Met
        50                  55                  60

Ile Gln Val Leu Asn Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Tyr Ile Ala Glu Asn Val Trp Asn Ala Ala
                100                 105                 110
```

<210> SEQ ID NO 211
<211> LENGTH: 336
<212> TYPE: DNA
<213> ORGANISM: Bacteriophage D802

<400> SEQUENCE: 211

```
atgaaaaaag aaattatgac aaaagcatgg aaaatcgcta agaagcagt tgagaagttc      60
```

```
ggtggtaaat ctatcgaata cattgcggaa gcaatgaaaa tggcttgggc tgctgcaaaa    120
ggcggaaacg ctagcttagc taaatttcaa gcggtagaag ctaaaatgcg caaagctggt    180
aaatactcaa tgattcaagt tttaaatttc gctaaggaag tgaaatttaa cgaagttatg    240
cacaaagctg gtgcttacta tggaatcgaa gtggtagctg acggagacag cattggtact    300 tattcatcg ctgaaaaagt ttgggaagta gcataa                                336
```

<210> SEQ ID NO 212
<211> LENGTH: 111
<212> TYPE: PRT
<213> ORGANISM: Bacteriophage D802

<400> SEQUENCE: 212

```
Met Lys Lys Glu Ile Met Thr Lys Ala Trp Lys Ile Ala Lys Glu Ala
1               5                   10                  15

Val Glu Lys Phe Gly Gly Lys Ser Ile Glu Tyr Ile Ala Glu Ala Met
            20                  25                  30

Lys Met Ala Trp Ala Ala Ala Lys Gly Gly Asn Ala Ser Leu Ala Lys
        35                  40                  45

Phe Gln Ala Val Glu Ala Lys Met Arg Lys Ala Gly Lys Tyr Ser Met
    50                  55                  60

Ile Gln Val Leu Asn Phe Ala Lys Glu Val Lys Phe Asn Glu Val Met
65                  70                  75                  80

His Lys Ala Gly Ala Tyr Tyr Gly Ile Glu Val Val Ala Asp Gly Asp
                85                  90                  95

Ser Ile Gly Thr Tyr Tyr Ile Ala Glu Lys Val Trp Glu Val Ala
            100                 105                 110
```

<210> SEQ ID NO 213
<211> LENGTH: 336
<212> TYPE: DNA
<213> ORGANISM: Bacteriophage N1024

<400> SEQUENCE: 213

```
atgaaaaaag aaattatgac aaaagcttgg gaaattgcta aaaacgcttc taaaaaattc     60
ggtggtaaag ctatcgaata catcgctgga gctatgaaaa tggcttgggc tgctgctaaa    120
gctggaaaca ctagcgtcgc taaattccaa gcggtagaag ctaaaatgcg caaagctgga    180
aaacattcaa tggtccaagt tttgaattt gcaaagaag ttaagttcaa cgaagtaatg      240
cacaaagttg gcacttatta cggcatcgaa gtagtagctg acggcgatag cattggtact    300
tactacatcg ctgaaaaagt ttgggatgca gcataa                               336
```

<210> SEQ ID NO 214
<211> LENGTH: 111
<212> TYPE: PRT
<213> ORGANISM: Bacteriophage N1024

<400> SEQUENCE: 214

```
Met Lys Lys Glu Ile Met Thr Lys Ala Trp Glu Ile Ala Lys Asn Ala
1               5                   10                  15

Ser Lys Lys Phe Gly Gly Lys Ala Ile Glu Tyr Ile Ala Gly Ala Met
            20                  25                  30

Lys Met Ala Trp Ala Ala Ala Lys Ala Gly Asn Thr Ser Val Ala Lys
        35                  40                  45

Phe Gln Ala Val Glu Ala Lys Met Arg Lys Ala Gly Lys His Ser Met
    50                  55                  60
```

```
Val Gln Val Leu Asn Phe Ala Lys Glu Val Lys Phe Asn Glu Val Met
65                  70                  75                  80

His Lys Val Gly Thr Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

<210> SEQ ID NO 215
<211> LENGTH: 336
<212> TYPE: DNA
<213> ORGANISM: Bacteriophage O1205

<400> SEQUENCE: 215
atgaaatcac aagtaatgag ccaagcatgg aaaatcgcta agaagcagt taagaaattc        60 ggtggtaaag ctatcgaata catctctgaa gctatgaaaa tggcttgggc tgctgccaag      120
ggtgaaaaca ctagcttaac taaatttcaa gctgttgagg aaaagatgcg taaagctggc      180
aaatactcaa tgattcaagt tcttgacttt gctaaagaag tgaaattcaa cgaagtaatg      240
cataaagttg gtgcttacta cggaattgaa gttattgctg acggagacag cattggtact      300
tactttatcg ctgaaaaagt ttgggatgta gcttaa                                336

<210> SEQ ID NO 216
<211> LENGTH: 111
<212> TYPE: PRT
<213> ORGANISM: Bacteriophage O1205

<400> SEQUENCE: 216

Met Lys Ser Gln Val Met Ser Gln Ala Trp Lys Ile Ala Lys Glu Ala
1               5                   10                  15

Val Lys Lys Phe Gly Gly Lys Ala Ile Glu Tyr Ile Ser Glu Ala Met
                20                  25                  30

Lys Met Ala Trp Ala Ala Ala Lys Gly Glu Asn Thr Ser Leu Thr Lys
            35                  40                  45

Phe Gln Ala Val Glu Glu Lys Met Arg Lys Ala Gly Lys Tyr Ser Met
        50                  55                  60

Ile Gln Val Leu Asp Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Ser Ile Gly Thr Tyr Phe Ile Ala Glu Lys Val Trp Asp Val Ala
            100                 105                 110

<210> SEQ ID NO 217
<211> LENGTH: 336
<212> TYPE: DNA
<213> ORGANISM: Bacteriophage P0095

<400> SEQUENCE: 217
atgaaaaaag aaattatgaa aaaagcatgg aaaatcgcta agaagcagt taagaagttc        60 ggcggcaaag ctatcgaata catcgcagaa gcattgaaaa tggcttggtc tgatgcaaag      120
ggtagtaata ctagcttagc taaattccaa gctgttgagg aaaagatgcg taaagctggc      180
aaatactcaa tgatccaagt tcttgatttt gctaaagaag tgaaatttaa cgaagtaatg      240
cacaaagctg gtgcttacta cggtatcgaa gttattgctg atggcgatag cattggtact      300
tattacattg ctgaaaaagt ttgggaagta gcttaa                                336
```

<210> SEQ ID NO 218
<211> LENGTH: 111
<212> TYPE: PRT
<213> ORGANISM: Bacteriophage P0095

<400> SEQUENCE: 218

Met Lys Lys Glu Ile Met Lys Lys Ala Trp Lys Ile Ala Lys Glu Ala
1               5                   10                  15

Val Lys Lys Phe Gly Gly Lys Ala Ile Glu Tyr Ile Ala Glu Ala Leu
                20                  25                  30

Lys Met Ala Trp Ser Asp Ala Lys Gly Ser Asn Thr Ser Leu Ala Lys
            35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Phe Asn Glu Val Met
65                  70                  75                  80

His Lys Ala Gly Ala Tyr Tyr Gly Ile Glu Val Ile Ala Asp Gly Asp
                85                  90                  95

Ser Ile Gly Thr Tyr Tyr Ile Ala Glu Lys Val Trp Glu Val Ala
            100                 105                 110

<210> SEQ ID NO 219
<211> LENGTH: 336
<212> TYPE: DNA
<213> ORGANISM: Bacteriophage P5641

<400> SEQUENCE: 219
atgaaaaaag aaattatgac aaaagcttgg gaaattgcta aaaacgcttc taaaaattc      60 ggtggtaaag ctatcgaata catcgctgga gctatgaaaa tggcttgggc tgctgctaaa    120
gctggaaaca ctagcgtcgc taaattccaa gcggtagaag ctaaaatgcg caaagctgga    180
aaacattcaa tggtccaagt tttgaatttt gcaaagaag ttaagttcaa cgaagtaatg     240
cacaaagttg gcgcttatta cggcatcgaa gtagtagctg acggcgatag cattggtact    300
tattacattg ctgaaaaagt ttgggaagta gcataa                              336

<210> SEQ ID NO 220
<211> LENGTH: 111
<212> TYPE: PRT
<213> ORGANISM: Bacteriophage P5641

<400> SEQUENCE: 220

Met Lys Lys Glu Ile Met Thr Lys Ala Trp Glu Ile Ala Lys Asn Ala
1               5                   10                  15

Ser Lys Lys Phe Gly Gly Lys Ala Ile Glu Tyr Ile Ala Gly Ala Met
                20                  25                  30

Lys Met Ala Trp Ala Ala Ala Lys Ala Gly Asn Thr Ser Val Ala Lys
            35                  40                  45

Phe Gln Ala Val Glu Ala Lys Met Arg Lys Ala Gly Lys His Ser Met
    50                  55                  60

Val Gln Val Leu Asn Phe Ala Lys Glu Val Lys Phe Asn Glu Val Met
65                  70                  75                  80

His Lys Val Gly Ala Tyr Tyr Gly Ile Glu Val Val Ala Asp Gly Asp
                85                  90                  95

Ser Ile Gly Thr Tyr Tyr Ile Ala Glu Lys Val Trp Glu Val Ala
            100                 105                 110

<210> SEQ ID NO 221
<211> LENGTH: 336
<212> TYPE: DNA
<213> ORGANISM: Bacteriophage P7602

<400> SEQUENCE: 221

```
atgaaaaaag aaattatgac aaacgcgtgg gaaattgcta aaaacgcttc taaaaaattc      60
ggtggtaaag ctatcgaata catcgcagaa gcattgaaaa tggcttggtc tgatgcaaag     120
ggtagtaata ctagcttagc taaattccaa gctgttgagg aaaagatgcg taaagctggc     180
aaatactcaa tgattcaagt tttaaatttc gctaaagaag tgaaattcaa tgaagtaatg     240
cacaaagaag gtgcttacta tggtatcgaa gtagtagctg acggagacag cattggtact     300
tattcattg ctgaaaaagt ttgggatgca gcgtaa                                336
```

<210> SEQ ID NO 222
<211> LENGTH: 111
<212> TYPE: PRT
<213> ORGANISM: Bacteriophage P7602

<400> SEQUENCE: 222

Met Lys Lys Glu Ile Met Thr Asn Ala Trp Glu Ile Ala Lys Asn Ala
1               5                   10                  15

Ser Lys Lys Phe Gly Gly Lys Ala Ile Glu Tyr Ile Ala Glu Ala Leu
            20                  25                  30

Lys Met Ala Trp Ser Asp Ala Lys Gly Ser Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asn Phe Ala Lys Glu Val Lys Phe Asn Glu Val Met
65                  70                  75                  80

His Lys Glu Gly Ala Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

<210> SEQ ID NO 223
<211> LENGTH: 336
<212> TYPE: DNA
<213> ORGANISM: Bacteriophage SFi18

<400> SEQUENCE: 223

```
atgaaaaaag aagttatgac aaacgcatgg aaaatcgcta agaagcagt taagaaattc      60
ggtggtaaag ctatcgaata catctctgaa gctatgaaaa tggcttgggc tgctgccaag     120
ggtgaaaaca ctagcttagc taaattccaa gctgttgagg aaaagatgcg taaagctggc     180
aaatactcaa tgattcaagt tcttgacttt gctaaagaag ttaaaatcaa cgaagtaatg     240
cataaagttg gtgcttacta cggaattgaa gttattgctg acggagacaa cattggtact     300
tactacattg ctgaaaaagt ttgggaagta gcataa                                336
```

<210> SEQ ID NO 224
<211> LENGTH: 111
<212> TYPE: PRT
<213> ORGANISM: Bacteriophage SFi18

<400> SEQUENCE: 224

Met Lys Lys Glu Val Met Thr Asn Ala Trp Lys Ile Ala Lys Glu Ala
1               5                   10                  15

Val Lys Lys Phe Gly Gly Lys Ala Ile Glu Tyr Ile Ser Glu Ala Met
            20                  25                  30

Lys Met Ala Trp Ala Ala Ala Lys Gly Glu Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Ile Asn Glu Val Met
65                  70                  75                  80

His Lys Val Gly Ala Tyr Tyr Gly Ile Glu Val Ile Ala Asp Gly Asp
                85                  90                  95

Asn Ile Gly Thr Tyr Tyr Ile Ala Glu Lys Val Trp Glu Val Ala
            100                 105                 110

<210> SEQ ID NO 225
<211> LENGTH: 336
<212> TYPE: DNA
<213> ORGANISM: Bacteriophage Sfi11

<400> SEQUENCE: 225
atgaaaaaag aagttatgac aaacgcatgg aaaatcgcta agaagcagt taagaaattc      60 ggtggtaaag ctatcgaata catctctgaa ggctatgaaa tggcttgggc tgctgccaag    120
ggtgaaaaca ctagcttagc taaattccaa gctgttgagg aaaagatgcg taaagctggc    180
aaatactcaa tgattcaagt tcttgacttt gctaaagaag ttaaaattca cgaagtaatg    240
cataaagttg gtgcttacta cggaattgaa gttattgctg acggagacaa cattggtact    300
tactacattg ctgaaaaagt ttgggaagta gcataa                              336

<210> SEQ ID NO 226
<211> LENGTH: 111
<212> TYPE: PRT
<213> ORGANISM: Bacteriophage Sfi11

<400> SEQUENCE: 226

Met Lys Lys Glu Val Met Thr Asn Ala Trp Lys Ile Ala Lys Glu Ala
1               5                   10                  15

Val Lys Lys Phe Gly Gly Lys Ala Ile Glu Tyr Ile Ser Glu Gly Tyr
            20                  25                  30

Glu Met Ala Trp Ala Ala Ala Lys Gly Glu Asn Thr Ser Leu Ala Lys
        35                  40                  45

Phe Gln Ala Val Glu Glu Lys Met Arg Lys Ala Gly Lys Tyr Ser Met
    50                  55                  60

Ile Gln Val Leu Asp Phe Ala Lys Glu Val Lys Phe Asn Glu Val Met
65                  70                  75                  80

His Lys Val Gly Ala Tyr Tyr Gly Ile Glu Val Ile Ala Asp Gly Asp
                85                  90                  95

Asn Ile Gly Thr Tyr Tyr Ile Ala Glu Lys Val Trp Glu Val Ala
            100                 105                 110

<210> SEQ ID NO 227
<211> LENGTH: 336
<212> TYPE: DNA
<213> ORGANISM: Bacteriophage Sfi19

<400> SEQUENCE: 227
atgaagaaag agattatgaa aaaagcgtgg gaaatcgcta agaagcagt taaaaaattc      60 ggtggcaaag ctatcgaata catcgcagaa gcattgaaaa tggcttggtc tgatgcaaag   120

-continued

```
ggtagtaata ctagcttagc taaattccaa gctgttgagg aaaagatgcg taaagctggc    180
aaatactcaa tgattcaagt tcttgacttt gctaaagaag ttaaattcaa tgaagtaatg    240
cacaaagaag gtgcttacta tggtatcgaa gtggtagctg acggagacag cattggtact    300
tactacattg ctgaaaaagt ttgggaagta gcataa                              336
```

<210> SEQ ID NO 228
<211> LENGTH: 111
<212> TYPE: PRT
<213> ORGANISM: Bacteriophage Sfi19

<400> SEQUENCE: 228

```
Met Lys Lys Glu Ile Met Lys Lys Ala Trp Glu Ile Ala Lys Glu Ala
1               5                   10                  15

Val Lys Lys Phe Gly Gly Lys Ala Ile Glu Tyr Ile Ala Glu Ala Leu
                20                  25                  30

Lys Met Ala Trp Ser Asp Ala Lys Gly Ser Asn Thr Ser Leu Ala Lys
            35                  40                  45

Phe Gln Ala Val Glu Glu Lys Met Arg Lys Ala Gly Lys Tyr Ser Met
        50                  55                  60

Ile Gln Val Leu Asp Phe Ala Lys Glu Val Lys Phe Asn Glu Val Met
65                  70                  75                  80

His Lys Glu Gly Ala Tyr Tyr Gly Ile Glu Val Val Ala Asp Gly Asp
                85                  90                  95

Ser Ile Gly Thr Tyr Tyr Ile Ala Glu Lys Val Trp Glu Val Ala
                100                 105                 110
```

<210> SEQ ID NO 229
<211> LENGTH: 333
<212> TYPE: DNA
<213> ORGANISM: Bacteriophage Sfi21

<400> SEQUENCE: 229

```
atgaaaaaaa ttatgacaaa cgcatggaaa atcgctaaag aagcagttaa gaaattcggt     60
ggtaaagcta tcgaatacat ctctgaagct atgaaaattg cttgggctga tgctaaagaa    120
ggaaacacta gcgtagctaa attccaagct gtagaagcta aaatgcgtaa agctggaaaa    180
cattcaatgg tgcaagtgtt gaatttcgct aaagaagtga aattcaacga agtaatgcac    240
aaagttggtg cttactacgg tatcgaagta atcgctgatg gtgatagcat tggtacttac    300
tacatttctg aaaaagtttg ggaagtagct taa                                 333
```

<210> SEQ ID NO 230
<211> LENGTH: 110
<212> TYPE: PRT
<213> ORGANISM: Bacteriophage Sfi21

<400> SEQUENCE: 230

```
Met Lys Lys Ile Met Thr Asn Ala Trp Lys Ile Ala Lys Glu Ala Val
1               5                   10                  15

Lys Lys Phe Gly Gly Lys Ala Ile Glu Tyr Ile Ser Glu Ala Met Lys
                20                  25                  30

Ile Ala Trp Ala Asp Ala Lys Glu Gly Asn Thr Ser Val Ala Lys Phe
            35                  40                  45

Gln Ala Val Glu Ala Lys Met Arg Lys Ala Gly Lys His Ser Met Val
        50                  55                  60

Gln Val Leu Asn Phe Ala Lys Glu Val Lys Phe Asn Glu Val Met His
65                  70                  75                  80
```

Lys Val Gly Ala Tyr Tyr Gly Ile Glu Val Ile Ala Asp Gly Asp Ser
                85                  90                  95

Ile Gly Thr Tyr Tyr Ile Ser Glu Lys Val Trp Glu Val Ala
            100                 105                 110

<210> SEQ ID NO 231
<211> LENGTH: 336
<212> TYPE: DNA
<213> ORGANISM: Bacteriophage Proph1

<400> SEQUENCE: 231
atgaaaaaag aaattatgaa aaagcatgg aaaatcgcta agaagcagt taagaagttc    60 ggcggcaaag ctatcgaata catcgcagaa gcattgaaaa tggcttggtc tgatgcaaag   120
ggtagtaata ctagcttagc taaattccaa gctgtagaag ataaaatgaa caaaaccgga   180
aaacactcaa tggtccaagt cttgaatttt gctaaagaag tgaatttcaa agaagtaatg   240
cataaagttg gtgcttacta cggtatcgaa gtagtagctg acggagacag cattggtact   300
tactacatcg ctgaaaaggt ttgggatgca gcttaa                             336

<210> SEQ ID NO 232
<211> LENGTH: 111
<212> TYPE: PRT
<213> ORGANISM: Bacteriophage Proph1

<400> SEQUENCE: 232

Met Lys Lys Glu Ile Met Lys Lys Ala Trp Lys Ile Ala Lys Glu Ala
1               5                   10                  15

Val Lys Lys Phe Gly Gly Lys Ala Ile Glu Tyr Ile Ala Glu Ala Leu
            20                  25                  30

Lys Met Ala Trp Ser Asp Ala Lys Gly Ser Asn Thr Ser Leu Ala Lys
        35                  40                  45

Phe Gln Ala Val Glu Asp Lys Met Asn Lys Thr Gly Lys His Ser Met
    50                  55                  60

Val Gln Val Leu Asn Phe Ala Lys Glu Val Asn Phe Lys Glu Val Met
65                  70                  75                  80

His Lys Val Gly Ala Tyr Tyr Gly Ile Glu Val Val Ala Asp Gly Asp
                85                  90                  95

Ser Ile Gly Thr Tyr Tyr Ile Ala Glu Lys Val Trp Asp Ala Ala
            100                 105                 110

<210> SEQ ID NO 233
<211> LENGTH: 111
<212> TYPE: DNA
<213> ORGANISM: Bacteriophage D1427

<400> SEQUENCE: 233
atgaaaaaag aagttatgac aaacgcgtgg gaaattgcta aaaacgcttc taaaaaattc    60
ggtggtaaag ctatcgaata catcgctgaa aacgtttgga acgcagcata a             111

<210> SEQ ID NO 234
<211> LENGTH: 36
<212> TYPE: PRT
<213> ORGANISM: Bacteriophage D1427

<400> SEQUENCE: 234

Met Lys Lys Glu Val Met Thr Asn Ala Trp Glu Ile Ala Lys Asn Ala
1               5                   10                  15

Ser Lys Lys Phe Gly Gly Lys Ala Ile Glu Tyr Ile Ala Glu Asn Val
            20                  25                  30

Trp Asn Ala Ala
        35

<210> SEQ ID NO 235
<211> LENGTH: 345
<212> TYPE: DNA
<213> ORGANISM: Bacteriophage D5691

<400> SEQUENCE: 235
atgaaatcac aagtaatgag cctagcatgg aaaatcttca aaaacgaaaa aaacgacgta      60 acttttctg aagcattgaa gtttgcttgg aaagccgtta acgtcaaaa tatggcagat      120 gatttctact tcttccattc ttcaaatgtt aaatttcaag gtgttaagaa atggtttgct     180
gaaaaagagt tccgtggacg caacaaaaaa gacttggcgt tcatgtcagt aagtgcaatc     240
agtgttaaag ggttggtcga agaaactgat aaagcagtta acttgaaat cgtgacacct      300 tatggggttt ctgctaaatg gtacccaaaa agtgtaattg cttaa                   345

<210> SEQ ID NO 236
<211> LENGTH: 114
<212> TYPE: PRT
<213> ORGANISM: Bacteriophage D5691

<400> SEQUENCE: 236

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
            20                  25                  30

Val Lys Arg Gln Asn Met Ala Asp Asp Phe Tyr Phe His Ser Ser
        35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Ser Ala Ile
65                  70                  75                  80

Ser Val Lys Gly Leu Val Glu Glu Thr Asp Lys Ala Val Lys Leu Glu
                85                  90                  95

Ile Val Thr Pro Tyr Gly Val Ser Ala Lys Trp Tyr Pro Lys Ser Val
            100                 105                 110

Ile Ala

<210> SEQ ID NO 237
<211> LENGTH: 345
<212> TYPE: DNA
<213> ORGANISM: Bacteriophage D6193

<400> SEQUENCE: 237
atgaaatcac aagtaatgag cctagcatgg aaaatcttca aaaacgaaaa aaacgatgta      60 acttttctg aagcgttgaa atttgcttgg aaagccgtta acgtcaaaa catggcggat       120 gattttact tcttccgttc ttcaaatgtt aaattccaag gtgttaagaa atggtttgct      180
gaaaaagaat ttcgtggacg caacaagaaa gacttggcgt ttatgtcagt aactgcaatc    240
agtgttaaag ggttgattga agaaactgat aaagcggtta agcttgaaat cgtaacacct    300
tatggagttt ctactaaatg gtatccaaag agtgtaattg cttaa                    345

<210> SEQ ID NO 238

```
<211> LENGTH: 114
<212> TYPE: PRT
<213> ORGANISM: Bacteriophage D6193

<400> SEQUENCE: 238
```

| | | | | | | | | | | | | | | |
|---|---|---|---|---|---|---|---|---|---|---|---|---|---|---|
| Met | Lys | Ser | Gln | Val | Met | Ser | Leu | Ala | Trp | Lys | Ile | Phe | Lys | Asn | Glu |
| 1 | | | | 5 | | | | | 10 | | | | | 15 |

Lys Asn Asp Val Thr Phe Ser Glu Ala Leu Lys Phe Ala Trp Lys Ala
                20                  25                  30

Val Lys Arg Gln Asn Met Ala Asp Asp Phe Tyr Phe Phe Arg Ser Ser
            35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Thr Ala Ile
65                  70                  75                  80

Ser Val Lys Gly Leu Ile Glu Glu Thr Asp Lys Ala Val Lys Leu Glu
                85                  90                  95

Ile Val Thr Pro Tyr Gly Val Ser Thr Lys Trp Tyr Pro Lys Ser Val
            100                 105                 110

Ile Ala

```
<210> SEQ ID NO 239
<211> LENGTH: 345
<212> TYPE: DNA
<213> ORGANISM: Bacteriophage D7035

<400> SEQUENCE: 239
```

```
atgaaatcac aagtaatgag cctagcatgg aaaattttca aaaacgaaaa aaacgacgta      60
actttttctg aagcattgaa gtttgcttgg aaagccgtta acgtcaaaa catggcggat      120
gatttctact tcttccgttc ttcaaacgtt aaattccaag gtgttaagaa atggtttgct      180
gaaaaagaat tcgtggacg caacaagaaa gacttggcgt ttatgtcagt aactgcaatc      240
agcattaaag ggttggttga agaaactgat aaagcggtta agcttgaaat cgtgacacct      300
tatggaattt ctactaaatg gtatccaaag agtgtaattg cttaa                      345
```

```
<210> SEQ ID NO 240
<211> LENGTH: 114
<212> TYPE: PRT
<213> ORGANISM: Bacteriophage D7035

<400> SEQUENCE: 240
```

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
                20                  25                  30

Val Lys Arg Gln Asn Met Ala Asp Asp Phe Tyr Phe Phe Arg Ser Ser
            35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Thr Ala Ile
65                  70                  75                  80

Ser Ile Lys Gly Leu Val Glu Glu Thr Asp Lys Ala Val Lys Leu Glu
                85                  90                  95

Ile Val Thr Pro Tyr Gly Ile Ser Thr Lys Trp Tyr Pro Lys Ser Val
            100                 105                 110

Ile Ala

<210> SEQ ID NO 241
<211> LENGTH: 345
<212> TYPE: DNA
<213> ORGANISM: Bacteriophage Proph1

<400> SEQUENCE: 241
atgaaatcac aagtaatgag cctagcatgg aaaatcttca aaaacgaaaa aaacgatgta    60 acttttctg aagcgttgaa atttgcttgg aaagccgtta acgtcaaaa catggcggat    120 gatttctact tcttccgttc ttcaaacgtt aaattccaag gtgttaagaa atggtttgct    180
gaaaaagaat tcgtggacg caacaagaaa gacttggcgt ttatgtcagt aactgcaatc    240
agcgttaaag ggttgatcga agaaactgat aaagcggtta agcttgaaat cgtaacacct    300
tatggagttt ctactaaatg gtatccaaag agtgtaattg cttaa    345

<210> SEQ ID NO 242
<211> LENGTH: 114
<212> TYPE: PRT
<213> ORGANISM: Bacteriophage Proph1

<400> SEQUENCE: 242

Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
            20                  25                  30

Val Lys Arg Gln Asn Met Ala Asp Asp Phe Tyr Phe Arg Ser Ser
        35                  40                  45

Asn Val Lys Phe Gln Gly Val Lys Lys Trp Phe Ala Glu Lys Glu Phe
    50                  55                  60

Arg Gly Arg Asn Lys Lys Asp Leu Ala Phe Met Ser Val Thr Ala Ile
65                  70                  75                  80

Ser Val Lys Gly Leu Ile Glu Glu Thr Asp Lys Ala Val Lys Leu Glu
                85                  90                  95

Ile Val Thr Pro Tyr Gly Val Ser Thr Lys Trp Tyr Pro Lys Ser Val
            100                 105                 110

Ile Ala

<210> SEQ ID NO 243
<211> LENGTH: 345
<212> TYPE: DNA
<213> ORGANISM: Bacteriophage Proph1

<400> SEQUENCE: 243
atgaaatcac aagtaatgag cctagcatgg aaaatcttca aaaacgaaaa aaacgatgta    60 acttttctg aagcgttgaa atttgcttgg aaagccgtta acgtcaaaa catggcggat    120 gatttctact tcttccgttc ttcaaacgtt aaattccaag gtgttaagaa atggtttgct    180
gaaaaagaat tcgtggacg caacaagaaa gacttggcgt ttatgtcagt aactgcaatc    240
agcattaaag ggttggttga agaaactgat aaagcggtta agcttgaaat cgtgacacct    300
tatggaattt ctactaaatg gtatccaaag agtgtaattg cttaa    345

<210> SEQ ID NO 244
<211> LENGTH: 114
<212> TYPE: PRT
<213> ORGANISM: Bacteriophage Proph1

<400> SEQUENCE: 244

```
Met Lys Ser Gln Val Met Ser Leu Ala Trp Lys Ile Phe Lys Asn Glu
1               5                   10                  15

Lys Asn Asp Val Thr Phe Ser Glu Ala Leu Lys Phe Ala Trp Lys Ala
                20                  25                  30

Val Lys Arg Gln Asn Met Ala Asp Asp Phe Tyr Phe Phe Arg Ser Ser
            35                  40                  45

Asn Val Lys Phe Gln Gly Val Lys Lys Trp Phe Ala Glu Lys Glu Phe
        50                  55                  60

Arg Gly Arg Asn Lys Lys Asp Leu Ala Phe Met Ser Val Thr Ala Ile
65                  70                  75                  80

Ser Ile Lys Gly Leu Val Glu Glu Thr Asp Lys Ala Val Lys Leu Glu
                85                  90                  95

Ile Val Thr Pro Tyr Gly Ile Ser Thr Lys Trp Tyr Pro Lys Ser Val
                100                 105                 110

Ile Ala
```

<210> SEQ ID NO 245
<211> LENGTH: 261
<212> TYPE: DNA
<213> ORGANISM: Bacteriophage 5093

<400> SEQUENCE: 245

```
gtgaaaacaa tggatgcata taaagaacaa tttcaagaat tacaagaata cgcttttaac      60
gttttaagag aatatcctct agacaagaca gcagttaatg tgctttctgc actcgttaac     120
tcaaaaaaga aagatcgcat cgagtttttt aaactaaaca aaggcgaaga tgccatgaaa     180
gtttattata atctagcaga tagcggaacg attgaaaaat atttagaaac atctgcattt     240
ttagattaca tcaatgaata a                                               261
```

<210> SEQ ID NO 246
<211> LENGTH: 86
<212> TYPE: PRT
<213> ORGANISM: Bacteriophage 5093

<400> SEQUENCE: 246

```
Met Lys Thr Met Asp Ala Tyr Lys Glu Gln Phe Gln Glu Leu Gln Glu
1               5                   10                  15

Tyr Ala Phe Asn Val Leu Arg Glu Tyr Pro Leu Asp Lys Thr Ala Val
                20                  25                  30

Asn Val Leu Ser Ala Leu Val Asn Ser Lys Lys Asp Arg Ile Glu
            35                  40                  45

Phe Phe Lys Leu Asn Lys Gly Glu Asp Ala Met Lys Val Tyr Tyr Asn
        50                  55                  60

Leu Ala Asp Ser Gly Thr Ile Glu Lys Tyr Leu Glu Thr Ser Ala Phe
65                  70                  75                  80

Leu Asp Tyr Ile Asn Glu
                85
```

<210> SEQ ID NO 247
<211> LENGTH: 252
<212> TYPE: DNA
<213> ORGANISM: Bacteriophage D4154

<400> SEQUENCE: 247

```
atggatacat ataagaaca atttcaaaaa ttacaagaat acgcttttaa cgttttaaga      60
gaataccctc tagataagac agcagttaat gtactttctg cactcgttaa ctcaaaaaag    120
```

```
aaagatcgca tcgagttttt taaactaaac aaaggcgaag atgccatgaa agtttattat    180
aatctagcag atagcggaac gattgaaaaa tatttagaaa catctgcatt tttagaatac    240
ataaatgaat aa                                                       252
```

<210> SEQ ID NO 248
<211> LENGTH: 83
<212> TYPE: PRT
<213> ORGANISM: Bacteriophage D4154

<400> SEQUENCE: 248

Met Asp Thr Tyr Lys Glu Gln Phe Gln Lys Leu Gln Glu Tyr Ala Phe
1               5                   10                  15

Asn Val Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Gly Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Ile Asn Glu

<210> SEQ ID NO 249
<211> LENGTH: 252
<212> TYPE: DNA
<213> ORGANISM: Bacteriophage D4160

<400> SEQUENCE: 249

```
atggatacat ataagaaca atttcaagaa ttacaagaat acgcttttaa cgttttaaga    60
gaatatcctc tagacaagac agcagttaat gtactttctg cactcgttaa ctcaaaaaag   120
aaagatcgca tcgagttttt taaactaaac aaagacgaag atgccatgaa agtttattat   180
aatctagcag atagcggaac gattgaaaaa tatttagaaa catctgcatt tttagaatac   240
atcaatgaat aa                                                      252
```

<210> SEQ ID NO 250
<211> LENGTH: 83
<212> TYPE: PRT
<213> ORGANISM: Bacteriophage D4160

<400> SEQUENCE: 250

Met Asp Thr Tyr Lys Glu Gln Phe Gln Glu Leu Gln Glu Tyr Ala Phe
1               5                   10                  15

Asn Val Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Asp Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Ile Asn Glu

<210> SEQ ID NO 251
<211> LENGTH: 252
<212> TYPE: DNA

<213> ORGANISM: Bacteriophage D4212

<400> SEQUENCE: 251

```
atggatacat ataagaaca atttcaagaa ttacaagaat acgcttttaa cattttaaga      60
gaatatcctc tagacaagac agcagttaat gtactttctg cactcgttaa ctcaaaaaag    120
aaagatcgca tcgagtttt taaactaaac aaagacgaag atgccatgaa agtttattat    180
aatctagcag atagcggaac gattgaaaaa tatttagaaa catctgcatt tttagaatac    240
atcaatgaat aa                                                        252
```

<210> SEQ ID NO 252
<211> LENGTH: 83
<212> TYPE: PRT
<213> ORGANISM: Bacteriophage D4212

<400> SEQUENCE: 252

Met Asp Thr Tyr Lys Glu Gln Phe Gln Glu Leu Gln Glu Tyr Ala Phe
1               5                   10                  15

Asn Ile Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Asp Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Ile Asn Glu

<210> SEQ ID NO 253
<211> LENGTH: 252
<212> TYPE: DNA
<213> ORGANISM: Bacteriophage D6193

<400> SEQUENCE: 253

```
atggatacat acaagaaca atttcaaaaa ttacaagaat acgctttta cgttttaaga      60
gaataccctc tagataagac agcagttaat gtactttctg cactcgttaa ctcaaaaaag    120
aaagatcgca tcgagtttt taaactaaac aaaggcgaag atgccatgaa agtttattat    180
aatctagcag atagcggaac gattgaaaaa tatttagaaa catctgcatt tttagaatac    240
acaaatgaat aa                                                        252
```

<210> SEQ ID NO 254
<211> LENGTH: 83
<212> TYPE: PRT
<213> ORGANISM: Bacteriophage D6193

<400> SEQUENCE: 254

Met Asp Thr Tyr Lys Glu Gln Phe Gln Lys Leu Gln Glu Tyr Ala Phe
1               5                   10                  15

Asn Val Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Gly Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Thr Asn Glu

<210> SEQ ID NO 255
<211> LENGTH: 252
<212> TYPE: DNA
<213> ORGANISM: Bacteriophage Sfi11

<400> SEQUENCE: 255

| | |
|---|---|
| atggatacat ataaagaaca atttcaagaa ttacaagaat acgcttttaa cattttaaga | 60 |
| gaatatcctc tagacaagac agcagttaat gtactttctg cactcgttaa ctcaaaaaag | 120 |
| aaagatcgca tcgagttttt taaacttaac aaagacgaag atgccatgaa agtttattat | 180 |
| aatctagcag atagcggaac gattgaaaaa tatttagaaa catctgcatt tttagaatac | 240 |
| atcaatgaat aa | 252 |

<210> SEQ ID NO 256
<211> LENGTH: 83
<212> TYPE: PRT
<213> ORGANISM: Bacteriophage Sfi11

<400> SEQUENCE: 256

Met Asp Thr Tyr Lys Glu Gln Phe Gln Glu Leu Gln Glu Tyr Ala Phe
1               5                   10                  15

Asn Ile Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Asp Glu Asp Ala Met Lys Val Tyr Tyr Asn Leu Ala Asp
    50                  55                  60

Ser Gly Thr Ile Glu Lys Tyr Leu Glu Thr Ser Ala Phe Leu Glu Tyr
65                  70                  75                  80

Ile Asn Glu

<210> SEQ ID NO 257
<211> LENGTH: 252
<212> TYPE: DNA
<213> ORGANISM: Bacteriophage Proph1

<400> SEQUENCE: 257

| | |
|---|---|
| atggatacat acaaagaaca atttcaagaa ttacaagaat acgcttttaa cgttttaaga | 60 |
| gaataccctc tagataagac agcagttaat gtactttctg cactcgttaa ctcaaaaaag | 120 |
| aaagatcgca tcgagttttt taaactaaac aaaggcgaag acgccatgaa agtttattat | 180 |
| aatctagcag atagcggaac gattgaaaaa tatttagaaa catctgcatt cttagaatac | 240 |
| atcaatgaat aa | 252 |

<210> SEQ ID NO 258
<211> LENGTH: 83
<212> TYPE: PRT
<213> ORGANISM: Bacteriophage Proph1

<400> SEQUENCE: 258

Met Asp Thr Tyr Lys Glu Gln Phe Gln Glu Leu Gln Glu Tyr Ala Phe
1               5                   10                  15

Asn Val Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys

```
                    35                  40                  45
Leu Asn Lys Gly Glu Asp Ala Met Lys Val Tyr Tyr Asn Leu Ala Asp
            50                  55                  60

Ser Gly Thr Ile Glu Lys Tyr Leu Glu Thr Ser Ala Phe Leu Glu Tyr
65                  70                  75                  80

Ile Asn Glu

<210> SEQ ID NO 259
<211> LENGTH: 252
<212> TYPE: DNA
<213> ORGANISM: Bacteriophage Proph1

<400> SEQUENCE: 259
atggatacat ataaagaaca atttcaagaa ttacaagaat acgcttttaa cgttttaaga      60
gaatatcctc tagacaagac agcagttaat gtactttctg cactcgttaa ctcaaaaaag    120
aaagatcgca tcgagttttt taaactaaac aaaggcgaag atgccatgaa agtttattat    180
agtctagcag atagcggaac gattgagaga tacttggaag tctgtggatt tttagagtac    240
atcaacgaat aa                                                         252

<210> SEQ ID NO 260
<211> LENGTH: 83
<212> TYPE: PRT
<213> ORGANISM: Bacteriophage Proph1

<400> SEQUENCE: 260

Met Asp Thr Tyr Lys Glu Gln Phe Gln Glu Leu Gln Glu Tyr Ala Phe
1               5                   10                  15

Asn Val Leu Arg Glu Tyr Pro Leu Asp Lys Thr Ala Val Asn Val Leu
            20                  25                  30

Ser Ala Leu Val Asn Ser Lys Lys Lys Asp Arg Ile Glu Phe Phe Lys
        35                  40                  45

Leu Asn Lys Gly Glu Asp Ala Met Lys Val Tyr Tyr Ser Leu Ala Asp
    50                  55                  60

Ser Gly Thr Ile Glu Arg Tyr Leu Glu Val Cys Gly Phe Leu Glu Tyr
65                  70                  75                  80

Ile Asn Glu

<210> SEQ ID NO 261
<211> LENGTH: 282
<212> TYPE: DNA
<213> ORGANISM: Bacteriophage D1024

<400> SEQUENCE: 261
atgataacta agaacaatt aaaagaatac tacagcgaac acttggaaga gctcgtcgaa      60
tgggcagacg atataaataa atatgcccta tttgcctacc tagatgaaga tgataacttg    120
tattgtggga ttaatcaact gtcctacaca caattcagag ttccaattca agctgaggtg    180
acagtggatg atgattggaa ctacgatttc ttcaaaaatc cagctgccta tgatggatgg    240
gatgaaactt tggaagaaat gttggaagaa ttaaatgatt aa                        282

<210> SEQ ID NO 262
<211> LENGTH: 93
<212> TYPE: PRT
<213> ORGANISM: Bacteriophage D1024

<400> SEQUENCE: 262
```

Met Ile Thr Lys Glu Gln Leu Lys Glu Tyr Tyr Ser Glu His Leu Glu
1               5                   10                  15

Glu Leu Val Glu Trp Ala Asp Asp Ile Asn Lys Ile Cys Leu Phe Ala
                20                  25                  30

Tyr Leu Asp Glu Asp Asp Asn Leu Tyr Cys Gly Ile Asn Gln Leu Ser
            35                  40                  45

Tyr Thr Gln Phe Arg Val Pro Ile Gln Ala Glu Val Thr Val Asp Asp
        50                  55                  60

Asp Trp Asn Tyr Asp Phe Phe Lys Asn Pro Ala Ala Tyr Asp Gly Trp
65                  70                  75                  80

Asp Glu Thr Leu Glu Glu Met Leu Glu Glu Leu Asn Asp
            85                  90

<210> SEQ ID NO 263
<211> LENGTH: 282
<212> TYPE: DNA
<213> ORGANISM: Bacteriophage D1811

<400> SEQUENCE: 263
atgataacta aagaacaatt aaaagaatac tacagcgaac acttggaaga gctcgtcgaa    60
tgggcagacg atataaataa atatgccta tttgcctacc tagatgaaga tgataacttg    120
tattgtggga ttaatcaact gtcctacaca caattcagag ttccaattca agctgaggtg   180
acagtggatg atgattggaa ctacgatttc ttcaaaaatc cagctgccta tgatggatgg   240
gatgaaactt tggaagaaat gttggaagaa ttaaatgatt aa                      282

<210> SEQ ID NO 264
<211> LENGTH: 93
<212> TYPE: PRT
<213> ORGANISM: Bacteriophage D1811

<400> SEQUENCE: 264

Met Ile Thr Lys Glu Gln Leu Lys Glu Tyr Tyr Ser Glu His Leu Glu
1               5                   10                  15

Glu Leu Val Glu Trp Ala Asp Asp Ile Asn Lys Ile Cys Leu Phe Ala
                20                  25                  30

Tyr Leu Asp Glu Asp Asp Asn Leu Tyr Cys Gly Ile Asn Gln Leu Ser
            35                  40                  45

Tyr Thr Gln Phe Arg Val Pro Ile Gln Ala Glu Val Thr Val Asp Asp
        50                  55                  60

Asp Trp Asn Tyr Asp Phe Phe Lys Asn Pro Ala Ala Tyr Asp Gly Trp
65                  70                  75                  80

Asp Glu Thr Leu Glu Glu Met Leu Glu Glu Leu Asn Asp
            85                  90

<210> SEQ ID NO 265
<211> LENGTH: 282
<212> TYPE: DNA
<213> ORGANISM: Bacteriophage D7035

<400> SEQUENCE: 265
atgataacta aagaacaatt aaaagaatac tacagcgaac acttggaaga gctcgtcgaa    60
tgggcagacg atataaataa atatgccta tttgcctacc tagatgaaga tgataacttg    120
tattgtggga taatcaact gtcctacaca caattcagag ttccaattca agctgaggtg    180
acagtggatg atgattggaa ctacgatttc ttcaaaaatc cagctgccta tgatggatgg   240
gatgaaactt tggaagaaat gttggaagaa ttaaatgatt aa                      282

<210> SEQ ID NO 266
<211> LENGTH: 93
<212> TYPE: PRT
<213> ORGANISM: Bacteriophage D7035

<400> SEQUENCE: 266

Met Ile Thr Lys Glu Gln Leu Lys Glu Tyr Tyr Ser Glu His Leu Glu
1               5                   10                  15

Glu Leu Val Glu Trp Ala Asp Asp Ile Asn Lys Ile Cys Leu Phe Ala
            20                  25                  30

Tyr Leu Asp Glu Asp Asn Leu Tyr Cys Gly Ile Asn Gln Leu Ser
        35                  40                  45

Tyr Thr Gln Phe Arg Val Pro Ile Gln Ala Glu Val Thr Val Asp Asp
    50                  55                  60

Asp Trp Asn Tyr Asp Phe Phe Asn Asn Pro Ala Ser Tyr Asp Gly Trp
65                  70                  75                  80

Asp Glu Thr Leu Glu Glu Met Leu Glu Glu Leu Asn Asp
                85                  90

<210> SEQ ID NO 267
<211> LENGTH: 141
<212> TYPE: DNA
<213> ORGANISM: Bacteriophage D3821

<400> SEQUENCE: 267
gtgaaaacaa tggatacata taagaacaa ttttattatt tggatcctat ttatattagt     60
gtggatatta ataggaggac ttttatttta ggaaaaagag ggcaatcgct ctcttttttt    120
tattgtaata aaacaattta a                                              141

<210> SEQ ID NO 268
<211> LENGTH: 46
<212> TYPE: PRT
<213> ORGANISM: Bacteriophage D3821

<400> SEQUENCE: 268

Met Lys Thr Met Asp Thr Tyr Lys Glu Gln Phe Tyr Tyr Leu Asp Pro
1               5                   10                  15

Ile Tyr Ile Ser Val Asp Ile Asn Arg Arg Thr Phe Ile Leu Gly Lys
            20                  25                  30

Arg Gly Gln Ser Leu Ser Phe Phe Tyr Cys Asn Lys Thr Ile
        35                  40                  45

<210> SEQ ID NO 269
<211> LENGTH: 225
<212> TYPE: DNA
<213> ORGANISM: Bacteriophage O1205

<400> SEQUENCE: 269
atgacacaaa ttaaagatgg ttggcacatg gtttatgacg aaaaagtgta tgtagagagc     60
gggaaagttg tccgtggaat aactaaagac aataacaatt ctgaaatagc ttgctaccct    120
tacgaataca caaagacta tgattgctgg attaacattt ctgggaaagt aactctatca    180
gcttatagat caggtcgtaa aaaagggaca aaatgtatga agtga                    225

<210> SEQ ID NO 270
<211> LENGTH: 74
<212> TYPE: PRT
<213> ORGANISM: Bacteriophage O1205

<400> SEQUENCE: 270

| Met | Thr | Gln | Ile | Lys | Asp | Gly | Trp | His | Met | Val | Tyr | Asp | Glu | Lys | Val |
| 1 | | | | 5 | | | | | 10 | | | | | 15 | |

| Tyr | Val | Glu | Ser | Gly | Lys | Val | Val | Arg | Gly | Ile | Thr | Lys | Asp | Asn | Asn |
| | | | | 20 | | | | | 25 | | | | | 30 | |

| Asn | Ser | Glu | Ile | Ala | Cys | Tyr | Pro | Tyr | Glu | Tyr | Asn | Lys | Asp | Tyr | Asp |
| | | 35 | | | | | 40 | | | | | 45 | | | |

| Cys | Trp | Ile | Asn | Ile | Ser | Gly | Lys | Val | Thr | Leu | Ser | Ala | Tyr | Arg | Ser |
| | 50 | | | | | 55 | | | | | 60 | | | | |

| Gly | Arg | Lys | Lys | Gly | Thr | Lys | Cys | Met | Lys |
| 65 | | | | | 70 | | | | |

<210> SEQ ID NO 271
<211> LENGTH: 225
<212> TYPE: DNA
<213> ORGANISM: Bacteriophage Sfi21

<400> SEQUENCE: 271

```
atgacacaaa ttaaagatgg ttggcacata gtttatgacg aaaaagtgta cgtagagagc    60
gggaaagttg tccgtggaat aactaaagac aataacaatt ctgaaatagc ttgctaccct   120
tacgaataca acgaagacta tgattgctgg attaacattt ctgggaaagt aactctatca   180
gcttatagat caggtcgtaa aaagggaca aatgtatga agtga                     225
```

<210> SEQ ID NO 272
<211> LENGTH: 74
<212> TYPE: PRT
<213> ORGANISM: Bacteriophage Sfi21

<400> SEQUENCE: 272

| Met | Thr | Gln | Ile | Lys | Asp | Gly | Trp | His | Ile | Val | Tyr | Asp | Glu | Lys | Val |
| 1 | | | | 5 | | | | | 10 | | | | | 15 | |

| Tyr | Val | Glu | Ser | Gly | Lys | Val | Val | Arg | Gly | Ile | Thr | Lys | Asp | Asn | Asn |
| | | | | 20 | | | | | 25 | | | | | 30 | |

| Asn | Ser | Glu | Ile | Ala | Cys | Tyr | Pro | Tyr | Glu | Tyr | Asn | Glu | Asp | Tyr | Asp |
| | | 35 | | | | | 40 | | | | | 45 | | | |

| Cys | Trp | Ile | Asn | Ile | Ser | Gly | Lys | Val | Thr | Leu | Ser | Ala | Tyr | Arg | Ser |
| | 50 | | | | | 55 | | | | | 60 | | | | |

| Gly | Arg | Lys | Lys | Gly | Thr | Lys | Cys | Met | Lys |
| 65 | | | | | 70 | | | | |

<210> SEQ ID NO 273
<211> LENGTH: 153
<212> TYPE: DNA
<213> ORGANISM: Bacteriophage D6264

<400> SEQUENCE: 273

```
ttgtttgaat gcttggcatc gtttcggtta aattctcgaa ctgtaacctc gacttttgt     60
cggggttttc ttttttttaca aaaaaatcta aattcctttta tcaaaagtgt tgacaaacta  120
tcatatatga tatataatgt atacataaga taa                                153
```

<210> SEQ ID NO 274
<211> LENGTH: 50
<212> TYPE: PRT
<213> ORGANISM: Bacteriophage D6264

<400> SEQUENCE: 274

Met Phe Glu Cys Leu Ala Ser Phe Arg Leu Asn Ser Arg Thr Val Thr
1               5                   10                  15

Ser Thr Phe Cys Arg Gly Phe Leu Phe Leu Gln Lys Asn Leu Asn Ser
                20                  25                  30

Phe Ile Lys Ser Val Asp Lys Leu Ser Tyr Met Ile Tyr Asn Val Tyr
            35                  40                  45

Ile Arg
    50

<210> SEQ ID NO 275
<211> LENGTH: 192
<212> TYPE: DNA
<213> ORGANISM: Bacteriophage D2759

<400> SEQUENCE: 275
atgaatgaaa gtgaattgct tgagcagttc tgcgtttctc tttgtgaatt tagctctaga      60
cagtggccac gagatgggtt tttagaccct attaaccgtg tggtctacat caatagggat     120
ttaccaaccg aaagacgttt aaaggtccta ctgcacgaat tagggcactt agaacacgac     180
cctaaacact aa                                                         192

<210> SEQ ID NO 276
<211> LENGTH: 63
<212> TYPE: PRT
<213> ORGANISM: Bacteriophage D2759

<400> SEQUENCE: 276

Met Asn Glu Ser Glu Leu Leu Glu Gln Phe Cys Val Ser Leu Cys Glu
1               5                   10                  15

Phe Ser Ser Arg Gln Trp Pro Arg Asp Gly Phe Leu Asp Pro Ile Asn
                20                  25                  30

Arg Val Val Tyr Ile Asn Arg Asp Leu Pro Thr Glu Arg Arg Leu Lys
            35                  40                  45

Val Leu Leu His Glu Leu Gly His Leu Glu His Asp Pro Lys His
        50                  55                  60

<210> SEQ ID NO 277
<211> LENGTH: 150
<212> TYPE: DNA
<213> ORGANISM: Bacteriophage D4091

<400> SEQUENCE: 277
ttgttggggg ctaagaccac cctttttgat ataatatacc tatatcaatg gcttcccacg      60
catacgcgca gatacgttct gagggaagtt ttttatttgc tttgttttga tagaaatgct     120
actatattaa tggatacagt taaaagctga                                      150

<210> SEQ ID NO 278
<211> LENGTH: 49
<212> TYPE: PRT
<213> ORGANISM: Bacteriophage D4091

<400> SEQUENCE: 278

Met Leu Gly Ala Lys Thr Thr Leu Phe Asp Ile Ile Tyr Leu Tyr Gln
1               5                   10                  15

Trp Leu Pro Thr His Thr Arg Arg Tyr Val Leu Arg Glu Val Phe Tyr
                20                  25                  30

Leu Leu Cys Phe Asp Arg Asn Ala Thr Ile Leu Met Asp Thr Val Lys
            35                  40                  45

Ser

<210> SEQ ID NO 279
<211> LENGTH: 150
<212> TYPE: DNA
<213> ORGANISM: Bacteriophage D5821

<400> SEQUENCE: 279

```
ttgttgggggg ttaagaccac ccttttttgat ataatatacc tatatcaatg gcttcccacg    60
catacgcgca gatacgttct gagggaagtt ttttatttgc tttgttttga tagaaatgct    120
actatattaa tggatacagt taaaagctga                                      150
```

<210> SEQ ID NO 280
<211> LENGTH: 49
<212> TYPE: PRT
<213> ORGANISM: Bacteriophage D5821

<400> SEQUENCE: 280

Met Leu Gly Val Lys Thr Thr Leu Phe Asp Ile Ile Tyr Leu Tyr Gln
1               5                   10                  15

Trp Leu Pro Thr His Thr Arg Arg Tyr Val Leu Arg Glu Val Phe Tyr
            20                  25                  30

Leu Leu Cys Phe Asp Arg Asn Ala Thr Ile Leu Met Asp Thr Val Lys
        35                  40                  45

Ser

<210> SEQ ID NO 281
<211> LENGTH: 138
<212> TYPE: DNA
<213> ORGANISM: Bacteriophage 5093

<400> SEQUENCE: 281

```
atgaggaggt gtcttttttt tggtttgctc aaaaaacgca acaatggtat aataattttt    60
gcaacgacaa accccctgca accacatgga cagatacgct ctgacgcagg gcttttttta    120
tttgctttat ttttataa                                                   138
```

<210> SEQ ID NO 282
<211> LENGTH: 45
<212> TYPE: PRT
<213> ORGANISM: Bacteriophage 5093

<400> SEQUENCE: 282

Met Arg Arg Cys Leu Phe Phe Gly Leu Leu Lys Lys Arg Asn Asn Gly
1               5                   10                  15

Ile Ile Ile Phe Ala Thr Thr Asn Pro Leu Gln Pro His Gly Gln Ile
            20                  25                  30

Arg Ser Asp Ala Gly Leu Phe Leu Phe Ala Leu Phe Leu
        35                  40                  45

<210> SEQ ID NO 283
<211> LENGTH: 423
<212> TYPE: DNA
<213> ORGANISM: Bacteriophage 5093

<400> SEQUENCE: 283

```
atgaaaatca atacgacaag agttaaaatg gtcttgaaga atgaggctat acctgctgat    60
tatttagaga gcgagattgg cattagtcgt tccgttgttg aaaaagtgag agaagatgag    120
agcgaattta aaaatttaac tcttgatttt gttgcgaaaa ttcaaaagtg gattgatgat    180
```

-continued

```
ggaaactaca ctttcagcta tgattacagc gacttgatag aagagttgga agaagatatt      240
gcagaaggtc taacggatga gtatatctat gttgtcagag acaatacaa cgaaatttta       300 gagaaatgcc caataattga ctactactac acttctgaag agattgaaga aggagatctc      360
gcagagaaga ccctaacagc ttctgccttg tctgaaatga acaggacaa cgaaatcttt       420 taa                                                                    423
```

<210> SEQ ID NO 284
<211> LENGTH: 140
<212> TYPE: PRT
<213> ORGANISM: Bacteriophage 5093

<400> SEQUENCE: 284

Met Lys Ile Asn Thr Thr Arg Val Lys Met Val Leu Lys Asn Glu Ala
1               5                   10                  15

Ile Pro Ala Asp Tyr Leu Glu Ser Glu Ile Gly Ile Ser Arg Ser Val
            20                  25                  30

Val Glu Lys Val Arg Glu Asp Glu Ser Glu Phe Lys Asn Leu Thr Leu
        35                  40                  45

Asp Phe Val Ala Lys Ile Gln Lys Trp Ile Asp Gly Asn Tyr Thr
    50                  55                  60

Phe Ser Tyr Asp Tyr Ser Asp Leu Ile Glu Glu Leu Glu Glu Asp Ile
65                  70                  75                  80

Ala Glu Gly Leu Thr Asp Glu Tyr Ile Tyr Val Arg Gly Gln Tyr
                85                  90                  95

Asn Glu Ile Leu Glu Lys Cys Pro Ile Ile Asp Tyr Tyr Tyr Thr Ser
            100                 105                 110

Glu Glu Ile Glu Glu Gly Asp Leu Ala Glu Lys Thr Leu Thr Ala Ser
        115                 120                 125

Ala Leu Ser Glu Met Lys Gln Asp Asn Glu Ile Phe
    130                 135                 140

<210> SEQ ID NO 285
<211> LENGTH: 423
<212> TYPE: DNA
<213> ORGANISM: Bacteriophage D4154

<400> SEQUENCE: 285

```
atgaaaatca atacgacaag agttaaaatg gtcttgaaga ataaggttat acctgctatt      60
tatttagaga tgagcttgg tatcagtcgt tctgttattg aaaaagtgag agatggcgag       120
cgaaaaatag agaatctaac gctcgaaaca attattaaag tccagaaatg gatagattcg     180
ggcaaatata ccttctctta tgattattcc gacttgatag aagagttgga agaagatatt     240
gcagaaggct tggtagatga gtatatctac gtagtcagag gtccgtataa tgaactttta    300
gataaatgcc caataattga ctactactac acttctgaag agattgaaga aggagatctc     360
gcagagaaga ccctaacagc ttctgtcttg gctgaaatga aaaggacaa cgaaatcttt      420 taa                                                                   423
```

<210> SEQ ID NO 286
<211> LENGTH: 140
<212> TYPE: PRT
<213> ORGANISM: Bacteriophage D4154

<400> SEQUENCE: 286

Met Lys Ile Asn Thr Thr Arg Val Lys Met Val Leu Lys Asn Lys Val

```
            1               5                  10                 15
          Ile Pro Ala Ile Tyr Leu Glu Asn Glu Leu Gly Ile Ser Arg Ser Val
                         20                  25                  30

Ile Glu Lys Val Arg Asp Gly Glu Arg Lys Ile Glu Asn Leu Thr Leu
                         35                  40                  45

Glu Thr Ile Ile Lys Val Gln Lys Trp Ile Asp Ser Gly Lys Tyr Thr
                         50                  55                  60

Phe Ser Tyr Asp Tyr Ser Asp Leu Ile Glu Glu Leu Glu Glu Asp Ile
           65                  70                  75                  80

Ala Glu Gly Leu Val Asp Glu Tyr Ile Tyr Val Arg Gly Pro Tyr
                             85                  90                  95

Asn Glu Leu Leu Asp Lys Cys Pro Ile Ile Asp Tyr Tyr Tyr Thr Ser
                         100                 105                 110

Glu Glu Ile Glu Glu Gly Asp Leu Ala Glu Lys Thr Leu Thr Ala Ser
                         115                 120                 125

Val Leu Ala Glu Met Lys Lys Asp Asn Glu Ile Phe
                         130                 135                 140
```

<210> SEQ ID NO 287
<211> LENGTH: 423
<212> TYPE: DNA
<213> ORGANISM: Bacteriophage D4160

<400> SEQUENCE: 287

```
atgaaaatca atacgacaag aattaaaatg gtcttgaaga atgaggctat acctgctatt      60
tatttagaaa atgagcttgg tatcagtcgt tctgttattg aaaaagtgag agaagacgag     120
agcgaattta aaatctaac tcttgatgtt gttgcgaaaa ttcaaaagtg gattgatgat     180
ggcaattaca cgtttagtta tgattacagt gaatttatcg aggaattaga agaagatctc     240
gctgagggtt taatagatga ttacctattc gttgttcgtg agattatga cgaagcctta      300
ggaaaatgtc ccatcattga ctattactac acttccgaag aaattgaaga aggagatctc     360
gcagagaaga ccctaacagc ttctgtcttg gctgaaatga aaaaggacaa cggaatctt t    420
taa                                                                   423
```

<210> SEQ ID NO 288
<211> LENGTH: 140
<212> TYPE: PRT
<213> ORGANISM: Bacteriophage D4160

<400> SEQUENCE: 288

```
          Met Lys Ile Asn Thr Thr Arg Ile Lys Met Val Leu Lys Asn Glu Ala
           1               5                  10                  15

Ile Pro Ile Tyr Leu Glu Asn Glu Leu Gly Ile Ser Arg Ser Val
                         20                  25                  30

Ile Glu Lys Val Arg Glu Asp Glu Ser Glu Phe Lys Asn Leu Thr Leu
                         35                  40                  45

Asp Val Ala Lys Ile Gln Lys Trp Ile Asp Asp Gly Asn Tyr Thr
                         50                  55                  60

Phe Ser Tyr Asp Tyr Ser Glu Phe Ile Glu Glu Leu Glu Glu Asp Leu
           65                  70                  75                  80

Ala Glu Gly Leu Ile Asp Asp Tyr Leu Phe Val Val Arg Gly Asp Tyr
                             85                  90                  95

Asp Glu Ala Leu Gly Lys Cys Pro Ile Ile Asp Tyr Tyr Tyr Thr Ser
                         100                 105                 110
```

Glu Glu Ile Glu Glu Gly Asp Leu Ala Glu Lys Thr Leu Thr Ala Ser
            115                 120                 125

Val Leu Ala Glu Met Lys Lys Asp Asn Gly Ile Phe
    130                 135                 140

<210> SEQ ID NO 289
<211> LENGTH: 423
<212> TYPE: DNA
<213> ORGANISM: Bacteriophage D5691

<400> SEQUENCE: 289
atgaaaatca atacaacaag agtcaacatg gtcttgaaga acgaggctat acctgctgat      60
tatttagaga acgtgattgg tatcagtcgt tccgttattg aaagagtgag agaagatgag     120
agcggattta aaaatttaac tcttgatgtt attgcgaaaa ttcaaaagtg gatagatgaa     180
ggaaactaca cgtttagtta tgattacagc gacttgatag aagagttgga agaagatatt     240
gcagaaggct tggtagatga gtatatctac gtagtcagag gtccttataa tgagatttta     300
gagaaatgcc caatcattga ctactactac acttctgaag aaattgaaga ggagatctc     360 gcagagaaga ccctgacagc ctctgcctta gctgaaatga agttagacaa caaaatcttt     420
taa                                                                   423

<210> SEQ ID NO 290
<211> LENGTH: 140
<212> TYPE: PRT
<213> ORGANISM: Bacteriophage D5691

<400> SEQUENCE: 290

Met Lys Ile Asn Thr Thr Arg Val Asn Met Val Leu Lys Asn Glu Ala
1               5                   10                  15

Ile Pro Ala Asp Tyr Leu Glu Asn Val Ile Gly Ile Ser Arg Ser Val
                20                  25                  30

Ile Glu Arg Val Arg Glu Asp Glu Ser Gly Phe Lys Asn Leu Thr Leu
            35                  40                  45

Asp Val Ile Ala Lys Ile Gln Lys Trp Ile Asp Glu Gly Asn Tyr Thr
    50                  55                  60

Phe Ser Tyr Asp Tyr Ser Asp Leu Ile Glu Glu Leu Glu Glu Asp Ile
65                  70                  75                  80

Ala Glu Gly Leu Val Asp Glu Tyr Ile Tyr Val Val Arg Gly Pro Tyr
                85                  90                  95

Asn Glu Ile Leu Glu Lys Cys Pro Ile Ile Asp Tyr Tyr Tyr Thr Ser
            100                 105                 110

Glu Glu Ile Glu Glu Gly Asp Leu Ala Glu Lys Thr Leu Thr Ala Ser
            115                 120                 125

Ala Leu Ala Glu Met Lys Leu Asp Asn Lys Ile Phe
    130                 135                 140

<210> SEQ ID NO 291
<211> LENGTH: 423
<212> TYPE: DNA
<213> ORGANISM: Bacteriophage D7035

<400> SEQUENCE: 291
atgaaaatca atacgacaag agttaacatg gtcttgaaga acaaagctat accagctaat      60
tatttagaaa ggaactggg aataaaccgt tcgacaatta caagagtgcg gaacggtgag     120
agaaagcttg agaatctaac gctcgaaaca atcataaaag tccagaaatg gatagattcg     180

```
ggcaaatata cattctctta tgattattcc gacttgatag aagagttgga agaagatatt    240
gaagaaggcc taacagatga gtatatctat gttgtcagag gtccgtataa tgaactttta    300
gagaaatgcc aataattga ctactactac acttctgaag agattgaaga aggagatctc    360
acagagaaga ccctaacagc ttctgccttg gctgagatga acaggataa cgaaatcttt    420 taa                                                                 423
```

```
<210> SEQ ID NO 292
<211> LENGTH: 140
<212> TYPE: PRT
<213> ORGANISM: Bacteriophage D7035

<400> SEQUENCE: 292
```

```
Met Lys Ile Asn Thr Thr Arg Val Asn Met Val Leu Lys Asn Lys Ala
1               5                   10                  15

Ile Pro Ala Asn Tyr Leu Glu Lys Glu Leu Gly Ile Asn Arg Ser Thr
            20                  25                  30

Ile Thr Arg Val Arg Asn Gly Glu Arg Lys Leu Glu Asn Leu Thr Leu
        35                  40                  45

Glu Thr Ile Ile Lys Val Gln Lys Trp Ile Asp Ser Gly Lys Tyr Thr
    50                  55                  60

Phe Ser Tyr Asp Tyr Ser Asp Leu Ile Glu Glu Leu Glu Glu Asp Ile
65                  70                  75                  80

Glu Glu Gly Leu Thr Asp Glu Tyr Ile Tyr Val Val Arg Gly Pro Tyr
                85                  90                  95

Asn Glu Leu Leu Glu Lys Cys Pro Ile Ile Asp Tyr Tyr Tyr Thr Ser
            100                 105                 110

Glu Glu Ile Glu Glu Gly Asp Leu Thr Glu Lys Thr Leu Thr Ala Ser
        115                 120                 125

Ala Leu Ala Glu Met Lys Gln Asp Asn Glu Ile Phe
    130                 135                 140
```

```
<210> SEQ ID NO 293
<211> LENGTH: 423
<212> TYPE: DNA
<213> ORGANISM: Bacteriophage O1205

<400> SEQUENCE: 293
```

```
atgataataa acactgcacg agttgaatta gttttaatga caaagctat accagcaaat     60 tatttagaaa gcgaaatagg tattagtcgt tcagcaatta ctagggtaag aaatgatgag    120
cgaaaaatag agaatctgaa gctcgaaaca atcataaaag tccagaaatg gatagattcg    180
ggcaaataca cattctctta tgattattcc gacttgatag aagagttgga agaagatatt    240
gcaaaaggtc tggcaggtaa gtatatctac gttgtcagag gaccatacaa cgagatttta    300
gagaaatgtc caatcattga ctattactac acttccgaag agattgaaga aggagagctc    360
gcagagaaga ccttgacagc ttctgtcttg gctgaaatga gtcagacaa cgaaatcttt    420 taa                                                                 423
```

```
<210> SEQ ID NO 294
<211> LENGTH: 140
<212> TYPE: PRT
<213> ORGANISM: Bacteriophage O1205

<400> SEQUENCE: 294
```

```
Met Ile Ile Asn Thr Ala Arg Val Glu Leu Val Leu Met Asn Lys Ala
1               5                   10                  15
```

Ile Pro Ala Asn Tyr Leu Glu Ser Glu Ile Gly Ile Ser Arg Ser Ala
                20                  25                  30

Ile Thr Arg Val Arg Asn Asp Glu Arg Lys Ile Glu Asn Leu Lys Leu
            35                  40                  45

Glu Thr Ile Ile Lys Val Gln Lys Trp Ile Asp Ser Gly Lys Tyr Thr
    50                  55                  60

Phe Ser Tyr Asp Tyr Ser Asp Leu Ile Glu Glu Leu Glu Glu Asp Ile
65                  70                  75                  80

Ala Lys Gly Leu Ala Gly Lys Tyr Ile Tyr Val Val Arg Gly Pro Tyr
                85                  90                  95

Asn Glu Ile Leu Glu Lys Cys Pro Ile Ile Asp Tyr Tyr Tyr Thr Ser
            100                 105                 110

Glu Glu Ile Glu Glu Gly Glu Leu Ala Glu Lys Thr Leu Thr Ala Ser
        115                 120                 125

Val Leu Ala Glu Met Lys Ser Asp Asn Glu Ile Phe
    130                 135                 140

<210> SEQ ID NO 295
<211> LENGTH: 396
<212> TYPE: DNA
<213> ORGANISM: Bacteriophage Proph1

<400> SEQUENCE: 295
atggtcttga agaacgaggc tatacctgct gattatttag agagcgagat tggcattagt      60
cgttccgttg ttgaaaaagt gagagaagat gagagcgaat ttaaaaattt aactcttgat     120
gttgttgcga aaattcaaaa gtggattgat gatggaaact acactttcag ctatgattac     180
agcgacctaa tcgaagaact ggaggaagat attgcagaag gcttggtaga tgagtatatc     240
tacgtagtca gaggtccgta taatgaactt ttagagaaat gcccaatcat tgactactac     300
tatacttctg aagaaattga gaagggggat cttgcagaga agaccttgat aacttctgtc     360
ttagctgaaa tgaagtcaga caacaaaatc ttttaa                               396

<210> SEQ ID NO 296
<211> LENGTH: 131
<212> TYPE: PRT
<213> ORGANISM: Bacteriophage Proph1

<400> SEQUENCE: 296

Met Val Leu Lys Asn Glu Ala Ile Pro Ala Asp Tyr Leu Glu Ser Glu
1               5                   10                  15

Ile Gly Ile Ser Arg Ser Val Val Glu Lys Val Arg Glu Asp Glu Ser
            20                  25                  30

Glu Phe Lys Asn Leu Thr Leu Asp Val Val Ala Lys Ile Gln Lys Trp
        35                  40                  45

Ile Asp Asp Gly Asn Tyr Thr Phe Ser Tyr Tyr Ser Asp Leu Ile
    50                  55                  60

Glu Glu Leu Glu Glu Asp Ile Ala Glu Gly Leu Val Asp Glu Tyr Ile
65                  70                  75                  80

Tyr Val Val Arg Gly Pro Tyr Asn Glu Leu Leu Glu Lys Cys Pro Ile
                85                  90                  95

Ile Asp Tyr Tyr Tyr Thr Ser Glu Glu Ile Glu Glu Gly Asp Leu Ala
            100                 105                 110

Glu Lys Thr Leu Ile Thr Ser Val Leu Ala Glu Met Lys Ser Asp Asn
        115                 120                 125

Lys Ile Phe
    130

<210> SEQ ID NO 297
<211> LENGTH: 423
<212> TYPE: DNA
<213> ORGANISM: Bacteriophage Sfi21

<400> SEQUENCE: 297

| | |
|---|---:|
| atgataataa atgttgcacg agttgaaaca gttttaatga acaatgctat accagctaat | 60 |
| tatttagaaa gagaaatagg aattagtcgt tcagcaatta ctagggtaag aaacggtgag | 120 |
| cgaaaaatag agaatctgaa gctcgaaaca atcataaaag tccagaaatg gatagattcg | 180 |
| ggcaaatata cattctctta tgattattcc gacttgatag aagagttgga agaagatatt | 240 |
| gcagaaggac taacggatga gtatatctac gttgtcagag gagcatacaa cgagattta | 300 |
| gagaaatgcc caatcattga ctattactac acttccgaag agattgaaga aggagatctc | 360 |
| gcagagaaga ccctaacagc ttctgccttg tctgaaatga acaggacaa cgaaatcttt | 420 |
| taa | 423 |

<210> SEQ ID NO 298
<211> LENGTH: 140
<212> TYPE: PRT
<213> ORGANISM: Bacteriophage Sfi21

<400> SEQUENCE: 298

Met Ile Ile Asn Val Ala Arg Val Glu Thr Val Leu Met Asn Asn Ala
1               5                   10                  15

Ile Pro Ala Asn Tyr Leu Glu Arg Glu Ile Gly Ile Ser Arg Ser Ala
            20                  25                  30

Ile Thr Arg Val Arg Asn Gly Glu Arg Lys Ile Glu Asn Leu Lys Leu
        35                  40                  45

Glu Thr Ile Ile Lys Val Gln Lys Trp Ile Asp Ser Gly Lys Tyr Thr
    50                  55                  60

Phe Ser Tyr Asp Tyr Ser Asp Leu Ile Glu Glu Leu Glu Glu Asp Ile
65                  70                  75                  80

Ala Glu Gly Leu Thr Asp Glu Tyr Ile Tyr Val Val Arg Gly Ala Tyr
                85                  90                  95

Asn Glu Ile Leu Glu Lys Cys Pro Ile Ile Asp Tyr Tyr Tyr Thr Ser
            100                 105                 110

Glu Glu Ile Glu Glu Gly Asp Leu Ala Glu Lys Thr Leu Thr Ala Ser
        115                 120                 125

Ala Leu Ser Glu Met Lys Gln Asp Asn Glu Ile Phe
    130                 135                 140

<210> SEQ ID NO 299
<211> LENGTH: 423
<212> TYPE: DNA
<213> ORGANISM: Bacteriophage TP-778L

<400> SEQUENCE: 299

| | |
|---|---:|
| atgataataa acactgcacg agttgaatta gttttaatga acaaagctat accagcaaat | 60 |
| tatttagaaa gagagatagg aattagtcgt tcagcaatta caagagttcg gaacggtgag | 120 |
| agaaagcttg agaacctaac ccttgaaact attatgacta ttcaaaagtg gatagatgaa | 180 |
| ggaaactatc gctttagtta cgattatagt gagcttatcg aagaccttga ggaagatatt | 240 |
| gcagaaggcc taacagatga gtatatctat gttgtcagag gtccgtataa tgaactttta | 300 |

```
gagaaatgtc caatcattga ctattactac acttccgaag agattgaaga aggaaatctc      360
gcagagaaga ccttgacagc ttctgtcttg gctgaaatga aacaggacaa cgaaatattt      420
taa                                                                    423
```

<210> SEQ ID NO 300
<211> LENGTH: 140
<212> TYPE: PRT
<213> ORGANISM: Bacteriophage TP-778L

<400> SEQUENCE: 300

```
Met Ile Ile Asn Thr Ala Arg Val Glu Leu Val Leu Met Asn Lys Ala
1               5                   10                  15

Ile Pro Ala Asn Tyr Leu Glu Arg Glu Ile Gly Ile Ser Arg Ser Ala
            20                  25                  30

Ile Thr Arg Val Arg Asn Gly Glu Arg Lys Leu Glu Asn Leu Thr Leu
        35                  40                  45

Glu Thr Ile Met Thr Ile Gln Lys Trp Ile Asp Glu Gly Asn Tyr Arg
    50                  55                  60

Phe Ser Tyr Asp Tyr Ser Glu Leu Ile Glu Asp Leu Glu Glu Asp Ile
65                  70                  75                  80

Ala Glu Gly Leu Thr Asp Glu Tyr Ile Tyr Val Arg Gly Pro Tyr
                85                  90                  95

Asn Glu Leu Leu Glu Lys Cys Pro Ile Ile Asp Tyr Tyr Tyr Thr Ser
            100                 105                 110

Glu Glu Ile Glu Glu Gly Asn Leu Ala Glu Lys Thr Leu Thr Ala Ser
        115                 120                 125

Val Leu Ala Glu Met Lys Gln Asp Asn Glu Ile Phe
    130                 135                 140
```

<210> SEQ ID NO 301
<211> LENGTH: 423
<212> TYPE: DNA
<213> ORGANISM: Bacteriophage TP-J34

<400> SEQUENCE: 301

```
atgaaaatca atacgacaag aattaaaatg gtcttgaaga atgaggctat acctgctatt      60
tatttagaaa atgagcttgg tatcagtcgt tctattattg aaaaagtgag agatgatgag      120
agcgaattta aaatctaac tcttgaaact attataaaaa tacaaagttt gataaattcg      180
ggcaaatata cattctctta tgattattcc gacttgatag aagagttgga agaagatatt      240
gcagaaggac taacggatga gtatatctac gttgtcagag gaccatacaa cgagatttta      300
gagaaatgtc caatcattga ctattactac acttccgaag agattgaaga aggaaatctc      360
gcagagaaga ccttgacagc ttctgtcttg gctgaaatga aacaggacaa cgaaatattt      420
taa                                                                    423
```

<210> SEQ ID NO 302
<211> LENGTH: 140
<212> TYPE: PRT
<213> ORGANISM: Bacteriophage TP-J34

<400> SEQUENCE: 302

```
Met Lys Ile Asn Thr Thr Arg Ile Lys Met Val Leu Lys Asn Glu Ala
1               5                   10                  15

Ile Pro Ala Ile Tyr Leu Glu Asn Glu Leu Gly Ile Ser Arg Ser Ile
            20                  25                  30
```

```
Ile Glu Lys Val Arg Asp Asp Glu Ser Glu Phe Lys Asn Leu Thr Leu
            35                  40                  45

Glu Thr Ile Ile Lys Ile Gln Ser Leu Ile Asn Ser Gly Lys Tyr Thr
     50                  55                  60

Phe Ser Tyr Asp Tyr Ser Asp Leu Ile Glu Glu Leu Glu Glu Asp Ile
 65                  70                  75                  80

Ala Glu Gly Leu Thr Asp Glu Tyr Ile Tyr Val Val Arg Gly Pro Tyr
                 85                  90                  95

Asn Glu Ile Leu Glu Lys Cys Pro Ile Ile Asp Tyr Tyr Tyr Thr Ser
            100                 105                 110

Glu Glu Ile Glu Glu Gly Asn Leu Ala Glu Lys Thr Leu Thr Ala Ser
            115                 120                 125

Val Leu Ala Glu Met Lys Gln Asp Asn Glu Ile Phe
            130                 135                 140

<210> SEQ ID NO 303
<211> LENGTH: 423
<212> TYPE: DNA
<213> ORGANISM: Bacteriophage Proph1

<400> SEQUENCE: 303
atgaaaatca atacgacaag agttaaaatg gtcttgaaga atgaggttat acctgctatt      60
tatttagaga atgagcttgg tatcagtcgt tctgttattg aaaaagtgag agatggcgag     120
cgaaaaatag agaatctaac tcttgaaacg attataaaaa ttcaaaagtg gatcgatgat     180
ggaaactaca ctttcagcta cgactatagc gacctaatcg aagaactgga ggaagatatt     240
gcagaaggct tggtagatga gtatatctac gtagtcagag gtccgtataa tgaacttta      300
gagaaatgcc caatcattga ctactactat acttctgaag aaattgaaga agggatctt      360
gcagagaaga ccttgataac ttctgtctta gctgaaatga agtcagacaa caaaatcttt     420
taa                                                                    423

<210> SEQ ID NO 304
<211> LENGTH: 140
<212> TYPE: PRT
<213> ORGANISM: Bacteriophage Proph1

<400> SEQUENCE: 304

Met Lys Ile Asn Thr Thr Arg Val Lys Met Val Leu Lys Asn Glu Val
 1               5                  10                  15

Ile Pro Ala Ile Tyr Leu Glu Asn Glu Leu Gly Ile Ser Arg Ser Val
             20                  25                  30

Ile Glu Lys Val Arg Asp Gly Glu Arg Lys Ile Glu Asn Leu Thr Leu
            35                  40                  45

Glu Thr Ile Ile Lys Ile Gln Lys Trp Ile Asp Asp Gly Asn Tyr Thr
     50                  55                  60

Phe Ser Tyr Asp Tyr Ser Asp Leu Ile Glu Glu Leu Glu Glu Asp Ile
 65                  70                  75                  80

Ala Glu Gly Leu Val Asp Glu Tyr Ile Tyr Val Val Arg Gly Pro Tyr
                 85                  90                  95

Asn Glu Leu Leu Glu Lys Cys Pro Ile Ile Asp Tyr Tyr Tyr Thr Ser
            100                 105                 110

Glu Glu Ile Glu Glu Gly Asp Leu Ala Glu Lys Thr Leu Ile Thr Ser
            115                 120                 125

Val Leu Ala Glu Met Lys Ser Asp Asn Lys Ile Phe
```

<210> SEQ ID NO 305
<211> LENGTH: 183
<212> TYPE: DNA
<213> ORGANISM: Bacteriophage D1126

<400> SEQUENCE: 305

```
atggaccaag ttaaattagt tttaatgaac aaagctatac cagctaatta tttagaaaga      60
caaactggtg ttagtcgttc agcaattact agggttagaa atggcgagcg aaaaatagaa     120
aatctaacac ttgaaacaat tattaaaatt caaagttgga tagactctga aatacgata     180
tag                                                                    183
```

<210> SEQ ID NO 306
<211> LENGTH: 60
<212> TYPE: PRT
<213> ORGANISM: Bacteriophage D1126

<400> SEQUENCE: 306

```
Met Asp Gln Val Lys Leu Val Leu Met Asn Lys Ala Ile Pro Ala Asn
1               5                   10                  15

Tyr Leu Glu Arg Gln Thr Gly Val Ser Arg Ser Ala Ile Thr Arg Val
            20                  25                  30

Arg Asn Gly Glu Arg Lys Ile Glu Asn Leu Thr Leu Glu Thr Ile Ile
        35                  40                  45

Lys Ile Gln Ser Trp Ile Asp Ser Glu Asn Thr Ile
    50                  55                  60
```

<210> SEQ ID NO 307
<211> LENGTH: 195
<212> TYPE: DNA
<213> ORGANISM: Bacteriophage D1128

<400> SEQUENCE: 307

```
atgataatta atgtggaccg agttaaagcg gttttaatgg ataaatctat accggcaaat      60
tatttagaaa tgcaaactgg cattagtcgt tcggcaatta ccagagtaag gaacggcgag     120
cgaaagatag aaaatctaac tatcggaaca attattaaaa ttcaaagttg gttggataga     180
aggatgatta gataa                                                       195
```

<210> SEQ ID NO 308
<211> LENGTH: 64
<212> TYPE: PRT
<213> ORGANISM: Bacteriophage D1128

<400> SEQUENCE: 308

```
Met Ile Ile Asn Val Asp Arg Val Lys Ala Val Leu Met Asp Lys Ser
1               5                   10                  15

Ile Pro Ala Asn Tyr Leu Glu Met Gln Thr Gly Ile Ser Arg Ser Ala
            20                  25                  30

Ile Thr Arg Val Arg Asn Gly Glu Arg Lys Ile Glu Asn Leu Thr Ile
        35                  40                  45

Gly Thr Ile Ile Lys Ile Gln Ser Trp Leu Asp Arg Arg Met Ile Arg
    50                  55                  60
```

<210> SEQ ID NO 309
<211> LENGTH: 183
<212> TYPE: DNA
<213> ORGANISM: Bacteriophage D4250

<400> SEQUENCE: 309

```
atggaccgag ttaaattagt tttaatgaac aaagctatac cagcaaattt tttagaaaga       60
caaactggag ttagtcgttc agcaattact agggttagaa ataacgagcg aaaaatagaa      120
aatctaacac ttgaaacaat tattaaaatt caaagttgga tagattctga caatacgata      180
tag                                                                    183
```

<210> SEQ ID NO 310
<211> LENGTH: 60
<212> TYPE: PRT
<213> ORGANISM: Bacteriophage D4250

<400> SEQUENCE: 310

```
Met Asp Arg Val Lys Leu Val Leu Met Asn Lys Ala Ile Pro Ala Asn
1               5                   10                  15

Phe Leu Glu Arg Gln Thr Gly Val Ser Arg Ser Ala Ile Thr Arg Val
                20                  25                  30

Arg Asn Asn Glu Arg Lys Ile Glu Asn Leu Thr Leu Glu Thr Ile Ile
            35                  40                  45

Lys Ile Gln Ser Trp Ile Asp Ser Asp Asn Thr Ile
        50                  55                  60
```

<210> SEQ ID NO 311
<211> LENGTH: 228
<212> TYPE: DNA
<213> ORGANISM: Bacteriophage D4252

<400> SEQUENCE: 311

```
ttgggaagaa ggataaggat aaagataaag ataatgataa taaatatgga ccaagttaaa       60 ttagtttta tgaacaaaga tataccagct aattttatag aaagacaaac tggtgttagt      120
cgttcagcaa ttactaaggt tagaaatggt gagcgaaaaa tagaaaatct aagacttgaa      180
acaattatta aaattcaaag ttggatagac tctgggaata cgatatag                   228
```

<210> SEQ ID NO 312
<211> LENGTH: 75
<212> TYPE: PRT
<213> ORGANISM: Bacteriophage D4252

<400> SEQUENCE: 312

```
Met Gly Arg Arg Ile Arg Ile Lys Ile Lys Ile Met Ile Ile Asn Met
1               5                   10                  15

Asp Gln Val Lys Leu Val Leu Met Asn Lys Asp Ile Pro Ala Asn Phe
                20                  25                  30

Ile Glu Arg Gln Thr Gly Val Ser Arg Ser Ala Ile Thr Lys Val Arg
            35                  40                  45

Asn Gly Glu Arg Lys Ile Glu Asn Leu Arg Leu Glu Thr Ile Ile Lys
        50                  55                  60

Ile Gln Ser Trp Ile Asp Ser Gly Asn Thr Ile
65                  70                  75
```

<210> SEQ ID NO 313
<211> LENGTH: 216
<212> TYPE: DNA
<213> ORGANISM: Bacteriophage D4273

<400> SEQUENCE: 313

```
ttgggaagta ggataaggat aatgataatt aatgtggacc gagttaaagc ggttttaatg       60
```

```
gataaatcta taccggcaaa ttatttagaa atgcaaactg gcattagtcg ttcggcaatt    120
accagagtaa ggaacggcga gcgaaagata gaaaatctaa ctatcggaac aattattaaa    180
attcaaagtt ggttggatag aaggatgatt agataa                              216
```

<210> SEQ ID NO 314
<211> LENGTH: 71
<212> TYPE: PRT
<213> ORGANISM: Bacteriophage D4273

<400> SEQUENCE: 314

```
Met Gly Ser Arg Ile Arg Ile Met Ile Ile Asn Val Asp Arg Val Lys
1               5                   10                  15

Ala Val Leu Met Asp Lys Ser Ile Pro Ala Asn Tyr Leu Glu Met Gln
            20                  25                  30

Thr Gly Ile Ser Arg Ser Ala Ile Thr Arg Val Arg Asn Gly Glu Arg
        35                  40                  45

Lys Ile Glu Asn Leu Thr Ile Gly Thr Ile Lys Ile Gln Ser Trp
    50                  55                  60

Leu Asp Arg Arg Met Ile Arg
65                  70
```

<210> SEQ ID NO 315
<211> LENGTH: 195
<212> TYPE: DNA
<213> ORGANISM: Bacteriophage D4276

<400> SEQUENCE: 315

```
atgataataa atatggaccg agttaaatta gttttaatga caaagatat accagctaat     60 tttttagaaa gacaaactgg tgttagtcgt tcagcaatta ctaaggttag aaatggtgag    120
cgaaaaatag aaaatctaac acttgaaaca attattaaaa ttcaaagttg gttagactct    180
gagaatacga tatag                                                     195
```

<210> SEQ ID NO 316
<211> LENGTH: 64
<212> TYPE: PRT
<213> ORGANISM: Bacteriophage D4276

<400> SEQUENCE: 316

```
Met Ile Ile Asn Met Asp Arg Val Lys Leu Val Leu Met Asn Lys Asp
1               5                   10                  15

Ile Pro Ala Asn Phe Leu Glu Arg Gln Thr Gly Val Ser Arg Ser Ala
            20                  25                  30

Ile Thr Lys Val Arg Asn Gly Glu Arg Lys Ile Glu Asn Leu Thr Leu
        35                  40                  45

Glu Thr Ile Ile Lys Ile Gln Ser Trp Leu Asp Ser Glu Asn Thr Ile
    50                  55                  60
```

<210> SEQ ID NO 317
<211> LENGTH: 195
<212> TYPE: DNA
<213> ORGANISM: Bacteriophage D6252

<400> SEQUENCE: 317

```
atgataataa acactgcacg agttgaatta gttttaatga caaagctat accagctaat     60 tttttagaaa gacaaactgg tgttagtcgt tcagcaatta ctagggttag agatggtgag    120
cgaaagatag aaaatctaac acttgaaaca attattaaaa ttcaaagttg gatagactct    180
```

```
gacaataaga tatag                                              195

<210> SEQ ID NO 318
<211> LENGTH: 64
<212> TYPE: PRT
<213> ORGANISM: Bacteriophage D6252

<400> SEQUENCE: 318

Met Ile Ile Asn Thr Ala Arg Val Glu Leu Val Leu Met Asn Lys Ala
1               5                   10                  15

Ile Pro Ala Asn Phe Leu Glu Arg Gln Thr Gly Val Ser Arg Ser Ala
            20                  25                  30

Ile Thr Arg Val Arg Asp Gly Glu Arg Lys Ile Glu Asn Leu Thr Leu
        35                  40                  45

Glu Thr Ile Ile Lys Ile Gln Ser Trp Ile Asp Ser Asp Asn Lys Ile
    50                  55                  60

<210> SEQ ID NO 319
<211> LENGTH: 216
<212> TYPE: DNA
<213> ORGANISM: Bacteriophage D6938

<400> SEQUENCE: 319
atgacaaaaa ggataaagac aatgataata aatatggacc gagttaaatt agttttaatg     60
aaaaaagata taccagctaa tttttagaa agacaaactg gtgttagtcg ttcagcaatt    120
actagggtta gaaatggtga gcgaaaaata gaaaatctaa cacttgaaac aattattaaa    180
attcaaagtt ggatagactc tgagaatacg atatag                              216

<210> SEQ ID NO 320
<211> LENGTH: 71
<212> TYPE: PRT
<213> ORGANISM: Bacteriophage D6938

<400> SEQUENCE: 320

Met Thr Lys Arg Ile Lys Thr Met Ile Ile Asn Met Asp Arg Val Lys
1               5                   10                  15

Leu Val Leu Met Lys Lys Asp Ile Pro Ala Asn Phe Leu Glu Arg Gln
            20                  25                  30

Thr Gly Val Ser Arg Ser Ala Ile Thr Arg Val Arg Asn Gly Glu Arg
        35                  40                  45

Lys Ile Glu Asn Leu Thr Leu Glu Thr Ile Ile Lys Ile Gln Ser Trp
    50                  55                  60

Ile Asp Ser Glu Asn Thr Ile
65                  70

<210> SEQ ID NO 321
<211> LENGTH: 195
<212> TYPE: DNA
<213> ORGANISM: Bacteriophage D7163

<400> SEQUENCE: 321
atgataataa acactgcacg agttgaatta gttttaatga caaagctat accagcaaat      60 tatttagaaa gacaaactgg tgttagtcgt tcagcaatta ctagggtgag gaatggtgag    120
cgaaagatag aaaatctaac acttgaaaca attattaaaa ttcaaagttg gatagactct    180
gacaataaga tatag                                                    195
```

```
<210> SEQ ID NO 322
<211> LENGTH: 64
<212> TYPE: PRT
<213> ORGANISM: Bacteriophage D7163

<400> SEQUENCE: 322

Met Ile Ile Asn Thr Ala Arg Val Glu Leu Val Leu Met Asn Lys Ala
1               5                   10                  15

Ile Pro Ala Asn Tyr Leu Glu Arg Gln Thr Gly Val Ser Arg Ser Ala
            20                  25                  30

Ile Thr Arg Val Arg Asn Gly Glu Arg Lys Ile Glu Asn Leu Thr Leu
        35                  40                  45

Glu Thr Ile Ile Lys Ile Gln Ser Trp Ile Asp Ser Asp Asn Lys Ile
    50                  55                  60

<210> SEQ ID NO 323
<211> LENGTH: 195
<212> TYPE: DNA
<213> ORGANISM: Bacteriophage P4761

<400> SEQUENCE: 323
atgataatta atgtggaccg agttaaagcg gttttaatgg ataaatctat atcagcaaat      60
tatttagaaa tagaaactgg cattagtcgt tcggcaatta ccagagtaag gaacggcgag     120
cgaaagatag aaaatctaac tatcggaaca attattaaaa ttcaaagttg gttggataga     180
aggatgatta gataa                                                     195

<210> SEQ ID NO 324
<211> LENGTH: 64
<212> TYPE: PRT
<213> ORGANISM: Bacteriophage P4761

<400> SEQUENCE: 324

Met Ile Ile Asn Val Asp Arg Val Lys Ala Val Leu Met Asp Lys Ser
1               5                   10                  15

Ile Ser Ala Asn Tyr Leu Glu Ile Glu Thr Gly Ile Ser Arg Ser Ala
            20                  25                  30

Ile Thr Arg Val Arg Asn Gly Glu Arg Lys Ile Glu Asn Leu Thr Ile
        35                  40                  45

Gly Thr Ile Ile Lys Ile Gln Ser Trp Leu Asp Arg Arg Met Ile Arg
    50                  55                  60

<210> SEQ ID NO 325
<211> LENGTH: 513
<212> TYPE: DNA
<213> ORGANISM: Bacteriophage D4090

<400> SEQUENCE: 325
atggtagtaa aaattaaaag aattgtttgg gttaaaaata atggttttga atcagagaa      60 cgtgagctag attgttactt taaaaatgat ggaagttaca aaaagagttc tggagattgg     120
gaaagtcgtt gttatgaaca attcggagat gaatttcaac tcattagaga tagcaaagca     180
ttagaatctt atagtggttt gacaagagat tatcaaaaag acttaaaaat cttgcgtaag     240
tataaacata gagatatgac tatttcagag tatgaagcaa tgaaatatgt cgtggagaat     300
tggacaaaag aatggtctca gtcacccttac agttatagtt tttatagttc aaaaaacatt    360 gactgggggtt acaaaccaga aggcagctta cgcatttctg accattggaa ttttggcgaa    420
aatggtgaac attgcccaac agctgaacca gttgatggct gggcagtatg taagtttgaa     480
```

```
aatggtaaat atcatttaat taaaaagttt taa                                    513
```

<210> SEQ ID NO 326
<211> LENGTH: 170
<212> TYPE: PRT
<213> ORGANISM: Bacteriophage D4090

<400> SEQUENCE: 326

```
Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Ser Lys Ala Leu Glu Ser Tyr
    50                  55                  60

Ser Gly Leu Thr Arg Asp Tyr Gln Lys Asp Leu Lys Ile Leu Arg Lys
65                  70                  75                  80

Tyr Lys His Arg Asp Met Thr Ile Ser Glu Tyr Ala Met Lys Tyr
                85                  90                  95

Val Val Glu Asn Trp Thr Lys Glu Trp Ser Gln Ser Pro Tyr Ser Tyr
            100                 105                 110

Ser Phe Tyr Ser Ser Lys Asn Ile Asp Trp Gly Tyr Lys Pro Glu Gly
        115                 120                 125

Ser Leu Arg Ile Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170
```

<210> SEQ ID NO 327
<211> LENGTH: 513
<212> TYPE: DNA
<213> ORGANISM: Bacteriophage D4254

<400> SEQUENCE: 327

```
atggtagtaa aaattaaaag aattgtttgg gttaaaaata atggttttga aatcagagaa    60
cgtgagctag attgttactt taaaaatgat ggaagttaca aaaaaagttc tggagattgg   120
gaaagtcgtt gttatgaaca attcggagat gaatttcaac tcattagaga tagcaaagca   180
ttagaatctt atagtggttt gacaagagat tatcaaaaag acttaaaaat cttgcgtaag   240
tataaacata gagatatgac tatttcagag tatgaagcaa tgaaatatgt cgtggagaat   300
tggacaaaag agtggtcaca atcaccatac agcaatagtt tctatagctc aaagatatt   360 gattggggct acaaaccaga aggtagctta agagtctcag accattggaa ttttggcgaa   420
aatggtgaac attgcccaac agctgaacca gttgatggct gggcagtatg taagtttgaa   480
aatggtaaat atcatttaat taaaaagttt taa                                513
```

<210> SEQ ID NO 328
<211> LENGTH: 170
<212> TYPE: PRT
<213> ORGANISM: Bacteriophage D4254

<400> SEQUENCE: 328

```
Met Val Val Lys Ile Lys Arg Ile Val Trp Val Lys Asn Asn Gly Phe
1               5                   10                  15
```

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Ser Lys Ala Leu Glu Ser Tyr
    50                  55                  60

Ser Gly Leu Thr Arg Asp Tyr Gln Lys Asp Leu Lys Ile Leu Arg Lys
65                  70                  75                  80

Tyr Lys His Arg Asp Met Thr Ile Ser Glu Tyr Glu Ala Met Lys Tyr
                85                  90                  95

Val Val Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170

<210> SEQ ID NO 329
<211> LENGTH: 474
<212> TYPE: DNA
<213> ORGANISM: Bacteriophage D4368

<400> SEQUENCE: 329
atggtagtaa aaattaaaag aattgtttgg gttaaaaata atggttttga aatcagagaa      60
cgtgagctag attgttactt taaaaatgat ggaagttaca aaaagagttc tggagattgg     120
gaaagtcgtt gttatgaaca attcggtaat aaacttcaac ttattaaaga cagtaaaaaa     180
ttagaatcgt acaacggatt aacaaaagat tatcaaaaag atttaaaaat cttacgtaaa     240
tgtggacgtt cggaaatgaa tgcaacagag tacgaagcaa tgaaatatgt tgaagaaaac     300
tggacaaaag agtggtcaca atcaccatac agcaatagtt tctatagctc taaagatatt     360
gattggggct acaaaccaga aggtagctta agagtctcag accattggaa ttttggcgaa     420
aatggtgaac attgcccaac agctgaacca gttgatggct gggcagtatt ttga           474

<210> SEQ ID NO 330
<211> LENGTH: 157
<212> TYPE: PRT
<213> ORGANISM: Bacteriophage D4368

<400> SEQUENCE: 330

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asn Lys Leu Gln Leu Ile Lys Asp Ser Lys Lys Leu Glu Ser Tyr
    50                  55                  60

Asn Gly Leu Thr Lys Asp Tyr Gln Lys Asp Leu Lys Ile Leu Arg Lys
65                  70                  75                  80

Cys Gly Arg Ser Glu Met Asn Ala Thr Glu Tyr Glu Ala Met Lys Tyr

```
                    85                  90                  95
Val Glu Glu Asn Trp Thr Lys Glu Trp Ser Gln Ser Pro Tyr Ser Asn
                100                 105                 110

Ser Phe Tyr Ser Ser Lys Asp Ile Asp Trp Gly Tyr Lys Pro Glu Gly
                115                 120                 125

Ser Leu Arg Val Ser Asp His Trp Asn Phe Gly Glu Asn Gly Glu His
                130                 135                 140

Cys Pro Thr Ala Glu Pro Val Asp Gly Trp Ala Val Phe
145                 150                 155

<210> SEQ ID NO 331
<211> LENGTH: 513
<212> TYPE: DNA
<213> ORGANISM: Bacteriophage D5700

<400> SEQUENCE: 331
atggtagtaa aaattaaaag aattgtttgg gttaaaaata atggttttga aatcagagaa      60
cgtgagctag attgttactt taaaaatgat ggaagttaca aaaaaagttc tggagattgg     120
gaaagtcgtt gttatgaaca attcggagat gaatttcagc tcattagaga tagcaaagca     180
ttagaatctt atagtggttt gacaagagat tatcaaaaag acttaaaaat cttgcgtaag     240
tataaacata gagatatgac tatttcagag tatgaagcaa tgaaatatgt cgtggagaat     300
tggacaaaag agtggtcaca atcaccatac agcaatagtt tctatagctc aaagatatt     360 gattggggct acaaaccaga aggtagctta agagtctcag accattggaa ttttggcgaa     420
aatggtgaac attgcccaac agctgaacca gttgatggct gggcagtatg taagtttgaa     480
aatggtaaat atcatttaat taaaaagttt taa                                 513

<210> SEQ ID NO 332
<211> LENGTH: 170
<212> TYPE: PRT
<213> ORGANISM: Bacteriophage D5700

<400> SEQUENCE: 332

Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
                20                  25                  30

Tyr Lys Lys Ser Ser Gly Asp Trp Glu Ser Arg Cys Tyr Glu Gln Phe
                35                  40                  45

Gly Asp Glu Phe Gln Leu Ile Arg Asp Ser Lys Ala Leu Glu Ser Tyr
        50                  55                  60

Ser Gly Leu Thr Arg Asp Tyr Gln Lys Asp Leu Lys Ile Leu Arg Lys
65                  70                  75                  80

Tyr Lys His Arg Asp Met Thr Ile Ser Glu Tyr Glu Ala Met Lys Tyr
                85                  90                  95

Val Val Glu Asn Trp Thr Lys Glu Trp Ser Gln Ser Pro Tyr Ser Asn
                100                 105                 110

Ser Phe Tyr Ser Ser Lys Asp Ile Asp Trp Gly Tyr Lys Pro Glu Gly
                115                 120                 125

Ser Leu Arg Val Ser Asp His Trp Asn Phe Gly Glu Asn Gly Glu His
                130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
```

<210> SEQ ID NO 333
<211> LENGTH: 513
<212> TYPE: DNA
<213> ORGANISM: Bacteriophage D7059

<400> SEQUENCE: 333

```
atggtagtaa aaattaaaag aattgtttgg gttaaaaata atggttttga aatcagagaa      60
cgtgagctag attgttactt taaaaatgat ggaagttaca aaaaaagttc tggagattgg     120
gaaagtcgtt gttatgaaca attcggagat gaatttcaac tcattagaga taacaaagca     180
ttagaatctt atagtggttt gacaagagat tatcaaaaag acttaaaaat cttgcgtaag     240
tataaacata gagatatgac tatttcagag tatgaagcaa tgaaatatgt cgtggagaat     300
tggacaaaag agtggtcaca atcaccatac agcaatagtt tctatagctc taaagatatt     360
gattggggct acaaaccaga aggtagctta agagtctcag accattggaa ttttggcgaa     420
aatggtgaac attgcccaac agctgaacca gttgatggct gggcagtatg taagtttgaa     480
aatggtaaat atcatttaat taaaaagttt taa                                  513
```

<210> SEQ ID NO 334
<211> LENGTH: 170
<212> TYPE: PRT
<213> ORGANISM: Bacteriophage D7059

<400> SEQUENCE: 334

```
Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Asn Lys Ala Leu Glu Ser Tyr
    50                  55                  60

Ser Gly Leu Thr Arg Asp Tyr Gln Lys Asp Leu Lys Ile Leu Arg Lys
65                  70                  75                  80

Tyr Lys His Arg Asp Met Thr Ile Ser Glu Tyr Glu Ala Met Lys Tyr
                85                  90                  95

Val Val Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170
```

<210> SEQ ID NO 335
<211> LENGTH: 513
<212> TYPE: DNA
<213> ORGANISM: Bacteriophage D7108

<400> SEQUENCE: 335

```
atggtagtaa aaattaaaag aattgtttgg gttaaaaata atggttttga aatcagagaa      60
```

```
cgtgagctag attgttactt taaaaatgat ggaagttaca aaaaaagttc tggagattgg      120
gaaagtcgtt gttatgaaca attcggagat gaatttcaac tcattagaga taacaaagca      180
ttagaatctt atagtggttt gacaagagat tatcaaaaag acttaaaaat cttgcgtaag      240
tataaacata gagatatgac tatttcagag tatgaagcaa tgaaatatgt cgtggagaat      300
tggacaaaag agtggtcaca atcaccatac agcaatagtt tttatagctc taaagatatt      360
gattggggct acaaaccaga aggtagctta agagtctcag accattggaa ttttggcgaa      420
aatggtgaac attgcccaac agctgaacca gttgatggct gggcagtatg taagtttgaa      480
aatggtaaat atcatttaat taaaaagttt taa                                   513
```

<210> SEQ ID NO 336
<211> LENGTH: 170
<212> TYPE: PRT
<213> ORGANISM: Bacteriophage D7108

<400> SEQUENCE: 336

```
Met Val Val Lys Ile Lys Arg Ile Val Trp Val Lys Asn Asn Gly Phe
1               5                   10                  15

Glu Ile Arg Glu Arg Glu Leu Asp Cys Tyr Phe Lys Asn Asp Gly Ser
            20                  25                  30

Tyr Lys Lys Ser Ser Gly Asp Trp Glu Ser Arg Cys Tyr Glu Gln Phe
        35                  40                  45

Gly Asp Glu Phe Gln Leu Ile Arg Asp Asn Lys Ala Leu Glu Ser Tyr
    50                  55                  60

Ser Gly Leu Thr Arg Asp Tyr Gln Lys Asp Leu Lys Ile Leu Arg Lys
65                  70                  75                  80

Tyr Lys His Arg Asp Met Thr Ile Ser Glu Tyr Glu Ala Met Lys Tyr
                85                  90                  95

Val Val Glu Asn Trp Thr Lys Glu Trp Ser Gln Ser Pro Tyr Ser Asn
            100                 105                 110

Ser Phe Tyr Ser Ser Lys Asp Ile Asp Trp Gly Tyr Lys Pro Glu Gly
        115                 120                 125

Ser Leu Arg Val Ser Asp His Trp Asn Phe Gly Glu Asn Gly Glu His
    130                 135                 140

Cys Pro Thr Ala Glu Pro Val Asp Gly Trp Ala Val Cys Lys Phe Glu
145                 150                 155                 160

Asn Gly Lys Tyr His Leu Ile Lys Lys Phe
                165                 170
```

<210> SEQ ID NO 337
<211> LENGTH: 225
<212> TYPE: DNA
<213> ORGANISM: Bacteriophage D4090

<400> SEQUENCE: 337

```
atgattaaaa cggaaatgat tgacgatatt ctcactttga ttgaagaaat tgaagctgtt       60
agcgataaga ataaagaaaa gtttattgaa aaatttgacg agttagaaac caatttacaa      120
gcattgaata aacaaaccac tgatgatttg gttgaaattt tacaagaaga ttattctgat      180
aattgggtag caaagagggt gattgaactt gttactaaca gctag                      225
```

<210> SEQ ID NO 338
<211> LENGTH: 74
<212> TYPE: PRT
<213> ORGANISM: Bacteriophage D4090

<400> SEQUENCE: 338

Met Ile Lys Thr Glu Met Ile Asp Asp Ile Leu Thr Leu Ile Glu Glu
1               5                   10                  15

Ile Glu Ala Val Ser Asp Lys Asn Lys Glu Lys Phe Ile Glu Lys Phe
            20                  25                  30

Asp Glu Leu Glu Thr Asn Leu Gln Ala Leu Asn Lys Gln Thr Thr Asp
        35                  40                  45

Asp Leu Val Glu Ile Leu Gln Glu Asp Tyr Ser Asp Asn Trp Val Ala
    50                  55                  60

Lys Glu Val Ile Glu Leu Val Thr Asn Ser
65                  70

<210> SEQ ID NO 339
<211> LENGTH: 225
<212> TYPE: DNA
<213> ORGANISM: Bacteriophage D4368

<400> SEQUENCE: 339
atgaataaaa tagaaatgat tgacgatatt ctcactttga ttgaagagat tgacgccatt    60
agtgataaga gtaaagaaac gtttttttgaa aaaattgatg agttggaaac aaatttacaa   120
gcattgaaca gacaaatcac tgatgaattg gttgaaattt acaagaaga ttattctgat    180 aattgggtag caaagaggt gattgaactt gttactaaca gctag                    225

<210> SEQ ID NO 340
<211> LENGTH: 74
<212> TYPE: PRT
<213> ORGANISM: Bacteriophage D4368

<400> SEQUENCE: 340

Met Asn Lys Ile Glu Met Ile Asp Asp Ile Leu Thr Leu Ile Glu Glu
1               5                   10                  15

Ile Asp Ala Ile Ser Asp Lys Ser Lys Glu Thr Phe Phe Glu Lys Ile
            20                  25                  30

Asp Glu Leu Glu Thr Asn Leu Gln Ala Leu Asn Arg Gln Ile Thr Asp
        35                  40                  45

Glu Leu Val Glu Ile Leu Gln Glu Asp Tyr Ser Asp Asn Trp Val Ala
    50                  55                  60

Lys Glu Val Ile Glu Leu Val Thr Asn Ser
65                  70

<210> SEQ ID NO 341
<211> LENGTH: 225
<212> TYPE: DNA
<213> ORGANISM: Bacteriophage D5700

<400> SEQUENCE: 341
atgattaaaa cggaaatgat tgacgatatt ctcactttga ttgaagaaat tgaagctgtt    60
agcgataaga ataagaaaaa gtttattgaa aaatttgacg agttagaaac caatttacaa   120
gcattgaata aacaaaccac tgatgatttg gttgaaattt acaagaaga ttattctgat    180 aattgggtag caaagaggt gattgaactt gtcgatgact actag                    225

<210> SEQ ID NO 342
<211> LENGTH: 74
<212> TYPE: PRT
<213> ORGANISM: Bacteriophage D5700

<400> SEQUENCE: 342

```
Met Ile Lys Thr Glu Met Ile Asp Asp Ile Leu Thr Leu Ile Glu Glu
1               5                   10                  15

Ile Glu Ala Val Ser Asp Lys Asn Lys Glu Lys Phe Ile Glu Lys Phe
                20                  25                  30

Asp Glu Leu Glu Thr Asn Leu Gln Ala Leu Asn Lys Gln Thr Thr Asp
            35                  40                  45

Asp Leu Val Glu Ile Leu Gln Glu Asp Tyr Ser Asp Asn Trp Val Ala
        50                  55                  60

Lys Glu Val Ile Glu Leu Val Asp Asp Tyr
65                  70
```

<210> SEQ ID NO 343
<211> LENGTH: 225
<212> TYPE: DNA
<213> ORGANISM: Bacteriophage D6961

<400> SEQUENCE: 343

```
atgattaaaa cggaaatgat tgacgatatt ctcactttga ttgaagaaat tgaagctgtt      60
agcgataaga ataaagaaaa gtttattgaa aaatttgatg agttagaaac caatttacaa     120
gcattgaata acaaaccac tgatgatttg gttgaaattt acaagaaga ttattctgat       180
aattgggtag caaaagaggt gattgaactt gtcgatgact actag                     225
```

<210> SEQ ID NO 344
<211> LENGTH: 74
<212> TYPE: PRT
<213> ORGANISM: Bacteriophage D6961

<400> SEQUENCE: 344

```
Met Ile Lys Thr Glu Met Ile Asp Asp Ile Leu Thr Leu Ile Glu Glu
1               5                   10                  15

Ile Glu Ala Val Ser Asp Lys Asn Lys Glu Lys Phe Ile Glu Lys Phe
                20                  25                  30

Asp Glu Leu Glu Thr Asn Leu Gln Ala Leu Asn Lys Gln Thr Thr Asp
            35                  40                  45

Asp Leu Val Glu Ile Leu Gln Glu Asp Tyr Ser Asp Asn Trp Val Ala
        50                  55                  60

Lys Glu Val Ile Glu Leu Val Asp Asp Tyr
65                  70
```

<210> SEQ ID NO 345
<211> LENGTH: 513
<212> TYPE: DNA
<213> ORGANISM: Bacteriophage D4090

<400> SEQUENCE: 345

```
atgagttata caagcccagt ttataacatt aaacgagtac ccattgacaa atccaagca      60
aacagttata atccaaatca tgtagcacct cccgaaatga aattgcttta taagtctatt    120
ttagaggacg gatacactat gccaatcgtt tgttattatc ttaaagacga ggataaatac    180
gagattgtag acggttttca ccgttacagc actatgctta accacaaaga tatttatgaa    240
cgtgagggtg gttgtttgcc agtatccgtt attgataagc caattagcga ccgcatggcg    300
tcaactatcc gacacaatcg agcgagaggg tcacatgata tcgacctaat gacaaacatt    360
gtcgctgacc ttgtagacag tggtatgtct gacgcttgga ttttaaaaaa tatcggaatg    420
gacgcagacg aattgttgcg tttgaaacaa ttaactggtt tagcgagttt gtttgcagac    480
```
aaagaattca gtaaatcatg ggatgtagaa taa 513

<210> SEQ ID NO 346
<211> LENGTH: 170
<212> TYPE: PRT
<213> ORGANISM: Bacteriophage D4090

<400> SEQUENCE: 346

```
Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
            20                  25                  30

Met Lys Leu Leu Tyr Lys Ser Ile Leu Glu Asp Gly Tyr Thr Met Pro
        35                  40                  45

Ile Val Cys Tyr Tyr Leu Lys Asp Glu Asp Lys Tyr Glu Ile Val Asp
    50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
    130                 135                 140

Leu Leu Arg Leu Lys Gln Leu Thr Gly Leu Ala Ser Leu Phe Ala Asp
145                 150                 155                 160

Lys Glu Phe Ser Lys Ser Trp Asp Val Glu
                165                 170
```

<210> SEQ ID NO 347
<211> LENGTH: 513
<212> TYPE: DNA
<213> ORGANISM: Bacteriophage D4368

<400> SEQUENCE: 347
atgagttata caagcccagt ttataacatt aaacgagtac ccattgacaa atccaagca 60 aacagttata atccaaatca tgtagcacct cccgaaatga aattgcttta taagtctatt 120
ttagaggacg gatacactat gccaatcgtt tgttattatc ttaaagacga ggataaatac 180
gagattgtag acggttttca ccgttacagc actatgctta accacaaaga tatttatgaa 240
cgtgagggtg gttgtttgcc agtatccgtt attgataagc caattagcga ccgcatggcg 300
tcaactatcc gacacaatcg agcgagaggg tcacatgata tcgacctaat gacaaacatt 360
gtcgctgacc ttgtagacag tggtatgtct gacgcttgga ttttaaaaaa tatcggaatg 420
gacgcagacg aattgttgcg tttgaaacaa ttaactggct tgtcgagttt gtttgcagac 480
aaagaattca gtaaatcatg ggatgtagaa taa 513

<210> SEQ ID NO 348
<211> LENGTH: 170
<212> TYPE: PRT
<213> ORGANISM: Bacteriophage D4368

<400> SEQUENCE: 348

```
Met Ser Tyr Thr Ser Pro Val Tyr Asn Ile Lys Arg Val Pro Ile Asp
1               5                   10                  15
```

Lys Ile Gln Ala Asn Ser Tyr Asn Pro Asn His Val Ala Pro Pro Glu
                20                  25                  30

Met Lys Leu Leu Tyr Lys Ser Ile Leu Glu Asp Gly Tyr Thr Met Pro
            35                  40                  45

Ile Val Cys Tyr Tyr Leu Lys Asp Glu Asp Lys Tyr Glu Ile Val Asp
        50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
130                 135                 140

Leu Leu Arg Leu Lys Gln Leu Thr Gly Leu Ser Ser Leu Phe Ala Asp
145                 150                 155                 160

Lys Glu Phe Ser Lys Ser Trp Asp Val Glu
                165                 170

<210> SEQ ID NO 349
<211> LENGTH: 513
<212> TYPE: DNA
<213> ORGANISM: Bacteriophage D4598

<400> SEQUENCE: 349
atgagttaca caagtccagt ttataacatt aaacgagtac ccattgacaa aattcaggca    60
aacagttata atccaaacca tgtagcacct cctgaaatga aactacttta caagtctatt   120
ttagaggatg gatacacaat gccaatcgtt tgttattatc ttaaagatga agataaatat   180
gagattgtag atggctttca ccgttatagc actatgctta accacaaaga tatttatgac   240
cgtgagggcg gttgtttgcc agtatccgtt attaataagc caatcagtga ccgtatggca   300
tcaactatcc gacataatcg agcgagaggg tcacatgata ttgacctaat gacaaacatt   360
gtcgctgacc ttgtagacag tggtatgtct gacgcttgga ttttaaaaaa tatcggaatg   420
gacgcagacg aattgttgcg tttgaaacaa ttaactggct tggcaagttt gtttgcagac   480
aaagaattca gtaaatcatg ggatgtagaa taa                                513

<210> SEQ ID NO 350
<211> LENGTH: 170
<212> TYPE: PRT
<213> ORGANISM: Bacteriophage D4598

<400> SEQUENCE: 350

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
                20                  25                  30

Met Lys Leu Leu Tyr Lys Ser Ile Leu Glu Asp Gly Tyr Thr Met Pro
            35                  40                  45

Ile Val Cys Tyr Tyr Leu Lys Asp Glu Asp Lys Tyr Glu Ile Val Asp
        50                  55                  60

Gly Phe His Arg Tyr Ser Thr Met Leu Asn His Lys Asp Ile Tyr Asp
65                  70                  75                  80

```
Arg Glu Gly Gly Cys Leu Pro Val Ser Val Ile Asn Lys Pro Ile Ser
                 85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
130                 135                 140

Leu Leu Arg Leu Lys Gln Leu Thr Gly Leu Ala Ser Leu Phe Ala Asp
145                 150                 155                 160

Lys Glu Phe Ser Lys Ser Trp Asp Val Glu
                165                 170

<210> SEQ ID NO 351
<211> LENGTH: 513
<212> TYPE: DNA
<213> ORGANISM: Bacteriophage D5700

<400> SEQUENCE: 351
atgagttata caagcccagt ttataacatt aaacgagtac ccattgacaa aatccaagca      60
aatagttata atccaaatca tgtagcacct cccgaaatga aattgcttta taagtctatt     120
ttagaggacg gatacactat gccaatcgtt tgttattatc ttaaagacga ggataaatac     180
gagattgtag acggttttca ccgttacagc actatgctta accacaaaga tatttatgaa     240
cgtgagggtg gttgtttgcc agtatccgtt attgataagc caattagcga ccgcatggcg     300
tcaactatcc gacacaatcg agcgagaggg tcacatgata tcgacctaat gacaaacatt     360
gtcgctgacc ttgtagacag tggtatgtct gacgcttgga ttttaaaaaa tatcggaatg     420
gacgcagacg aattgttgcg tttgaaacaa ttaactggct tggcaagttt gtttgcagac     480
aaagaattca gtaaatcatg ggatgtagaa taa                                  513

<210> SEQ ID NO 352
<211> LENGTH: 170
<212> TYPE: PRT
<213> ORGANISM: Bacteriophage D5700

<400> SEQUENCE: 352

Met Ser Tyr Thr Ser Pro Val Tyr Asn Ile Lys Arg Val Pro Ile Asp
1               5                  10                  15

Lys Ile Gln Ala Asn Ser Tyr Asn Pro Asn His Val Ala Pro Pro Glu
            20                  25                  30

Met Lys Leu Leu Tyr Lys Ser Ile Leu Glu Asp Gly Tyr Thr Met Pro
        35                  40                  45

Ile Val Cys Tyr Tyr Leu Lys Asp Glu Asp Lys Tyr Glu Ile Val Asp
    50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
130                 135                 140
```

```
Leu Leu Arg Leu Lys Gln Leu Thr Gly Leu Ala Ser Leu Phe Ala Asp
145                 150                 155                 160

Lys Glu Phe Ser Lys Ser Trp Asp Val Glu
                165                 170

<210> SEQ ID NO 353
<211> LENGTH: 513
<212> TYPE: DNA
<213> ORGANISM: Bacteriophage D6938

<400> SEQUENCE: 353
atgagttaca caagtccagt ttataacatt aaacgagtac ctattgataa aattcaggca      60
aacagttata atccaaacca tgtagcacct cctgaaatga aactacttta caagtctatt     120
ttagaggatg ggtacacaat gccaatcgtt tgttattatc ttaaagatga agataaaatat    180 gagattgtag atggctttca tcgctatagc actatgctta accacaaaga tatttatgac    240
cgtgagggcg gttgtttgcc agtatccgtt attaataaac cgattagtga ccgcatggcg    300
tcaactatcc gacacaaccg ggcgagaggg tcacatgata ttgacctaat gacaaacatt    360
gttgctgacc ttgtagatag tggcatgtct gacgcttgga ttttgaaaaa tatcggaatg    420
gacgcagacg aattgttgcg gttgaaacag ttaactggtt tagctagtct atttgcagac    480
aaagaattca gtaaatcgtg gatcgtagaa taa                                 513

<210> SEQ ID NO 354
<211> LENGTH: 170
<212> TYPE: PRT
<213> ORGANISM: Bacteriophage D6938

<400> SEQUENCE: 354

Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
                20                  25                  30

Met Lys Leu Leu Tyr Lys Ser Ile Leu Glu Asp Gly Tyr Thr Met Pro
            35                  40                  45

Ile Val Cys Tyr Tyr Leu Lys Asp Glu Asp Lys Tyr Glu Ile Val Asp
        50                  55                  60

Gly Phe His Arg Tyr Ser Thr Met Leu Asn His Lys Asp Ile Tyr Asp
65                  70                  75                  80

Arg Glu Gly Gly Cys Leu Pro Val Ser Val Ile Asn Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
130                 135                 140

Leu Leu Arg Leu Lys Gln Leu Thr Gly Leu Ala Ser Leu Phe Ala Asp
145                 150                 155                 160

Lys Glu Phe Ser Lys Ser Trp Ile Val Glu
                165                 170

<210> SEQ ID NO 355
<211> LENGTH: 513
<212> TYPE: DNA
<213> ORGANISM: Bacteriophage D7059
```

<400> SEQUENCE: 355

```
atgagttaca caagtccagt ttataacatt aaacgagtac ccattgacaa aatccaagca      60
aacagttata atccaaatca tgtagcacct cccgaaatga aattgcttta taagtctatt    120
ttagaggacg gatacactat gccaatcgtt tgttattatc ttaaagacga ggataaatac    180
gagattgtag acggttttca ccgttacagc actatgctta accacaaaga tatttatgaa    240
cgtgagggtg gttgtttgcc agtatccgtt attgataagc caattagcga ccgcatggcg    300
tcaactatcc gacacaatcg agcgagaggg tcacatgata tcgacctaat gacaaacatt    360
gtcgccgacc ttgtagacag tggtatgtct gacgcttgga ttttaaaaaa tatcggaatg    420
gacgcagacg aattgttgcg tttgaaacaa ttaactggct tggcaagttt gtttgcagac    480
aaagaattca gtaaatcatg ggatgtagaa taa                                 513
```

<210> SEQ ID NO 356
<211> LENGTH: 170
<212> TYPE: PRT
<213> ORGANISM: Bacteriophage D7059

<400> SEQUENCE: 356

```
Met Ser Tyr Thr Ser Pro Val Tyr Asn Ile Lys Arg Val Pro Ile Asp
1               5                   10                  15

Lys Ile Gln Ala Asn Ser Tyr Asn Pro Asn His Val Ala Pro Pro Glu
            20                  25                  30

Met Lys Leu Leu Tyr Lys Ser Ile Leu Glu Asp Gly Tyr Thr Met Pro
        35                  40                  45

Ile Val Cys Tyr Tyr Leu Lys Asp Glu Asp Lys Tyr Glu Ile Val Asp
    50                  55                  60

Gly Phe His Arg Tyr Ser Thr Met Leu Asn His Lys Asp Ile Tyr Glu
65                  70                  75                  80

Arg Glu Gly Gly Cys Leu Pro Val Ser Val Ile Asp Lys Pro Ile Ser
                85                  90                  95

Asp Arg Met Ala Ser Thr Ile Arg His Asn Arg Ala Arg Gly Ser His
            100                 105                 110

Asp Ile Asp Leu Met Thr Asn Ile Val Ala Asp Leu Val Asp Ser Gly
        115                 120                 125

Met Ser Asp Ala Trp Ile Leu Lys Asn Ile Gly Met Asp Ala Asp Glu
    130                 135                 140

Leu Leu Arg Leu Lys Gln Leu Thr Gly Leu Ala Ser Leu Phe Ala Asp
145                 150                 155                 160

Lys Glu Phe Ser Lys Ser Trp Asp Val Glu
                165                 170
```

<210> SEQ ID NO 357
<211> LENGTH: 180
<212> TYPE: DNA
<213> ORGANISM: Bacteriophage D4090

<400> SEQUENCE: 357

```
atgcctaaag tttccgagag caaacggaaa gcaaatgaca atgggacaa aaagaacaaa       60
gaacgcaagc agtatatcaa cagacgttct gtcgcaagga actttattaa gaatatggaa    120
ggcgaagata ttccagaatt taaaaaacta atagaagaaa gagcttccaa aatcaaataa    180
```

<210> SEQ ID NO 358
<211> LENGTH: 59

```
<212> TYPE: PRT
<213> ORGANISM: Bacteriophage D4090

<400> SEQUENCE: 358

Met Pro Lys Val Ser Glu Ser Lys Arg Lys Ala Asn Asp Lys Trp Asp
1               5                   10                  15

Lys Lys Asn Lys Glu Arg Lys Gln Tyr Ile Asn Arg Arg Ser Val Ala
            20                  25                  30

Arg Asn Phe Ile Lys Asn Met Glu Gly Glu Asp Ile Pro Glu Phe Lys
        35                  40                  45

Lys Leu Ile Glu Glu Arg Ala Ser Lys Ile Lys
    50                  55

<210> SEQ ID NO 359
<211> LENGTH: 180
<212> TYPE: DNA
<213> ORGANISM: Bacteriophage D4254

<400> SEQUENCE: 359
atgcctaaag tttccgagag caaacggaaa gcaaatgaca atgggacaa aaagaacaaa      60 gaacgcaagc agtatattaa cagacgttct gtcgcaagga actttattaa gaatatggaa    120
gacgaagata ttccagaatt taaaaaacta atggaagaaa gagcttccaa atcaaataa     180

<210> SEQ ID NO 360
<211> LENGTH: 59
<212> TYPE: PRT
<213> ORGANISM: Bacteriophage D4254

<400> SEQUENCE: 360

Met Pro Lys Val Ser Glu Ser Lys Arg Lys Ala Asn Asp Lys Trp Asp
1               5                   10                  15

Lys Lys Asn Lys Glu Arg Lys Gln Tyr Ile Asn Arg Arg Ser Val Ala
            20                  25                  30

Arg Asn Phe Ile Lys Asn Met Glu Asp Glu Asp Ile Pro Glu Phe Lys
        35                  40                  45

Lys Leu Met Glu Glu Arg Ala Ser Lys Ile Lys
    50                  55

<210> SEQ ID NO 361
<211> LENGTH: 180
<212> TYPE: DNA
<213> ORGANISM: Bacteriophage D4368

<400> SEQUENCE: 361
atgcctaaag tttccgagag caaacggaaa gcaaatgaca atgggacaa aaagaacaaa      60 gaacgcaagc agtatattaa cagacgttct gtcgcaagga actttattaa gaatatggaa    120
gacgaagata ttccagaatt taaaaaacta atggaagaaa gaacttccaa atcaaataa     180

<210> SEQ ID NO 362
<211> LENGTH: 59
<212> TYPE: PRT
<213> ORGANISM: Bacteriophage D4368

<400> SEQUENCE: 362

Met Pro Lys Val Ser Glu Ser Lys Arg Lys Ala Asn Asp Lys Trp Asp
1               5                   10                  15

Lys Lys Asn Lys Glu Arg Lys Gln Tyr Ile Asn Arg Arg Ser Val Ala
            20                  25                  30
```

Arg Asn Phe Ile Lys Asn Met Glu Asp Glu Asp Ile Pro Glu Phe Lys
        35                  40                  45

Lys Leu Met Glu Glu Arg Thr Ser Lys Ile Lys
    50                  55

<210> SEQ ID NO 363
<211> LENGTH: 198
<212> TYPE: DNA
<213> ORGANISM: Bacteriophage D6961

<400> SEQUENCE: 363
atgcctaaag tctcagaaag caaacggaga gcgaataata aatgggataa aaaaaataaa      60
gaacgtaaac aatatataaa caaacgttcc gttgcaagaa actttattaa gaacatggaa     120
gatgaagatg ttccggaatt taaaaaacta atggaagaaa gagcttccaa acaaataaa     180 acgtgtttta gttcatga                                                   198

<210> SEQ ID NO 364
<211> LENGTH: 65
<212> TYPE: PRT
<213> ORGANISM: Bacteriophage D6961

<400> SEQUENCE: 364

Met Pro Lys Val Ser Glu Ser Lys Arg Arg Ala Asn Asn Lys Trp Asp
1               5                   10                  15

Lys Lys Asn Lys Glu Arg Lys Gln Tyr Ile Asn Lys Arg Ser Val Ala
            20                  25                  30

Arg Asn Phe Ile Lys Asn Met Glu Asp Glu Asp Val Pro Glu Phe Lys
        35                  40                  45

Lys Leu Met Glu Glu Arg Ala Ser Lys Thr Asn Lys Thr Cys Phe Ser
    50                  55                  60

Ser
65

<210> SEQ ID NO 365
<211> LENGTH: 180
<212> TYPE: DNA
<213> ORGANISM: Bacteriophage D7059

<400> SEQUENCE: 365
atgcctaaag tttccgagag caaacggaaa gcaaacgaca aatgggataa aaataacaaa      60
gaacgcaagc agtatattaa cagacgttct gtcgcaagga actttattaa gaatatggaa     120
gacgaagata ttccagaatt taaaaaacta atggaagaaa gaacttccaa aatcaaataa     180

<210> SEQ ID NO 366
<211> LENGTH: 59
<212> TYPE: PRT
<213> ORGANISM: Bacteriophage D7059

<400> SEQUENCE: 366

Met Pro Lys Val Ser Glu Ser Lys Arg Lys Ala Asn Asp Lys Trp Asp
1               5                   10                  15

Lys Asn Asn Lys Glu Arg Lys Gln Tyr Ile Asn Arg Arg Ser Val Ala
            20                  25                  30

Arg Asn Phe Ile Lys Asn Met Glu Asp Glu Asp Ile Pro Glu Phe Lys
        35                  40                  45

Lys Leu Met Glu Glu Arg Thr Ser Lys Ile Lys
    50                  55

<210> SEQ ID NO 367
<211> LENGTH: 246
<212> TYPE: DNA
<213> ORGANISM: Bacteriophage D4250

<400> SEQUENCE: 367

```
atgaagttaa ctaatcaaca gaatcaagcc tttaagaaat tcaaaaattt gagagttgga      60
gctctattta tggagcaagg aacaggtaag acaagagtag cactagagtt aatcagaaaa     120
acagatgctg atttagcctt gttctttttgt ccgttttcaa ccaaaaacaa tcttttatct    180
gagattgaaa atggggaat tgatattgaa tttatggtgt atggatatga acgatttca       240
tcatag                                                                246
```

<210> SEQ ID NO 368
<211> LENGTH: 81
<212> TYPE: PRT
<213> ORGANISM: Bacteriophage D4250

<400> SEQUENCE: 368

```
Met Lys Leu Thr Asn Gln Gln Asn Gln Ala Phe Lys Lys Phe Lys Asn
1               5                   10                  15

Leu Arg Val Gly Ala Leu Phe Met Glu Gln Gly Thr Gly Lys Thr Arg
            20                  25                  30

Val Ala Leu Glu Leu Ile Arg Lys Thr Asp Ala Asp Leu Ala Leu Phe
        35                  40                  45

Phe Cys Pro Phe Ser Thr Lys Asn Asn Leu Leu Ser Glu Ile Glu Lys
    50                  55                  60

Trp Gly Ile Asp Ile Glu Phe Met Val Tyr Gly Tyr Glu Thr Ile Ser
65                  70                  75                  80

Ser
```

<210> SEQ ID NO 369
<211> LENGTH: 177
<212> TYPE: DNA
<213> ORGANISM: Bacteriophage D4254

<400> SEQUENCE: 369

```
gtggaaacag aaccaaattt tcaaataata tgttataata aaagtacctc gtttgaggta      60
ttttttatc ttacaactgc acccgaattt tttcaggtgt ttttttttcg cccaaaaatc     120
acccgaaaac tttgggaaaa gctagaaaaa ataaaaataa acgaggtaaa aacatag        177
```

<210> SEQ ID NO 370
<211> LENGTH: 58
<212> TYPE: PRT
<213> ORGANISM: Bacteriophage D4254

<400> SEQUENCE: 370

```
Met Glu Thr Glu Pro Asn Phe Gln Ile Ile Cys Tyr Asn Lys Ser Thr
1               5                   10                  15

Ser Phe Glu Val Phe Phe Tyr Leu Thr Thr Ala Pro Glu Phe Phe Gln
            20                  25                  30

Val Phe Phe Arg Pro Lys Ile Thr Arg Lys Leu Trp Glu Lys Leu
        35                  40                  45

Glu Lys Ile Lys Ile Asn Glu Val Lys Thr
    50                  55
```

<210> SEQ ID NO 371

<210> SEQ ID NO 371
<211> LENGTH: 204
<212> TYPE: DNA
<213> ORGANISM: Bacteriophage D6961

<400> SEQUENCE: 371

```
gtggaaacag aaccaaattt tcaaataata tgttataata aaagtacctc gtttgaggta      60
ttttttatct tacaactgca cccgaatttt ttcaggtgtt ttttttgccc aaaaatcacc    120
caaaaacttt gggaaaagct agaaaaaata aaaaataaac gaggtaaaaa catagtatgt    180
tttactaatt ttcaagctga ttaa                                            204
```

<210> SEQ ID NO 372
<211> LENGTH: 67
<212> TYPE: PRT
<213> ORGANISM: Bacteriophage D6961

<400> SEQUENCE: 372

```
Met Glu Thr Glu Pro Asn Phe Gln Ile Ile Cys Tyr Asn Lys Ser Thr
1               5                   10                  15

Ser Phe Glu Val Phe Phe Ile Leu Gln Leu His Pro Asn Phe Phe Arg
            20                  25                  30

Cys Phe Phe Cys Pro Lys Ile Thr Gln Lys Leu Trp Glu Lys Leu Glu
        35                  40                  45

Lys Ile Lys Asn Lys Arg Gly Lys Asn Ile Val Cys Phe Thr Asn Phe
    50                  55                  60

Gln Ala Asp
65
```

<210> SEQ ID NO 373
<211> LENGTH: 159
<212> TYPE: DNA
<213> ORGANISM: Bacteriophage D4263

<400> SEQUENCE: 373

```
atgggtttta cggttacatg ttgcaataac ctgcggtcac tgagtaacca taaccactac      60
tgctgctttc ttcgcctcgt tttcgtccca actaaaattg aaatcatacc aataatctgg    120
tttatcttta gggtgtctca cggatttcaa acggtgtga                            159
```

<210> SEQ ID NO 374
<211> LENGTH: 52
<212> TYPE: PRT
<213> ORGANISM: Bacteriophage D4263

<400> SEQUENCE: 374

```
Met Gly Phe Thr Val Thr Cys Cys Asn Asn Leu Arg Ser Leu Ser Asn
1               5                   10                  15

His Asn His Tyr Cys Cys Phe Leu Arg Leu Val Phe Val Pro Thr Lys
            20                  25                  30

Ile Glu Ile Ile Pro Ile Ile Trp Phe Ile Phe Arg Val Ser His Gly
        35                  40                  45

Phe Gln Thr Val
    50
```

<210> SEQ ID NO 375
<211> LENGTH: 453
<212> TYPE: DNA
<213> ORGANISM: Bacteriophage D4445

<400> SEQUENCE: 375

```
ttggaatact tggcatcgtt tcggttaaat tctcgaactg taacctcgac ttttagtcga    60
ggttttcttt ttttgcaaaa aaaactaaat tccttaataa ataaaaataa aaactataaa   120
aacttagtac agcttcattt attctcaaat tttatatatt ttcgttcaag aattgttctg   180
ttgttaaacc taaagcgcga gcgaaatcat cagctttatt cagcgggaac acccgactac   240
ctgaaagata tcttgtttga atcccagct ttatttgcat tgacatggaa ctgttgtcta    300
aatagctttt tattatcgtt gtttctcata tttaatagta taacattat acaaagttc     360 ccaaaaataa acaatatgtt cccaaaaata aacttttttc atattttttt gattttagtg   420
ttgacaaatg ggaacgtgtt agatatacta taa                                 453
```

<210> SEQ ID NO 376
<211> LENGTH: 150
<212> TYPE: PRT
<213> ORGANISM: Bacteriophage D4445

<400> SEQUENCE: 376

```
Met Glu Tyr Leu Ala Ser Phe Arg Leu Asn Ser Arg Thr Val Thr Ser
1               5                   10                  15

Thr Phe Ser Arg Gly Phe Leu Phe Leu Gln Lys Lys Leu Asn Ser Leu
            20                  25                  30

Ile Asn Lys Asn Lys Asn Tyr Lys Asn Leu Val Gln Leu His Leu Phe
        35                  40                  45

Ser Asn Phe Ile Tyr Phe Arg Ser Arg Ile Val Leu Leu Asn Leu
    50                  55                  60

Lys Arg Glu Arg Asn His Gln Leu Tyr Ser Ala Gly Thr Pro Asp Tyr
65                  70                  75                  80

Leu Lys Asp Ile Leu Phe Glu Ile Pro Ala Leu Phe Ala Leu Thr Trp
                85                  90                  95

Asn Cys Cys Leu Asn Ser Phe Leu Leu Ser Leu Phe Leu Ile Phe Asn
            100                 105                 110

Ser Ile Asn Ile Ile Gln Lys Phe Pro Lys Ile Asn Asn Met Phe Pro
        115                 120                 125

Lys Ile Asn Phe Phe His Ile Phe Leu Ile Leu Val Leu Thr Asn Gly
    130                 135                 140

Asn Val Leu Asp Ile Leu
145                 150
```

<210> SEQ ID NO 377
<211> LENGTH: 282
<212> TYPE: DNA
<213> ORGANISM: Bacteriophage D4446

<400> SEQUENCE: 377

```
atggaagttg aacaaagact agaacaacta agacaagatt ggttgaaaca cccaaattta    60
acagatactt taaagaata tctaaacgaa tatttttacg atgattattc ttattgtgag   120
aaatgtgata ggattgccag cgatagcgat tggttttggt atgaaggcga agactatacg   180 gatttttac acattgattg taataaagaa aaatttacg aagcaacaaa aaaaacctct    240
ggaaggagga gaccagagga aaacataaaa ggagaaagtt ag                      282
```

<210> SEQ ID NO 378
<211> LENGTH: 93
<212> TYPE: PRT
<213> ORGANISM: Bacteriophage D4446

<400> SEQUENCE: 378

```
Met Glu Val Glu Gln Arg Leu Glu Gln Leu Arg Gln Asp Trp Leu Lys
1               5                   10                  15

His Pro Asn Leu Thr Asp Thr Leu Lys Glu Tyr Leu Asn Glu Tyr Phe
            20                  25                  30

Tyr Asp Asp Tyr Ser Tyr Cys Glu Lys Cys Asp Arg Ile Ala Ser Asp
                35                  40                  45

Ser Asp Trp Phe Trp Tyr Glu Gly Asp Tyr Thr Asp Phe Leu His
    50                  55                  60

Ile Asp Cys Asn Lys Glu Lys Phe Tyr Glu Ala Thr Lys Lys Thr Ser
65                  70                  75                  80

Gly Arg Arg Arg Pro Glu Glu Asn Ile Lys Gly Glu Ser
                85                  90
```

<210> SEQ ID NO 379
<211> LENGTH: 228
<212> TYPE: DNA
<213> ORGANISM: Bacteriophage D4446

<400> SEQUENCE: 379

```
atgaaaacta agacacttgg gcgccgttta agacgtttaa gaaaaatcaa tggagaaaca      60
caaaaggaat tgccgaaaa ttttggaaga cattatagaa ccgttcaaaa ttgggagcta     120
gattgttcaa taccagacgt tttcacagca atggcattgg cagaatatta taacatggac    180
gttgaagaat tggtgaatgg agaagatgac tatgacaaag aatttga                  228
```

<210> SEQ ID NO 380
<211> LENGTH: 75
<212> TYPE: PRT
<213> ORGANISM: Bacteriophage D4446

<400> SEQUENCE: 380

```
Met Lys Thr Lys Thr Leu Gly Arg Arg Leu Arg Arg Leu Arg Lys Ile
1               5                   10                  15

Asn Gly Glu Thr Gln Lys Glu Phe Ala Glu Asn Phe Gly Arg His Tyr
            20                  25                  30

Arg Thr Val Gln Asn Trp Glu Leu Asp Cys Ser Ile Pro Asp Val Phe
        35                  40                  45

Thr Ala Met Ala Leu Ala Glu Tyr Tyr Asn Met Asp Val Glu Glu Leu
    50                  55                  60

Val Asn Gly Glu Asp Asp Tyr Asp Lys Glu Phe
65                  70                  75
```

<210> SEQ ID NO 381
<211> LENGTH: 378
<212> TYPE: DNA
<213> ORGANISM: Bacteriophage D4446

<400> SEQUENCE: 381

```
atggagaaga tgactatgac aaagaatttt gaaattttta aaaaggctg ggataatgtt      60 caacaagtag taatgaata cagcaaaaaa ctcgttgaaa acagtcaaga aaatgtaacc     120
aaccgagata gtgaagagta tcagcaaatc aaggtaaag ataacgtaat tagtccaaac    180
cactatgtaa ccgataaggg ttttgaagtg tttgacgtgc aagaagcttt tatccacgaa    240
ttaaaaggaa tggcagctag ttactggtgc aatgttgtga agtatatttt gagatttcaa    300
agaaagaatg gagtggaaga cttaaaaaaa gctaagtact acttggaaaa attaattgaa    360
aaagaggaag gtaaataa                                                   378
```

<210> SEQ ID NO 382
<211> LENGTH: 125
<212> TYPE: PRT
<213> ORGANISM: Bacteriophage D4446

<400> SEQUENCE: 382

```
Met Glu Lys Met Thr Met Thr Lys Asn Phe Glu Asn Phe Lys Lys Gly
1               5                   10                  15

Trp Asp Asn Val Gln Gln Val Val Asn Glu Tyr Ser Lys Lys Leu Val
            20                  25                  30

Glu Asn Ser Gln Glu Asn Val Thr Asn Arg Asp Ser Glu Glu Tyr Gln
        35                  40                  45

Gln Ile Lys Gly Lys Asp Asn Val Ile Ser Pro Asn His Tyr Val Thr
    50                  55                  60

Asp Lys Gly Phe Glu Val Phe Asp Val Gln Glu Ala Phe Ile His Glu
65                  70                  75                  80

Leu Lys Gly Met Ala Ala Ser Tyr Trp Cys Asn Val Val Lys Tyr Ile
                85                  90                  95

Leu Arg Phe Gln Arg Lys Asn Gly Val Glu Asp Leu Lys Lys Ala Lys
            100                 105                 110

Tyr Tyr Leu Glu Lys Leu Ile Glu Lys Glu Glu Gly Lys
        115                 120                 125
```

<210> SEQ ID NO 383
<211> LENGTH: 546
<212> TYPE: DNA
<213> ORGANISM: Bacteriophage D4446

<400> SEQUENCE: 383

```
atgaataaac aagaagcaat tgaactagta aaaaatactt catacagtgt accaattgat    60
agcccagtga acatcttac agaagataca gttatcaata ttatcaaaca gcttgatgaa   120
ccagagaaag ctacagtgcc agattttgta gcaaaataca ttgaagaaag cagagaattt   180
gacagaaaat taaatgacgc tttatcttac tcaaacacta ccgtcgcaat ggacgactgg   240
tttgaagaaa acgaagtaga caacacggaa atatttgcta aggcatggct tcacggctat   300
gaagtagaaa agaaaaaact ttacacagtt gaaattccag accctaatgc aagtggttac   360
ggtaagacat tccttggcag agatgatgat ggaaaagtag tgctatctac ttggactggt   420
tttagttcca ttgaatttgc tgatgattgg aaacaatcag aacgtgcaca gttgacagaa   480
gatgaaatta aaaaaggttt tacttgggct tggaatgaag ggtttgccga agaggtgaaa   540
gaatga                                                              546
```

<210> SEQ ID NO 384
<211> LENGTH: 181
<212> TYPE: PRT
<213> ORGANISM: Bacteriophage D4446

<400> SEQUENCE: 384

```
Met Asn Lys Gln Glu Ala Ile Glu Leu Val Lys Asn Thr Ser Tyr Ser
1               5                   10                  15

Val Pro Ile Asp Ser Pro Val Lys His Leu Thr Glu Asp Thr Val Ile
            20                  25                  30

Asn Ile Ile Lys Gln Leu Asp Glu Pro Glu Lys Ala Thr Val Pro Asp
        35                  40                  45

Phe Val Ala Lys Tyr Ile Glu Glu Ser Arg Glu Phe Asp Arg Lys Leu
```

```
            50                  55                  60
Asn Asp Ala Leu Ser Tyr Ser Asn Thr Thr Val Ala Met Asp Asp Trp
 65                  70                  75                  80

Phe Glu Glu Asn Glu Val Asp Asn Thr Glu Ile Phe Ala Lys Ala Trp
                 85                  90                  95

Leu His Gly Tyr Glu Val Glu Lys Glu Lys Leu Tyr Thr Val Glu Ile
            100                 105                 110

Pro Asp Pro Asn Ala Ser Gly Tyr Gly Lys Thr Phe Leu Gly Arg Asp
        115                 120                 125

Asp Asp Gly Lys Val Val Leu Ser Thr Trp Thr Gly Phe Ser Ser Ile
    130                 135                 140

Glu Phe Ala Asp Asp Trp Lys Gln Ser Glu Arg Ala Gln Leu Thr Glu
145                 150                 155                 160

Asp Glu Ile Lys Lys Gly Phe Thr Trp Ala Trp Asn Glu Gly Phe Ala
                165                 170                 175

Glu Glu Val Lys Glu
            180

<210> SEQ ID NO 385
<211> LENGTH: 162
<212> TYPE: DNA
<213> ORGANISM: Bacteriophage D4446

<400> SEQUENCE: 385
atgaaacgct tgtagtaac aggttacaaa gatggttggt ttgtcttctc atttcctta      60 aacgccataa actcttatta tgctatccaa tatgcaagcg aagatgaatt ggtagaaggt     120
atggagttcg ataagctggt tataaaagag gtgaaagaat ga                        162

<210> SEQ ID NO 386
<211> LENGTH: 53
<212> TYPE: PRT
<213> ORGANISM: Bacteriophage D4446

<400> SEQUENCE: 386

Met Lys Arg Phe Val Val Thr Gly Tyr Lys Asp Gly Trp Phe Val Phe
 1               5                  10                  15

Ser Phe Pro Leu Asn Ala Ile Asn Ser Tyr Tyr Ala Ile Gln Tyr Ala
             20                  25                  30

Ser Glu Asp Glu Leu Val Glu Gly Met Glu Phe Asp Lys Leu Val Ile
         35                  40                  45

Lys Glu Val Lys Glu
     50

<210> SEQ ID NO 387
<211> LENGTH: 147
<212> TYPE: DNA
<213> ORGANISM: Bacteriophage D4446

<400> SEQUENCE: 387
atgaacataa aagaggtgtt ctgtattgat tgctatgaat ggaaaaagaa agaagactta      60
acagggagca aattttccaa tgatatttta tattgcaaag aatgtggtta cgccttagtt     120
cgtacgtgtg accgtaataa caaatga                                         147

<210> SEQ ID NO 388
<211> LENGTH: 48
<212> TYPE: PRT
<213> ORGANISM: Bacteriophage D4446
```

<400> SEQUENCE: 388

Met Asn Ile Lys Glu Val Phe Cys Ile Asp Cys Tyr Glu Trp Lys Lys
1               5                   10                  15

Lys Glu Asp Leu Thr Gly Ser Lys Phe Ser Asn Asp Ile Leu Tyr Cys
            20                  25                  30

Lys Glu Cys Gly Tyr Ala Leu Val Arg Thr Cys Asp Arg Asn Asn Lys
        35                  40                  45

<210> SEQ ID NO 389
<211> LENGTH: 165
<212> TYPE: DNA
<213> ORGANISM: Bacteriophage D547

<400> SEQUENCE: 389
atgacaaaca ttgttgctga ccttgtagat agtggcatgt ctgacgcttg gattttgaaa    60
aacattggga tggatgctga cgaattgctg cgactaaagc aacttagcgg actggcttcc   120
ttgttcaaag ataaggaatt cactacagct tgggaagtag gataa                   165

<210> SEQ ID NO 390
<211> LENGTH: 54
<212> TYPE: PRT
<213> ORGANISM: Bacteriophage D547

<400> SEQUENCE: 390

Met Thr Asn Ile Val Ala Asp Leu Val Asp Ser Gly Met Ser Asp Ala
1               5                   10                  15

Trp Ile Leu Lys Asn Ile Gly Met Asp Ala Asp Glu Leu Leu Arg Leu
            20                  25                  30

Lys Gln Leu Ser Gly Leu Ala Ser Leu Phe Lys Asp Lys Glu Phe Thr
        35                  40                  45

Thr Ala Trp Glu Val Gly
    50

<210> SEQ ID NO 391
<211> LENGTH: 273
<212> TYPE: DNA
<213> ORGANISM: Bacteriophage D5691

<400> SEQUENCE: 391
atggaaactt ataaagaata caaacaacaa cagaaagaag aacgtgaaag agtaagagcg    60
cttcgtagtg aagtattttc aggcaacgct gaaaagcttg cgacagatat tgtaaggatt   120
tcgagcggag atgtttataa aattatccca cgttttggga ctagatatga aaaaagtcca   180
atcatcaaat tagacccaga agaagtagaa cgccacatca agaagctcg tgaagtcaga    240 gaacttgcga aaattatggc aagcaaagaa tag                                273

<210> SEQ ID NO 392
<211> LENGTH: 90
<212> TYPE: PRT
<213> ORGANISM: Bacteriophage D5691

<400> SEQUENCE: 392

Met Glu Thr Tyr Lys Glu Tyr Lys Gln Gln Gln Lys Glu Glu Arg Glu
1               5                   10                  15

Arg Val Arg Ala Leu Arg Ser Glu Val Phe Ser Gly Asn Ala Glu Lys
            20                  25                  30

Leu Ala Thr Asp Ile Val Arg Ile Ser Ser Gly Asp Val Tyr Lys Ile

```
                35                  40                  45
Ile Pro Arg Phe Gly Thr Arg Tyr Glu Lys Ser Pro Ile Ile Lys Leu
         50                  55                  60
Asp Pro Glu Glu Val Glu Arg His Ile Lys Glu Ala Arg Glu Val Arg
 65                  70                  75                  80
Glu Leu Ala Lys Ile Met Ala Ser Lys Glu
                 85                  90

<210> SEQ ID NO 393
<211> LENGTH: 243
<212> TYPE: DNA
<213> ORGANISM: Bacteriophage D5700

<400> SEQUENCE: 393
atggcagtag tggtcgaagc ctcagcatta tgctggggct ttttttgtta taatataacct    60 atatcaatgg cctcccacgc atacgcgcag atacgttctg atgggaggtt tttttgttg    120 ccgttaaaac ggacaaaaaa atttaaaaag tttgatttta tgttgataaa tacacgcata    180
agcgtgtata atgtaattaa agataaggaa agcgaggaaa caaaaatggg tagtaaaaat    240
taa                                                                  243

<210> SEQ ID NO 394
<211> LENGTH: 80
<212> TYPE: PRT
<213> ORGANISM: Bacteriophage D5700

<400> SEQUENCE: 394

Met Ala Val Val Val Glu Ala Ser Ala Leu Cys Trp Gly Phe Phe Cys
 1               5                  10                  15
Tyr Asn Ile Pro Ile Ser Met Ala Ser His Ala Tyr Ala Gln Ile Arg
                20                  25                  30
Ser Asp Gly Arg Phe Phe Leu Leu Pro Leu Lys Arg Thr Lys Lys Phe
            35                  40                  45
Lys Lys Phe Asp Phe Ile Val Asp Asn Thr Arg Ile Ser Val Tyr Asn
 50                  55                  60
Val Ile Lys Asp Lys Glu Ser Glu Glu Asn Lys Asn Gly Ser Lys Asn
 65                  70                  75                  80

<210> SEQ ID NO 395
<211> LENGTH: 471
<212> TYPE: DNA
<213> ORGANISM: Bacteriophage D5839

<400> SEQUENCE: 395
ttgctggggc ttttttttgtg ttataataga ataaaaaaac aaatagatga ggtaagaaaa    60
acggctattg acctgtatcg tgaactggat atccaatcgt tggagcaaag attggaaaag    120
aacgaagaaa acactcaacg cttcctccaa caaacagcca aaagcttaaa ccaagacaag    180
actgaactat ctctccgaac tgaccagtta gggcgtagtg ttgaaaagat tgaaaacaaa    240
ctagacgaca tgtacgctaa gaacgaacta gacttgaaat tccagatgat ggatcaaaag    300
attgacgcta aatttgatac ctttggtcaa cgcatggaaa acatgttctt agcacaaacc    360
aataggcaac ttgaggaaca agccaagaat agaaagaat tcacatattg gtttatttgc    420
attcttgtag ctatcgctgt tattgctatt cctgtttggt tcggcaaata a             471

<210> SEQ ID NO 396
<211> LENGTH: 156
```

```
<212> TYPE: PRT
<213> ORGANISM: Bacteriophage D5839

<400> SEQUENCE: 396

Met Leu Gly Leu Phe Leu Cys Tyr Asn Arg Ile Lys Lys Gln Ile Asp
1               5                   10                  15

Glu Val Arg Lys Thr Ala Ile Asp Leu Tyr Arg Glu Leu Asp Ile Gln
                20                  25                  30

Ser Leu Glu Gln Arg Leu Glu Lys Asn Glu Glu Asn Thr Gln Arg Phe
            35                  40                  45

Leu Gln Gln Thr Ala Lys Ser Leu Asn Gln Asp Lys Thr Glu Leu Ser
        50                  55                  60

Leu Arg Thr Asp Gln Leu Gly Arg Ser Val Glu Lys Ile Glu Asn Lys
65                  70                  75                  80

Leu Asp Asp Met Tyr Ala Lys Asn Glu Leu Asp Leu Lys Phe Gln Met
                85                  90                  95

Met Asp Gln Lys Ile Asp Ala Lys Phe Asp Thr Phe Gly Gln Arg Met
                100                 105                 110

Glu Asn Met Phe Leu Ala Gln Thr Asn Arg Gln Leu Glu Glu Gln Ala
            115                 120                 125

Lys Asn Arg Lys Glu Phe Thr Tyr Trp Phe Ile Cys Ile Leu Val Ala
        130                 135                 140

Ile Ala Val Ile Ala Ile Pro Val Trp Phe Gly Lys
145                 150                 155

<210> SEQ ID NO 397
<211> LENGTH: 204
<212> TYPE: DNA
<213> ORGANISM: Bacteriophage D5839

<400> SEQUENCE: 397
atgtcatttt ttacgtcaac aaaaacggca acgtcaactt ttttcatagc aagtaataga      60
atacttgcat catttcgatt aaattctcga actgtacacc cgtcttttt aggtgggttt     120 tttgttttgc aaaaaaatct aaatttattt atcaaaagca ttgacaaact atcatgtatg    180
atatataata tacttataag ataa                                           204

<210> SEQ ID NO 398
<211> LENGTH: 67
<212> TYPE: PRT
<213> ORGANISM: Bacteriophage D5839

<400> SEQUENCE: 398

Met Ser Phe Phe Thr Ser Thr Lys Thr Ala Thr Ser Thr Phe Phe Ile
1               5                   10                  15

Ala Ser Asn Arg Ile Leu Ala Ser Phe Arg Leu Asn Ser Arg Thr Val
                20                  25                  30

His Pro Ser Phe Leu Gly Gly Phe Phe Val Leu Gln Lys Asn Leu Asn
            35                  40                  45

Leu Phe Ile Lys Ser Ile Asp Lys Leu Ser Cys Met Ile Tyr Asn Ile
        50                  55                  60

Leu Ile Arg
65

<210> SEQ ID NO 399
<211> LENGTH: 129
<212> TYPE: DNA
<213> ORGANISM: Bacteriophage D6252
```

<400> SEQUENCE: 399
atgttactaa tagtgacatt cagttatatc ataaattatt tgttgttcga tttgggaagt    60
agcttaatta aaaaggaga aagaaaatgc tactataaag gatttaagac aaagaaggat   120
gtaatctaa                                                         129

<210> SEQ ID NO 400
<211> LENGTH: 42
<212> TYPE: PRT
<213> ORGANISM: Bacteriophage D6252

<400> SEQUENCE: 400

Met Leu Leu Ile Val Thr Phe Ser Tyr Ile Ile Asn Tyr Leu Leu Phe
1               5                   10                  15

Asp Leu Gly Ser Ser Leu Ile Lys Lys Gly Glu Arg Lys Cys Tyr Tyr
            20                  25                  30

Lys Gly Phe Lys Thr Lys Lys Asp Val Ile
        35                  40

<210> SEQ ID NO 401
<211> LENGTH: 159
<212> TYPE: DNA
<213> ORGANISM: Bacteriophage D6252

<400> SEQUENCE: 401
ttggagtgct tatattttag gaaaaaagag ggcgcttgct ctcttttttt tatgtattca    60
ataaaaagta tactttataa attttagagt tattttgtta aaaactcaaa aaaacttgaa   120
aaaaaatcaa gaaaactgtt gacattgaat tttgtttaa                         159

<210> SEQ ID NO 402
<211> LENGTH: 28
<212> TYPE: PRT
<213> ORGANISM: Bacteriophage D6252

<400> SEQUENCE: 402

Met Glu Cys Leu Tyr Phe Arg Lys Lys Glu Gly Ala Cys Ser Leu Phe
1               5                   10                  15

Phe Met Tyr Ser Ile Lys Ser Ile Leu Tyr Lys Phe
            20                  25

<210> SEQ ID NO 403
<211> LENGTH: 690
<212> TYPE: DNA
<213> ORGANISM: Bacteriophage D7130

<400> SEQUENCE: 403
ttggatattt acgtttatac tgatgaatca ggagtatttg ataaagaaca tgaaacaata    60
tatgtttatg gtggagtgat tttttttaact tctgaggaca aagagaattc aggtagaaga   120
tatatatatg cggaaaaagc actaagaaaa agccatagta attataggaa aggggaactg   180
aaagcaagta ggcttaaaaa tagacataaa gccagtttgt ttaggtcgct taatagggaa   240
ataaaatttt ctatagtggt gagtattggc agggtgcatg ataggatttt ttgtgagaaa   300
aaaagtaagc agcgttactt agattatgtt tacaaagttg gtttgaaaaa ggtgttacaa   360
cgtcttgtag cagattgtaa aatagagact accgaagtag atacgatcag tattttaca    420 gatgagcata gtactgcgac taatggaaaa tatgagttaa gagaggcgct gttaaacgag   480
tttaaatatg gcacgtttaa cccagactgg aatatttttt atcctcccctt attcgaaaaa   540

```
ctatctagtt taactgttga atactgtaat tcagctaaaa agccacatat acgtatggca    600
gatataatag cgaatagagc atattatctt gcaaagaatg atcttttggg agagttggga    660
gagaaaacta tatcaatcca cttcccttag                                    690
```

<210> SEQ ID NO 404
<211> LENGTH: 229
<212> TYPE: PRT
<213> ORGANISM: Bacteriophage D7130

<400> SEQUENCE: 404

```
Met Asp Ile Tyr Val Tyr Thr Asp Glu Ser Gly Val Phe Asp Lys Glu
1               5                   10                  15

His Glu Thr Ile Tyr Val Tyr Gly Gly Val Ile Phe Leu Thr Ser Glu
            20                  25                  30

Asp Lys Glu Asn Ser Gly Arg Arg Tyr Ile Tyr Ala Glu Lys Ala Leu
        35                  40                  45

Arg Lys Ser His Ser Asn Tyr Arg Lys Gly Glu Leu Lys Ala Ser Arg
    50                  55                  60

Leu Lys Asn Arg His Lys Ala Ser Leu Phe Arg Ser Leu Asn Arg Glu
65                  70                  75                  80

Ile Lys Phe Ser Ile Val Val Ser Ile Gly Arg Val His Asp Arg Ile
                85                  90                  95

Phe Cys Glu Lys Lys Ser Lys Gln Arg Tyr Leu Asp Tyr Val Tyr Lys
            100                 105                 110

Val Gly Leu Lys Lys Val Leu Gln Arg Leu Val Ala Asp Cys Lys Ile
        115                 120                 125

Glu Thr Thr Glu Val Asp Thr Ile Ser Ile Phe Thr Asp Glu His Ser
    130                 135                 140

Thr Ala Thr Asn Gly Lys Tyr Glu Leu Arg Glu Ala Leu Leu Asn Glu
145                 150                 155                 160

Phe Lys Tyr Gly Thr Phe Asn Pro Asp Trp Asn Ile Phe Tyr Pro Pro
                165                 170                 175

Leu Phe Glu Lys Leu Ser Ser Leu Thr Val Glu Tyr Cys Asn Ser Ala
            180                 185                 190

Lys Lys Pro His Ile Arg Met Ala Asp Ile Ile Ala Asn Arg Ala Tyr
        195                 200                 205

Tyr Leu Ala Lys Asn Asp Leu Phe Gly Glu Leu Gly Glu Lys Thr Ile
    210                 215                 220

Ser Ile His Phe Pro
225
```

<210> SEQ ID NO 405
<211> LENGTH: 135
<212> TYPE: DNA
<213> ORGANISM: Bacteriophage D7130

<400> SEQUENCE: 405

```
ttggagagtt gggagagaaa actatatcaa tccacttccc ttagttttag aaagaggcga    60
ggctgtaagc ctctttttat tataatggtc aagtatgtgg gattttgctt aattctgttc   120
atgacattag ggtag                                                   135
```

<210> SEQ ID NO 406
<211> LENGTH: 44
<212> TYPE: PRT
<213> ORGANISM: Bacteriophage D7130

<400> SEQUENCE: 406

Met Glu Ser Trp Glu Arg Lys Leu Tyr Gln Ser Thr Ser Leu Ser Phe
1               5                   10                  15

Arg Lys Arg Arg Gly Cys Lys Pro Leu Phe Ile Ile Met Val Lys Tyr
            20                  25                  30

Val Gly Phe Cys Leu Ile Leu Phe Met Thr Leu Gly
        35                  40

<210> SEQ ID NO 407
<211> LENGTH: 150
<212> TYPE: DNA
<213> ORGANISM: Bacteriophage M5728

<400> SEQUENCE: 407
gtgcacaaaa agggaattca tataaaaaaa gtcggctatt ttagtcgact cttttttta      60 tgtcatgtaa acagcagtat agcgttttct attatgttat cgatgtcgtg tcgtttctct   120 aacttttca atgttggaa acttttctga                                       150

<210> SEQ ID NO 408
<211> LENGTH: 49
<212> TYPE: PRT
<213> ORGANISM: Bacteriophage M5728

<400> SEQUENCE: 408

Met His Lys Lys Gly Ile His Ile Lys Lys Val Gly Tyr Phe Ser Arg
1               5                   10                  15

Leu Phe Phe Leu Cys His Val Asn Ser Ser Ile Ala Phe Ser Ile Met
            20                  25                  30

Leu Ser Met Ser Cys Arg Phe Ser Asn Phe Phe Lys Cys Trp Lys Leu
        35                  40                  45

Phe

<210> SEQ ID NO 409
<211> LENGTH: 141
<212> TYPE: DNA
<213> ORGANISM: Bacteriophage M5782

<400> SEQUENCE: 409
ttgttggggg ggctaagacg cccccttttt gatatatcaa cggcctccca cccgtctttt      60
ttaggtgggt tttttgtttt gcaaaaaatt ttttatcaa agtacggat acatacaaag     120 aatacgcttt taacgtttta a                                              141

<210> SEQ ID NO 410
<211> LENGTH: 46
<212> TYPE: PRT
<213> ORGANISM: Bacteriophage M5782

<400> SEQUENCE: 410

Met Leu Gly Gly Leu Arg Arg Pro Leu Phe Asp Ile Ser Thr Ala Ser
1               5                   10                  15

His Pro Ser Phe Leu Gly Gly Phe Phe Val Leu Gln Lys Ile Phe Leu
            20                  25                  30

Ser Lys Val Arg Ile His Thr Lys Asn Thr Leu Leu Thr Phe
        35                  40                  45

<210> SEQ ID NO 411
<211> LENGTH: 438

```
<212> TYPE: DNA
<213> ORGANISM: Bacteriophage P3681

<400> SEQUENCE: 411
atgaacgaaa tagcattatc ggacaatctt gcacagattg aacttgaaat caatcatcat    60
aagcagattg caggtcagtc tatttgggaa atcggcaggc gtttaaatca tgttaaagag   120
cacgatttag cgcatgggca atttatggaa tgggttgaaa aacttggtat aaatcaacca   180
gaagccaatc gtatgatgag agttgctaaa gaactaccaa attcttcaac gttgagtaat   240
ttaggaagca cggctctcta cttaatcgcc actcttccag atgatgaaaa gcaagaacaa   300
attgaaaaga ttgagcaagg tgaatcacca acggtcagag aattgcaaga gataaagcgt   360
cgtctcaaac tcaaagacca agcactggaa gcggtcaagg gtgagttgga acgtgctata   420
cttggtatta aagtttaa                                                 438

<210> SEQ ID NO 412
<211> LENGTH: 145
<212> TYPE: PRT
<213> ORGANISM: Bacteriophage P3681

<400> SEQUENCE: 412

Met Asn Glu Ile Ala Leu Ser Asp Asn Leu Ala Gln Ile Glu Leu Glu
1               5                   10                  15

Ile Asn His His Lys Gln Ile Ala Gly Gln Ser Ile Trp Glu Ile Gly
            20                  25                  30

Arg Arg Leu Asn His Val Lys Glu His Asp Leu Ala His Gly Gln Phe
        35                  40                  45

Met Glu Trp Val Glu Lys Leu Gly Ile Asn Gln Pro Glu Ala Asn Arg
    50                  55                  60

Met Met Arg Val Ala Lys Glu Leu Pro Asn Ser Ser Thr Leu Ser Asn
65                  70                  75                  80

Leu Gly Ser Thr Ala Leu Tyr Leu Ile Ala Thr Leu Pro Asp Asp Glu
                85                  90                  95

Lys Gln Glu Gln Ile Glu Lys Ile Glu Gln Gly Glu Ser Pro Thr Val
            100                 105                 110

Arg Glu Leu Gln Glu Ile Lys Arg Arg Leu Lys Leu Lys Asp Gln Ala
        115                 120                 125

Leu Glu Ala Val Lys Gly Glu Leu Glu Arg Ala Ile Leu Gly Ile Lys
    130                 135                 140

Val
145

<210> SEQ ID NO 413
<211> LENGTH: 438
<212> TYPE: DNA
<213> ORGANISM: Bacteriophage P3684

<400> SEQUENCE: 413
atgaacgaaa tagcattatc ggacaatctt gcacagattg aacttgaaat caatcatcat    60
aagcagattg caggtcagtc tatttgggaa atcggcaggc gtttaaatca tgttaaagag   120
cacgatttag cgcatgggca atttatggaa tgggttgaaa aacttggtat aaatcaacca   180
gaagccaatc gtatgatgag agttgctaaa gaactaccaa attcttcaac gttgagtaat   240
ttaggaagca cggctctcta cttaatcgcc actcttccag atgatgaaaa gcaagaacaa   300
attgaaaaga ttgagcaagg tgaatcacca acggtcagag aattgcaaga gataaagcgt   360
```

-continued

```
cgtctcaaac tcaaagacca agaactggaa gcggtcaagg gtgagttgga acgtgctata       420
cttggtatta aagtttaa                                                     438
```

<210> SEQ ID NO 414
<211> LENGTH: 145
<212> TYPE: PRT
<213> ORGANISM: Bacteriophage P3684

<400> SEQUENCE: 414

```
Met Asn Glu Ile Ala Leu Ser Asp Asn Leu Ala Gln Ile Glu Leu Glu
1               5                   10                  15

Ile Asn His His Lys Gln Ile Ala Gly Gln Ser Ile Trp Glu Ile Gly
            20                  25                  30

Arg Arg Leu Asn His Val Lys Glu His Asp Leu Ala His Gly Gln Phe
        35                  40                  45

Met Glu Trp Val Glu Lys Leu Gly Ile Asn Gln Pro Glu Ala Asn Arg
    50                  55                  60

Met Met Arg Val Ala Lys Glu Leu Pro Asn Ser Ser Thr Leu Ser Asn
65                  70                  75                  80

Leu Gly Ser Thr Ala Leu Tyr Leu Ile Ala Thr Leu Pro Asp Asp Glu
                85                  90                  95

Lys Gln Glu Gln Ile Glu Lys Ile Glu Gln Gly Glu Ser Pro Thr Val
            100                 105                 110

Arg Glu Leu Gln Glu Ile Lys Arg Arg Leu Lys Leu Lys Asp Gln Glu
        115                 120                 125

Leu Glu Ala Val Lys Gly Glu Leu Glu Arg Ala Ile Leu Gly Ile Lys
    130                 135                 140

Val
145
```

<210> SEQ ID NO 415
<211> LENGTH: 336
<212> TYPE: DNA
<213> ORGANISM: Bacteriophage P4761

<400> SEQUENCE: 415

```
atggaagaat tagaacaagc gtttgaaaat cttgatgatt ggtatctatc aagcatgaaa       60
gacagtgctt acaaggattt tgggaaatac gaaattcgct tatcaaatca ttcggcagac      120
aataaatatc atgacctaga aaatggtcgc ttaatcgtta atgttaaagc tagtaaattg      180
aacttcgttg atatcatcga gaataaaatc tataaaatca ttgagaaaat tgaaactctc      240
gatttagaca agtacagatt tattaacgct actaaaatgg aaaacgatat caaatgttat      300
tacaagggat ttaagacaaa gaaggatgtg atctaa                                336
```

<210> SEQ ID NO 416
<211> LENGTH: 111
<212> TYPE: PRT
<213> ORGANISM: Bacteriophage P4761

<400> SEQUENCE: 416

```
Met Glu Glu Leu Glu Gln Ala Phe Glu Asn Leu Asp Asp Trp Tyr Leu
1               5                   10                  15

Ser Ser Met Lys Asp Ser Ala Tyr Lys Asp Phe Gly Lys Tyr Glu Ile
            20                  25                  30

Arg Leu Ser Asn His Ser Ala Asp Asn Lys Tyr His Asp Leu Glu Asn
        35                  40                  45
```

Gly Arg Leu Ile Val Asn Val Lys Ala Ser Lys Leu Asn Phe Val Asp
            50                  55                  60

Ile Ile Glu Asn Lys Ile Tyr Lys Ile Glu Lys Ile Glu Thr Leu
 65                  70                  75                  80

Asp Leu Asp Lys Tyr Arg Phe Ile Asn Ala Thr Lys Met Glu Asn Asp
                 85                  90                  95

Ile Lys Cys Tyr Tyr Lys Gly Phe Lys Thr Lys Lys Asp Val Ile
            100                 105                 110

<210> SEQ ID NO 417
<211> LENGTH: 177
<212> TYPE: DNA
<213> ORGANISM: Bacteriophage P5641

<400> SEQUENCE: 417
atgacagatg cgcacaaaaa agctgttaag aagtggaata aaaacaacag agaacataga      60
aattatctaa acaagcgttc atcagctcgt ggtttcatca gaataatgc gactgctgaa     120 gatttgagag agctagagga gcttattgca gaaagaagaa aaagaattt taggtaa        177

<210> SEQ ID NO 418
<211> LENGTH: 58
<212> TYPE: PRT
<213> ORGANISM: Bacteriophage P5641

<400> SEQUENCE: 418

Met Thr Asp Ala His Lys Lys Ala Val Lys Lys Trp Asn Lys Asn
 1               5                  10                  15

Arg Glu His Arg Asn Tyr Leu Asn Lys Arg Ser Ser Ala Arg Gly Phe
                 20                  25                  30

Ile Arg Asn Asn Ala Thr Ala Glu Asp Leu Arg Glu Leu Glu Glu Leu
             35                  40                  45

Ile Ala Glu Arg Arg Lys Lys Asn Phe Arg
             50                  55

<210> SEQ ID NO 419
<211> LENGTH: 294
<212> TYPE: DNA
<213> ORGANISM: Bacteriophage P7573

<400> SEQUENCE: 419
ttgttaaacc taaagcgcga gcgaaatcat cagctttatt cagcgggaac accgactac      60 ctgaaagata tcttgtttga atcccagct ttatttgcat tgacatggaa ctgttgtcta    120
aatagctttt tattatcgtt gtttctcata tttaatagta taacattat acaaaagttc    180 ccaaaaaata aacaatatgt tcccaaaaat aaactttttt catattttttt tgattttagt    240 gttgacaaat gggaacgtgt tagatatact ataattgttc taaggaacaa gtaa           294

<210> SEQ ID NO 420
<211> LENGTH: 97
<212> TYPE: PRT
<213> ORGANISM: Bacteriophage P7573

<400> SEQUENCE: 420

Met Leu Asn Leu Lys Arg Glu Arg Asn His Gln Leu Tyr Ser Ala Gly
 1               5                  10                  15

Thr Pro Asp Tyr Leu Lys Asp Ile Leu Phe Glu Ile Pro Ala Leu Phe
                 20                  25                  30

Ala Leu Thr Trp Asn Cys Cys Leu Asn Ser Phe Leu Leu Ser Leu Phe 35                  40                  45

Leu Ile Phe Asn Ser Ile Asn Ile Ile Gln Lys Phe Pro Lys Asn Lys
             50                  55                  60

Gln Tyr Val Pro Lys Asn Lys Leu Phe Ser Tyr Phe Phe Asp Phe Ser
 65                  70                  75                  80

Val Asp Lys Trp Glu Arg Val Arg Tyr Thr Ile Ile Val Leu Arg Asn
                 85                  90                  95

Lys

<210> SEQ ID NO 421
<211> LENGTH: 105
<212> TYPE: DNA
<213> ORGANISM: Bacteriophage P7601

<400> SEQUENCE: 421
ttgcaaaaaa aatatataat tttttataaa aacagtttcc gtctggtcgc aaaaatcgac    60
ttgaatggat tgaaaacaat cttgaaaaca ttcgataaaa aataa                   105

<210> SEQ ID NO 422
<211> LENGTH: 34
<212> TYPE: PRT
<213> ORGANISM: Bacteriophage P7601

<400> SEQUENCE: 422

Met Gln Lys Lys Tyr Ile Ile Phe Tyr Lys Asn Ser Phe Arg Leu Val
 1               5                  10                  15

Ala Lys Ile Asp Leu Asn Gly Leu Lys Thr Ile Leu Lys Thr Phe Asp
             20                  25                  30

Lys Lys

<210> SEQ ID NO 423
<211> LENGTH: 105
<212> TYPE: DNA
<213> ORGANISM: Bacteriophage P7602

<400> SEQUENCE: 423
ttgcgcacac acaagcataa gggaaaattt tgttgggggg ggctaagacg ccccctttt    60 gatataatat acctatatca acggcctccc acccgtcttt tttag                   105

<210> SEQ ID NO 424
<211> LENGTH: 34
<212> TYPE: PRT
<213> ORGANISM: Bacteriophage P7602

<400> SEQUENCE: 424

Met Arg Thr His Lys His Lys Gly Lys Phe Cys Trp Gly Gly Leu Arg
 1               5                  10                  15

Arg Pro Leu Phe Asp Ile Ile Tyr Leu Tyr Gln Arg Pro Pro Thr Arg
             20                  25                  30

Leu Phe

<210> SEQ ID NO 425
<211> LENGTH: 132
<212> TYPE: DNA
<213> ORGANISM: Bacteriophage P9853

<400> SEQUENCE: 425
atgctggggc ttttttttaa tataaatgct actatattaa tggatacagt taaaagagaa    60

```
gcatccagat atgatggatt ttatggacct gatagattgg tatttagaaa atcgcaaacc    120
ataagatatt ga                                                        132
```

<210> SEQ ID NO 426
<211> LENGTH: 43
<212> TYPE: PRT
<213> ORGANISM: Bacteriophage P9853

<400> SEQUENCE: 426

```
Met Leu Gly Leu Phe Phe Asn Ile Asn Ala Thr Ile Leu Met Asp Thr
1               5                   10                  15
Val Lys Arg Glu Ala Ser Arg Tyr Asp Gly Phe Tyr Gly Pro Asp Arg
            20                  25                  30
Leu Val Phe Arg Lys Ser Gln Thr Ile Arg Tyr
        35                  40
```

<210> SEQ ID NO 427
<211> LENGTH: 222
<212> TYPE: DNA
<213> ORGANISM: Bacteriophage TP-778L

<400> SEQUENCE: 427

```
atgtacgcta agaacgaact agatttgaaa ttccagatga tggatcaaaa gattgacgct     60
aaatttgata cctttggtca acgcatggaa aacatgttct tagcacaaac caataggcaa    120
cttgaggaac aagccaagaa tagaaaagaa ttcacatatt ggtttatttg cattcttgta    180
gctatcgctg ttattgctat tcctgtttgg ttcggcaaat aa                       222
```

<210> SEQ ID NO 428
<211> LENGTH: 73
<212> TYPE: PRT
<213> ORGANISM: Bacteriophage TP-778L

<400> SEQUENCE: 428

```
Met Tyr Ala Lys Asn Glu Leu Asp Leu Lys Phe Gln Met Met Asp Gln
1               5                   10                  15
Lys Ile Asp Ala Lys Phe Asp Thr Phe Gly Gln Arg Met Glu Asn Met
            20                  25                  30
Phe Leu Ala Gln Thr Asn Arg Gln Leu Glu Glu Gln Ala Lys Asn Arg
        35                  40                  45
Lys Glu Phe Thr Tyr Trp Phe Ile Cys Ile Leu Val Ala Ile Ala Val
    50                  55                  60
Ile Ala Ile Pro Val Trp Phe Gly Lys
65                  70
```

<210> SEQ ID NO 429
<211> LENGTH: 222
<212> TYPE: DNA
<213> ORGANISM: Bacteriophage TP-J34

<400> SEQUENCE: 429

```
atgtacgcta agaacgaact agacttgaaa ttccagatga tggatcaaaa gattgacgct     60
aaatttgata cctttggtca acgcatggaa aacatgttct tagcacaaac caataggcaa    120
cttgaggaac aagccaagaa tagaaaagaa ttcacatatt ggtttatttg cattcttgta    180
gctatcgctg ttattgctat tcctgtttgg ttcggcaaat aa                       222
```

<210> SEQ ID NO 430
<211> LENGTH: 73

<212> TYPE: PRT
<213> ORGANISM: Bacteriophage TP-J34

<400> SEQUENCE: 430

```
Met Tyr Ala Lys Asn Glu Leu Asp Leu Lys Phe Gln Met Met Asp Gln
1               5                   10                  15

Lys Ile Asp Ala Lys Phe Asp Thr Phe Gly Gln Arg Met Glu Asn Met
            20                  25                  30

Phe Leu Ala Gln Thr Asn Arg Gln Leu Glu Gln Ala Lys Asn Arg
        35                  40                  45

Lys Glu Phe Thr Tyr Trp Phe Ile Cys Ile Leu Val Ala Ile Ala Val
    50                  55                  60

Ile Ala Ile Pro Val Trp Phe Gly Lys
65                  70
```

<210> SEQ ID NO 431
<211> LENGTH: 183
<212> TYPE: DNA
<213> ORGANISM: Bacteriophage D3820

<400> SEQUENCE: 431

```
atggatacat ataagaaca attttattat ttggatccta tttatattag tgtggatatt       60
aataggagga ctttattttt aggaaaaaga gggcaatcgc tctcttttt tattgtaata      120 aaacaattta aaatataac taaaaaaact tcaaaaaaat cgaaaaaaaa tattgacaaa      180
taa                                                                  183
```

<210> SEQ ID NO 432
<211> LENGTH: 60
<212> TYPE: PRT
<213> ORGANISM: Bacteriophage D3820

<400> SEQUENCE: 432

```
Met Asp Thr Tyr Lys Glu Gln Phe Tyr Tyr Leu Asp Pro Ile Tyr Ile
1               5                   10                  15

Ser Val Asp Ile Asn Arg Arg Thr Phe Ile Leu Gly Lys Arg Gly Gln
            20                  25                  30

Ser Leu Ser Phe Phe Ile Val Ile Lys Gln Phe Lys Asn Ile Thr Lys
        35                  40                  45

Lys Thr Ser Lys Lys Ser Lys Lys Asn Ile Asp Lys
    50                  55                  60
```

<210> SEQ ID NO 433
<211> LENGTH: 177
<212> TYPE: DNA
<213> ORGANISM: Bacteriophage P7574

<400> SEQUENCE: 433

```
atgctgggc ttttttgtg ttataatatg aatgagatgt caatccccc acatcctttt        60 atggacagat acgttctgag tgggggtttt tttgttttgc tatttttaa cctaacagcc     120 cgtaattccc ccacctctaa ggtggcggga tgtaagggct tcggtctagt gcagtga       177
```

<210> SEQ ID NO 434
<211> LENGTH: 58
<212> TYPE: PRT
<213> ORGANISM: Bacteriophage P7574

<400> SEQUENCE: 434

```
Met Leu Gly Leu Phe Leu Cys Tyr Asn Met Asn Glu Met Ser Ile Pro
```

```
              1               5                  10                 15
Pro His Pro Phe Met Asp Arg Tyr Val Leu Ser Gly Gly Phe Val
                         20                  25                 30

Leu Leu Phe Phe Asn Leu Thr Ala Arg Asn Ser Pro Thr Ser Lys Val
             35                  40                  45

Ala Gly Cys Lys Gly Phe Gly Leu Val Gln
    50                  55

<210> SEQ ID NO 435
<211> LENGTH: 195
<212> TYPE: DNA
<213> ORGANISM: Bacteriophage D1422

<400> SEQUENCE: 435
atgttcagcg accttgtgcg ttcgaaagtg tataagggaa cattttgttg tgggctaaga        60 ccccctttt  ttgatataat atatctatat caatgtcctc ccacgcataa gcgcagatac       120
gttctgaggg aggttttta  tttgttttat tttgataaaa atgctactat attaacggat       180
acagttaaaa gctga                                                         195

<210> SEQ ID NO 436
<211> LENGTH: 64
<212> TYPE: PRT
<213> ORGANISM: Bacteriophage D1422

<400> SEQUENCE: 436

Met Phe Ser Asp Leu Val Arg Ser Lys Val Tyr Lys Gly Thr Phe Cys
1               5                  10                  15

Cys Gly Leu Arg Pro Pro Phe Phe Asp Ile Ile Tyr Leu Tyr Gln Cys
                20                  25                  30

Pro Pro Thr His Lys Arg Arg Tyr Val Leu Arg Glu Val Phe Tyr Leu
            35                  40                  45

Phe Tyr Phe Asp Lys Asn Ala Thr Ile Leu Thr Asp Thr Val Lys Ser
    50                  55                  60

<210> SEQ ID NO 437
<211> LENGTH: 195
<212> TYPE: DNA
<213> ORGANISM: Bacteriophage D5861

<400> SEQUENCE: 437
atgttcagcg accttgtgcg ttcgcaagtg tataagggaa cattttgttg tgggctaaga        60 ccccctttt  ttgatataat atatctatat caatgtcctc ccacgcataa gcgcagatac       120
gttctgaggg aggtttttta tttgttttat tttgatataa atgctactat aataatggat       180
acagttaaaa gctga                                                         195

<210> SEQ ID NO 438
<211> LENGTH: 64
<212> TYPE: PRT
<213> ORGANISM: Bacteriophage D5861

<400> SEQUENCE: 438

Met Phe Ser Asp Leu Val Arg Ser Gln Val Tyr Lys Gly Thr Phe Cys
1               5                  10                  15

Cys Gly Leu Arg Pro Pro Phe Phe Asp Ile Ile Tyr Leu Tyr Gln Cys
                20                  25                  30

Pro Pro Thr His Lys Arg Arg Tyr Val Leu Arg Glu Val Phe Tyr Leu
            35                  40                  45
```

Phe Tyr Phe Asp Ile Asn Ala Thr Ile Ile Met Asp Thr Val Lys Ser
    50                  55                  60

<210> SEQ ID NO 439
<211> LENGTH: 264
<212> TYPE: DNA
<213> ORGANISM: Bacteriophage P3681

<400> SEQUENCE: 439
atgaatagca tgaaaaagcc ccacactgcg gaaaacggcg atttaattca tacaacagaa      60
gacaacgagg cttcagatat atcaatcatt acaatttcgt tgttcgcaa aacgaacaag     120 caaatattga aaaattcgaa agtttgccta aaacgttaca agctcaagta tctaaaccat    180
ctgccaatcc agaggttaat caagcagtat tcgacggaga tatcaaagca aaagaaatt    240 atagctcttg aaaaaaatga gtga                                            264

<210> SEQ ID NO 440
<211> LENGTH: 87
<212> TYPE: PRT
<213> ORGANISM: Bacteriophage P3681

<400> SEQUENCE: 440

Met Asn Ser Met Lys Lys Pro His Thr Ala Glu Asn Gly Asp Leu Ile
1               5                   10                  15

His Thr Thr Glu Asp Asn Glu Ala Ser Asp Ile Ser Ile Ile Thr Ile
            20                  25                  30

Ser Phe Val Arg Lys Thr Asn Lys Gln Ile Leu Lys Asn Ser Lys Val
        35                  40                  45

Cys Leu Lys Arg Tyr Lys Leu Lys Tyr Leu Asn His Leu Pro Ile Gln
    50                  55                  60

Arg Leu Ile Lys Gln Tyr Ser Thr Glu Ile Ser Lys Gln Lys Glu Ile
65                  70                  75                  80

Ile Ala Leu Glu Lys Asn Glu
                85

<210> SEQ ID NO 441
<211> LENGTH: 243
<212> TYPE: DNA
<213> ORGANISM: Bacteriophage P3684

<400> SEQUENCE: 441
atgaatagca tgaaaaagcc ccacactgcg gaaaacggcg atttaattca tacaacagaa      60
gacaacgagg cttcagatat atcaatcatt acaatttcgt tgttcgcaa aacgaacaag     120 caaatattga aaaattcgaa agtttgccta aaacgttaca agctcaagta tctaaaccat    180
ctgccaatcc agaggttaat caagcagtat tcgacggaga tatcaaagca aaagaatat    240 tga                                                                   243

<210> SEQ ID NO 442
<211> LENGTH: 80
<212> TYPE: PRT
<213> ORGANISM: Bacteriophage P3684

<400> SEQUENCE: 442

Met Asn Ser Met Lys Lys Pro His Thr Ala Glu Asn Gly Asp Leu Ile
1               5                   10                  15

His Thr Thr Glu Asp Asn Glu Ala Ser Asp Ile Ser Ile Ile Thr Ile
            20                  25                  30

Ser Phe Val Arg Lys Thr Asn Lys Gln Ile Leu Lys Asn Ser Lys Val
         35                  40                  45

Cys Leu Lys Arg Tyr Lys Leu Lys Tyr Leu Asn His Leu Pro Ile Gln
     50                  55                  60

Arg Leu Ile Lys Gln Tyr Ser Thr Glu Ile Ser Lys Gln Lys Glu Tyr
 65                  70                  75                  80

<210> SEQ ID NO 443
<211> LENGTH: 81
<212> TYPE: DNA
<213> ORGANISM: Bacteriophage D2767

<400> SEQUENCE: 443
atgttcagcg accttgtgcg ttcgaaagtg tataagggaa catttgttg tgggctaaga    60 ccccccttt ttttgatata a                                              81

<210> SEQ ID NO 444
<211> LENGTH: 26
<212> TYPE: PRT
<213> ORGANISM: Bacteriophage D2767

<400> SEQUENCE: 444

Met Phe Ser Asp Leu Val Arg Ser Lys Val Tyr Lys Gly Thr Phe Cys
 1               5                  10                  15

Cys Gly Leu Arg Pro Pro Phe Phe Leu Ile
             20                  25

<210> SEQ ID NO 445
<211> LENGTH: 153
<212> TYPE: DNA
<213> ORGANISM: Bacteriophage D6660

<400> SEQUENCE: 445
atggcagtag tggtcgaagc ctcagcattt tgctggggc ttttttttgtg ttataatatg    60 aaacatcatt ttatggacag atatttgctt tgttttgata aaatgctac tatattaatg   120 gtcttcgata aactctctct cgccctgact tga                                153

<210> SEQ ID NO 446
<211> LENGTH: 50
<212> TYPE: PRT
<213> ORGANISM: Bacteriophage D6660

<400> SEQUENCE: 446

Met Ala Val Val Val Glu Ala Ser Ala Phe Leu Leu Gly Leu Phe Leu
 1               5                  10                  15

Cys Tyr Asn Met Lys His His Phe Met Asp Arg Tyr Leu Leu Cys Phe
             20                  25                  30

Asp Lys Asn Ala Thr Ile Leu Met Val Phe Asp Lys Leu Ser Leu Ala
         35                  40                  45

Leu Thr
     50

<210> SEQ ID NO 447
<211> LENGTH: 276
<212> TYPE: DNA
<213> ORGANISM: Bacteriophage D802

<400> SEQUENCE: 447
atgataacta agaacaatt aaaaggatac tacagcgaac acttggaaga gctcgtcgaa    60

```
tgggcagacg atataaataa aatcgcttat gagatagatg ggaaaagtca tcaaactaag    120
ataggttggg tgaatgatag attaaaagac cattttatga agaaaaaggg ggttttagtt    180
attcattaca ccaatgagca agtcgaaaca gcctacaatg agtgggtaaa aattacagag    240
gaggcgttta atggattctt taataacaca atctaa                              276
```

<210> SEQ ID NO 448
<211> LENGTH: 91
<212> TYPE: PRT
<213> ORGANISM: Bacteriophage D802

<400> SEQUENCE: 448

```
Met Ile Thr Lys Glu Gln Leu Lys Gly Tyr Tyr Ser Glu His Leu Glu
1               5                   10                  15

Glu Leu Val Glu Trp Ala Asp Asp Ile Asn Lys Ile Ala Tyr Glu Ile
            20                  25                  30

Asp Gly Lys Ser His Gln Thr Lys Ile Gly Trp Val Asn Asp Arg Leu
        35                  40                  45

Lys Asp His Phe Met Lys Glu Lys Gly Val Leu Val Ile His Tyr Thr
    50                  55                  60

Asn Glu Gln Val Glu Thr Ala Tyr Asn Glu Trp Val Lys Ile Thr Glu
65                  70                  75                  80

Glu Ala Phe Asn Gly Phe Phe Asn Asn Thr Ile
                85                  90
```

<210> SEQ ID NO 449
<211> LENGTH: 138
<212> TYPE: DNA
<213> ORGANISM: Bacteriophage P9871

<400> SEQUENCE: 449

```
atggcagcag tggtcgaagc ctcagcattt ttgctggggc ttttttttgtg ttataatatg    60 aatgagatgt caatcccccc acatcctttt atggacagat acgttctgat gggaagtttt    120
ttatttgctt tgttttga                                                   138
```

<210> SEQ ID NO 450
<211> LENGTH: 45
<212> TYPE: PRT
<213> ORGANISM: Bacteriophage P9871

<400> SEQUENCE: 450

```
Met Ala Ala Val Val Glu Ala Ser Ala Phe Leu Leu Gly Leu Phe Leu
1               5                   10                  15

Cys Tyr Asn Met Asn Glu Met Ser Ile Pro Pro His Pro Phe Met Asp
            20                  25                  30

Arg Tyr Val Leu Met Gly Ser Phe Leu Phe Ala Leu Phe
        35                  40                  45
```

<210> SEQ ID NO 451
<211> LENGTH: 147
<212> TYPE: DNA
<213> ORGANISM: Bacteriophage D4254

<400> SEQUENCE: 451

```
atggcagtag tggtcgaagc ctcagcatta tgctggggct tttttttgtgt tataatatac    60 ctatatcaat ggcctcccac gcatacgcgc agatacgttc tgatgggagg ttttttttgtt    120 gccgttaaaa cggacaaaaa aatttaa                                         147
```

<210> SEQ ID NO 452
<211> LENGTH: 48
<212> TYPE: PRT
<213> ORGANISM: Bacteriophage D4254

<400> SEQUENCE: 452

Met Ala Val Val Glu Ala Ser Ala Leu Cys Trp Gly Phe Phe Cys
1               5                   10                  15

Val Ile Ile Tyr Leu Tyr Gln Trp Pro Pro Thr His Thr Arg Arg Tyr
            20                  25                  30

Val Leu Met Gly Gly Phe Phe Val Ala Val Lys Thr Asp Lys Lys Ile
        35                  40                  45

<210> SEQ ID NO 453
<211> LENGTH: 120
<212> TYPE: DNA
<213> ORGANISM: Bacteriophage D4753

<400> SEQUENCE: 453
gtggtcgaag cctcagcatt atgctggggc ttttttgtg ttataataca tatatcaatg    60
gcttcccacg catacgcgca gatacgttct gagggaagtt tttatttgc ttttttttga   120

<210> SEQ ID NO 454
<211> LENGTH: 39
<212> TYPE: PRT
<213> ORGANISM: Bacteriophage D4753

<400> SEQUENCE: 454

Met Val Glu Ala Ser Ala Leu Cys Trp Gly Phe Phe Cys Val Ile Ile
1               5                   10                  15

His Ile Ser Met Ala Ser His Ala Tyr Ala Gln Ile Arg Ser Glu Gly
            20                  25                  30

Ser Phe Leu Phe Ala Phe Phe
        35

<210> SEQ ID NO 455
<211> LENGTH: 126
<212> TYPE: DNA
<213> ORGANISM: Bacteriophage D5944

<400> SEQUENCE: 455
atggcagtag tggtcgaagc ctcagcattt tgctggggct ttttttgtgt tataatatac    60
atggaacgac aaaccccctg catccacatg gacagatacg ctctgacgca gggcttttt   120 atttga                                                            126

<210> SEQ ID NO 456
<211> LENGTH: 41
<212> TYPE: PRT
<213> ORGANISM: Bacteriophage D5944

<400> SEQUENCE: 456

Met Ala Val Val Val Glu Ala Ser Ala Phe Cys Trp Gly Phe Phe Cys
1               5                   10                  15

Val Ile Ile Tyr Met Glu Arg Gln Thr Pro Cys Ile His Met Asp Arg
            20                  25                  30

Tyr Ala Leu Thr Gln Gly Phe Phe Ile
        35                  40

<210> SEQ ID NO 457
<211> LENGTH: 132
<212> TYPE: DNA
<213> ORGANISM: Bacteriophage P0095

<400> SEQUENCE: 457

```
atggcagcag tggtcgaagc ctcagcattt tgctggggc ttttttttgtg ttataatata    60 cctatatcaa tggcttccca cgcatacgcg cagatacgtt ctgagggagg ttttttgttt   120
gctttatttt ga                                                       132
```

<210> SEQ ID NO 458
<211> LENGTH: 43
<212> TYPE: PRT
<213> ORGANISM: Bacteriophage P0095

<400> SEQUENCE: 458

Met Ala Ala Val Val Glu Ala Ser Ala Phe Leu Leu Gly Leu Phe Leu
1               5                   10                  15

Cys Tyr Asn Ile Pro Ile Ser Met Ala Ser His Ala Tyr Ala Gln Ile
            20                  25                  30

Arg Ser Glu Gly Gly Phe Leu Phe Ala Leu Phe
        35                  40

<210> SEQ ID NO 459
<211> LENGTH: 519
<212> TYPE: DNA
<213> ORGANISM: Bacteriophage D6961

<400> SEQUENCE: 459

```
atggaaaatt actctagtcc agtgtataat attaaaaaaa tcccgattga aaaaattcaa    60
gcgaatagct ataaccccaa ccatgtagcg acaccagaaa tgaagttgtt atatgaatcc   120
atcaaagcag acggatacac aatgcctatc gtttgttatt atcttaaaga tgaagacaaa   180
tacgagattg tagatggctt tcaccgttat acaactatgc ttaatcataa agatatttac   240
gaacgagaga atggctgttt acctgtatct gttattgata aaccattaga ggagcgcatg   300
gcttctacag tacgcacaa tcgagcaaga ggtagtcatg atattggctt aatggctaat   360
attgtaactg aattggttga tagcggaatg tctgatgcca agttatgaa agtcttgga    420 atggacgcag acgagttatt aagattaaaa caggttagcg gtttagcaag tttgtttgca   480
aacaaggagt tcagtaaatc gtgggatata aaaaaatag                          519
```

<210> SEQ ID NO 460
<211> LENGTH: 172
<212> TYPE: PRT
<213> ORGANISM: Bacteriophage D6961

<400> SEQUENCE: 460

Met Glu Asn Tyr Ser Ser Pro Val Tyr Asn Ile Lys Lys Ile Pro Ile
1               5                   10                  15

Glu Lys Ile Gln Ala Asn Ser Tyr Asn Pro Asn His Val Ala Thr Pro
            20                  25                  30

Glu Met Lys Leu Leu Tyr Glu Ser Ile Lys Ala Asp Gly Tyr Thr Met
        35                  40                  45

Pro Ile Val Cys Tyr Tyr Leu Lys Asp Glu Asp Lys Tyr Glu Ile Val
    50                  55                  60

Asp Gly Phe His Arg Tyr Thr Thr Met Leu Asn His Lys Asp Ile Tyr
65                  70                  75                  80

Glu Arg Glu Asn Gly Cys Leu Pro Val Ser Val Ile Asp Lys Pro Leu
                85                  90                  95

Glu Glu Arg Met Ala Ser Thr Val Arg His Asn Arg Ala Arg Gly Ser
            100                 105                 110

His Asp Ile Gly Leu Met Ala Asn Ile Val Thr Glu Leu Val Asp Ser
        115                 120                 125

Gly Met Ser Asp Ala Lys Val Met Lys Ser Leu Gly Met Asp Ala Asp
130                 135                 140

Glu Leu Leu Arg Leu Lys Gln Val Ser Gly Leu Ala Ser Leu Phe Ala
145                 150                 155                 160

Asn Lys Glu Phe Ser Lys Ser Trp Asp Ile Lys Lys
                165                 170

<210> SEQ ID NO 461
<211> LENGTH: 516
<212> TYPE: DNA
<213> ORGANISM: Bacteriophage D4250

<400> SEQUENCE: 461
atgcaaacat actctagccc tgtatataat attaagcgcg tgcctattga gaaaattcaa    60
gcaaacagct acaatcctaa ccatgtagca agcccgaaaa tgaagttgct ttaccaatcc   120
atcaaagaag atggttacac aatgccaatc gtatgttatt accttgagga tgaagataag   180
tatgaaattg tggacggttt ccatcggtat acaacgatga agaacacaa ggatatctat   240
gaaagagagg agggtgtct accagtttct gttatagata aaccaatcag tgaccgaatg   300
gcatcaacta tcagacacaa tagagcaaga gggtcgcacg acatcggtct gatgactaat   360
atcatttctg acctagttga ttctgggatg tcagatgcgt ggattatgaa aaatattggt   420
atggatgctg atgaattact acgactaaaa caagttagcg gactggcttc cttgttcaaa   480
gataaggaat tcacgacagc ttgggaagaa ggataa                             516

<210> SEQ ID NO 462
<211> LENGTH: 171
<212> TYPE: PRT
<213> ORGANISM: Bacteriophage D4250

<400> SEQUENCE: 462

Met Gln Thr Tyr Ser Ser Pro Val Tyr Asn Ile Lys Arg Val Pro Ile
1               5                   10                  15

Glu Lys Ile Gln Ala Asn Ser Tyr Asn Pro Asn His Val Ala Ser Pro
            20                  25                  30

Glu Met Lys Leu Leu Tyr Gln Ser Ile Lys Glu Asp Gly Tyr Thr Met
        35                  40                  45

Pro Ile Val Cys Tyr Tyr Leu Glu Asp Glu Asp Lys Tyr Glu Ile Val
50                  55                  60

Asp Gly Phe His Arg Tyr Thr Thr Met Lys Glu His Lys Asp Ile Tyr
65                  70                  75                  80

Glu Arg Glu Glu Gly Cys Leu Pro Val Ser Val Ile Asp Lys Pro Ile
                85                  90                  95

Ser Asp Arg Met Ala Ser Thr Ile Arg His Asn Arg Ala Arg Gly Ser
            100                 105                 110

His Asp Ile Gly Leu Met Thr Asn Ile Ile Ser Asp Leu Val Asp Ser
        115                 120                 125

Gly Met Ser Asp Ala Trp Ile Met Lys Asn Ile Gly Met Asp Ala Asp
130                 135                 140

Glu Leu Leu Arg Leu Lys Gln Val Ser Gly Leu Ala Ser Leu Phe Lys
145                 150                 155                 160

Asp Lys Glu Phe Thr Thr Ala Trp Glu Glu Gly
                165                 170

<210> SEQ ID NO 463
<211> LENGTH: 516
<212> TYPE: DNA
<213> ORGANISM: Bacteriophage D4252

<400> SEQUENCE: 463
atgcaaacat actctagccc tgtatataat attaagcgcg tgcctattga taaaattcaa      60
gcaaacagct acaatcctaa ccatgtagca agcccagaaa tgaagttgct ttatcaatcc     120
atcaaagaag atggttacac aatgccaatc gtatgttatt accttgagga tgaagataag     180
tatgaaattg tggacggttt tcatcggtat acaacgatga agaacacaa ggatatctat      240 gaaagagagg agggtgtct accagtgtct gtcatagata aaccaatcag tgaccgaatg      300
gcatcaacta tcagacacaa tagagcaaga ggttcgcacg catcggtct gatgactaat      360 atcatttctg acctagttga ttctgggatg tcagatgcgt ggattatgaa aaatattggt     420
atggatgctg atgaattact acgactaaaa caagttagcg gactggcttc cttgttcaaa     480
gataaggaat tcacgacagc ttgggaagaa ggataa                              516

<210> SEQ ID NO 464
<211> LENGTH: 171
<212> TYPE: PRT
<213> ORGANISM: Bacteriophage D4252

<400> SEQUENCE: 464

Met Gln Thr Tyr Ser Ser Pro Val Tyr Asn Ile Lys Arg Val Pro Ile
1               5                   10                  15

Asp Lys Ile Gln Ala Asn Ser Tyr Asn Pro Asn His Val Ala Ser Pro
            20                  25                  30

Glu Met Lys Leu Leu Tyr Gln Ser Ile Lys Glu Asp Gly Tyr Thr Met
        35                  40                  45

Pro Ile Val Cys Tyr Tyr Leu Glu Asp Glu Asp Lys Tyr Glu Ile Val
    50                  55                  60

Asp Gly Phe His Arg Tyr Thr Thr Met Lys Glu His Lys Asp Ile Tyr
65                  70                  75                  80

Glu Arg Glu Glu Gly Cys Leu Pro Val Ser Val Ile Asp Lys Pro Ile
                85                  90                  95

Ser Asp Arg Met Ala Ser Thr Ile Arg His Asn Arg Ala Arg Gly Ser
            100                 105                 110

His Asp Ile Gly Leu Met Thr Asn Ile Ile Ser Asp Leu Val Asp Ser
        115                 120                 125

Gly Met Ser Asp Ala Trp Ile Met Lys Asn Ile Gly Met Asp Ala Asp
    130                 135                 140

Glu Leu Leu Arg Leu Lys Gln Val Ser Gly Leu Ala Ser Leu Phe Lys
145                 150                 155                 160

Asp Lys Glu Phe Thr Thr Ala Trp Glu Glu Gly
                165                 170

<210> SEQ ID NO 465
<211> LENGTH: 513
<212> TYPE: DNA
<213> ORGANISM: Bacteriophage D4276

<400> SEQUENCE: 465

```
atgcaaacat actatagccc tgtatataat attaagcgcg tgcctattga gaaaattcaa      60
gcaaacagct acaatcctaa ccatgtagca agcccagaaa tgaagttgct ttatcaatcc     120
atcaaagaag atggttacac aatgccaatc gtatgttatt accttgagga tgaagataag     180
tatgaaattg tggacggttt ccatcggtat acaacgatga agaacacaa ggatatctat      240
gaaagagagg aggggtgtct accagtttct gtcatagata aaccaatcag tgaccgaatg     300
gcatcgacta tcagacacaa tagagcaaga gggtcgcacg acatcggtct gatgactaat     360
atcatttctg acctagttga ttctgggatg tcagatgcgt ggattatgaa aaatattggt     420
atggatgctg atgaattact acgactaaaa caagttagcg gactggcttc cttgttcaaa     480
gataaggaat tcacgacagc ttgggaagaa tga                                  513
```

<210> SEQ ID NO 466
<211> LENGTH: 170
<212> TYPE: PRT
<213> ORGANISM: Bacteriophage D4276

<400> SEQUENCE: 466

```
Met Gln Thr Tyr Tyr Ser Pro Val Tyr Asn Ile Lys Arg Val Pro Ile
1               5                   10                  15
Glu Lys Ile Gln Ala Asn Ser Tyr Asn Pro Asn His Val Ala Ser Pro
            20                  25                  30
Glu Met Lys Leu Leu Tyr Gln Ser Ile Lys Glu Asp Gly Tyr Thr Met
        35                  40                  45
Pro Ile Val Cys Tyr Tyr Leu Glu Asp Glu Asp Lys Tyr Glu Ile Val
    50                  55                  60
Asp Gly Phe His Arg Tyr Thr Thr Met Lys Glu His Lys Asp Ile Tyr
65                  70                  75                  80
Glu Arg Glu Glu Gly Cys Leu Pro Val Ser Val Ile Asp Lys Pro Ile
                85                  90                  95
Ser Asp Arg Met Ala Ser Thr Ile Arg His Asn Arg Ala Arg Gly Ser
            100                 105                 110
His Asp Ile Gly Leu Met Thr Asn Ile Ile Ser Asp Leu Val Asp Ser
        115                 120                 125
Gly Met Ser Asp Ala Trp Ile Met Lys Asn Ile Gly Met Asp Ala Asp
    130                 135                 140
Glu Leu Leu Arg Leu Lys Gln Val Ser Gly Leu Ala Ser Leu Phe Lys
145                 150                 155                 160
Asp Lys Glu Phe Thr Thr Ala Trp Glu Glu
                165                 170
```

<210> SEQ ID NO 467
<211> LENGTH: 225
<212> TYPE: DNA
<213> ORGANISM: Bacteriophage D5691

<400> SEQUENCE: 467

```
atggcacaaa ttaaagatgg ttggcataaa gtttataacg aaaatgttta tgttgaaaac      60
gaaaaagtag tacgaggaac aaaaaaagat tataacggtt ctgaggtcac ttgttatcct     120
tacgaatacg ataaaaacca agattgttgg attaatattt ctgggaaagc aactctttct     180
tcttatagag caggactcaa aaaaggcact aagtgtatga agtaa                     225
```

<210> SEQ ID NO 468

```
<211> LENGTH: 74
<212> TYPE: PRT
<213> ORGANISM: Bacteriophage D5691

<400> SEQUENCE: 468

Met Ala Gln Ile Lys Asp Gly Trp His Lys Val Tyr Asn Glu Asn Val
1               5                   10                  15

Tyr Val Glu Asn Glu Lys Val Val Arg Gly Thr Lys Lys Asp Tyr Asn
            20                  25                  30

Gly Ser Glu Val Thr Cys Tyr Pro Tyr Glu Tyr Asp Lys Asn Gln Asp
        35                  40                  45

Cys Trp Ile Asn Ile Ser Gly Lys Ala Thr Leu Ser Ser Tyr Arg Ala
    50                  55                  60

Gly Leu Lys Lys Gly Thr Lys Cys Met Lys
65                  70

<210> SEQ ID NO 469
<211> LENGTH: 138
<212> TYPE: DNA
<213> ORGANISM: Bacteriophage D1024

<400> SEQUENCE: 469
atgttcagcg accttgtgcg ttcgaaagtg tataagggaa cattttgttg tgggctaaga      60
cccccttttt ttgatataat atatctatat caatgtcctc ccacgcataa gcgcagatac     120
gtgctgagtc ttcgataa                                                   138

<210> SEQ ID NO 470
<211> LENGTH: 45
<212> TYPE: PRT
<213> ORGANISM: Bacteriophage D1024

<400> SEQUENCE: 470

Met Phe Ser Asp Leu Val Arg Ser Lys Val Tyr Lys Gly Thr Phe Cys
1               5                   10                  15

Cys Gly Leu Arg Pro Pro Phe Phe Asp Ile Ile Tyr Leu Tyr Gln Cys
            20                  25                  30

Pro Pro Thr His Lys Arg Arg Tyr Val Leu Ser Leu Arg
        35                  40                  45

<210> SEQ ID NO 471
<211> LENGTH: 123
<212> TYPE: DNA
<213> ORGANISM: Bacteriophage D1018

<400> SEQUENCE: 471 atgctgggc ttttttgtg ttataatatg aatgagatgt caatccccc acatcctttt         60 atggacagat acgttctgag tgggggtttt tttgttttgc tattttttaa aaatgtggta    120
taa                                                                   123

<210> SEQ ID NO 472
<211> LENGTH: 40
<212> TYPE: PRT
<213> ORGANISM: Bacteriophage D1018

<400> SEQUENCE: 472

Met Leu Gly Leu Phe Leu Cys Tyr Asn Met Asn Glu Met Ser Ile Pro
1               5                   10                  15

Pro His Pro Phe Met Asp Arg Tyr Val Leu Ser Gly Gly Phe Phe Val
            20                  25                  30
```

Leu Leu Phe Phe Lys Asn Val Val
        35                  40

<210> SEQ ID NO 473
<211> LENGTH: 141
<212> TYPE: DNA
<213> ORGANISM: Bacteriophage D5738

<400> SEQUENCE: 473
atgctggggc ttttttttgtg ttataatatg aatgagatgt caatcccccc acatccttttt    60 atggacagat acgttctgag tgggggtttt ttgttttgct attttttaaa aatgtggtat    120
aatataaata tccattcata a                                               141

<210> SEQ ID NO 474
<211> LENGTH: 46
<212> TYPE: PRT
<213> ORGANISM: Bacteriophage D5738

<400> SEQUENCE: 474

Met Leu Gly Leu Phe Leu Cys Tyr Asn Met Asn Glu Met Ser Ile Pro
1               5                   10                  15

Pro His Pro Phe Met Asp Arg Tyr Val Leu Ser Gly Gly Phe Leu Phe
            20                  25                  30

Cys Tyr Phe Leu Lys Met Trp Tyr Asn Ile Asn Ile His Ser
        35                  40                  45

<210> SEQ ID NO 475
<211> LENGTH: 258
<212> TYPE: DNA
<213> ORGANISM: Bacteriophage D4276

<400> SEQUENCE: 475
atgaagaaat tttggcatag cggtatgatt gacaagaagg ttattgaaaa acgtaaacaa    60
gatgattata tgaataaatt acacaggact attcttgagt tgagtataaa accacctgaa   120
cccgaacctt ggtacagaca tccagaaatg agagcattgt tggataggat tgattctatg   180
gacatgatag attggtattc aaaatatcta aacatcgca aaccatacga taattatagt    240
ggagaattag agaaatga                                                  258

<210> SEQ ID NO 476
<211> LENGTH: 85
<212> TYPE: PRT
<213> ORGANISM: Bacteriophage D4276

<400> SEQUENCE: 476

Met Lys Lys Phe Trp His Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Asp Ser Met Asp Met Ile Asp
    50                  55                  60

Trp Tyr Ser Lys Tyr Leu Lys His Arg Lys Pro Tyr Asp Asn Tyr Ser
65                  70                  75                  80

Gly Glu Leu Glu Lys
                85

<210> SEQ ID NO 477
<211> LENGTH: 180
<212> TYPE: DNA
<213> ORGANISM: Bacteriophage 5093

<400> SEQUENCE: 477
atgaagaaat tttggcgtag tggaatgatt gacaagaagg ttatcgaaaa acgacaacaa    60
gaagagtata ttaataagtt acataggact attcttgagt tgagtataaa accacctgaa   120
ccagaacctt ggtacagaca tccagaaatg agagcattgt tggatagaat tgatgattag   180

<210> SEQ ID NO 478
<211> LENGTH: 59
<212> TYPE: PRT
<213> ORGANISM: Bacteriophage 5093

<400> SEQUENCE: 478

Met Lys Lys Phe Trp Arg Ser Gly Met Ile Asp Lys Lys Val Ile Glu
1               5                   10                  15

Lys Arg Gln Gln Glu Glu Tyr Ile Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Asp Asp
    50                  55

<210> SEQ ID NO 479
<211> LENGTH: 198
<212> TYPE: DNA
<213> ORGANISM: Bacteriophage D4154

<400> SEQUENCE: 479
atgaagaagt tttggcgtag tggaatgatt gacaagaaag ttattgaaaa acgacaacaa    60
gatgattata tgaataagtt acataggact attcttgagt tgagtataaa accacctgaa   120
cccgaacctt ggtacagaca tccagaaatg agagcatttt tggataggat ttatgattcg   180
agaagcaatt taaagtaa                                                  198

<210> SEQ ID NO 480
<211> LENGTH: 65
<212> TYPE: PRT
<213> ORGANISM: Bacteriophage D4154

<400> SEQUENCE: 480

Met Lys Lys Phe Trp Arg Ser Gly Met Ile Asp Lys Lys Val Ile Glu
1               5                   10                  15

Lys Arg Gln Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Phe Leu Asp Arg Ile Tyr Asp Ser Arg Ser Asn Leu
    50                  55                  60

Lys
65

<210> SEQ ID NO 481
<211> LENGTH: 180
<212> TYPE: DNA
<213> ORGANISM: Bacteriophage D4160

-continued

<400> SEQUENCE: 481
atgaagaaat tttggcgtag tggaatgatt gacaagaaaa ttattgcgaa acgtgaacag    60
gatgagtatt tgaataaatt acacaggact attcttgagt tgagtagaaa accacctgaa   120
caagaacctt ggtacagaca tccagaaatg agagcattgt tggatagaat tgatgattag   180

<210> SEQ ID NO 482
<211> LENGTH: 59
<212> TYPE: PRT
<213> ORGANISM: Bacteriophage D4160

<400> SEQUENCE: 482

Met Lys Lys Phe Trp Arg Ser Gly Met Ile Asp Lys Lys Ile Ile Ala
1               5                   10                  15

Lys Arg Glu Gln Asp Glu Tyr Leu Asn Lys Leu His Arg Thr Ile Leu
            20                  25                  30

Glu Leu Ser Arg Lys Pro Pro Glu Gln Glu Pro Trp Tyr Arg His Pro
        35                  40                  45

Glu Met Arg Ala Leu Leu Asp Arg Ile Asp Asp
    50                  55

<210> SEQ ID NO 483
<211> LENGTH: 180
<212> TYPE: DNA
<213> ORGANISM: Bacteriophage D5925

<400> SEQUENCE: 483
atgaaaaaat tttggcatag cggtatgatt gacaagaaag ttattgaaaa acgtaaacaa    60
gatgattata tgaataagtt acataggact attcttgagt tgagtataaa accacctgaa   120
ccagaacctt ggtacagaca tccagaaatg agagcattgt tggataggat tgatgattag   180

<210> SEQ ID NO 484
<211> LENGTH: 59
<212> TYPE: PRT
<213> ORGANISM: Bacteriophage D5925

<400> SEQUENCE: 484

Met Lys Lys Phe Trp His Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Asp Asp
    50                  55

<210> SEQ ID NO 485
<211> LENGTH: 198
<212> TYPE: DNA
<213> ORGANISM: Bacteriophage D6193

<400> SEQUENCE: 485
atgaagaagt tttggcgtag tggaatgatt gacaagaaag ttattgaaaa acgacaacaa    60
gatgattata tgaataagtt acataggact attcttgagt tgagtataaa accacctgaa   120
cccgaacctt ggtacagaca tccagaaatg agagcattgt tggataggat ttatgattcg   180
agaagcaatt taaagtaa                                                 198

```
<210> SEQ ID NO 486
<211> LENGTH: 65
<212> TYPE: PRT
<213> ORGANISM: Bacteriophage D6193

<400> SEQUENCE: 486
```

Met Lys Lys Phe Trp Arg Ser Gly Met Ile Asp Lys Lys Val Ile Glu
1               5                   10                  15

Lys Arg Gln Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Tyr Asp Ser Arg Ser Asn Leu
    50                  55                  60

Lys
65

```
<210> SEQ ID NO 487
<211> LENGTH: 180
<212> TYPE: DNA
<213> ORGANISM: Bacteriophage TP-J34

<400> SEQUENCE: 487
atgaagaaat tttggcgtag tggaatgatt gacaagaagg ttattgaaaa acgtaaacaa     60
gatgattata tgaataaatt acacaggact attcttgagt tgagtataaa accacctgaa    120
ccagaaccct tggtacagac atccagaaat gagagcattgt tggatagaat tgatgattag   180

<210> SEQ ID NO 488
<211> LENGTH: 59
<212> TYPE: PRT
<213> ORGANISM: Bacteriophage TP-J34

<400> SEQUENCE: 488
```

Met Lys Lys Phe Trp Arg Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Glu Pro Trp Tyr Arg His Pro
        35                  40                  45

Glu Met Arg Ala Leu Leu Asp Arg Ile Asp Asp
    50                  55

```
<210> SEQ ID NO 489
<211> LENGTH: 180
<212> TYPE: DNA
<213> ORGANISM: Bacteriophage Proph1

<400> SEQUENCE: 489
atgaagaaat tttggcgtag tggcatgatt gacaagaagg ttattgaaaa acgtaaacaa     60
gatgattata tgaataaatt acacaggact attcttgagt tgagtataaa accacctgaa    120
cccgaaccct tggtacagac atccagaaat gagagcattgt tggataggat tgatgattag   180

<210> SEQ ID NO 490
<211> LENGTH: 59
<212> TYPE: PRT
<213> ORGANISM: Bacteriophage Proph1

<400> SEQUENCE: 490
```

Met Lys Lys Phe Trp Arg Ser Gly Met Ile Asp Lys Lys Val Ile Glu

```
             1               5                  10                 15
Lys Arg Lys Gln Asp Asp Tyr Met Asn Lys Leu His Arg Thr Ile Leu
             20                 25                 30

Glu Leu Ser Ile Lys Pro Pro Glu Pro Glu Pro Trp Tyr Arg His Pro
         35                 40                 45

Glu Met Arg Ala Leu Leu Asp Arg Ile Asp Asp
     50                 55

<210> SEQ ID NO 491
<211> LENGTH: 177
<212> TYPE: DNA
<213> ORGANISM: Bacteriophage D1126

<400> SEQUENCE: 491
atgaagaaat tttggcgtag tggcatgatt gacaagaagg ttattaaaaa acgtaaacag     60
gaagagtata tgaataagat gcataggact attcttgaat taaaaaatga gaagcatcca    120
gatatgatgg attttatgga cctgatagat tggtatttag aaaatcgcaa accataa       177

<210> SEQ ID NO 492
<211> LENGTH: 58
<212> TYPE: PRT
<213> ORGANISM: Bacteriophage D1126

<400> SEQUENCE: 492

Met Lys Lys Phe Trp Arg Ser Gly Met Ile Asp Lys Lys Val Ile Lys
1               5                  10                 15

Lys Arg Lys Gln Glu Glu Tyr Met Asn Lys Met His Arg Thr Ile Leu
             20                 25                 30

Glu Leu Lys Asn Glu Lys His Pro Asp Met Met Asp Phe Met Asp Leu
         35                 40                 45

Ile Asp Trp Tyr Leu Glu Asn Arg Lys Pro
     50                 55

<210> SEQ ID NO 493
<211> LENGTH: 189
<212> TYPE: DNA
<213> ORGANISM: Bacteriophage D3607

<400> SEQUENCE: 493
atgaagaaat tttggcatag cggtatgatc gacaagaaag ttattgaaaa acgtaaacag     60
gatgagtatt tgaataaatt acacaggact attcttgagt taaaaaatga gaagcatcca    120
gatatgatgg attttatgga cctgatagat tggtatttag agaatcgcaa accacgagat    180
attgattag                                                            189

<210> SEQ ID NO 494
<211> LENGTH: 62
<212> TYPE: PRT
<213> ORGANISM: Bacteriophage D3607

<400> SEQUENCE: 494

Met Lys Lys Phe Trp His Ser Gly Met Ile Asp Lys Lys Val Ile Glu
1               5                  10                 15

Lys Arg Lys Gln Asp Glu Tyr Leu Asn Lys Leu His Arg Thr Ile Leu
             20                 25                 30

Glu Leu Lys Asn Glu Lys His Pro Asp Met Met Asp Phe Met Asp Leu
         35                 40                 45

Ile Asp Trp Tyr Leu Glu Asn Arg Lys Pro Arg Asp Ile Asp
```

<210> SEQ ID NO 495
<211> LENGTH: 189
<212> TYPE: DNA
<213> ORGANISM: Bacteriophage D4252

<400> SEQUENCE: 495

```
atgaagaaat tttggcatag cggtatgatt gacaagaagg ttattgaaaa acgtaaacag      60
gaagaatgta ttaatgaact gcataggact attcttgagt tgaaaaatga aagcatcca     120 gatatgatgg attttatgga cctgatagat tggtatttag aaaatcgcaa accacgagat    180
atttattag                                                             189
```

<210> SEQ ID NO 496
<211> LENGTH: 62
<212> TYPE: PRT
<213> ORGANISM: Bacteriophage D4252

<400> SEQUENCE: 496

```
Met Lys Lys Phe Trp His Ser Gly Met Ile Asp Lys Lys Val Ile Glu
1               5                   10                  15

Lys Arg Lys Gln Glu Glu Cys Ile Asn Glu Leu His Arg Thr Ile Leu
            20                  25                  30

Glu Leu Lys Asn Glu Lys His Pro Asp Met Met Asp Phe Met Asp Leu
        35                  40                  45

Ile Asp Trp Tyr Leu Glu Asn Arg Lys Pro Arg Asp Ile Tyr
    50                  55                  60
```

<210> SEQ ID NO 497
<211> LENGTH: 183
<212> TYPE: DNA
<213> ORGANISM: Bacteriophage D4487

<400> SEQUENCE: 497

```
atgatcgaca agaaagttat tgaaaaacgt aaacaggatg agtatttgaa taaattacac      60
aggactattc ttgagttaaa aaatgagaag catccagata tgatagattt tatggacctg    120
atagatttta tggacctgat agattggtat ttagagaatc gcaaaccacg agatattgat    180
tag                                                                   183
```

<210> SEQ ID NO 498
<211> LENGTH: 60
<212> TYPE: PRT
<213> ORGANISM: Bacteriophage D4487

<400> SEQUENCE: 498

```
Met Ile Asp Lys Lys Val Ile Glu Lys Arg Lys Gln Asp Glu Tyr Leu
1               5                   10                  15

Asn Lys Leu His Arg Thr Ile Leu Glu Leu Lys Asn Glu Lys His Pro
            20                  25                  30

Asp Met Ile Asp Phe Met Asp Leu Ile Asp Phe Met Asp Leu Ile Asp
        35                  40                  45

Trp Tyr Leu Glu Asn Arg Lys Pro Arg Asp Ile Asp
    50                  55                  60
```

<210> SEQ ID NO 499
<211> LENGTH: 189
<212> TYPE: DNA
<213> ORGANISM: Bacteriophage D6938

<400> SEQUENCE: 499

```
atgaataaat tttggcatag cggtatgatc gacaagaaag ttattgaaaa ccgtaaacag      60
gaagaatata ttaataaact gcatagcact attcttgaat tgaaaaatga aagcatcca     120
gatatgatgg attttatgga cctgatagat tggtatttag aaaatcgcaa accacaagat    180
attgattag                                                            189
```

<210> SEQ ID NO 500
<211> LENGTH: 62
<212> TYPE: PRT
<213> ORGANISM: Bacteriophage D6938

<400> SEQUENCE: 500

```
Met Asn Lys Phe Trp His Ser Gly Met Ile Asp Lys Lys Val Ile Glu
1               5                   10                  15
Asn Arg Lys Gln Glu Glu Tyr Ile Asn Lys Leu His Ser Thr Ile Leu
            20                  25                  30
Glu Leu Lys Asn Glu Lys His Pro Asp Met Met Asp Phe Met Asp Leu
        35                  40                  45
Ile Asp Trp Tyr Leu Glu Asn Arg Lys Pro Gln Asp Ile Asp
    50                  55                  60
```

<210> SEQ ID NO 501
<211> LENGTH: 189
<212> TYPE: DNA
<213> ORGANISM: Bacteriophage P5641

<400> SEQUENCE: 501

```
atgaagaaat tttggcgtag tggcatgatt gacaataagg ttattgaaaa acgtaaacaa      60
gatgattata tgaataaatt acacaggact attcttgagt tgacccgtga aattgaattg    120
agacgtggcc cagatatgat ggatttcatg gatctgatag attggtattt aaacagccgc    180
aaaccgtag                                                            189
```

<210> SEQ ID NO 502
<211> LENGTH: 62
<212> TYPE: PRT
<213> ORGANISM: Bacteriophage P5641

<400> SEQUENCE: 502

```
Met Lys Lys Phe Trp Arg Ser Gly Met Ile Asp Asn Lys Val Ile Glu
1               5                   10                  15
Lys Arg Lys Gln Asp Asp Tyr Met Asn Lys Leu His Arg Thr Ile Leu
            20                  25                  30
Glu Leu Thr Arg Glu Ile Glu Leu Arg Arg Gly Pro Asp Met Met Asp
        35                  40                  45
Phe Met Asp Leu Ile Asp Trp Tyr Leu Asn Ser Arg Lys Pro
    50                  55                  60
```

<210> SEQ ID NO 503
<211> LENGTH: 216
<212> TYPE: DNA
<213> ORGANISM: Bacteriophage D1765

<400> SEQUENCE: 503

```
atgaagaagt tttggcatag cggtatgatt gacaagaaag ttattgaaaa acgccaacat      60
gatgagtata taaataaaat acataagact attattgagt tgaggaaaga accacctgaa    120
```

```
cctaaacctt gctcttgtca caaagatata gatattaatg ctttgattaa tgatattgag    180
tgggatgatt attatacatg gtttaaagat aaataa                              216

<210> SEQ ID NO 504
<211> LENGTH: 71
<212> TYPE: PRT
<213> ORGANISM: Bacteriophage D1765

<400> SEQUENCE: 504

Met Lys Lys Phe Trp His Ser Gly Met Ile Asp Lys Lys Val Ile Glu
1               5                   10                  15

Lys Arg Gln His Asp Glu Tyr Ile Asn Lys Ile His Lys Thr Ile Ile
            20                  25                  30

Glu Leu Arg Lys Glu Pro Pro Glu Pro Lys Pro Cys Ser Cys His Lys
        35                  40                  45

Asp Ile Asp Ile Asn Ala Leu Ile Asn Asp Ile Glu Trp Asp Asp Tyr
    50                  55                  60

Tyr Thr Trp Phe Lys Asp Lys
65                  70

<210> SEQ ID NO 505
<211> LENGTH: 216
<212> TYPE: DNA
<213> ORGANISM: Bacteriophage D4212

<400> SEQUENCE: 505
atgaagaaat tttggcgtag tggaatgatt gacaagaagg ttattgaaaa acgtaaacaa    60
gatgattata tgaataaatt acacaggact attcttgagt tgagtataaa accacctgaa   120
cctaaacctt gctcttgtca caaagatata gatattaatg ctttgattaa tgatattgag   180
tgggatgatt attatacatg gtttaaagat aaataa                             216

<210> SEQ ID NO 506
<211> LENGTH: 71
<212> TYPE: PRT
<213> ORGANISM: Bacteriophage D4212

<400> SEQUENCE: 506

Met Lys Lys Phe Trp Arg Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30

Glu Leu Ser Ile Lys Pro Pro Glu Pro Lys Pro Cys Ser Cys His Lys
        35                  40                  45

Asp Ile Asp Ile Asn Ala Leu Ile Asn Asp Ile Glu Trp Asp Asp Tyr
    50                  55                  60

Tyr Thr Trp Phe Lys Asp Lys
65                  70

<210> SEQ ID NO 507
<211> LENGTH: 216
<212> TYPE: DNA
<213> ORGANISM: Bacteriophage D4250

<400> SEQUENCE: 507
atgaagaaat tttggcgtag tggcatgatt gacaagaagg ttattgaaaa acgtaaacag    60
gaagagtata tgaataagat gcataggact attcttgagt tgagtataaa accacctgaa   120
cctaaacctt gctcttgtca caaagatata gatattaatg ctttgattaa tgatattgag   180
```

```
tgggatgatt attatacatg gtttaaagat aaataa                                216
```

<210> SEQ ID NO 508
<211> LENGTH: 71
<212> TYPE: PRT
<213> ORGANISM: Bacteriophage D4250

<400> SEQUENCE: 508

```
Met Lys Lys Phe Trp Arg Ser Gly Met Ile Asp Lys Lys Val Ile Glu
1               5                   10                  15

Lys Arg Lys Gln Glu Glu Tyr Met Asn Lys Met His Arg Thr Ile Leu
            20                  25                  30

Glu Leu Ser Ile Lys Pro Pro Glu Pro Lys Pro Cys Ser Cys His Lys
        35                  40                  45

Asp Ile Asp Ile Asn Ala Leu Ile Asn Asp Ile Glu Trp Asp Asp Tyr
    50                  55                  60

Tyr Thr Trp Phe Lys Asp Lys
65                  70
```

<210> SEQ ID NO 509
<211> LENGTH: 192
<212> TYPE: DNA
<213> ORGANISM: Bacteriophage D4282

<400> SEQUENCE: 509

```
atgattgaca agaaggttat tgaaaaacgt aaacaagatg attatatgaa taaattacac     60
aggactattc ttgagttgag tataaaacca cctgaaccta aaccttgctc ttgtcacaaa    120
gatatagata ttaatgcttt gattaatgat attgagtggg atgattatta tacatggttt    180
aaagataaat aa                                                        192
```

<210> SEQ ID NO 510
<211> LENGTH: 63
<212> TYPE: PRT
<213> ORGANISM: Bacteriophage D4282

<400> SEQUENCE: 510

```
Met Ile Asp Lys Lys Val Ile Glu Lys Arg Lys Gln Asp Asp Tyr Met
1               5                   10                  15

Asn Lys Leu His Arg Thr Ile Leu Glu Leu Ser Ile Lys Pro Pro Glu
            20                  25                  30

Pro Lys Pro Cys Ser Cys His Lys Asp Ile Asp Ile Asn Ala Leu Ile
        35                  40                  45

Asn Asp Ile Glu Trp Asp Asp Tyr Tyr Thr Trp Phe Lys Asp Lys
    50                  55                  60
```

<210> SEQ ID NO 511
<211> LENGTH: 216
<212> TYPE: DNA
<213> ORGANISM: Bacteriophage D7163

<400> SEQUENCE: 511

```
atgaagaaat tttggcatag cggtatgatt gacaagaaag ttattaaaaa acgtaaacag     60
gaagaatata tgaataaact tcaaagaatt atccttgagt tgagtataaa accacctgaa    120
cctaaacctt gctcttgtca caagatatata gatattaatg ctttgattaa tgatattgag    180
tgggatgatt attatacatg gtttaaagat aaataa                              216
```

-continued

```
<210> SEQ ID NO 512
<211> LENGTH: 71
<212> TYPE: PRT
<213> ORGANISM: Bacteriophage D7163

<400> SEQUENCE: 512
```

Met Lys Lys Phe Trp His Ser Gly Met Ile Asp Lys Lys Val Ile Lys
1               5                   10                  15

Lys Arg Lys Gln Glu Glu Tyr Met Asn Lys Leu Gln Arg Ile Ile Leu
            20                  25                  30

Glu Leu Ser Ile Lys Pro Pro Glu Pro Lys Pro Cys Ser Cys His Lys
        35                  40                  45

Asp Ile Asp Ile Asn Ala Leu Ile Asn Asp Ile Glu Trp Asp Asp Tyr
    50                  55                  60

Tyr Thr Trp Phe Lys Asp Lys
65                  70

```
<210> SEQ ID NO 513
<211> LENGTH: 213
<212> TYPE: DNA
<213> ORGANISM: Bacteriophage O1205

<400> SEQUENCE: 513
atgaagaagt tttggcatag cggtatgatt gacaagaaaa ttattgaaaa acgtgaacat      60
gatgagtatt tgaataaatt acatatgact attattgagt tgagaaaaga accacctgaa     120
actaaacctt gctcttgtca caaaaatgta gatattaatg aattaattaa ctatattgag     180
tggaatgatt attatacatg gtttaaagat taa                                  213

<210> SEQ ID NO 514
<211> LENGTH: 70
<212> TYPE: PRT
<213> ORGANISM: Bacteriophage O1205

<400> SEQUENCE: 514
```

Met Lys Lys Phe Trp His Ser Gly Met Ile Asp Lys Lys Ile Ile Glu
1               5                   10                  15

Lys Arg Glu His Asp Glu Tyr Leu Asn Lys Leu His Met Thr Ile Ile
            20                  25                  30

Glu Leu Arg Lys Glu Pro Pro Glu Thr Lys Pro Cys Ser Cys His Lys
        35                  40                  45

Asn Val Asp Ile Asn Glu Leu Ile Asn Tyr Ile Glu Trp Asn Asp Tyr
    50                  55                  60

Tyr Thr Trp Phe Lys Asp
65                  70

```
<210> SEQ ID NO 515
<211> LENGTH: 183
<212> TYPE: DNA
<213> ORGANISM: Bacteriophage D4263

<400> SEQUENCE: 515
atgaagaaat tttggcatag cggtatgatc gacaagaaag ttattgaaaa acgtaaacag      60
gatgagtatt tgaataaatt acacaggact attcttgaga tagactttcc aattcaacgt     120
gtttgtcacc ggtcactatc accgacaccc ataacggtgc ccacggaaac ccttgatata     180
taa                                                                   183

<210> SEQ ID NO 516
```

```
<211> LENGTH: 60
<212> TYPE: PRT
<213> ORGANISM: Bacteriophage D4263

<400> SEQUENCE: 516

Met Lys Lys Phe Trp His Ser Gly Met Ile Asp Lys Lys Val Ile Glu
1               5                   10                  15

Lys Arg Lys Gln Asp Glu Tyr Leu Asn Lys Leu His Arg Thr Ile Leu
            20                  25                  30

Glu Ile Asp Phe Pro Ile Gln Arg Val Cys His Arg Ser Leu Ser Pro
        35                  40                  45

Thr Pro Ile Thr Val Pro Thr Glu Thr Leu Asp Ile
    50                  55                  60

<210> SEQ ID NO 517
<211> LENGTH: 135
<212> TYPE: DNA
<213> ORGANISM: Bacteriophage D6252

<400> SEQUENCE: 517
atgaagaaat tttggcatag cggtatgatt gacaagaaag ttattaaaaa acgtaaacag      60
gaagagtata tgaataagat gcataggact attcttgagt tgagtataaa accaatagaa     120
gaaatggttt tttaa                                                      135

<210> SEQ ID NO 518
<211> LENGTH: 44
<212> TYPE: PRT
<213> ORGANISM: Bacteriophage D6252

<400> SEQUENCE: 518

Met Lys Lys Phe Trp His Ser Gly Met Ile Asp Lys Lys Val Ile Lys
1               5                   10                  15

Lys Arg Lys Gln Glu Glu Tyr Met Asn Lys Met His Arg Thr Ile Leu
            20                  25                  30

Glu Leu Ser Ile Lys Pro Ile Glu Glu Met Val Phe
        35                  40

<210> SEQ ID NO 519
<211> LENGTH: 267
<212> TYPE: DNA
<213> ORGANISM: Bacteriophage Sfi19

<400> SEQUENCE: 519
atgaagaaat tttggcgtag tggaatgatt gacaagaagg ttattgaaaa acgtaaacaa      60
gatgattata tgaataaatt acacaggact attcttgagt tgagtataaa accacctgaa     120
cctaaacctt gctcttgtca caagatata gatattaatg ctttgattaa tgatattgag     180
tgggatgatt gggtagatga agtgttggaa tatataaata aatgggtaaa taagataaa     240 gctgatgtgg aggtattaga taaatga                                         267

<210> SEQ ID NO 520
<211> LENGTH: 88
<212> TYPE: PRT
<213> ORGANISM: Bacteriophage Sfi19

<400> SEQUENCE: 520

Met Lys Lys Phe Trp Arg Ser Gly Met Ile Asp Lys Lys Val Ile Glu
1               5                   10                  15

Lys Arg Lys Gln Asp Asp Tyr Met Asn Lys Leu His Arg Thr Ile Leu
            20                  25                  30
```

```
                    20                  25                  30
Glu Leu Ser Ile Lys Pro Pro Glu Pro Lys Pro Cys Ser Cys His Lys
                35                  40                  45

Asp Ile Asp Ile Asn Ala Leu Ile Asn Asp Ile Glu Trp Asp Asp Trp
            50                  55                  60

Val Asp Glu Val Leu Glu Tyr Ile Asn Lys Trp Val Asn Lys Asp Lys
65                  70                  75                  80

Ala Asp Val Glu Val Leu Asp Lys
                85
```

<210> SEQ ID NO 521
<211> LENGTH: 633
<212> TYPE: DNA
<213> ORGANISM: Bacteriophage D4234

<400> SEQUENCE: 521

```
atgaccaccc cacaaaagtt tcttagtatc agggaattgc ttaaaccact ccctagcaac    60
ggtgttaagt ttcctaagtt ctctgcactc tatcacgaaa gccaagtggg agcgtggcag   120
aagaaaatga gtaagcgaag acaccaagca aaggtacaag tagctatgga taagaaccgt   180
ggtgaactag ttcctcgtga gttagaggac ttctctaact ggcaacgtgc tagacaaatg   240
aaagcacgct atcaagagaa ggtggctaac aagcgtaagg actacctaca caaactaacc   300
acttatcttg ttaagactta tgatgttatc gtgattgagg acttgaaagc taagaacttg   360
atgaagaacc attacttagc taaatcaatc gctaacgctt catggcatga gtttaagaga   420
ctgctagaat acaagtgttc gtggtatggc aaggaactta ttgttgttcc ggctcaccat   480
actagtcaag agtgttctaa ctgtcaccac aattcaggta agaaaccgct ccatatccgt   540
gagtggatgt gtgataattg tggtactcac catgatagag acattaacgc aagtatcaat   600
atcttgcacc gtggacttgc cacgttaaat taa                                 633
```

<210> SEQ ID NO 522
<211> LENGTH: 210
<212> TYPE: PRT
<213> ORGANISM: Bacteriophage D4234

<400> SEQUENCE: 522

```
Met Thr Thr Pro Gln Lys Phe Leu Ser Ile Arg Glu Leu Leu Lys Pro
1               5                   10                  15

Leu Pro Ser Asn Gly Val Lys Phe Pro Lys Phe Ser Ala Leu Tyr His
                20                  25                  30

Glu Ser Gln Val Gly Ala Trp Gln Lys Lys Met Ser Lys Arg Arg His
            35                  40                  45

Gln Ala Lys Val Gln Val Ala Met Asp Lys Asn Arg Gly Glu Leu Val
        50                  55                  60

Pro Arg Glu Leu Glu Asp Phe Ser Asn Trp Gln Arg Ala Arg Gln Met
65                  70                  75                  80

Lys Ala Arg Tyr Gln Glu Lys Val Ala Asn Lys Arg Lys Asp Tyr Leu
                85                  90                  95

His Lys Leu Thr Thr Tyr Leu Val Lys Thr Tyr Asp Val Ile Val Ile
            100                 105                 110

Glu Asp Leu Lys Ala Lys Asn Leu Met Lys Asn His Tyr Leu Ala Lys
        115                 120                 125

Ser Ile Ala Asn Ala Ser Trp His Glu Phe Lys Arg Leu Leu Glu Tyr
    130                 135                 140
```

Lys Cys Ser Trp Tyr Gly Lys Glu Leu Ile Val Val Pro Ala His His
145                 150                 155                 160

Thr Ser Gln Glu Cys Ser Asn Cys His His Asn Ser Gly Lys Lys Pro
                165                 170                 175

Leu His Ile Arg Glu Trp Met Cys Asp Asn Cys Gly Thr His His Asp
            180                 185                 190

Arg Asp Ile Asn Ala Ser Ile Asn Ile Leu His Arg Gly Leu Ala Thr
            195                 200                 205

Leu Asn
    210

<210> SEQ ID NO 523
<211> LENGTH: 303
<212> TYPE: DNA
<213> ORGANISM: Bacteriophage D4620

<400> SEQUENCE: 523
atgtcaacag ttttcttgat ttttttttcaa gttttttttga tttttattatt aaacatcttg    60 aaaattagta aaacatacta tatattgttc tttgtatgta tccattgttt ttacctcgtt   120 ttttttatttt ttatcgaatg ttttccaagt tgctctcaat ccattctagt ctattttggc   180
gaccagacgg aaactgtttt tataaaaaaa tatatatttt tttgcaaaac aaaaaccctg   240
actaattcaa gtcagggcaa gagagagttt atcgaagact cagcttttaa ctgtatccat   300
taa                                                                 303

<210> SEQ ID NO 524
<211> LENGTH: 100
<212> TYPE: PRT
<213> ORGANISM: Bacteriophage D4620

<400> SEQUENCE: 524

Met Ser Thr Val Phe Leu Ile Phe Phe Gln Val Phe Leu Ile Leu Leu
1               5                   10                  15

Leu Asn Ile Leu Lys Ile Ser Lys Thr Tyr Tyr Ile Leu Phe Phe Val
            20                  25                  30

Cys Ile His Cys Phe Tyr Leu Val Phe Leu Phe Ile Glu Cys Phe
        35                  40                  45

Pro Ser Cys Ser Gln Ser Ile Leu Val Tyr Phe Gly Asp Gln Thr Glu
    50                  55                  60

Thr Val Phe Ile Lys Lys Tyr Ile Phe Phe Cys Lys Thr Lys Thr Leu
65                  70                  75                  80

Thr Asn Ser Ser Gln Gly Lys Arg Glu Phe Ile Glu Asp Ser Ala Phe
                85                  90                  95

Asn Cys Ile His
            100

<210> SEQ ID NO 525
<211> LENGTH: 303
<212> TYPE: DNA
<213> ORGANISM: Bacteriophage D5930

<400> SEQUENCE: 525
atgtcaacag ttttcttgat ttttttttcaa gtttttcttga ttttttttatt aaacatcttg    60 aaaattagta aaacatacta tatattgttc tttgtatgta tccattgttt ttacctcgtt   120 ttttttatttt ttatcgaatg ttttccaagt tgctctcaat ccattctagt ctattttggc   180
gaccagacgg aaactgtttt tataaaaaaa tatatatttt tttgcaaaac aaaaaccctg   240

```
actaattcaa gtcagggtga gagagagttt atcgaagact cagcttttaa ctgtattcat    300
taa                                                                  303
```

<210> SEQ ID NO 526
<211> LENGTH: 100
<212> TYPE: PRT
<213> ORGANISM: Bacteriophage D5930

<400> SEQUENCE: 526

```
Met Ser Thr Val Phe Leu Ile Phe Phe Gln Val Phe Leu Ile Phe Leu
1               5                   10                  15

Leu Asn Ile Leu Lys Ile Ser Lys Thr Tyr Tyr Ile Leu Phe Phe Val
            20                  25                  30

Cys Ile His Cys Phe Tyr Leu Val Phe Leu Phe Phe Ile Glu Cys Phe
        35                  40                  45

Pro Ser Cys Ser Gln Ser Ile Leu Val Tyr Phe Gly Asp Gln Thr Glu
    50                  55                  60

Thr Val Phe Ile Lys Lys Tyr Ile Phe Phe Cys Lys Thr Lys Thr Leu
65                  70                  75                  80

Thr Asn Ser Ser Gln Gly Glu Arg Glu Phe Ile Glu Asp Ser Ala Phe
                85                  90                  95

Asn Cys Ile His
            100
```

<210> SEQ ID NO 527
<211> LENGTH: 303
<212> TYPE: DNA
<213> ORGANISM: Bacteriophage P0091

<400> SEQUENCE: 527

```
atgtcaacag ttttcttgat ttttttcaa gttttcttga tttttttatt aaacatcttg    60
aaaattagta aaacatacta tatattgttc tttgtatgta tccattgttt ttacctcgtt   120
tttttatttt ttatcgaatg ttttccaagt tgctctcaat ccattctagt ctattttggt   180
gaccagacgg aaactgtttt tataaaaaaa tatatatttt tttgcaaaac aaaaaccctg   240
actaattcaa gtcagggtga gagagagttt atcgaagata acagctttta ctgtaaccat   300
taa                                                                 303
```

<210> SEQ ID NO 528
<211> LENGTH: 100
<212> TYPE: PRT
<213> ORGANISM: Bacteriophage P0091

<400> SEQUENCE: 528

```
Met Ser Thr Val Phe Leu Ile Phe Phe Gln Val Phe Leu Ile Phe Leu
1               5                   10                  15

Leu Asn Ile Leu Lys Ile Ser Lys Thr Tyr Tyr Ile Leu Phe Phe Val
            20                  25                  30

Cys Ile His Cys Phe Tyr Leu Val Phe Leu Phe Phe Ile Glu Cys Phe
        35                  40                  45

Pro Ser Cys Ser Gln Ser Ile Leu Val Tyr Phe Gly Asp Gln Thr Glu
    50                  55                  60

Thr Val Phe Ile Lys Lys Tyr Ile Phe Phe Cys Lys Thr Lys Thr Leu
65                  70                  75                  80

Thr Asn Ser Ser Gln Gly Glu Arg Glu Phe Ile Glu Asp Asn Ser Phe
                85                  90                  95
```

-continued

Tyr Cys Asn His
         100

<210> SEQ ID NO 529
<211> LENGTH: 231
<212> TYPE: DNA
<213> ORGANISM: Bacteriophage P0093

<400> SEQUENCE: 529
ttgatttttt ttaaagtttt tttgatttta ttattaaaca acttgaaaat tagtaaaaca      60
tactatatat tgttctttgt atgtatccat tgttttacc tcgttttttt attttttatc     120 gaatatttc cagattgttt tcaatccatt caagtcgatt tttgcgacca gacgaaact     180 gtttttataa aaattatat atttttttg caaaacaaaa accctgacta a               231

<210> SEQ ID NO 530
<211> LENGTH: 76
<212> TYPE: PRT
<213> ORGANISM: Bacteriophage P0093

<400> SEQUENCE: 530

Met Ile Phe Phe Lys Val Phe Leu Ile Leu Leu Asn Asn Leu Lys
1               5                   10                  15

Ile Ser Lys Thr Tyr Tyr Ile Leu Phe Phe Val Cys Ile His Cys Phe
            20                  25                  30

Tyr Leu Val Phe Leu Phe Phe Ile Glu Tyr Phe Pro Asp Cys Phe Gln
        35                  40                  45

Ser Ile Gln Val Asp Phe Cys Asp Gln Thr Glu Thr Val Phe Ile Lys
    50                  55                  60

Asn Tyr Ile Phe Phe Leu Gln Asn Lys Asn Pro Asp
65                  70                  75

<210> SEQ ID NO 531
<211> LENGTH: 246
<212> TYPE: DNA
<213> ORGANISM: Bacteriophage P0094

<400> SEQUENCE: 531
atgtcaatag ttttcttgat ttttttaaa gttttttga ttttattatt aaacaacttg      60
aaaattagta aaacatacta tattgttc tttgtatgta tccattgttt ttacctcgtt     120
tttttatttt ttatcgaata ttttccagat tgttttcaat ccattcaagt cgattttgc     180 gaccagacgg aaactgtttt tataaaaaaa tatatatttt ttttgcaaaa caaaaccct     240 gactaa                                                                246

<210> SEQ ID NO 532
<211> LENGTH: 81
<212> TYPE: PRT
<213> ORGANISM: Bacteriophage P0094

<400> SEQUENCE: 532

Met Ser Ile Val Phe Leu Ile Phe Phe Lys Val Phe Leu Ile Leu Leu
1               5                   10                  15

Leu Asn Asn Leu Lys Ile Ser Lys Thr Tyr Tyr Ile Leu Phe Phe Val
            20                  25                  30

Cys Ile His Cys Phe Tyr Leu Val Phe Leu Phe Phe Ile Glu Tyr Phe
        35                  40                  45

Pro Asp Cys Phe Gln Ser Ile Gln Val Asp Phe Cys Asp Gln Thr Glu

Thr Val Phe Ile Lys Lys Tyr Ile Phe Phe Leu Gln Asn Lys Asn Pro
65                  70                  75                  80

Asp

<210> SEQ ID NO 533
<211> LENGTH: 234
<212> TYPE: DNA
<213> ORGANISM: Bacteriophage P7632

<400> SEQUENCE: 533
atgtcaacag ttttcttgat ttttttttcaa gttttttttga tttttttttata tatttacttt      60 aaaattagta aaacatacta tatattgttc tttgtatgta tccattgttt ttttattttt        120
tatcgaatgt tttccaagtt gctctcaatc cattctagtc tattttggcg accagacgga        180
aactgttttt ataaaaaaat atatatttttt ttgcaaaaca aaacccctga ctaa             234

<210> SEQ ID NO 534
<211> LENGTH: 77
<212> TYPE: PRT
<213> ORGANISM: Bacteriophage P7632

<400> SEQUENCE: 534

Met Ser Thr Val Phe Leu Ile Phe Phe Gln Val Phe Leu Ile Phe Leu
1               5                   10                  15

Tyr Ile Tyr Phe Lys Ile Ser Lys Thr Tyr Tyr Ile Leu Phe Phe Val
                20                  25                  30

Cys Ile His Cys Phe Phe Ile Phe Tyr Arg Met Phe Ser Lys Leu Leu
            35                  40                  45

Ser Ile His Ser Ser Leu Phe Trp Arg Pro Asp Gly Asn Cys Phe Tyr
        50                  55                  60

Lys Lys Ile Tyr Ile Phe Leu Gln Asn Lys Asn Pro Asp
65                  70                  75

<210> SEQ ID NO 535
<211> LENGTH: 219
<212> TYPE: DNA
<213> ORGANISM: Bacteriophage P7952

<400> SEQUENCE: 535 ttgattttttt ttcaagttttt cttgattttttt ttattaaaca tcttgaaaat tagtaaaaca      60
tactatatat tgttctttgt atgtatccat tgttttttat ttttatcga atgttttcca        120 agttgctctc aatccattct agtctatttt ggcgaccaga cggaaactgt ttttataaaa        180 aaatatatata ttttttttgca aaacaaaaac cctgactaa                              219

<210> SEQ ID NO 536
<211> LENGTH: 72
<212> TYPE: PRT
<213> ORGANISM: Bacteriophage P7952

<400> SEQUENCE: 536

Met Ile Phe Phe Gln Val Phe Leu Ile Phe Leu Leu Asn Ile Leu Lys
1               5                   10                  15

Ile Ser Lys Thr Tyr Tyr Ile Leu Phe Phe Val Cys Ile His Cys Phe
                20                  25                  30

Leu Phe Phe Ile Glu Cys Phe Pro Ser Cys Ser Gln Ser Ile Leu Val
            35                  40                  45

Tyr Phe Gly Asp Gln Thr Glu Thr Val Phe Ile Lys Lys Ile Tyr Ile
 50                  55                  60

Phe Leu Gln Asn Lys Asn Pro Asp
 65                  70

<210> SEQ ID NO 537
<211> LENGTH: 198
<212> TYPE: DNA
<213> ORGANISM: Bacteriophage D5738

<400> SEQUENCE: 537
ttgtttattt ttgggaactg ttgtataatg tttatactat atatatcatg tatgatagtt     60
tgtcaacagt tttacctaaa ttattttagt ttttttgca aaaaagaaa acctcgacta      120 aaagtcgagg ttacagttcg agaatttaac cgaaacgata ccaagtattc caacaattat    180
attaccactt ttctatga                                                 198

<210> SEQ ID NO 538
<211> LENGTH: 65
<212> TYPE: PRT
<213> ORGANISM: Bacteriophage D5738

<400> SEQUENCE: 538

Met Phe Ile Phe Gly Asn Cys Cys Ile Met Phe Ile Leu Tyr Ile Ser
 1               5                  10                  15

Cys Met Ile Val Cys Gln Gln Phe Tyr Leu Asn Tyr Phe Ser Phe Phe
                20                  25                  30

Cys Lys Lys Arg Lys Pro Arg Leu Lys Val Glu Val Thr Val Arg Glu
            35                  40                  45

Phe Asn Arg Asn Asp Thr Lys Tyr Ser Asn Asn Tyr Ile Thr Thr Phe
     50                  55                  60

Leu
 65

<210> SEQ ID NO 539
<211> LENGTH: 189
<212> TYPE: DNA
<213> ORGANISM: Bacteriophage D5839

<400> SEQUENCE: 539
gtgagttctg aacatagtat tcaaaatcaa attcgagtgg aattatccaa ggctggcaac     60
atggtattta gaattaacgt tggtaaagtc agaatggctg atggacgttg gtttgatact    120
ggagcaccaa aaggatttg tgacctgttt ggatttagac cagctactgt aatagcactt    180
atctattag                                                           189

<210> SEQ ID NO 540
<211> LENGTH: 62
<212> TYPE: PRT
<213> ORGANISM: Bacteriophage D5839

<400> SEQUENCE: 540

Met Ser Ser Glu His Ser Ile Gln Asn Gln Ile Arg Val Glu Leu Ser
 1               5                  10                  15

Lys Ala Gly Asn Met Val Phe Arg Ile Asn Val Gly Lys Val Arg Met
                20                  25                  30

Ala Asp Gly Arg Trp Phe Asp Thr Gly Ala Pro Lys Gly Phe Cys Asp
            35                  40                  45

Leu Phe Gly Phe Arg Pro Ala Thr Val Ile Ala Leu Ile Tyr

<210> SEQ ID NO 541
<211> LENGTH: 141
<212> TYPE: DNA
<213> ORGANISM: Bacteriophage P0093

<400> SEQUENCE: 541
ttgccaatcc tctttattgt cggtaacgca cagggagcaa gtcactgcac tagaccgaag    60
cccttacatc ccgccacctt agaggtgggg gaattacggg ctgttaggtt aaaaaaagca   120
aacaaaaaag ccccagcata a                                             141

<210> SEQ ID NO 542
<211> LENGTH: 46
<212> TYPE: PRT
<213> ORGANISM: Bacteriophage P0093

<400> SEQUENCE: 542

Met Pro Ile Leu Phe Ile Val Gly Asn Ala Gln Gly Ala Ser His Cys
1               5                   10                  15

Thr Arg Pro Lys Pro Leu His Pro Ala Thr Leu Glu Val Gly Glu Leu
            20                  25                  30

Arg Ala Val Arg Leu Lys Lys Ala Asn Lys Lys Ala Pro Ala
        35                  40                  45

<210> SEQ ID NO 543
<211> LENGTH: 171
<212> TYPE: DNA
<213> ORGANISM: Bacteriophage P7152

<400> SEQUENCE: 543
atgtcaacag ttttcttgat ttttttttcaa gttttcttga ttttttttatt aaacatcttg    60 aaaattagta aaacatacta tatattgttc tttgtatgta tccattgttt tttattttt   120 tatcgaatgt tttccaagtt gctctcaatc cattctagtc tattttggtg a            171

<210> SEQ ID NO 544
<211> LENGTH: 56
<212> TYPE: PRT
<213> ORGANISM: Bacteriophage P7152

<400> SEQUENCE: 544

Met Ser Thr Val Phe Leu Ile Phe Phe Gln Val Phe Leu Ile Phe Leu
1               5                   10                  15

Leu Asn Ile Leu Lys Ile Ser Lys Thr Tyr Tyr Ile Leu Phe Phe Val
            20                  25                  30

Cys Ile His Cys Phe Phe Ile Phe Tyr Arg Met Phe Ser Lys Leu Leu
        35                  40                  45

Ser Ile His Ser Ser Leu Phe Trp
    50                  55

<210> SEQ ID NO 545
<211> LENGTH: 144
<212> TYPE: DNA
<213> ORGANISM: Bacteriophage P7954

<400> SEQUENCE: 545
ttgatttttt ttcaagtttt cttgattttt ttattaaaca tcttgaaaat tagtaaaaca    60
tactatatat tgttctttgt atgtatccat tgttttttt attttttatc gaatgttttc   120

```
caagttgctc tcaatccatt ctag                                              144
```

<210> SEQ ID NO 546
<211> LENGTH: 47
<212> TYPE: PRT
<213> ORGANISM: Bacteriophage P7954

<400> SEQUENCE: 546

```
Met Ile Phe Phe Gln Val Phe Leu Ile Phe Leu Leu Asn Ile Leu Lys
1               5                   10                  15

Ile Ser Lys Thr Tyr Tyr Ile Leu Phe Phe Val Cys Ile His Cys Phe
            20                  25                  30

Phe Tyr Phe Leu Ser Asn Val Phe Gln Val Ala Leu Asn Pro Phe
        35                  40                  45
```

<210> SEQ ID NO 547
<211> LENGTH: 171
<212> TYPE: DNA
<213> ORGANISM: Bacteriophage P7953

<400> SEQUENCE: 547

```
ttggtcttag cccccaacaa aacgttccct tatgcttgtg tgtgcgcaag caatagggcg      60
ctgaacctaa tcagtctttt accttttgca ctagataaat tgtatctagg ttatccaatt    120 acatttatc aaattatcat ttataagtca aataaaaaag ccccagcata a               171
```

<210> SEQ ID NO 548
<211> LENGTH: 56
<212> TYPE: PRT
<213> ORGANISM: Bacteriophage P7953

<400> SEQUENCE: 548

```
Met Val Leu Ala Pro Asn Lys Thr Phe Pro Tyr Ala Cys Val Cys Ala
1               5                   10                  15

Ser Asn Arg Ala Leu Asn Leu Ile Ser Leu Leu Pro Phe Ala Leu Asp
            20                  25                  30

Lys Leu Tyr Leu Gly Tyr Pro Ile Thr Phe Tyr Gln Ile Ile Ile Tyr
        35                  40                  45

Lys Ser Asn Lys Lys Ala Pro Ala
    50                  55
```

<210> SEQ ID NO 549
<211> LENGTH: 198
<212> TYPE: DNA
<213> ORGANISM: Bacteriophage P7955

<400> SEQUENCE: 549

```
ttgagaataa atgaagctgt actaagtttt tatagttttt atttttattt attaaggaat      60
ttagtttttt tttgcaaaaa agaaaacct cgactaaaag tcgaggttac agttcgagaa     120
tttaaccgaa acgatgccaa gtattccaac aattatatga aatagcaaa caaaagagc      180 tacgagatta tctcatag                                                  198
```

<210> SEQ ID NO 550
<211> LENGTH: 65
<212> TYPE: PRT
<213> ORGANISM: Bacteriophage P7955

<400> SEQUENCE: 550

```
Met Arg Ile Asn Glu Ala Val Leu Ser Phe Tyr Ser Phe Tyr Phe Tyr
1               5                   10                  15
```

```
Leu Leu Arg Asn Leu Val Phe Phe Cys Lys Lys Arg Lys Pro Arg Leu
            20                  25                  30

Lys Val Glu Val Thr Val Arg Glu Phe Asn Arg Asn Asp Ala Lys Tyr
            35                  40                  45

Ser Asn Asn Tyr Met Lys Ile Ala Asn Lys Lys Ser Tyr Glu Ile Ile
    50                  55                  60

Ser
65

<210> SEQ ID NO 551
<211> LENGTH: 195
<212> TYPE: DNA
<213> ORGANISM: Bacteriophage Sequence3

<400> SEQUENCE: 551
ttgttctacc tattgactaa agcgagtttt tacctctctc tttatcttat gtatacatta      60
catatcatat atgatagtct gccaactgtt tttataaaaa aatatatatt tttttgcaaa     120
acaaaaaccc tgactaattc aagtcagggt gagagagagt ttatcgaaga ctcagctttt    180
aactgtattc attaa                                                      195

<210> SEQ ID NO 552
<211> LENGTH: 64
<212> TYPE: PRT
<213> ORGANISM: Bacteriophage Sequence3

<400> SEQUENCE: 552

Met Phe Tyr Leu Leu Thr Lys Ala Ser Phe Tyr Leu Ser Leu Tyr Leu
1               5                   10                  15

Met Tyr Thr Leu His Ile Ile Tyr Asp Ser Leu Pro Thr Val Phe Ile
            20                  25                  30

Lys Lys Tyr Ile Phe Phe Cys Lys Thr Lys Thr Leu Thr Asn Ser Ser
            35                  40                  45

Gln Gly Glu Arg Glu Phe Ile Glu Asp Ser Ala Phe Asn Cys Ile His
    50                  55                  60
```

ANTI-CRISPR GENES AND PROTEINS AND METHODS OF USE

CROSS-REFERENCE TO RELATED APPLICATIONS

This application claims priority to U.S. Provisional Patent Application No. 62/488,969, filed Apr. 24, 2017 and U.S. Provisional Patent Application No. 62/510,896, filed May 25, 2017, the disclosure of which are herein incorporated by reference in their entirety.

FIELD

The application relates to the field of molecular biology, in particular to anti-CRISPR genes and anti-CRISPR proteins, and methods of use in various biotechnology applications.

REFERENCE TO SEQUENCE LISTING SUBMITTED ELECTRONICALLY

The official copy of the sequence listing is submitted electronically via EFS-Web as an ASCII formatted sequence listing with a file named 20191021_NB41267USPCT_SeqLst.txt created on Oct. 21, 2019 and having a size of 404 kbs kilobytes and is filed concurrently with the specification. The sequence listing contained in this ASCII formatted document is part of the specification and is herein incorporated by reference in its entirety.

BACKGROUND

Bacteriophage-host dynamics are a clear example of an evolutionary arms race (Labrie et al. 2010; Samson et al. 2013) in which each bacterial defense mechanism, such as restriction enzymes, might be countered in turn by a phage mechanism, such as phage T4's heavily modified DNA. A pronounced biotechnological interest arose in finding proteins specifically inhibiting bacterial CRISPR-Cas immune systems, which could then serve to modulate the activity of the CRISPR-derived genome-editing tools (such as SpCas9) in vivo and limit off-target activity. However, given the relative ease of bypassing the CRISPR-Cas system—a single point mutation in a targeted region is sufficient (Barangou et al. 2007)—it wasn't clear whether such a system would even exist.

This doubt was laid to rest with the discovery of four anti-CRISPR (ACR) genes in *Pseudomonas* temperate phages, with activity against the type I-F system (Bondy-Denomy et al. 2013). Type I systems are distantly related to type II systems (Makarova et al. 2015; Makarova et al. 2017), such as the type II-A system of *Streptococcus pyogenes* (source of the genome-editing tool SpCas9) (Jinek et al. 2012). The targets of these four ACRs are distinct (Bondy-Denomy et al. 2015), and subsequent work on two of these proteins (Maxwell et al. 2016; Chowdhury et al. 2017) revealed that the mechanisms of action span from interacting directly with the targeting RNA, to mimicking DNA in order to bind to the cleavage complex's active site. While these ACRs shared little similarity to known sequences, bioinformatic searches in similar gene neighborhoods assisted by an association with helix-turn-helix (HTH) motifs enabled the discovery ACRs with activity against type I-E (Pawluk et al. 2014), both type I-E and type I-F (Pawluk et al. 2016a), and subsequently against type II-C (Pawluk et al. 2016b). Most recently, this bioinformatic approach identified ACRs in prophages of *Listeria* strains whose native type II-A systems appeared to target their own genomes (Rauch et al. 2017). In the case of two of these, a moderate activity against SpCas9 could be demonstrated.

Although several ACRs have recently been discovered, there is still a need to discover additional ACRs not only having a broad spectrum of action in terms of bacterial species but also being highly effective against CRISPR-Cas systems to be targeted.

BRIEF SUMMARY

In one embodiment, the present disclosure provides proteins (anti-CRISPR proteins) interfering with a function of a CRISPR-Cas system from a bacterial strain, as well as genes encoding these proteins (anti-CRISPR genes), constructs and vector comprising these genes.

Also provided are bacterial strains as well as phages comprising these anti-CRISPR genes and expressing said anti-CRISPR proteins.

In another embodiment, methods to downmodulate, in a bacterial strain, the activity of a CRISPR-Cas system against target nucleic acids—based on expressing in said bacterial strain a gene (anti-CRISPR gene) encoding a protein which interferes with a function of a CRISPR-Cas system or based on introducing in said bacterial strain a protein (anti-CRISPR protein) which interferes with a function of a CRISPR-Cas system against target nucleic acids—are provided In still a further embodiment, methods—based on expressing anti-CRISPR genes—to downmodulate, in a bacterial strain, the CRISPR-Cas-mediated immunity against a given target nucleic acid are provided In another embodiment, the invention also discloses methods—based on expressing anti-CRISPR genes—to decrease the CRISPR-mediated instability of a plasmid in a bacterial strain.

Also provided herein are methods—based on expressing anti-CRISPR genes—to increase the efficiency of gene transfer methods in a bacterial strain.

In another embodiment, the invention also discloses methods—based on expressing anti-CRISPR genes—to favor the screening of a bacterial mechanism providing resistance against a virulent phage other than a given CRISPR-Cas mediated resistance.

Methods—based on expressing anti-CRISPR genes—to enrich a bacterial population in bacteriophage-insensitive mutants (BIMs) other than BIMs due to a given CRISPR-Cas system, are also disclosed.

Also provided herein are methods to identify a gene (anti-CRISPR gene) encoding a protein (anti-CRISPR protein), which interferes with the interference function of a given CRISPR-Cas system.

Another embodiment provided herein are methods—based on modulating the expression of anti-CRISPR genes—to induce the death of a bacterial population

SEQUENCES

Figure 1:
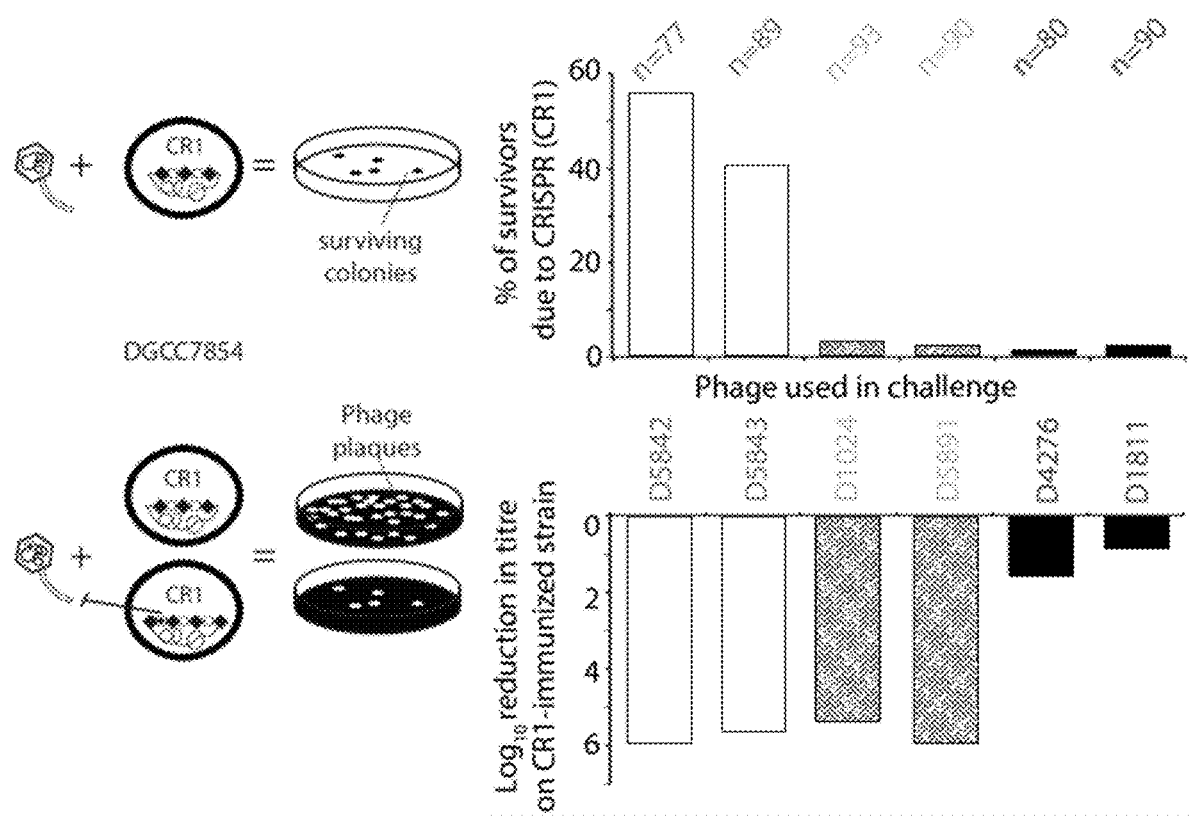
FIG. 1 provides one embodiment of a schematic for the discovery of virulent phages impeding CRISPR-based immunity. (Top) When a virulent phage is used to challenge a bacterium, phage-resistant survivors might be isolated. Six virulent phages infecting *Streptococcus thermophilus* DGCC7854 generated differing frequencies of CRISPR-immune survivors. (Bottom) When comparing these same phages plated on the phage-sensitive wild-type strain DGCC7854 and a CRISPR-immunized mutant targeting a sequence conserved in all six phages, a large reduction in phage titer was expected. Phages D4276 and D1811 suffered a much smaller reduction in titer than the other four related phages. Phage names and associated data are divided according to CRISPR-interacting phenotypes; permissive (white), impeded adaptation (fractal pattern), and restrictive (black).

A sequence listing encompassing 552 sequences is electronically submitted together with this application. Some of these anti-CRISPR gene sequences and anti-CRISPR protein sequences are also disclosed below:

```
/anti-CRISPR gene isolated from bacteriophage O1205
                                                              SEQ ID NO: 1
ATGGCATACGGAAAAAGCAGATACAACTCATATAGGAAACGCAGTTTCAATAGAAGCGATAAGCAACGTAGAGAATAC

GCACAAGAAATGGATAGATTAGAACAAACATTTGAAAAACTTGATGGTTGGTATCTATCTAGCATGAAAGATAGTGCGT

ATAAAGATTTCGGAAAATACGAAATTCGCTTATCAAATCATTCAGCAGACAACAAATATCATGACCTAGAAAATGGTCGT

TTAATTGTTAATGTCAAAGCAAGTAAATTGAAATTCGTTGATATCAAATGTTACTATAAGGGATTTAAGACAAAGAAGGA

TGTAATCTAA

/anti-CRISPR protein encoded by SEQ ID NO: 1
                                                              SEQ ID NO: 2
MAYGKSRYNSYRKRSFNRSDKQRREYAQEMDRLEQTFEKLDGWYLSSMKDSAYKDFGKYEIRLSNHSADNKYHDLENGRLIV

NVKASKLKFVDIKCYYKGFKTKKDVI

/anti-CRISPR gene isolated from Bacteriophage Sfi21
                                                              SEQ ID NO: 3
ATGGCATACGGAAAAAGTAGATATAACTCATATAGAAAGCGCAGTTTTAACAGAAGTAATAAGCAACGTAGAGAATACG

CACAAGAAATGGATAGATTAGAGAAAGCTTTCGAAAATCTTGACGGATGGTATCTATCTAGCATGAAAGATAGTGCGTA

CAAAGATTTCGGAAAATACGAAATTCGCTTATCAAATCATTCAGCAGACAACAAATATCATGACCTAGAAAATGGTCGTT
```

TAATTGTTAATGTCAAAGCAAGTAAATTGAACTTCGTTGATATCATCGAGAACAAACTTGATAAAATCATTGAGAAGATT

GATACTCTTGATTTAGATAAGTACAGATTCATTAATGCTACTAAATTGGAACGTGATATCAAATGCTACTATAAAGGCTAT

AAGACAAAGAAGGATGTAATCTAA

/anti-CRISPR protein encoded by SEQ ID NO: 3

SEQ ID NO: 4

MAYGKSRYNSYRKRSFNRSNKQRREYAQEMDRLEKAFENLDGWYLSSMKDSAYKDFGKYEIRLSNHSADNKYHDLENGRLIV

NVKASKLNFVDIIENKLDKIIEKIDTLDLDKYRFINATKLERDIKCYYKGYKTKKDVI

/anti-CRISPR gene isolated from Bacteriophage TP-778L

SEQ ID NO: 5

ATGGCATACGGAAAAAGCAGATACAACTCATATAGAAAACGTAGTTTCAACATAAGTGACACAAAGCGTAGGGAATATG

CAAAAGAAATGGAGAAATTAGAACAAGCATTTGAAAAGCTAGATGGTTGGTATCTATCTAGCATGAAGGATAGTGCATA

CAAGGATTTTGGAAAATACGAAATCCGCTTATCAAATCATTCAGCAGACAATAAATATCATGACCTAGAAAATGGTCGTT

TAATTGTTAATGTTAAAGCAAGTAAATTGAACTTCGTTGATATCATCGAAAACAAACTTGATAAAATCATCGAGAAGATT

GATAAGCTTGATTTAGATAAGTACAGATTTATTAACGCTACTAGAATGGAGCATGACATTAAATGCTACTATAAAGGATT

TAAGACAAAGAAAGATGTAATCTAA

/anti-CRISPR protein encoded by SEQ ID NO: 5

SEQ ID NO: 6

MAYGKSRYNSYRKRSFNISDTKRREYAKEMEKLEQAFEKLDGWYLSSMKDSAYKDFGKYEIRLSNHSADNKYHDLENGRLIVN

VKASKLNFVDIIENKLDKIIEKIDKLDLDKYRFINATRMEHDIKCYYKGFKTKKDVI

/anti-CRISPR gene isolated from the genome of *Streptococcus* sp. HMSC072D07

SEQ ID NO: 7

ATGGCATTTGGCAAGAACAGATACAATCCATACAGGAAACGTAGTTTTAATCGTAGTGATAAACAATGTCGAGAGTATG

CTCAGGCAATGGACGAACTAGAACAAGCCTTTGAGGAACTTGATGGATGGCACTTATCTAGTATGATGGATAGTGCTTAT

AAGAATTTTGAAAAGTACCAGGTTCGCCTATCAAATCATTCAGCAGACAACCAATATCATGACTTAGAAAATGGTTACTT

GATTGTCAATGTTAAAGCAAGTAAATTGAACTTTGTCGATATTATCGAAAATAAATTGGATAAGATTTTAGAGAAAGTAG

ACAAGCTTGATCTTGATAAGTATAGGTTTATCAATGCGACCAATCTGGAACATGATATTAAATGTTATCTCAAAGGCTATA

AGACGAAAAAAGACGTGATTTAA

/anti-CRISPR protein encoded by SEQ ID NO: 7

SEQ ID NO: 8

MAFGKNRYNPYRKRSFNRSDKQCREYAQAMDELEQAFEELDGWHLSSMMDSAYKNFEKYQVRLSNHSADNQYHDLENGY

LIVNVKASKLNFVDIIENKLDKILEKVDKLDLDKYRFINATNLEHDIKCYLKGYKTKKDVI

/anti-CRISPR gene isolated from Bacteriophage D4276

SEQ ID NO: 9

ATGGCATACGGAAAAAGTAGATATAACTCATATAGAAAGCGCAGTTTTAACAGAAGTAATAAGCAACGTAGAGAATACG

CACAAGAAATGGATAGATTAGAGAAAGCTTTCGAAAATCTTGACGGATGGTATCTATCTAGCATGAAAGACAGTGCTTA

CAAGGATTTTGGGAAATACGAAATTCGCTTATCAAATCATTCGGCAGACAACAAATATCACGACTTAGAAAACGGTCGTT

TAATTGTTAATATTAAAGCTAGTAAATTGAATTTCGTTGATATCATCGAGAATAAGCTTGATAAAATAATCGAGAAGATTG

ATAAGCTTGATTTAGATAAGTACCGATTCATCAATGCGACCAACCTAGAGCATGATATCAAATGCTATTACAAGGGGTTT

AAAACGAAAAAGGAGGTAATCTAA

/anti-CRISPR protein encoded by SEQ ID NO: 9

SEQ ID NO: 10

MAYGKSRYNSYRKRSFNRSNKQRREYAQEMDRLEKAFENLDGWYLSSMKDSAYKDFGKYEIRLSNHSADNKYHDLENGRLIV

NIKASKLNFVDIIENKLDKIIEKIDKLDLDKYRFINATNLEHDIKCYYKGFKTKKEVI

/anti-CRISPR gene isolated from Bacteriophage D1126

SEQ ID NO: 11

ATGGCATACGGAAAAAGCAGATACAATTCATATAGGAAGCGAAACTTCTCTATAAGCGACAATCAGCGTAGGGAATATG

CTAAAAAAATGAAGGAGTTAGAACAAGCGTTTGAAAACCTTGACGGATGGTATCTATCTAGCATGAAAGATAGTGCGTA

CAAAGATTTCGGAAAATACGAAATTCGCTTATCAAATCATTCAGCAGACAATAGATATCATGACCTAGAAAATGGTCGCT

TAATCGTTAATGTTAAAGCTAGTAAATTGAACTTCGTTGATATCATCGAGAATAAACTTGGTAAAATCATTGAGAAGATT

-continued

GATACTCTTGATTTAGATAAGTACAGATTCATTAATGCTACTAAATTGGAACGTGATATCAAATGCTACTATAAAGGCTAT

AAGACAAAGAAGGATGTAATCTAA

/anti-CRISPR protein encoded by SEQ ID NO: 11

SEQ ID NO: 12

MAYGKSRYNSYRKRNFSISDNQRREYAKKMKELEQAFENLDGWYLSSMKDSAYKDFGKYEIRLSNHSADNRYHDLENGRLIV

NVKASKLNFVDIIENKLGKIIEKIDTLDLDKYRFINATKLERDIKCYYKGYKTKKDVI

/anti-CRISPR gene isolated from Bacteriophage D4250

SEQ ID NO: 13

ATGGCATACGGAAAAAGTAGATATAACTCATATAGAAAACGCAGTTTCAACAGAAGCGATAAACAGCGTAGAGAATACG

CACAAGCAATGGAAGAATTAGAGCAAGCATTTGAAAACTTTGATGATTGGTATCTATCAAGCATGAAAGACAGTGCTTA

CAAGGATTTTGGGAAATACGAAATTCGCTTATCAAATCATTCGGCAGACAACAAATATCACGACTTAGAAAACGGTCGTT

TAATTGTTAATATTAAAGCTAGTAAATTGAATTTCGTTGATATCATCGAGAATAAGCTTGATAAAATAATCGAGAAGATTG

ATAAGCTTGATTTAGATAAGTACCGATTCATCAATGCGACCAACCTAGAGCATGATATCAAATGCTATTACAAGGGGTTT

AAAACGAAAAAGGAGGTAATCTAA

/anti-CRISPR protein encoded by SEQ ID NO: 13

SEQ ID NO: 14

MAYGKSRYNSYRKRSFNRSDKQRREYAQAMEELEQAFENFDDWYLSSMKDSAYKDFGKYEIRLSNHSADNKYHDLENGRLIV

NIKASKLNFVDIIENKLDKIIEKIDKLDLDKYRFINATNLEHDIKCYYKGFKTKKEVI

/anti-CRISPR gene isolated from Bacteriophage D4252

SEQ ID NO: 15

ATGGCATACGGAAAAAGCAGATACAACTCATATAGAAAGCGCAGTTTTAACAGAAGTGATAAGCAACGTAGAGAATAC

GCTAAAAAAATGAAGGAGTTAGAACAAGCGITTGAAAACCTTGATGGITGGTATCTATCGAGCATGAATGACAGTGCTT

ATAAAAATTTTGGCAAATATGAAGTTCGATTGTCAAATCATTCGGCAGATAATAAATATCACGACATAGAAAACGGTCGT

TTAATTGTTAATGTTAAAGCTAGTAAATTGAATTTCGTTGATATCATCGAGAACAAGCTTGATAAAATAATCGAGAAGATT

GATAAGCTTGATTTAGATAAGTACCGATTCATCAACGCTACCAATCTAGAGCATAATATTAAATGCTATTACAAGGGATTT

AAGACAAAGAAGGATGTAATATAA

/anti-CRISPR protein encoded by SEQ ID NO: 15

SEQ ID NO: 16

MAYGKSRYNSYRKRSFNRSDKQRREYAKKMKELEQAFENLDGWYLSSMNDSAYKNFGKYEVRLSNHSADNKYHDIENGRLI

VNVKASKLNFVDIIENKLDKIIEKIDKLDLDKYRFINATNLEHNIKCYYKGFKTKKDVI

/anti-CRISPR gene isolated from Bacteriophage D4598

SEQ ID NO: 17

ATGGCATACGGAAAAAGTAGATATAACTCATATAGAAAACGCAGTTTCAACAGAAGCGATAAACAGCGTGGAGAATAC

GCACAAGCAATGGAAGAATTAGAGCAAGCATTTGAAAACTTTGATGATTGGTATCTATCAAGCATGAAAGACAGTGCTT

ACAAGGATTTTGGGAAATACGAAATTCGCTTATCAAATCATTCGGCAGACAATAAATATCATGACCTAGAAAATGGTCGC

TTAATCGTTAATGTTAAAGCTAGTAAATTGAACTTCGTCGATATCATCGAGAATAAAATCGATAAAATCATTGAGAAGATT

GATAAGCTTGATTTAGATAAGTACCGATTCATCAACGCTACCAACCTAGAGCATGATATCAAATGTTATTACAAGGGAITT

AAGACAAAAAAGGATGTAATCTAA

/anti-CRISPR protein encoded by SEQ ID NO: 17

SEQ ID NO: 18

MAYGKSRYNSYRKRSFNRSDKQRGEYAQAMEELEQAFENFDDWYLSSMKDSAYKDFGKYEIRLSNHSADNKYHDLENGRLIV

NVKASKLNFVDIIENKIDKIIEKIDKLDLDKYRFINATNLEHDIKCYYKGFKTKKDVI

/anti-CRISPR gene isolated from the genome of a *Streptococcus mutans* strain

SEQ ID NO: 19

ATGGCATTTGGAAAAGAAGATATAACTCGTATCGTAAACGCAGTTTTAATAGAAGTGATAAGCAACGTCGAGAATATG

CACAAGCAATGGAAGAACTTGAACAAACATTTGAAAATCTTGAAGGTTGGAATTTATCAAGCATGAAAGATAGTGCTTAT

AAAGATTATGATAAATATGAAGTTCGACTTTCAAATCATTCAGCTGATAATCAATATCATAACTTACAAGATGGTAAATTA

ATCATCAATATCAAAGCTAGTAAAATGAATTTTGTTTGGATTATAGAAAATAAACTTGATGCAATTCTTGAAAAAGTAAAT

-continued

AAGTTAGACCTTAGCAAATACAGATTTATTAATGCTACAAGTTTAGATCATGATATCAAATGTTATTACAAAAATTATAAA

ACAAAGAAAGATGTAATTTAA

/anti-CRISPR protein encoded by SEQ ID NO: 19

SEQ ID NO: 20

MAFGKRRYNSYRKRSFNRSDKQRREYAQAMEELEQTFENLEGWNLSSMKDSAYKDYDKYEVRLSNHSADNQYHNLQDGKLI

INIKASKMNFVWIIENKLDAILEKVNKLDLSKYRFINATSLDHDIKCYYKNYKTKKDVI

/anti-CRISPR gene isolated from the genome of a *Streptococcus mutans* strain

SEQ ID NO: 21

ATGGCATTTGGAACAAGAAGATATAATTCATATCGTAAACGCAGTTTTAATAGAAGTGATAAGCAACGTCGAGAATATG

CACAAGCAATGGAAGAACTTGAACAAACATTTGAAAATCTTGAAGATTGGAATTTGTCGAGCATGAAAGATAGTGCTTA

TAAAGATTATGATAAATATGAAGTTCGACTTTCAAATCATTCAGCTGATAATCAATATCATAACTTACAAGATGGTAAATT

AATCATCAATATCAAAGCTAGTAAAATGAATTTTGTTTGGATTATAGAAAATAAACTTGATGCAATTCTTGAAAAAGTAAA

TAAGTTAGACCTTAGCAGATACAGATTTATTAATGCTACAAATTTAGAACATGATATCAAATGTTATTACAAAAATTATAA

AACAAAGAAAGATGTAATTTAA

/anti-CRISPR protein encoded by SEQ ID NO: 21

SEQ ID NO: 22

MAFGTRRYNSYRKRSFNRSDKQRREYAQAMEELEQTFENLEDWNLSSMKDSAYKDYDKYEVRLSNHSADNQYHNLQDGKLI

INIKASKMNFVWIIENKLDAILEKVNKLDLSRYRFINATNLEHDIKCYYKNYKTKKDVI

/anti-CRISPR gene isolated from the genome of a *Streptococcus mutans* strain

SEQ ID NO: 23

ATGGCATTTGGAACAAGAAGATATAATTCATATCGTAAACGCAGTTTTAATAGAAGTGATAAGCAACGTCGAGAATATG

CACAAGCAATGGAAGAACTTGAACAAACATTTGAAAATCTTGAAGATTGGAATTTGTCGAGCATGAAAGATAGTGCTTA

TAAAGATTATGATAAATATGAAGTTAGACTTTCAAATCATTCAGCTGATAATCAATATCATAACTTACAAGATGGTAAATT

AATCATCAATATCAAAGCTAGTAAAATGAATTTTGTTTGGATTATAGAAAATAAACTTGATGTAATTCTTGAAAAAGTAAA

TAAGTTAGACCTTAGCAAATACAGATTTATTAATGCTACAAGTTTAGATCATGATATCAAATGTTATTACAAAAATTATAA

AACAAAGAAAGATGTAATCTAA

/anti-CRISPR protein encoded by SEQ ID NO: 23

SEQ ID NO: 24

MAFGTRRYNSYRKRSFNRSDKQRREYAQAMEELEQTFENLEDWNLSSMKDSAYKDYDKYEVRLSNHSADNQYHNLQDGKLI

INIKASKMNFVWIIENKLDVILEKVNKLDLSKYRFINATSLDHDIKCYYKNYKTKKDVI

/anti-CRISPR gene isolated from the genome of a *Streptococcus mutans* strain

SEQ ID NO: 25

ATGGCATTTGGAACAAGAAGATATAATTCATATCGTAAACGCAATTTTAATAGAAGTGATAAACAACGTCGAGAATATGC

ACAAGCAATGGAAGAACTTGAACAAACATTTGAAAATCTTGAAGATTGGAATTTGTCGAGCATGAAAGATAGTGCTTAT

AAAGATTATGATAAATTTGAAGTTCGACTTTCAAATCATTCAGCTGATAATCAATATCATAACTTACAAGATGGTAAATTA

ATCATCAATATCAAAGCTAGTAAAATGAATTTTGTTTGGATTATAGAAAATAAACTTGATGCAATTCTTGAAAAGGTAAAT

AAGTTAGACCTTAGCAAATACAGATTTATTAATGCTACAAGTTTAGATCATGATATCAAATGTTATTACAAAAATTATAAA

ACAAAAAAAGATGTAATTTAA

/anti-CRISPR protein encoded by SEQ ID NO: 25

SEQ ID NO: 26

MAFGTRRYNSYRKRNFNRSDKQRREYAQAMEELEQTFENLEDWNLSSMKDSAYKDYDKFEVRLSNHSADNQYHNLQDGKL

IINIKASKMNFVWIIENKLDAILEKVNKLDLSKYRFINATSLDHDIKCYYKNYKTKKDVI

/anti-CRISPR gene isolated from Bacteriophage D1811

SEQ ID NO: 27

ATGAAAATAAATGACGACATCAAAGAGTTAATTTTAGAATATATGAGCCGTTACTTCAAATTCGAGAACGACTTTTATAA

ACTGCCAGGCATCAAGTTCACTGATGCAAATTGGCAGAAGTTCAAAAATGGAGGCACTGACATTGAGAAGATGGGGGC

GGCACGAGTAAACGCCATGCTCGACTGCCTATTCGACGATTTCGAGCTTGCTATGATTGGCAAGGCTCAAACTAATTATT

ACAATGATAATTCACTAAAGATGAACATGCCATTTTACACTTACTATGACATGTTCAAAAAGCAGCAACTTCTAAAATGGC

TTAAAAATAACCGTGATGATGTCATCGGCGGAACTGGTAGGATGTACACAGCAAGTGGTAATTACATTGCTAACGCTTAT

-continued

TTAGAGGTGGCATTAGAATCGAGCTCGCTTGGTAGTGGCTCTTACATGCTTCAAATGAGGTTTAAAGACTATTCAAAAGG

TCAAGAACCTATTCCGTCAGGTCGTCAGAATCGACTTGAATGGATTGAAAACAATCTCGAAAACATTCGATAA

/anti-CRISPR protein encoded by SEQ ID NO: 27

SEQ ID NO: 28

MKINDDIKELILEYMSRYFKFENDFYKLPGIKFTDANWQKFKNGGTDIEKMGAARVNAMLDCLFDDFELAMIGKAQTNYYND

NSLKMNMPFYTYYDMFKKQQLLKWLKNNRDDVIGGTGRMYTASGNYIANAYLEVALESSSLGSGSYMLQMRFKDYSKGQE

PIPSGRQNRLEWIENNLENIR

/anti-CRISPR gene isolated from Bacteriophage D1024

SEQ ID NO: 29

ATGAAAATAAATGACGACATCAAAGAGTTAATTTTAGAATATATGAGCCGTTACTTCAAATTCGAGAACGACTTTTATAA

ACTGCCAGGCATCAAGTTCACTGATGCAAATTGGCAGAAGTTCAAAAATGGAGGCACTGACATTGAGAAGATGGGGGC

GGCACGAGTAAATGCCATGCTTTCCTGCCTATTCGAGGATTTTGAGCTTGCAATGATTGGCAAGGCTCAAACTAATTATT

ACATTGATAACTCACTTAAATTGAACATGCCATTTTACGCTTACTATGACATGTTCAAAAAGCAACTTCTTATAAATTGGCT

TAAAAATAACCGTGATGATGTCATCTGCGGAACTGGTAGGATGTACACAGCAAGTGGTAATTACATTGCTAACGCTTATT

TAGAGGTGGCATTAGAATCTAGCCGTCTGGGTGGTGGTGAGTACATGTTGCAAATGCGTTTTAAAAATTATTCAAGAAG

TCAAGAACCTATTCCGTCTGGTCGTCAGAATCGACTTGAATGGATTGAAAACAATCTTGAAAACATTCGATAA

/anti-CRISPR protein encoded by SEQ ID NO: 29

SEQ ID NO: 30

MKINDDIKELILEYMSRYFKFENDFYKLPGIKFTDANWQKFKNGGTDIEKMGAARVNAMLSCLFEDFELAMIGKAQTNYYIDN

SLKLNMPFYAYYDMFKKQLLINWLKNNRDDVICGTGRMYTASGNYIANAYLEVALESSRLGGGEYMLQMRFKNYSRSQEPIP

SGRQNRLEWIENNLENIR

/anti-CRISPR gene isolated from Bacteriophage D4530

SEQ ID NO: 31

ATGAAAATCAATAATGACATCAAAGAGCTAATTTTGGAATATGTAAGTCGCTATTTTAAATTTGAAAACGACTTCTACAAA

TTGCCAGGCATCAAATTCACTGATGCAAATTGGCAAAAATTCAAGAATGGAGATACTTCCATCGAGAAGATGGGGGCAG

CACGAGTAAATGCCATGCTTGACTGCCTGTTCGAAGATTTTGAGCTTGCAATGATTGGCAAGGCTCAAACTAATTATTAC

AATGATAATTCACTAAAGATGAACATGCCATTTTACACTTACTATGACATGTTCAAAAAGCAGCAACTTCTAAAATGGCTT

AAAAATAACCGTGATGATGTCATCTGCGGAACTGGTAGGATGTACACAGCAAGTGGTAATTACATTGCTAACGCTTATTT

AGAAATTGCGTTAGAATCTAGCCGTCTGGGTAGTGGCTCTTACATGCTTCAAATGAGATTCAAAGACTATTCAAGAAGTC

AAGAACCTATTCCGTCTGGTCGCCAAAATAGACTAGAATGGATTGAGAGCAACTTGGAAAACATTCGATAA

/anti-CRISPR protein encoded by SEQ ID NO: 31

SEQ ID NO: 32

MKINNDIKELILEYVSRYFKFENDFYKLPGIKFTDANWQKFKNGDTSIEKMGAARVNAMLDCLFEDFELAMIGKAQTNYYDN

SLKMNMPFYTYYDMFKKQQLLKWLKNNRDDVICGTGRMYTASGNYIANAYLEIALESSRLGSGSYMLQMRFKDYSRSQEPIP

SGRQNRLEWIESNLENIR

/anti-CRISPR gene isolated from Bacteriophage D2759

SEQ ID NO: 33

ATGAAAATCAATAATGACATCAAAGAGCTAATTTTGGAATATGTAAGTCGCTATTTTAAATTTGAAAACGACTTCTACAAA

TTGCCAGGCATCAAATTCACTGATGCAAATTGGCAAAAATTCAAGAATGGAGATACTTCCATCGAGAAGATGGGGGCAG

CACGAGTAAATGCCATGCTTGACTGCCTATTCGACGATTTTGAGCTTGCTTTGATTGGCAAGGCTCAAACTAATTATTACA

TTGATAACTCACTTAAATTGAACATGCCATTTTACGCTTACTATGACATGTTCAAAAAGCAGCAACTTCTAAAATGGCTTA

AAAATAACCGTGATGATGTCATCTGCGGAACTGGTAGGATGTACACAGCAAGTGGTAATTACATTGCTAACTCTTATTTA

GAGGTAGCGTTAGAATCTAGCCGTCTGGGTAGTGGCTCTTACATGCTTCAAATGAGATTCAAAGACTATTCAAGAAGTCA

AGAACCTATTCCATCTGGTCGCCAAAATAGACTAGAATGGATTGAGAGCAACTTGGAAAACATTCGATAA

/anti-CRISPR protein encoded by SEQ ID NO: 33

SEQ ID NO: 34

MKINNDIKELILEYVSRYFKFENDFYKLPGIKFTDANWQKFKNGDTSIEKMGAARVNAMLDCLFDDFELALIGKAQTNYYIDNS

LKLNMPFYAYYDMFKKQQLLKWLKNNRDDVICGTGRMYTASGNYIANSYLEVALESSRLGSGSYMLQMRFKDYSRSQEPIPS

GRQNRLEWIESNLENIR

/anti-CRISPR gene isolated from Bacteriophage D1297

SEQ ID NO: 35

ATGAAAATCAATAATGACATCAAAGAGCTAATTTTGGAATATGTAAGTCGCTATTTTAAATTTGAAAACGACTTCTACAAA

TTGCAAGGCATCAAATTCACTGATGCAAATTGGCAAAAATTCAAGAATGGAGATACTTCCATCGAGAAGATGGGGGCAG

CACGAGTAAATGCCATGCTTGACTGCCTATTCGACGATTTTGAGCTTGCTTTGATTGGCAAGGCTCAACAAGAATACTATT

CGGATAATTCCTTGAAATTGAACATGCCATTTTACGCTTACTATGACATGTTCAAAAAGCAGCAACTTCTAAAATGGCTTA

AAAATAACCGTGATGATGTCATCTGCGGAACTGGTAGGATGTACACAGCAAGTGGTAATTACATTGCTAACTCTTATTTA

GAGGTAGCGTTAGAATCTAGCCGTCTGGGTAGTGGCTCTTACATGCTTCAAATGAGATTCAAAGACTATTCAAGAAGTCA

AGAACCTATTCCGTCAGGTCGCAAAAACCGACTTGAGTGGATTGAAAACAATCTGGAAAATATTCGATAA

/anti-CRISPR protein encoded by SEQ ID NO: 35

SEQ ID NO: 36

MKINNDIKELILEYVSRYFKFENDFYKLQGIKFTDANWQKFKNGDTSIEKMGAARVNAMLDCLFDDFELALIGKAQQEYYSDN

SLKLNMPFYAYYDMFKKQQLLKWLKNNRDDVICGTGRMYTASGNYIANSYLEVALESSRLGSGSYMLQMRFKDYSRSQEPIP

SGRKNRLEWIENNLENIR

/anti-CRISPR gene isolated from Bacteriophage M5728

SEQ ID NO: 37

ATGAAAATCAATAATGACATCAAAGAGCTAATTTTGGAATATGTAAGTCGCTATTTTAAATTTGAAAACGACTTCTACAAA

TTGCCAGGCATCAAATTCACTGATGCAAATTGGCAAAAATTCAAGAATGGAGATACTTCCATCGAGAAGATGGGGGCAG

CACGAGTAAATGCCATGCTTGACTGCCTATTCGACGATTTTGAGCTTGCTTTTATTGGCAAGGCTCAACAAGAATACTATT

CGGATAATTCCTTGAAATTGAACATGCCATTTTACGCTTACTATGACATGTTCAAAAAGCAGCAACTTCTAAAATGGCTTA

AAAATAACCGTGATGATGTCATCTGCGGAACTGGTAGGATGTACACAGCAAGTGGTAATTACATTGCTAACTCTTATTTA

GAGGTAGCGTTAGAATCTAGCCGTCTGGGTAGTGGCTCTTACATGCTTCAAATGAGATTCAAAGACTATTCAAGAAGTCA

AGAACCTATTCCATCTGGTCGCCAAAATAGACTAGAATGGATTGAAAACAATCTTGAGAATATTCGATAA

/anti-CRISPR protein encoded by SEQ ID NO: 37

SEQ ID NO: 38

MKINNDIKELILEYVSRYFKFENDFYKLPGIKFTDANWQKFKNGDTSIEKMGAARVNAMLDCLFDDFELAFIGKAQQEYYSDNS

LKLNMPFYAYYDMFKKQQLLKWLKNNRDDVICGTGRMYTASGNYIANSYLEVALESSRLGSGSYMLQMRFKDYSRSQEPIPS

GRQNRLEWIENNLENIR

/anti-CRISPR gene isolated from Bacteriophage D4419

SEQ ID NO: 39

ATGAAAATCAATAATGACATCAAAGAGCTAATTTTGGAATATGTAAGTCGCTATTTTAAATTTGAAAACGACTTCTACAAA

TTGCCAGGCATCAAATTCACTGATGCAAATTGGCAAAAATTCAAGAATGGAGATACTTCCATCGAGAAGATGGGGGCAG

CACGAGTAAATGCCATGCTTGACTGCCTATTCGACGATTTTGAGCTTGCTTTGATTGGCAAGGCTCAACAAGAATACTATT

CGGATAATTCCTTGAAATTGAACATGCCATTTTACGCTTACTATGACATGTTCAAAAAGCAGCAACTTCTAAAATGGCTTA

AAAATAACCGTGATGATGTCATCTGCGGAACTGGTAGGATGTACACAGCAAGTGGTAATTACATTGCTAACTCTTATTTA

GAGGTAGCGTTAGAATCTAGCCGTCTGGGTAGTGGCTCTTACATGCTTCAAATGAGATTCAAAGACTATTCAAGAAGTCA

AGAACCTATTCCATCTGGTCGCCAAAATAGACTAGAATGGATTGAGAGCAACTTGGAAAACATTCGATAA

/anti-CRISPR protein encoded by SEQ ID NO: 39

SEQ ID NO: 40

MKINNDIKELILEYVSRYFKFENDFYKLPGIKFTDANWQKFKNGDTSIEKMGAARVNAMLDCLFDDFELALIGKAQQEYYSDNS

LKLNMPFYAYYDMFKKQQLLKWLKNNRDDVICGTGRMYTASGNYIANSYLEVALESSRLGSGSYMLQMRFKDYSRSQEPIPS

GRQNRLEWIESNLENIR

-continued

/anti-CRISPR gene isolated from Bacteriophage D5891
SEQ ID NO: 41
ATGAAAATCAATAATGACATCAAAGAGCTAATTTTGGAATATGTAAGTCGCTATTTTAAATTTGAAAACGACTTCTACAAA

TTGCCAGGCATCAAATTCACTGATGCAAATTGGCAAAAATTCAAGAATGGAGATACTTCCATCGAGAAGATGGGGCAG

CACGAGTAAATGCCATGCTTGACTGCCTATTCGACGATTTTGAGCTTGCTTTTATTGGCAAGGCTCAACAAGAATACTATT

CGGATAATTCCTTGAAATTGAACATGCCATTTTACGCTTACTATGACATGTTCAAAAAGCAGCAACTTCTAAAATGGCTTA

AAAATAACCGTGATGATGTCATCTGCGGAACTGGTAGGATGTACACAGCAAGTGGTAATTACATTGCTAACTCTTATTTA

GAGGTAGCGTTAGAATCTAGCCGTCTGGGTAGTGGCTCTTACATGCTTCAAATGAGATTCAAAGACTATTCAAGAAGTCA

AGAACCTATTCCATCTGGTCGCCAAAATAGACTAGAATGGATTGAGAGCAACTTGGAAAACATTCGATAA

/anti-CRISPR protein encoded by SEQ ID NO: 41
SEQ ID NO: 42
MKINNDIKELILEYVSRYFKFENDFYKLPGIKFTDANWQKFKNGDTSIEKMGAARVNAMLDCLFDDFELAFIGKAQQEYYSDNS LKLNMPFYAYYDMFKKQQLLKWLKNNRDDVICGTGRMYTASGNYIANSYLEVALESSRLGSGSYMLQMRFKDYSRSQEPIPS

GRQNRLEWIESNLENIR

/anti-CRISPR gene isolated from Bacteriophage ALQ13.2
SEQ ID NO: 43
ATGAAAATCAATAATGACATCAAAGAGCTAATTTTGGAATATGTAAGTCGCTATTTTAAATTTGAAAACGACTTCTACAAA

TTGCCAGGCATCAAATTCACTGATGCAAATTGGCAAAAATTCAAGAACGGAGATACTTCCATCGAGAAGATGGGGCAG

CACGAGTAAATGCCATGCTTGACTGCCTATTCGACGATTTTGAGCTTGCTTTGATTGGCAAGGCTCAACAAGAATACTATT

CGGATAATTCCTTGAAATTGAACATGCCATTTTACGCTTACTATGACATGTTAAAAAAGCAGCAACTTCTAAAATGGCTTA

AAAATAACCGTGATGATGTCATCTGCGGAACTGGTAGGATGTACACAGCAAGTGGTAATTACATTGCTAACTCTTATTTA

GAGGTAGCGTTAGAATCTAGCCGTCTGGGTAGTGGCTCTTACATGCTTCAAATGAGATTCAAAGACTATTCAAGAAGTCA

AGAACCTATTCCATCTGGTCGCCAAAATAGACTAGAATGGATTGAGAGCAACTTGGAAAACATTCGATGA

/anti-CRISPR protein encoded by SEQ ID NO: 43
SEQ ID NO: 44
MKINNDIKELILEYVSRYFKFENDFYKLPGIKFTDANWQKFKNGDTSIEKMGAARVNAMLDCLFDDFELALIGKAQQEYYSDNS LKLNMPFYAYYDMLKKQQLLKWLKNNRDDVICGTGRMYTASGNYIANSYLEVALESSRLGSGSYMLQMRFKDYSRSQEPIPS

GRQNRLEWIESNLENIR

/anti-CRISPR gene isolated from Bacteriophage D802
SEQ ID NO: 45
ATGAAAATCAATAATGACATCAAAGAGCTAATTTTGGAATATGTAAGTCGCTATTTTAAATTCGAGAACGACTTTTACAG

ATTGCCTGGCATCAAATTCACTGATGCCAACTGGCAAAAATTCAAGAATGGAGGCACTGCCATTGAGAAGATGGGAGCA

GCACGAGTTAATGCCATGCTTTCCTGCCTATTCGAGGATTTTGAGCTTGCAATGATTGGCAAGGCTCAATATGAATACTAT

TCGGATAATTCCTTGAAATTGAACATGCCATTTTACGCTTACTATGACATGTTCAAAAAGCAGCAACTTCTAAAATGGCTT

AAAAATAACCGTGATGATGTCATCGGCGGAACTGGTAGAATGTACACGTCAAGCGGTAGTTACATTGCTAACGCTTATTT

AGAAATTGCGTTAGAATCTAGCCGTCTGGGTAGTGGCTCTTACATGCTTCAAATGAGATTCAAAGACTATTCAAGAAGTC

AAGAACCTATTCCGTCTGGTCGCCAAAATAGACTTGAATGGATTGAGAGCAACTTGGAAAACATTCGATAA

/anti-CRISPR protein encoded by SEQ ID NO: 45
SEQ ID NO: 46
MKINNDIKELILEYVSRYFKFENDFYRLPGIKFTDANWQKFKNGGTAIEKMGAARVNAMLSCLFEDFELAMIGKAQYEYYSDN SLKLNMPFYAYYDMFKKQQLLKWLKNNRDDVIGGTGRMYTSSGSYIANAYLEIALESSRLGSGSYMLQMRFKDYSRSQEPIPS

GRQNRLEWIESNLENIR

/anti-CRISPR gene isolated from Bacteriophage 73
SEQ ID NO: 47
ATGAAAATCAATAATGACATCAAAGAGCTAATTTTGGAATATGTAAGTCGCTATTTTAAATTTGAAAACGACTTCTACAAA

TTACCTGGCATCAAATTCACTGATGCCAACTGGCAAAAATTCAAGAATGGAGATACTTCCATCGAGAAGATGGGGCAG

CACGAGTAAATGCCATGCTTGACTGCCTATTCGAGGATTTTGAGCTTGCAATGATTGGCAAGGCTCAAACTAATTATTAC

ATTGATAACTCACTTAAATTGAACATGCCATTTTACGCTTACTATGACATGTTCAAAAAGCAGCAACTTCTAAAATGGCTT

```
AAAAATAACCGTGATGATGTCATCGGCGGAACTGGTAGGATGTACACAGCAAGTGGTAATTACATTGCTAACGCTTATTT

AGAGGTGGCATTAGAATCGAGCTCGCTTGGTAGTGGCTCTTACATGCTTCAAATGAGGTTTAAAGACTATTCAAAAGGTC

AAGAACCTATTCCGTCAGGTCGTCAGAATCGACTTGAATGGATTGAAAACAATCTCGAAAACATTCGATAA
```

/anti-CRISPR protein encoded by SEQ ID NO: 47

SEQ ID NO: 48

```
MKINNDIKELILEYVSRYFKFENDFYKLPGIKFTDANWQKFKNGDTSIEKMGAARVNAMLDCLFEDFELAMIGKAQTNYYIDNS

LKLNMPFYAYYDMFKKQQLLKWLKNNRDDVIGGTGRMYTASGNYIANAYLEVALESSSLGSGSYMLQMRFKDYSKGQEPIPS

GRQNRLEWIENNLENIR
```

/anti-CRISPR gene isolated from Bacteriophage DT1

SEQ ID NO: 49

```
ATGAAAATCAATAATGACATCAAAGAGCTAATTTTGGAATATGTAAGTCGCTATTTTAAATTTGAAAACGACTTCTACAAA

TTACCTGGCATCAAATTCACTGATGCCAACTGGCAAAAATTCAAGAATGGAGAAACTTCAATCGAAAAAATGGGAGCAG

CACGAGTTAATGCCATGCTTTCATGCCTATTCGAGGATTTTGAGCTTGCAATGATTGGCAAGGCTCAAACTAATTATTACA

TTGATAACTCACTTAAATTGAACATGCCATTTTACGCTTACTATGACATGTTCAAAAAGCAACTTCTTATAAATTGGCTTAA

AAATAACCGTGATGATGTCATCGGCGGAACTGGTAGGATGTACACAGCAAGTGGTAATTACATTGCTAACGCTTATTTAG

AGGTGGCATTAGAATCAAGCTCGCTIGGTAGTGGCTCTTACATGATCCAAATGAGGTTTAAAGACTATTCAAAAGGTCAA

GAACCTATTCCGTCAGGTCGCAAAAACCGACTTGAGTGGATTGAAAACAATCTGGAAAATATTCGATAA
```

/anti-CRISPR protein encoded by SEQ ID NO: 49

SEQ ID NO: 50

```
MKINNDIKELILEYVSRYFKFENDFYKLPGIKFTDANWQKFKNGETSIEKMGAARVNAMLSCLFEDFELAMIGKAQTNYYIDNS

LKLNMPFYAYYDMFKKQLLINWLKNNRDDVIGGTGRMYTASGNYIANAYLEVALESSSLGSGSYMIQMRFKDYSKGQEPIPS

GRKNRLEWIENNLENIR
```

/anti-CRISPR gene isolated from Bacteriophage D1427

SEQ ID NO: 51

```
ATGAAAATCAATAATGACATCAAAGAGCTAATTTTGGAATATGTAAGTCGCTATTTTAAATTTGAAAACGACTTCTACAAA

TTACCTGGCATCAAATTCACTGATGCCAACTGGCAAAAATTCAAGAATGGAGAAACTTCAATCGAAAAAATGGGAGCAG

CACGAGTTAATGCCATGCTTTCATGCCTATTCGAGGATTTTGAGCTTGCAATGATTGGCAAGGCTCAAACTAATTATTACA

TTGATAACTCACTTAAATTGAACATGCCATTTTACGCTTACTATGACATGTTCAAAAAGCAACTTCTTATAAATTGGCTTAA

AAATAACCGTGATGATGTCATCGGCGGAACTGGTAGGATGTACACAGCAAGTGGTAATTACATTGCTAACGCTTATTTAG

AGGTGGCATTAGAATCAAGCTCGCTIGGTAGTGGCTCTTACATGATCCAAATGAGGTTTAAAGACTATTCAAAAGGTCAA

GAACCTATTCCGTCAGGTCGCAAAATAGACTAGAATGGATTGAGAGCAACTTGGAAAACATTCGATAA
```

/anti-CRISPR protein encoded by SEQ ID NO: 51

SEQ ID NO: 52

```
MKINNDIKELILEYVSRYFKFENDFYKLPGIKFTDANWQKFKNGETSIEKMGAARVNAMLSCLFEDFELAMIGKAQTNYYIDNS

LKLNMPFYAYYDMFKKQLLINWLKNNRDDVIGGTGRMYTASGNYIANAYLEVALESSSLGSGSYMIQMRFKDYSKGQEPIPS

GRQNRLEWIESNLENIR
```

/anti-CRISPR gene isolated from Bacteriophage N1162

SEQ ID NO: 53

```
ATGAAAATCAATAATGACATCAAAGAGCTAATTTTGGAATATGTAAGTCGCTATTTTAAATTTGAAAACGACTTCTACAAA

TTACCTGGCATCAAATTCACTGATGCCAACTGGCAAAAATTCAAGAATGGAGATACTTCCATCGAGAAGATGGGGCAG

CACGAGTAAATGCCATGCTTGACTGCCTATTCGAGGATTTTGAGCTTGCAATGATTGGCAAGGCTCAAACTAATTATTAC

ATTGATAACTCACTTAAATTGAACATGCCATTTTACGCTTACTATGACATGTTCAAAAAGCAGCAACTTCTAAAATGGCTT

AAAAATAACCGTGATGATGTCATCGGCGGAACTGGTAGGATGTACACATCAACCGGTAATTACATTGCTAACGCTTATTT

AGAAATTGCGTTAGAATCTAGCCGTCTGGGTAGTGGCTCTTACATGATCCAAATGAGGTTTAAAGACTATTCAAAAGGTC

AAGAACCTATTCCGTCTGGTCGTCAGAATCGACTTGAATGGATTGAAAACAATCTGGAAAATATTCGATAA
```

/anti-CRISPR protein encoded by SEQ ID NO: 53
SEQ ID NO: 54
MKINNDIKELILEYVSRYFKFENDFYKLPGIKFTDANWQKFKNGDTSIEKMGAARVNAMLDCLFEDFELAMIGKAQTNYYIDNS LKLNMPFYAYYDMFKKQQLLKWLKNNRDDVIGGTGRMYTSTGNYIANAYLEIALESSRLGSGSYMIQMRFKDYSKGQEPIPS

GRQNRLEWIENNLENIR

/anti-CRISPR gene isolated from Bacteriophage D1018
SEQ ID NO: 55
ATGAAAATCAATAATGATATCAAAGAGCTAATTTTGGAATATGTAAGTCGCTATTTTAAATTTGAAAACGACTTCTACAAA

TTGCCAGACATCAAGTTCACAGATGCTAATTGGCAAAAATTTAAGAATGGAGAAACTTCAATCGAAAAAATGGGAGCAG

CACGAGTAAATGCCATGCTTGACTGCCTATTCGAGGATTTTGAGCTTGCAATGATTGGCAAGGCTCAAACTAATTATTAC

ATTGATAACTCACTTAAATTGAACATGCCATTTTACGCTTACTATGACATGTTCAAAAAGCAGCAACTTCTAAAATGGCTT

AAAAATAACCGTGATGATGTCATCGGCGGAACTGGTAGGATGTACACATCAACCGGTAATTACATTGCTAACGCTTATTT

AGAAATTGCGTTAGAATCTAGCCGTCTGGGTAGTGGCTCTTACATGATCCAAATGAGGTTTAAAGACTATTCAAAAGGTC

AAGAACCTATTCCGTCTGGTCGTCAGAATCGACTTGAATGGATTGAAAACAATCTGGAAAATATTCGATAA

/anti-CRISPR protein encoded by SEQ ID NO: 55
SEQ ID NO: 56
MKINNDIKELILEYVSRYFKFENDFYKLPDIKFTDANWQKFKNGETSIEKMGAARVNAMLDCLFEDFELAMIGKAQTNYYIDNS LKLNMPFYAYYDMFKKQQLLKWLKNNRDDVIGGTGRMYTSTGNYIANAYLEIALESSRLGSGSYMIQMRFKDYSKGQEPIPS

GRQNRLEWIENNLENIR

/anti-CRISPR gene isolated from Bacteriophage D3577
SEQ ID NO: 57
ATGAAAATAAACAACGATATCAAAGAGCTAATTTTGGAATACGCTAAACGTTATTTCAAGTTTGAAAACGACTTCTACAA

ACTGCCAGACATCAAATTCACTGATGCCAACTGGCAAAAATTTAAGAATGGAGAAACTTCCATCGAAAAAATGGGAGCA

GCACGAGTTAATGCCATGCTTTCCTGCCTGTTCGACGATTTTGAGCTTGCTATGATTGGCAAGGCTCAAACTAATTATTAC

AATGATAACTCACTTAAATTGAACATGCCATTTTACGCTTACTATGACATGTTCAAAAAGCAGCAACTTCTAAAATGGCTT

AAAAATAACCGTGATGATATCATCTGCGGAACTGGTAGAATGTACACTTCAAGAGGTAGTTACATTGCTAACGCTTATTT

AGAGGTAGCGTTAGAATCAAGCTTGCTTGGTAGTGGCTCTTACATGCTTCAAATGAGGTTCAAAGACTATTCAAAAAGTC

AAGAACCTATTCCATCTGGTCGTCAGAATCGACTTGAATGGATTGAGAGCAACTTGGAAAATATTCGATAA

/anti-CRISPR protein encoded by SEQ ID NO: 57
SEQ ID NO: 58
MKINNDIKELILEYAKRYFKFENDFYKLPDIKFTDANWQKFKNGETSIEKMGAARVNAMLSCLFDDFELAMIGKAQTNYYNDN SLKLNMPFYAYYDMFKKQQLLKWLKNNRDDIICGTGRMYTSRGSYIANAYLEVALESSLLGSGSYMLQMRFKDYSKSQEPIPS

GRQNRLEWIESNLENIR

/anti-CRISPR gene isolated from Bacteriophage CHPC577
SEQ ID NO: 59
ATGAAAATAAACAACGATATCAAAGAGCTAATTTTGGAATATGGAAGTCGCTATTTTAAATTTGAAAACGACTTCTACAA

ACTGCCTGGCATCAAGTTCACTGATGCTAATTGGCAAAAATTCAAAAATGGTGATACTTTAATCGAAAAAATGGGGGCA

GCACGAGTAAATGCCATGCTTGACTGCCTGTTCGACGATTTTGAGCTTGCTATGATTGGCAAGGCTCAAACTAATTATTAC

AATGATAATTCCTTGAAATTGAACATGCCATTTTACGCTTACTATGACATGTTCAAAAAGCAACAGCTTATACATTGGCTC

AAAAACAACCGTGATGACATCGTAGGCGGAACTGGTAGACTGTACACTTCAAGCGGTAGTTACATTGCTAACGCTTATTT

AGAAATTGCATTAGAATCGAGCTCGCTTGGTAGTGGCTCTTACATGCTTCAAATGAGATTCAAAAACTATTCAAAAAGTC

AAGAACCTATTCCATCTGGTCGCCAGAATCGACTTGAATGGATTGAAAACAATCTTGAGAATATTCGATAA

/anti-CRISPR protein encoded by SEQ ID NO: 59
SEQ ID NO: 60
MKINNDIKELILEYGSRYFKFENDFYKLPGIKFTDANWQKFKNGDTLIEKMGAARVNAMLDCLFDDFELAMIGKAQTNYYND NSLKLNMPFYAYYDMFKKQQLIHWLKNNRDDIVGGTGRLYTSSGSYIANAYLEIALESSSLGSGSYMLQMRFKNYSKSQEPIPS

GRQNRLEWIENNLENIR

-continued

/anti-CRISPR gene isolated from Bacteriophage D4237

SEQ ID NO: 61

ATGAAAATAAATAACGACATCAAAGAATTAATTTTAGAATATATGAGCCGTTACTTCAAATTCGAAAACGACTTCTACAAA

TTGCCAGACATCAAGTTCACAGATGCTAATTGGCAAAAATTTAAGAATGGAGAAACTTCAATCGAAAAAATGGGAGCAG

CACGAGTTAATGCCATGCTCAACTGCCTATTCGAAGATTTTGAGCTTGCTATGATTGGCAAGGCTCAAATTAATTATTACA

ATGATAACTCACTTAAAATGAACATGCCATTTTACGCTTACTATGATATGTTCAAAAAACAACAGCTTCTAAAATGGCTTA

AAGATCACCATGATGACATCATCGGAGGAGCTGGCAGAATGTACACATCAACCGGTAGTTACATTGCTAATGCTTATTTA

GAGGTAGCGTTAGAATCAAGCTCGCTTGGTGATGGTGAGTACATGTTGCAAATGCGTTTTAAAAATTATTCACGAAGTCA

AGAACCTATTCCGTCAGGTCGCAAAAACCGACTTGAGTGGATTGAAAACAATCTGGAAAATATTCGATAA

/anti-CRISPR protein encoded by SEQ ID NO: 61

SEQ ID NO: 62

MKINNDIKELILEYMSRYFKFENDFYKLPDIKFTDANWQKFKNGETSIEKMGAARVNAMLNCLFEDFELAMIGKAQINYYNDN

SLKMNMPFYAYYDMFKKQQLLKWLKDHHDDIIGGAGRMYTSTGSYIANAYLEVALESSSLGDGEYMLQMRFKNYSRSQEPIP

SGRKNRLEWIENNLENIR

/anti-CRISPR gene isolated from Bacteriophage 9874

SEQ ID NO: 63

ATGAAAATAAATGACGACATCAAAGAATTAATTTTAGAATATATGAGCCGTTACTTCAAATTCGAGAACGACTTCTACAA

ATTGCCTGACATCAAATTCACTGATGCCAACTGGCAAAAATTCAAAAATGGAGATACTTCCATCGAAGAAGATGGGGGCA

GCACGAGTAAATGCCATGCTTGACTGCCTATTCGAAGATTTCGAACTTGCCATGATTGGCAAGGCTCAACAAGAATACTA

TTTGGATAATTCACTAAAGATGAACATGCCATTTTACGCTTATTATGATATGTTCAAGAAAAAACAGCTCGTCAAATGGCT

TAAAGATCACCATGATGACATCCTAGGCGGAACTGGTAGGATGTACACTTCAGACGGTAGTTACATTGCTAACTCTTATT

TAGAGGTAGCGTTAGAATCTAGCCGTCTGGGTAGTGGCTCTTACATGCTTCAAATGAGATTCAAAGACTATTCAAGAAGT

CAAGAACCCATTCCGTCAGGTCGCAAAAACCGACTTGAGTGGATTGAAAACAATCTGGAAAATATTCGATAA

/anti-CRISPR protein encoded by SEQ ID NO: 63

SEQ ID NO: 64

MKINDDIKELILEYMSRYFKFENDFYKLPDIKFTDANWQKFKNGDTSIEKMGAARVNAMLDCLFEDFELAMIGKAQQEYYLDN

SLKMNMPFYAYYDMFKKQLVKWLKDHHDDILGGTGRMYTSDGSYIANSYLEVALESSRLGSGSYMLQMRFKDYSRSQEPIP

SGRKNRLEWIENNLENIR

/anti-CRISPR gene isolated from Bacteriophage 5093

SEQ ID NO: 65

ATGGAAATCAACAACGATATCAAAGAGTTAATTTTGGAATACGTGAAAAGATACTTCAAGTTCGAGAACGACTTCTACAA

ATTGCCTGACATCAAATTCACTGATGCCAACTGGCAGAAGTTCAAAAATGGCGAAACAGCCATTGAGAAGATGGGGGCA

GCACGAGTAAACGCAATGCTCGACTGCCTATTCGAAGATTTTGAGCTTGCCATGATTGGCAAGGCTCAAACTAATTATTA

TATTGATAACTCGCTTAAATTAAACATGCCATTTTATGCTTACTATGATATGTTTAAGAAACAACAGCTCGTCAAATGGCTT

GAAACTAGTCGTGAAGACATCATCGGAGGGGCTGGCAGAATGTACACTTCAGACGGTAGTTACATTGCTAACGCTTATTT

AGAAGTAGCGTTAGAATCAAGCTCGCTTGGTGATAGTGAATACATGTTGCAAATGCGTTTTAAAAATTATTCAAAAAGTC

AAGAACCTATTCCGTCTGGTCGTCAAAATAGACTGGAATGGATTGAAAACAATCTTAAAAACATTCGATAA

/anti-CRISPR protein encoded by SEQ ID NO: 65

SEQ ID NO: 66

MEINNDIKELILEYVKRYFKFENDFYKLPDIKFTDANWQKFKNGETAIEKMGAARVNAMLDCLFEDFELAMIGKAQTNYYIDNS

LKLNMPFYAYYDMFKKQQLVKWLETSREDIIGGAGRMYTSDGSYIANAYLEVALESSSLGDSEYMLQMRFKNYSKSQEPIPSG

RQNRLEWIENNLKNIR

/anti-CRISPR gene isolated from Bacteriophage D4154

SEQ ID NO: 67

ATGCTAATAAATAACGACATCAAAGAGTTGATTTTGGAATACGTCAAACGCTATTTTAAATATGAAAATGACTTCTACAG

ATTGCCGGGCATCAAGTTTACCGATGCAAATTGGCAGAAGTTTAAAAATGGCGACACTTCCATCGAAGAATGGGGGCA

GCACGAGTAAACGCCATGCTCGACTGCCTATTCGAAGATTTTGAGCTTGCCATGATTGGTAAGGCTCAAACCAATTATTA

TATCAATAATTCATTGAAAATGAATATGCCGTTTTACGCTTACTATGATATGTTCAAGAAGGAACAGCTTATGAAATGGCT

TGAAACCAGCCGTGAAGACATCATAGGCGGAACTGGCAGGATGTACACTTCAGACGGTAGTTACATTGCTAACGCTTAT

TTGGAAATTGCATTAGAATCGAGCTCGCTTGGTAGTGGCTCTTACATGCTTCAAATGCGTTTTAAAGATTATTCAAAAGGT

CAAGAGCCTATCCCGTCTGGTCGTCAAAACCGACTTGAGTGGATTGAAAACAATCTTGAAAACATTCGATAA

/anti-CRISPR protein encoded by SEQ ID NO: 67

SEQ ID NO: 68

MLINNDIKELILEYVKRYFKYENDFYRLPGIKFTDANWQKFKNGDTSIEKMGAARVNAMLDCLFEDFELAMIGKAQTNYYINN

SLKMNMPFYAYYDMFKKEQLMKWLETSREDIIGGTGRMYTSDGSYIANAYLEIALESSSLGSGSYMLQMRFKDYSKGQEPIPS

GRQNRLEWIENNLENIR

/anti-CRISPR gene isolated from the genome of *Streptococcus thermophilus* DGCC11758

SEQ ID NO: 69

ATGCTAATAAATAACGACATCAAAGAGTTGATTTTGGAATACGTCAAACGCTATTTTAAATTTGAAAATGACTTCTACAGA

TTGCCGGGCATCAAGTTTACCGATGCAAATTGGCAGAAGTTTAAAAATGGCGACACTGCCATTGAGAAGATGGGGGCAT

CACGAGTAAACTCTATGCTTGACTGCCTGTTCGAAGATTTTGAGCTTGCTATGATTGGCAAGGCTCAAGATGAATACTATT

TGGATAATTCACTAAAGATGAACATGCCATTTTACGCTTATTATGATATGTTCAAGAAAAAACAGCTCGTCAAATGGCTTA

AAGATCACCATGATGACATCCTAGGCGGAACTGGTAGGATGTATACTTCAAGCGGCAATTACATTGCTAACGCTTATTTA

GAGGTAGCGTTAGAATCAAGCTCGCTTGGTAGTGGCTCTTACATGATTCAAATGCGTTTTAAAAATTATTCAAAAGGTCA

AGAGCCTATCCCGTCTGGTCGTCAAAACCGACTTGAGTGGATTGAAAAAAACTTGGAGAACATTCGATAA

/anti-CRISPR protein encoded by SEQ ID NO: 69

SEQ ID NO: 70

MLINNDIKELILEYVKRYFKFENDFYRLPGIKFTDANWQKFKNGDTAIEKMGASRVNSMLDCLFEDFELAMIGKAQDEYYLDNS

LKMNMPFYAYYDMFKKKQLVKWLKDHHDDILGGTGRMYTSSGNYIANAYLEVALESSSLGSGSYMIQMRFKNYSKGQEPIPS

GRQNRLEWIEKNLENIR

/anti-CRISPR gene isolated from the genome of *Streptococcus thermophilus* DSM 20617

SEQ ID NO: 71

ATGGAAATCAACAACGATATTAAACAACTGATCTTGGAATACGCTAAACGTTATTTCAAGTTTGAGAACGACTTTTATAAA

CTGCCAGGCATCAAGTTCACTGATGCAAATTGGCAGAAGTTCAAAAATGGAGGCACTGCCATTGAGAAGATGGGGGCA

GCACGAGTAAACGCCATGCTCGACTGCCTATTCGAAGATTTCGAGCTTGCAATGATTGGCAAGGCTCAACAAGAATACTA

TTCGGATAATTCCTTGAAAGTAAATATGGCATTCTATGCTTATTACGATCAATTCAAAAAACAACAGCTTATGAAATGGCT

TAAAGATAATCACGATGACATCATAGGAGGGACTGGTAGAATGTACACGTCAAGCGGTAGTTACATTGCTAACGCTTATT

TAGAAATTGCGTTAGAATCTAGCCGTCTGGGTGGTGGTTCTTACATGATCCAAATGAGGTTTAAAGACTATTCAAAAGGT

CAAGAACCTATTCCGTCTGGTCGTCAGAATCGACTTGAATGGATTGAGAGCAACTTGGAAAACATTCGATAA

/anti-CRISPR protein encoded by SEQ ID NO: 71

SEQ ID NO: 72

MEINNDIKQLILEYAKRYFKFENDFYKLPGIKFTDANWQKFKNGGTAIEKMGAARVNAMLDCLFEDFELAMIGKAQQEYYSD

NSLKVNMAFYAYYDQFKKQQLMKWLKDNHDDIIGGTGRMYTSSGSYIANAYLEIALESSRLGGGSYMIQMRFKDYSKGQEPI

PSGRQNRLEWIESNLENIR

/anti-CRISPR gene isolated from Bacteriophage Sfi19

SEQ ID NO: 73

ATGGAAATCAACAACGACATTAAACAACTGATCTTGGAATACGTGGACGCTATTTTAAATTTGAAAATGACTTCTACAA

ATTGCCCGGCATCAAATTCACTGATGCCAATTGGCAGAAGTTCAAAAATGGCGATACTTCCATCGAAAAGATGGGAGCA

GCACGAGTAAACGCAATGCTTGACTGCCTGTTCGAAGATTTCGAACTTGCCATGATTGGCAAGGCTCAAACTAATTATTA

TATTGATAATTCCCTTAAATTAAACATGCCATTTTACGCTTATTATGATATGTTCAAGAAGGAACAGCTTATGAAATGGCTT

AAAGATCACCATGATGACATCATAGGCGGAACTGGTAGGATGTATACATTTCAAGCGGTAGCTACATTGCTAACGCTTATTT

GGAAATTGCACTAGAATCAAGTACGCTTGGTGGTGGTGAGTACATGTTGCAAATGCGCTTTAAAAATTATTCACGAAGCC

AAGAACCTATTCCATCAGGTCGCAAAAATAGACTTGAATGGATTGAAAACAATCTTGAAAACATTCGATAA

/anti-CRISPR protein encoded by SEQ ID NO: 73
SEQ ID NO: 74
MEINNDIKQLILEYVGRYFKFENDFYKLPGIKFTDANWQKFKNGDTSIEKMGAARVNAMLDCLFEDFELAMIGKAQTNYYIDN SLKLNMPFYAYYDMFKKEQLMKWLKDHHDDIIGGTGRMYISSGSYIANAYLEIALESSTLGGGEYMLQMRFKNYSRSQEPIPS

GRKNRLEWIENNLENIR

/anti-CRISPR gene isolated from Bacteriophage Sfi11
SEQ ID NO: 75
ATGGAAATCAACAACGACATTAAACAACTGATCTTGGAATACGTGGGACGCTATTTTAAATTTGAAAATGACTTCTACAA

ATTGCCCGGCATCAAATTCACTGATGCCAATTGGCAGAAGTTCAAAAATGGCGATACTTCCATCGAAAGATGGGAGCA

GCACGAGTAAACGCAATGCTTGACTGCCTGTTCGAAGATTTCGAACTTGCCATGATTGGCAAGGCTCAAACTAATTATTA

TATTGATAATTCCCTTAAATTAAACATGCCATTTTACGCTTATTATGATATGTTCAAGAAGGAACAGCTTATGAAATGGCTT

AAAGATCACCATGATGACATCATAGGCGGAACTGGTAGGATGTACACTTCAAGCGGTAGCTACATTGCTAACGCTTATTT

GGAAATTGCACTAGAATCAAGTACGCTTGGTGGTGGTGAGTACATGTTGCAAATGCGCTTTAAAAATTATTCACGAAGCC

AAGAACCTATTCCATCAGGTCGCAAAAATAGACTTGAATGGATTGAAAACAATCTTGAAAACATTCGATAA

/anti-CRISPR protein encoded by SEQ ID NO: 75
SEQ ID NO: 76
MEINNDIKQLILEYVGRYFKFENDFYKLPGIKFTDANWQKFKNGDTSIEKMGAARVNAMLDCLFEDFELAMIGKAQTNYYIDN SLKLNMPFYAYYDMFKKEQLMKWLKDHHDDIIGGTGRMYTSSGSYIANAYLEIALESSTLGGGEYMLQMRFKNYSRSQEPIPS

GRKNRLEWIENNLENIR

/anti-CRISPR gene isolated from the genome of *Streptococcus thermophilus* M17PTZA496
SEQ ID NO: 77
ATGGAAATCAACAAAGACATCAAAGAGTTGATTTTGGAATACGTCAAACGCTATTTTAAATTTGAAAATGATTTCTACAG

ATTGCCGGGCATCAAGTTTACCGATGCCAACTGGCAAAAATTCAAGAATGGAGATACTTCCATCGAGAAGATGGGGGCA

GCACGAGTAAACGCCATGCTTGACTGCCTGTTCGAAGATTTCGAACTTGCTATGATTGGCAAGGCTCAAGATGAATACTA

TTTGGATAATTCACTTAAGTTTAATATGGCATTCCATACTTATTACGATCAATTTAAAAAACAACAGCTTATGAAATGGCTT

GAAACTAGCCTCGAAGACATCATAGGCGGAACTGGTAGGATGTACACTTCAAGCGGTAGTTACATTGCTAACGCTTATTT

GGAAATTGCACTAGAATCAAGCTCGCTTGGTGGTGGTGAGTACATGTTGCAAATGCGTTTTAAAAATTATTCACGAAGCC

AAGAACCTATTCCGTCAGGTCGCAAAAACCGACTTGAGTGGATTGAAAACAATCTGGAAAATATCCGATAA

/anti-CRISPR protein encoded by SEQ ID NO: 77
SEQ ID NO: 78
MEINKDIKELILEYVKRYFKFENDFYRLPGIKFTDANWQKFKNGDTSIEKMGAARVNAMLDCLFEDFELAMIGKAQDEYYLDN SLKFNMAFHTYYDQFKKQQLMKWLETSLEDIIGGTGRMYTSSGSYIANAYLEIALESSSLGGGEYMLQMRFKNYSRSQEPIPSG

RKNRLEWIENNLENIR

/anti-CRISPR gene isolated from Bacteriophage D4769
SEQ ID NO: 79
ATGAAAATCAATAATGACATCAAAGAGCTAATTTTGGAATATGTAAGTCGCTATTTTAAATTTGAAAACGACTTCTACAAA

TTACCTGGCATCAAATTCACTGATGCCAACTGGCAAAAATTCAAGAATGGAGATACTTCCATCGAGAAGATGGGGGCAG

CACGAGTAAACGCCATGCTTGACTGCCTGTTCGAAGATTTCGAACTTGCTATGATTGGCAAGGCTCAAGATGAATACTAT

TTTGGATAATTCACTTAAGTTTAATATGGCATTCCATACTTATTACGATCAATTTAAAAAACAACAGCTTATGAAATGGCTT

GAAACTAGCCTCGAAGACATCATAGGCGGAACTGGTAGGATGTACACTTCAAGCGGTAGTTACATTGCTAACGCTTATTT

GGAAATTGCACTAGAATCAAGCTCGCTTGGTGGTGGTGAGTACATGTTGCAAATGCGTTTTAAAAATTATTCACGAAGCC

AAGAACCTATTCCGTCAGGTCGCAAAAACCGACTTGAGTGGATTGAAAACAATCTGGAAAATATCCGATAA

/anti-CRISPR protein encoded by SEQ ID NO: 79
SEQ ID NO: 80
MKINNDIKELILEYVSRYFKFENDFYKLPGIKFTDANWQKFKNGDTSIEKMGAARVNAMLDCLFEDFELAMIGKAQDEYYLDN SLKFNMAFHTYYDQFKKQQLMKWLETSLEDIIGGTGRMYTSSGSYIANAYLEIALESSSLGGGEYMLQMRFKNYSRSQEPIPSG

RKNRLEWIENNLENIR

-continued

/anti-CRISPR gene isolated from Bacteriophage D5691

SEQ ID NO: 81

ATGATTATAAATATTGATATCAAGGAATTGATTTTAGAGTATATGAGTAGATACTTCAAATTTGAAAATGATTTCTACAAA

CTCCCCGGCATCAAATTCACTGATGCCAATTGGCAAAAATTTAAGAATGGTGACACTTCCATCGAAAAGATGGGAGCGG

CTCGAGTAAATGCCATGCTCGACTGTCTATTCGATGACTTTGAACTTGCTATGATTGGCAAGGCTCAAATTAATTATTACA

TAGACAATTCCCTTAAATTGAACATGCCATTCTATGCTTATTATGACATGTTCAAAAAACAACAACTGATCAAATGGATTG

AAACCAGCCGTGATGATGTCATCGGAGGAACTGGCAGGATGTATACAGCAAGCGGAAGCTACATAGCTAACGCTTATCT

AGAAATAGCACTAGAATCTAGCTCTCTGGGTGGTGGCTCTTATATGCTTCAAATGAGATTCAAAAACTACTCACGAAGCC

AAGAGCCAATACCATCTGGTCGGAAAAACCGACTTGAGTGGATTGAGAGCAACTTGGAAAACATTAGATAA

/anti-CRISPR protein encoded by SEQ ID NO: 81

SEQ ID NO: 82

MIINIDIKELILEYMSRYFKFENDFYKLPGIKFTDANWQKFKNGDTSIEKMGAARVNAMLDCLFDDFELAMIGKAQINYYIDNSL

KLNMPFYAYYDMFKKQQLIKWIETSRDDVIGGTGRMYTASGSYIANAYLEIALESSSLGGGSYMLQMRFKNYSRSQEPIPSGR

KNRLEWIESNLENIR

/anti-CRISPR gene isolated from the genome of Streptococcus sp. HMSC10E12

SEQ ID NO: 83

ATGGAAATCAACAATGACATCAAAGAGTTAATCTTGGAATACGTGGGACGCTATTTCAAGTTTGAAAATGATTTTTACAA

ATTGCCGGGCATCAAATTTACCGATGCAAATTGGCAAAAATTCAAAAACGGTGATACATCCATCGAGAAAATGGGGGCG

GCACGAGTAAACGCAATGCTCGACTGCCTATTCGATGATTTCGAGCTTGCTATGATTGGCAAGGCTCAAACTGATTATTA

CATTGATAACTCACTTAAATTGAACATGCCATTTTATGCTTATTATGACATGTTCAAAAAACAACAGCTTCTAAAATGGATT

GAGAATAGTCGTGAAGACATCATCGGAGGGGCTGGCAGAATGTACACAGCGGGCGGTAATTGGATTTCTAGCGCTTATT

TAGAGATCGCATTAGAATCTAGTTCCATCGGTGGCGGTGGCTATATGCTTCAAATGCGGTTCAAAAACTACTCAAGAGAC

CCTAGACCGATTCCAGCAGGCCACCAAAATCGTCTCGAATGGATTGAAAACAACTTGGAGAATATCCGATAA

/anti-CRISPR protein encoded by SEQ ID NO: 83

SEQ ID NO: 84

MEINNDIKELILEYVGRYFKFENDFYKLPGIKFTDANWQKFKNGDTSIEKMGAARVNAMLDCLFDDFELAMIGKAQTDYYIDN

SLKLNMPFYAYYDMFKKQQLLKWIENSREDIIGGAGRMYTAGGNWISSAYLEIALESSSIGGGGYMLQMRFKNYSRDPRPIPA

GHQNRLEWIENNLENIR

/anti-CRISPR gene isolated from the genome of Streptococcus sp. HSISS2

SEQ ID NO: 85

ATGGAAATCAACAATGACATCAAGGACCTAATTTTAGAATACGTAGGACGATATTTTCGATTTGAAAACGACTTCTACAA

ACTTCCCAGAATCAAGTTTACCGATTCCAATTGGCAAAAATTCAAGAACGGTGACACTTCCATCGAAAAAATGGGAGCTG

GCAGAGTGAACGCAATGCTCGATTGTCTATTTGATGATTTTGAGCTTGCTATGATTGGTAAGGCTCAAACCGATTACTAC

ATGGACAATTCTTTAAAGATGAATATGCCATTTTATGCCTATTATGACCAATTTAAGAAACAGCAACTATTGAAATGGATC

GAGAATAGTAGAGAGGATATCATAGGCGGTGCTGGCAGAATGTACACAGCTAGTGGGAATTGGATTTCTAGTGCCTATT

TAGAAATTGCATTGGAATCCAGCTCGTTAGGTGGTGGTGAGTACATGTTGCAAATGCGTTTCAAAGACTACTCACGAAGC

CAAGAGCCGATACCAGCAGGCCGCCAGAATCGACTTGAGTGGATTGAGAATAATTTGGAGAATATTCGATAA

/anti-CRISPR protein encoded by SEQ ID NO: 85

SEQ ID NO: 86

MEINNDIKDLILEYVGRYFRFENDFYKLPRIKFTDSNWQKFKNGDTSIEKMGAGRVNAMLDCLFDDFELAMIGKAQTDYYMD

NSLKMNMPFYAYYDQFKKQQLLKWIENSREDIIGGAGRMYTASGNWISSAYLEIALESSSLGGGEYMLQMRFKDYSRSQEPIP

AGRQNRLEWIENNLENIR

DETAILED DESCRIPTION

CRISPR-Cas Systems, Organization, Activity and Classification

CRISPR-Cas systems are encoded by CRISPR-cas loci. "CRISPR-cas loci" means a DNA segment, located in the bacterial genome, which includes a CRISPR locus and one or more cas genes. CRISPR is an acronym for "clustered regularly interspaced short palindromic repeats".

The term "CRISPR locus" as used herein means a DNA segment, which includes a CRISPR array as well as a leader sequence. CRISPR loci typically consist of several noncontiguous, direct, and highly conserved DNA repeats (CRISPR repeats) that are separated by stretches of unique, nonrepetitive, and similarly-sized sequences (CRISPR spacers). CRISPR repeats and CRISPR spacers form together a CRISPR array.

As used herein, the term "CRISPR array" refers to the DNA segment which includes all of the CRISPR repeats and spacers of a CRISPR locus, starting with the first nucleotide of the first CRISPR repeat and ending with the last nucleotide of the last (terminal) CRISPR repeat. Typically, each spacer sequence in a CRISPR array is located between two repeats and consequently, a CRISPR array locus includes one more repeat than spacer sequences. In other words, a CRISPR array comprises one or more [repeat-spacer] units (i.e., a CRISPR spacer sequence associated with a repeat sequence), followed by a terminal repeat.

As used herein, the terms "CRISPR repeat," "repeat sequence," or "repeat" have the conventional meaning as used in the art—i.e., multiple, short, direct repeating sequences, which show little or no sequence variation within a given CRISPR array. Many repeat sequences are partially palindromic, having the potential to form stable, conserved secondary structures.

As used herein, "CRISPR spacer", "spacer sequence," or "spacer" refer to the nonrepetitive sequences that are located between two repeats in a CRISPR array. As used herein, "protospacer" refers to the sequence within the target nucleic acid which corresponds to a given CRISPR spacer. Protospacer acquisition in many CRISPR-Cas systems requires recognition of a short protospacer adjacent motif (PAM) in the target nucleic acid. These motifs are located in the direct vicinity of the protospacer (typically less than 10 nucleotides outside of the sequence) and appear to be specific to each CRISPR-Cas system.

As used herein, a "CRISPR leader," "leader sequence," or "leader" refers to a low-complexity, A/T-rich, noncoding sequence of up to several hundred base pairs that is located on one side of the repeat-spacer array, immediately upstream of the first repeat.

As used herein, the term "cas gene" (for CRISPR-associated) has its conventional meaning as used in the art where it refers to a gene that is coupled to, associated with, close to, or in the vicinity of a CRISPR array. The expression "cas gene" includes, but is not limited to, cas, csn, csm and cmr genes, depending upon the type of CRISPR-Cas system. Thus, the person skilled in the art can easily identify based on conventional protein comparison bioinformatics tools (such as BLAST), whether a gene associated with a CRISPR locus encodes a Cas protein characteristic of any CRISPR-Cas system. The expression "Cas protein" encompasses Cas, Csn, Csm and Cmr proteins, depending upon the type of CRISPR-Cas system.

CRISPR-Cas system activity, including the activity providing immunity against target nucleic acids, involves two distinct functions: the adaptation function and the interference function. As used herein, "adaptation function" refers to the stage by which a fragment of a target nucleic acid (protospacer) is incorporated into the CRISPR array as a new spacer, in the form of a new repeat-spacer unit. As used herein, "interference function" refers to the stage by which the CRISPR array is transcribed as a precursor transcript (pre-crRNA), the pre-crRNA being possibly processed and matured to produce CRISPR RNAs (crRNAs), and whereby the crRNAs together with Cas protein(s) specifically target and cleave the target nucleic acids.

The adaptation function of a CRISPR-Cas system can be assayed by exposing to a virulent phage a bacterial strain comprising said CRISPR-Cas system (said bacterial being sensitive to said virulent phage), selecting bacteriophage-resistant strains (i.e., strains which are resistant to this phage), and checking whether this resistance is conferred by the addition—in the CRISPR array of said CRISPR-Cas system—of at least one repeat-spacer unit.

The interference function of a CRISPR-Cas system can be assayed by exposing a bacterial strain comprising said CRISPR-Cas system to a virulent phage (the CRISPR array of said CRISPR-Cas system comprising a spacer corresponding to a protospacer found in the genome of said virulent phage), and measuring the phage titer. A phage titer which is significantly reduced (i.e., a reduction of at least 2 Log or at least 99%) as compared to the same exposure with a bacterial strain not comprising in its CRISPR array said spacer is indicative of a functional interference function. In contrast, a phage titer, which is not significantly reduced is indicative of an interference function which is decreased or is inhibited.

The classification used herein—for the distinction between class 1 type CRISPR-Cas systems and class 2 CRISPR-Cas systems—is the one described in Makarova et al. 2015 (on the basis of the genes encoding the effector molecules). Thus, as defined herein "class 1 type CRISPR-Cas systems" refer to CRISPR-Cas systems possessing multisubunit crRNA—effector complexes. In contrast, "class 2 type CRISPR-Cas systems" as defined herein refer to CRISPR-Cas systems functioning with a single protein as effector complex (such as Cas9).

The classification used here—for the distinction between the different CRISPR-Cas system types within the class 2 CRISPR-Cas systems—is the one described in Schmakov et al. 2017. As defined herein, "class 2 type II CRISPR-Cas system" refers to CRISPR-Cas systems comprising the cas9 gene among its cas genes. As defined herein, "class 2 type II-A CRISPR-Cas system" refers to CRISPR-Cas systems comprising cas9 and csn2 genes. As defined herein, "class 2 type II-B CRISPR-Cas system" refers to CRISPR-Cas systems comprising the cas9 and cas4 genes. As defined herein, "class 2 type II-C CRISPR-Cas system" refers to CRISPR-Cas systems comprising the cas9 gene but neither the csn2 nor the cas4 gene. As defined herein, "class 2 type V CRISPR-Cas system" refers to CRISPR-Cas systems comprising the cas12 gene (cas12a, 12b or 12c gene) in its cas genes. As defined herein, "class 2 type VI CRISPR-Cas system" refers to CRISPR-Cas systems comprising the cas13 gene (cas13a, 13b or 13c gene) in its cas genes.

In *Streptococcus thermophilus*, although CRISPR1 and CRISPR3 belong to class 2 type II-A systems, they are significantly different in terms of sequence including Cas9 sequence. For the distinction of CRISPR1 and CRISPR3, reference is made herein to the publication of Chylinski et al. 2014, where the CRISPR1-Cas system is represented by the Cas9 sequence of LMD-9 116628213, and the CRISPR3-Cas system is represented by the Cas9 sequence of LMD-9 116627542.

Anti-CRISPR Proteins

The invention is directed to proteins, which interfere with a function of a bacterial CRISPR-Cas system involved in the immunity of a bacterial strain against target nucleic acids and their uses in various methods. Such proteins are called herein "anti-CRISPR proteins".

By "interfere with a function of a bacterial CRISPR-Cas system", it is meant that the anti-CRISPR protein as defined herein significantly downmodulates the activity of the CRISPR-Cas system, i.e., decreases, from partial to complete inhibition, the activity of the CRISPR-Cas system. Such downmodulation can be assayed by providing a bacterial strain which is resistant to a given virulent phage, said resistance being mediated by a given CRISPR-Cas system (i.e., the CRISPR array of said given CRISPR-Cas system comprises a spacer corresponding to a protospacer found in the genome of the virulent phage); producing in said bacterial strain an anti-CRISPR protein (interfering with a function of a bacterial CRISPR-Cas system); and exposing said bacterial strain to said given virulent phage, wherein an increase of the titer of said virulent phage by more than 1 Log (i.e. more than 90%) is recorded as compared to a control. In the assay above, the control is the same bacterial strain—but not producing said anti-CRISPR protein—and exposed to the same virulent phage in the same conditions. In an embodiment, the increase in the titer of said virulent phage is more than 95% as compared to a control. In an embodiment, the increase in the titer of said virulent phage is more than 98% as compared to a control. In an embodiment, the increase of the titer of said virulent phage is more than 2 Log (more than 99%) as compared to a control. In an embodiment, the increase in the titer of said virulent phage is more than 3 Log as compared to a control. In an embodiment, the increase in the titer of said virulent phage is more than 4 Log as compared to a control.

As used herein, the term "virulent phage" is synonymous to "infectious phage", and includes both lytic and temperate phages.

As used herein, "exposing a bacterial strain to a phage" means that bacterial cells and phage particles are physically mixed together (e.g., in the same medium) in conditions such that the phage particles are in contact with the bacterial cells.

By "a function of a bacterial CRISPR-Cas system", it is meant "at least one function" of a CRISPR-Cas system, such as for example the adaptation function or the interference function. In an embodiment, the anti-CRISPR protein used herein interferes with the interference function of a CRISPR-Cas system. In an embodiment, the anti-CRISPR protein used herein interferes with the adaptation function of a CRISPR-Cas system. In an embodiment, the anti-CRISPR protein used herein interferes with both the adaptation function and the interference function of a CRISPR-Cas system.

In an embodiment, the anti-CRISPR protein as used herein interferes with a function, in particular with the adaptation function and/or the interference function, of a class 2 CRISPR-Cas system. In an embodiment, the anti-CRISPR protein as defined herein interferes with a function, in particular with the adaptation function and/or the interference function, of a class 2 type II CRISPR-Cas system. In an embodiment, the anti-CRISPR protein as used herein interferes with a function, in particular with the adaptation function and/or the interference function, of a class 2 type II-A CRISPR-Cas system.

In an embodiment, and optionally in combination with any interferred function of the CRISPR-Cas system defined above, said anti-CRISPR protein interferes with a function of a class 2 type II, in particular a class 2 type II-A CRISPR-Cas system, of a Gram-positive bacterial strain. In an embodiment, said anti-CRISPR protein interferes with a function of a class 2 type II, in particular a class 2 type II-A CRISPR-Cas system, of a lactic acid bacterial strain. In an embodiment, said anti-CRISPR protein interferes with a function of a class 2 type II, in particular a class 2 type II-A CRISPR-Cas system, of a *Streptococcus* species strain. In an embodiment, said anti-CRISPR protein interferes with a function of a class 2 type II, in particular a class 2 type II-A CRISPR-Cas system, of a *Streptococcus thermophilus* strain. In an embodiment, said anti-CRISPR protein interferes with a function of a CRISPR1-Cas system of a *Streptococcus thermophilus*. In an embodiment, said anti-CRISPR protein interferes with a function of a CRISPR3-Cas system of a *Streptococcus thermophilus* strain. In an embodiment, said anti-CRISPR protein interferes with a function of a class 2 type II, in particular a class 2 type II-A CRISPR-Cas system, of a *Streptococcus pyogenes* strain. In an embodiment, said anti-CRISPR protein interferes with a function of a class 2 type II, in particular a class 2 type II-A CRISPR-Cas system, of a *Staphylococcus* species strain. In an embodiment, said anti-CRISPR protein interferes with a function of a class 2 type II, in particular a class 2 type II-A CRISPR-Cas system, of a *Staphylococcus aureus* strain.

As discussed herein, the Cas9 protein is the effector molecule found in the class 2 type II CRISPR-Cas systems. Cas9 has been shown to act not only in the interference function but also in the adaptation function of the CRISPR-Cas system, for the immunity against target nucleic acids. In an embodiment, said anti-CRISPR protein as used herein downmodulates the activity of a Cas9 protein or Cas9 derivatives. As defined herein "downmodulating the activity of a Cas9 protein", means that said anti-CRISPR protein decreases, from partial to complete inhibition, at least one of the interference activity of the Cas9 protein or the adaptation activity of the Cas9 protein. In an embodiment, the anti-CRISPR protein downmodulates the adaptation activity of the Cas9 protein. In an embodiment, the anti-CRISPR protein downmodulates the interference activity of the Cas9 protein. In an embodiment, the anti-CRISPR protein downmodulates the adaptation activity and the interference activity of the Cas9 protein.

Cas9 has been shown to display several activities on the target nucleic acid: (1) the adaptation-based activity of Cas9, (2) the RuvC-based nuclease activity of Cas9, (3) the HNH-based nuclease activity of Cas9, (4) the REC1-based recognition activity of Cas9, and (5) the REC2-based recognition activity of Cas9. Thus, in an embodiment, the anti-CRISPR protein downmodulates at least one, in particular one, of the following activities of the Cas9 protein: (1) the adaptation-based activity of Cas9, (2) the RuvC-based nuclease activity of Cas9, (3) the HNH-based nuclease activity of Cas9, (4) the REC1-based recognition activity of Cas9, and (5) the REC2-based recognition activity of Cas9. In an embodiment, the anti-CRISPR protein downmodulates the adaptation-based activity of Cas9 protein. In an embodiment, the anti-CRISPR protein downmodulates the RuvC-based nuclease activity of Cas9 protein. In an embodiment, the anti-CRISPR protein downmodulates the HNH-based nuclease activity of Cas9 protein. In an embodiment, the anti-CRISPR protein downmodulates the REC1-based recognition activity of Cas9 protein. In an embodiment, the anti-CRISPR protein downmodulates the REC2-based recognition activity of Cas9 protein.

In an embodiment, and optionally in combination with any downmodulated subactivities of the Cas9 protein defined above, said anti-CRISPR protein downmodulates the activity of a Cas9 protein of a Gram-positive bacterial strain. In an embodiment, said anti-CRISPR protein downmodulates the activity of a Cas9 protein of a lactic acid bacterial strain. In an embodiment, said anti-CRISPR protein downmodulates the activity of a Cas9 protein of a *Streptococcus* species strain. In an embodiment, said anti-CRISPR protein downmodulates the activity of a Cas9 protein of a *Streptococcus thermophilus* strain. In an embodiment, said anti-CRISPR protein downmodulates the activity of the Cas9 protein of a CRISPR1-Cas system of a *Streptococcus thermophilus*. In an embodiment, said anti- CRISPR protein downmodulates the activity of the Cas9 protein of a CRISPR3-Cas system of a *Streptococcus thermophilus*. In an embodiment, said anti-CRISPR protein downmodulates the activity of a Cas9 protein of a *Streptococcus pyogenes* strain. In an embodiment, said anti-CRISPR protein downmodulates the activity of a Cas9 protein of a *Staphylococcus* species strain. In an embodiment, said anti-CRISPR protein downmodulates the activity of a Cas9 protein of a *Staphylococcus aureus* strain.

The downmodulation of the activity of a Cas9 protein (including its several activities described herein) can be assayed by providing a bacterial strain which is resistant to a given virulent phage, said resistance being mediated by a given class 2 type II CRISPR-Cas system (i.e., the CRISPR array of said given class 2 type II CRISPR-Cas system comprises a spacer corresponding to a protospacer found in the genome of the virulent phage); producing in said bacterial strain an anti-CRISPR protein (interfering with a function of a bacterial CRISPR-Cas system); and exposing said bacterial strain to said given virulent phage, wherein an increase of the titer of said virulent phage by more than 1 Log (i.e. more than 90%) is recorded as compared to a control. In the assay above, the control is the same bacterial strain—but not producing said anti-CRISPR protein—and exposed to the same virulent phage in the same conditions. In an embodiment, the increase in the titer of said virulent phage is more than 95% as compared to a control. In an embodiment, the increase in the titer of said virulent phage is more than 98% as compared to a control. In an embodiment, the increase of the titer of said virulent phage is more than 2 Log (more than 99%) as compared to a control. In an embodiment, the increase in the titer of said virulent phage is more than 3 Log as compared to a control. In an embodiment, the increase in the titer of said virulent phage is more than 4 Log as compared to a control.

By "Cas9 derivatives", it is meant a Cas9, which is devoid of at least one of its activities, such as for example a Cas9 protein devoid of its nuclease activity (a nuclease-null Cas9, also known as "dCas9").

Some anti-CRISPR proteins, which have been shown to interfere with a function of a CRISPR-Cas system, in particular a class 2 type II CRISPR-Cas system, more particularly a class 2 type II-A CRISPR-Cas system, are described herein. These anti-CRISPR proteins as such are part of the invention, and can be used in the methods of the invention.

In an embodiment, the invention is directed to a protein, which has the sequence as defined in a SEQ ID NO of a Acr family selected from the group consisting of Acr1, Acr2, Acr3, Acr4, Acr5, Acr6, Acr7, Acr8, Acr9, Acr10, Acr11, Acr12, Acr13, Acr14, Acr15, Acr16, Acr17, Acr18, Acr19, Acr20, Acr21, Acr22, Acr23, Acr24, Acr25, Acr26, Acr27, Acr28, Acr29, Acr30, Acr31, Acr32, Acr33, Acr34, Acr35, Acr36, Acr37, Acr38, Acr39, Acr40, Acr41, Acr42, Acr43, Acr44, Acr45, Acr46, Acr47, Acr48, Acr49, Acr50, Acr51, Acr52, Acr53, Acr54, Acr55, Acr56, Acr57, Acr58, Acr59, Acr60, Acr61, Acr62, Acr63, Acr64, Acr65, Acr66, Acr67, Acr68, Acr69, Acr70, Acr71, Acr72, Acr73, Acr74, Acr75, Acr76, Acr77, Acr78, Acr79, Acr80, Acr81, Acr82, Acr83, Acr84, Acr85 and Acr86 families of Table 1 (i.e., selected from the group consisting of Acr1 to Acr86 families of Table 1).

TABLE 1

Acr families, and corresponding ACR genes and ACR proteins

| Acr family | SEQ ID of ACR gene | SEQ ID of ACR protein |
|---|---|---|
| Acr1 | SEQ ID NO: 1, 3, 5, 7, 9, 11, 13, 15, 17, 19, 21, 23, 25 | SEQ ID NO: 2, 4, 6, 8, 10, 12, 14, 16, 18, 20, 22, 24, 26 |
| Acr2 | SEQ ID NO: 27, 29, 31, 33, 35, 37, 39, 41, 43, 45, 47, 49, 51, 53, 55, 57, 59, 61, 63, 65, 67, 69, 71, 73, 75, 77, 79, 81, 83, 85 | 28, 30, 32, 34, 36, 38, 40, 42, 44, 46, 48, 50, 52, 54, 56, 58, 60, 62, 64, 66, 68, 70, 72, 74, 76, 78, 80, 82, 84, 86 |
| Acr3 | SEQ ID NO: 87, 89 | SEQ ID NO: 88, 90 |
| Acr4 | SEQ ID NO: 91, 93, 95, 97, 99, 101, 103, 105, 107, 109, 111, 113, 115, 117, 119 | SEQ ID NO: 92, 94, 96, 98, 100, 102, 104, 106, 108, 110, 112, 114, 116, 118, 120 |
| Acr5 | SEQ ID NO: 121, 123, 125, 127, 129, 131, 133 | SEQ ID NO: 122, 124, 126, 128, 130, 132, 134 |
| Acr 6 | SEQ ID NO: 135, 137, 139, 141 | SEQ ID NO: 136, 138, 140, 142 |
| Acr7 | SEQ ID NO: 143 | SEQ ID NO: 144 |
| Acr8 | SEQ ID NO: 145, 147, 149, 151, 153, 155, 157 | SEQ ID NO: 146, 148, 150, 152, 154, 156, 158 |
| Acr9 | SEQ ID NO: 159, 161, 163 | SEQ ID NO: 160, 162, 164 |
| Acr10 | SEQ ID NO: 165 | SEQ ID NO: 166 |
| Acr11 | SEQ ID NO: 167, 169 | SEQ ID NO: 168, 170 |
| Acr12 | SEQ ID NO: 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231 | SEQ ID NO: 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232 |
| Acr13 | SEQ ID NO: 233 | SEQ ID NO: 234 |
| Acr14 | SEQ ID NO: 235, 237, 239, 241, 243 | SEQ ID NO: 236, 238, 240, 242, 244 |
| Acr15 | SEQ ID NO: 245, 247, 249, 251, 253, 255, 257, 259 | SEQ ID NO: 246, 248, 250, 252, 254, 256, 258, 260 |
| Acr16 | SEQ ID NO: 261, 263, 265 | SEQ ID NO: 262, 264, 266 |
| Acr17 | SEQ ID NO: 267 | SEQ ID NO: 268 |
| Acr18 | SEQ ID NO: 269, 271 | SEQ ID NO: 270, 272 |
| Acr19 | SEQ ID NO: 273 | SEQ ID NO: 274 |
| Acr20 | SEQ ID NO: 275 | SEQ ID NO: 276 |
| Acr21 | SEQ ID NO: 277, 279 | SEQ ID NO: 278, 280 |
| Acr22 | SEQ ID NO: 281 | SEQ ID NO: 282 |
| Acr23 | SEQ ID NO: 283, 285, 287, 289, 291, 293, 295, 297, 299, 301, 303 | SEQ ID NO: 284, 286, 288, 290, 292, 294, 296, 298, 300, 302, 304 |

TABLE 1-continued

Acr families, and corresponding ACR genes and ACR proteins

| Acr family | SEQ ID of ACR gene | SEQ ID of ACR protein |
|---|---|---|
| Acr24 | SEQ ID NO: 305, 307, 309, 311, 313, 315, 317, 319, 321, 323 | SEQ ID NO: 306, 308, 310, 312, 314, 316, 318, 320, 322, 324 |
| Acr25 | SEQ ID NO: 325, 327, 329, 331, 333, 335 | SEQ ID NO: 326, 328, 330, 332, 334, 336 |
| Acr26 | SEQ ID NO: 337, 339, 341, 343 | SEQ ID NO: 338, 340, 342, 344 |
| Acr27 | SEQ ID NO: 345, 347, 349, 351, 353, 355 | SEQ ID NO: 346, 348, 350, 352, 354, 356 |
| Acr28 | SEQ ID NO: 357, 359, 361, 363, 365 | SEQ ID NO: 358, 360, 362, 364, 366 |
| Acr29 | SEQ ID NO: 367 | SEQ ID NO: 368 |
| Acr30 | SEQ ID NO: 369, 371 | SEQ ID NO: 370, 372 |
| Acr31 | SEQ ID NO: 373 | SEQ ID NO: 374 |
| Acr32 | SEQ ID NO: 375 | SEQ ID NO: 376 |
| Acr33 | SEQ ID NO: 377 | SEQ ID NO: 378 |
| Acr34 | SEQ ID NO: 379 | SEQ ID NO: 380 |
| Acr35 | SEQ ID NO: 381 | SEQ ID NO: 382 |
| Acr36 | SEQ ID NO: 383 | SEQ ID NO: 384 |
| Acr37 | SEQ ID NO: 385 | SEQ ID NO: 386 |
| Acr38 | SEQ ID NO: 387 | SEQ ID NO: 388 |
| Acr39 | SEQ ID NO: 389 | SEQ ID NO: 390 |
| Acr40 | SEQ ID NO: 391 | SEQ ID NO: 392 |
| Acr41 | SEQ ID NO: 393 | SEQ ID NO: 394 |
| Acr42 | SEQ ID NO: 395 | SEQ ID NO: 396 |
| Acr43 | SEQ ID NO: 397 | SEQ ID NO: 398 |
| Acr44 | SEQ ID NO: 399 | SEQ ID NO: 400 |
| Acr45 | SEQ ID NO: 401 | SEQ ID NO: 402 |
| Acr46 | SEQ ID NO: 403 | SEQ ID NO: 404 |
| Acr47 | SEQ ID NO: 405 | SEQ ID NO: 406 |
| Acr48 | SEQ ID NO: 407 | SEQ ID NO: 408 |
| Acr49 | SEQ ID NO: 409 | SEQ ID NO: 410 |
| Acr50 | SEQ ID NO: 411, 413 | SEQ ID NO: 412, 414 |
| Acr51 | SEQ ID NO: 415 | SEQ ID NO: 416 |
| Acr52 | SEQ ID NO: 417 | SEQ ID NO: 418 |
| Acr53 | SEQ ID NO: 419 | SEQ ID NO: 420 |
| Acr54 | SEQ ID NO: 421 | SEQ ID NO: 422 |
| Acr55 | SEQ ID NO: 423 | SEQ ID NO: 424 |
| Acr56 | SEQ ID NO: 425 | SEQ ID NO: 426 |
| Acr57 | SEQ ID NO: 427, 429 | SEQ ID NO: 428, 430 |
| Acr58 | SEQ ID NO: 431 | SEQ ID NO: 432 |
| Acr59 | SEQ ID NO: 433 | SEQ ID NO: 434 |
| Acr60 | SEQ ID NO: 435, 437 | SEQ ID NO: 436, 438 |
| Acr61 | SEQ ID NO: 439, 441 | SEQ ID NO: 440, 442 |
| Acr62 | SEQ ID NO: 443 | SEQ ID NO: 444 |
| Acr63 | SEQ ID NO: 445 | SEQ ID NO: 446 |
| Acr64 | SEQ ID NO: 447 | SEQ ID NO: 448 |
| Acr65 | SEQ ID NO: 449, 451, 453, 457, 459 | SEQ ID NO: 450, 452, 454, 456, 458 |
| Acr66 | SEQ ID NO: 459 | SEQ ID NO: 460 |
| Acr67 | SEQ ID NO: 461, 463, 465 | SEQ ID NO: 462, 464, 466 |
| Acr68 | SEQ ID NO: 467 | SEQ ID NO: 468 |
| Acr 69 | SEQ ID NO: 469 | SEQ ID NO: 470 |
| Acr70 | SEQ ID NO: 471, 473 | SEQ ID NO: 472, 474 |
| Acr71 | SEQ ID NO: 475 | SEQ ID NO: 476 |
| Acr72 | SEQ ID NO: 477, 479, 481, 483, 485, 487, 489 | SEQ ID NO: 478, 480, 482, 484, 486, 488, 490 |
| Acr73 | SEQ ID NO: 491, 493, 495, 497, 499, 501 | SEQ ID NO: 492, 494, 496, 498, 500, 502 |
| Acr74 | SEQ ID NO: 503, 505, 507, 509, 511, 513 | SEQ ID NO: 504, 506, 508, 510, 512, 514 |
| Acr75 | SEQ ID NO: 515 | 516 |
| Acr76 | SEQ ID NO: 517 | 518 |
| Acr77 | SEQ ID NO: 519 | 520 |
| Acr78 | SEQ ID NO: 521 | 522 |
| Acr79 | SEQ ID NO: 523, 525, 527, 529, 531, 533, 535 | 524, 526, 528, 530, 532, 534, 536 |
| Acr80 | SEQ ID NO: 537 | SEQ ID NO: 538 |
| Acr81 | SEQ ID NO: 539 | SEQ ID NO: 540 |
| Acr82 | SEQ ID NO: 541 | SEQ ID NO: 542 |
| Acr83 | SEQ ID NO: 543, 545 | SEQ ID NO: 544, 546 |
| Acr84 | SEQ ID NO: 547 | SEQ ID NO: 548 |
| Acr85 | SEQ ID NO: 549 | SEQ ID NO: 550 |
| Acr86 | SEQ ID NO: 551 | SEQ ID NO: 552 |

In an embodiment, the invention is directed to a protein, which has the sequence as defined in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, the invention is directed to a protein, which has the sequence as defined in SEQ ID NO: 2, 4, 6, 8, 10, 12, 14, 16, 18, 20, 22, 24 or 26. In an embodiment, the invention is directed to a protein, which has the sequence as defined in SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86. In an embodiment, the invention is directed to a protein, which has the sequence as defined in a SEQ ID NO of a Acr family selected from the group consisting of Acr3 to Acr86 families of Table 1. In an embodiment, the invention is directed to a protein, which has the sequence as defined in SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, the invention is directed to a protein, which has the sequence as defined in SEQ ID NO: 10 or SEQ ID NO: 28. In an embodiment, the invention is directed to a protein, which has the sequence as defined in SEQ ID NO: 10. In an embodiment, the invention is directed to a protein, which has the sequence as defined in SEQ ID NO: 28. In an embodiment, where an anti-CRISPR protein is specified as having a given amino acid sequence (SEQ ID), it is understood that the anti-CRISPR protein comprises said amino acid sequence. In an embodiment, where an anti-CRISPR protein is specified as having a given amino acid sequence, it is understood that the anti-CRISPR protein consists of said amino acid sequence.

In an embodiment, the invention is also directed to a protein which has a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86. In an embodiment, the invention is also directed to a protein which has a sequence having at least 70% similarity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or has a sequence having at least 90% identity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552.

In an embodiment, the invention is directed to a protein, which has the sequence having at least 70% similarity with SEQ ID NO: 10 or with SEQ ID NO: 28 or has a sequence having at least 90% identity with SEQ ID NO:10 or with SEQ ID NO:28. In an embodiment, the invention is directed to a protein, which has the sequence having at least 70% similarity with SEQ ID NO: 10 or has a sequence having at least 90% identity with SEQ ID NO:10. the invention is directed to a protein, which has the sequence having at least 70% similarity with SEQ ID NO: 28 or has a sequence having at least 90% identity with SEQ ID NO:28. When a protein is defined herein by its amino acid sequence having a percentage of identity or percentage of similarity to a specific SEQ ID, these proteins are still functional as anti-CRISPR proteins as defined herein. Thus, a protein defined by an amino acid sequence having a percentage of identity or percentage of similarity to a specific SEQ ID keeps an anti-CRISPR functionality, i.e., keeps the ability to interfere with a function of a bacterial CRISPR-Cas system (as defined herein).

In an embodiment, a protein defined by an amino acid sequence having a percentage of identity or percentage of similarity to a specific SEQ ID keeps the anti-CRISPR functionality of the protein it is identical or similar to. In an embodiment, a protein defined by an amino acid sequence having a percentage of identity or percentage of similarity to a specific SEQ ID keeps at least one, in particular 1, 2 or 3, in particular all, of the following features of the protein it is identical or similar to:
  it interferes with the same function(s) of a CRISPR-Cas system as the protein it is identical or similar to (in particular with the interference function and/or the adaptation function);
  it interferes with the same CRISPR-Cas system type as the protein they are identical or similar to (in particular with a class 2 CRISPR-Cas system, with a class 2 type II CRISPR-Cas system, with a class 2 type II-A CRISPR-Cas system);
  if applicable, it downmodulates the activity of a Cas9 protein, if the protein—it is identical or similar to—downmodulates the activity of a Cas9 protein;
  if applicable, it downmodulates the same subactivity(ies) of a Cas9 protein as the protein it is identical or similar (if this protein downmodulates the activity of a Cas9 protein).

In an embodiment, the invention is also directed to a protein which has a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein interferes with the interference function of a class 2 type II CRISPR-Cas system. In an embodiment, the invention is also directed to a protein which has a sequence having at least 70% similarity with a SEQ ID NO of a Acr family selected from the group consisting of Acr1 to Acr86 families of Table 1, or has a sequence having at least 90% identity with a SEQ ID NO of a Acr family selected from the group consisting of Acr1 to Acr86 families of Table 1, wherein said protein interferes with the interference function of a class 2 type II CRISPR-Cas system. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein interferes with the interference function of a class 2 type II-A CRISPR-Cas system. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II CRISPR-Cas system. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II-A CRISPR-Cas system. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II-A CRISPR-Cas system of a *Streptococcus* species strain. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II-A CRISPR-Cas system of a *Streptococcus thermophilus*. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a CRISPR1-Cas system of a *Streptococcus thermophilus*. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a CRISPR3-Cas system of a *Streptococcus thermophilus*. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II-A CRISPR-Cas system of a *Streptococcus pyogenes*. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II-A CRISPR-Cas system of a *Staphylococcus* species strain. In an embodiment, the invention is also directed to a protein which has a sequence having at least 70% similarity with or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II-A CRISPR-Cas system of a *Staphylococcus aureus*.

In an embodiment, a protein which has a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 encompasses a protein which has a sequence having at least 75%, at least 80%, at least 85%, at least 90%, at least 95%, at least 98% or at least 99% similarity respectively with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, a protein which has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 encompasses a protein which has a sequence having at least 91%, at least 92%, at least 93%, at least 94%, at least 95%, at least 96%, at least 97%, at least 98% or at least 99% similarity respectively with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, where an anti-CRISPR protein is specified as having an amino acid sequence similar to or identical to a given SEQ ID, it is understood that the anti-CRISPR protein comprises said amino acid sequence. In an embodiment, where an anti-CRISPR protein is specified as having an amino acid sequence similar to or identical to a given SEQ ID, it is understood that the anti-CRISPR protein consists of said amino acid sequence.

A protein which has a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 as defined herein or which has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 may differ from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 by 1 to 15 amino acid residues, 1 to 10, such as 6 to 10, less than or equals to 5, less than or equals to 4, 3, 2, or even 1 amino acid residue.

Sequences as defined in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 have been shown to contain a coiled-coil motif which is expected to act in a nucleic acid binding role. Thus, in an embodiment, a protein which has a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 as defined herein or which has sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 as defined herein keeps a functional coiled-coil motif as found in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86.

In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein interferes with the interference function of a class 2 type II CRISPR-Cas system. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein interferes with the interference function of a class 2 type II-A CRISPR-Cas system. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a class 2 type II CRISPR-Cas system. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a class 2 type II-A CRISPR-Cas system. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a class 2 type II-A CRISPR-Cas system of a *Streptococcus* species strain. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a class 2 type II-A CRISPR-Cas system of a *Streptococcus thermophilus*. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a CRISPR1-Cas system of a *Streptococcus thermophilus*. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a CRISPR3-Cas system of a *Streptococcus thermophilus*. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a class 2 type II-A CRISPR-Cas system of a *Streptococcus pyogenes*. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a class 2 type II-A CRISPR-Cas system of a *Staphylococcus* species strain. In an embodiment, the invention is also directed to a protein which has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, wherein said protein downmodulates the activity of the Cas9 protein of a class 2 type II-A CRISPR-Cas system of a *Staphylococcus aureus*.

In an embodiment, a protein which has a sequence having at least 70% similarity with SEQ ID NO: 2, 4, 6, 8, 10, 12, 14, 16, 18, 20, 22, 24 or 26 encompasses a protein which has a sequence having at least 75%, at least 80%, at least 85%, at least 90%, at least 95%, at least 98% or at least 99% similarity respectively with SEQ ID NO: 2, 4, 6, 8, 10, 12, 14, 16, 18, 20, 22, 24 or 26. In an embodiment, a protein which has a sequence having at least 90% identity with SEQ ID NO: 2, 4, 6, 8, 10, 12, 14, 16, 18, 20, 22, 24 or 26 encompasses a protein which has a sequence having at least 91%, at least 92%, at least 93%, at least 94%, at least 95%, at least 96%, at least 97%, at least 98% or at least 99% similarity respectively with SEQ ID NO: 2, 4, 6, 8, 10, 12, 14, 16, 18, 20, 22, 24 or 26. In an embodiment, where an anti-CRISPR protein is specified as having an amino acid sequence similar to or identical to a given SEQ ID, it is understood that the anti-CRISPR protein comprises said amino acid sequence. In an embodiment, where an anti-CRISPR protein is specified as having an amino acid sequence similar to or identical to a given SEQ ID, it is understood that the anti-CRISPR protein consists of said amino acid sequence.

A protein which has a sequence having at least 70% similarity with SEQ ID NO: 2, 4, 6, 8, 10, 12, 14, 16, 18, 20, 22, 24 or 26 as defined herein or which has a sequence having at least 90% identity with SEQ ID NO: 2, 4, 6, 8, 10, 12, 14, 16, 18, 20, 22, 24 or 26 may differ from SEQ ID NO: 2, 4, 6, 8, 10, 12, 14, 16, 18, 20, 22, 24 or 26 by 1 to 15 amino acid residues, 1 to 10, such as 6 to 10, less than or equals to 5, less than or equals to 4, 3, 2, or even 1 amino acid residue.

Sequences as defined in SEQ ID NO: 2, 4, 6, 8, 10, 12, 14, 16, 18, 20, 22, 24 or 26 have been shown to contain a coiled-coil motif which is expected to act in a nucleic acid binding role. Thus, in an embodiment, a protein which has a sequence having at least 70% similarity with SEQ ID NO: 2, 4, 6, 8, 10, 12, 14, 16, 18, 20, 22, 24 or 26 as defined herein or which has sequence having at least 90% identity with SEQ ID NO: 2, 4, 6, 8, 10, 12, 14, 16, 18, 20, 22, 24 or 26 as defined herein keeps a functional coiled-coil motif as found in SEQ ID NO: 2, 4, 6, 8, 10, 12, 14, 16, 18, 20, 22, 24 or 26.

In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein interferes with the interference function of a class 2 type II CRISPR-Cas system. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein interferes with the interference function of a class 2 type II-A CRISPR-Cas system. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a class 2 type II CRISPR-Cas system. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a class 2 type II-A CRISPR-Cas system. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a class 2 type II-A CRISPR-Cas system of a *Streptococcus* species strain. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a class 2 type II-A CRISPR-Cas system of a *Streptococcus thermophilus*. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a CRISPR1-Cas system of a *Streptococcus thermophilus*. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a CRISPR3-Cas system of a *Streptococcus thermophilus*. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a class 2 type II-A CRISPR-Cas system of a *Streptococcus pyogenes*. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a class 2 type II-A CRISPR-Cas system of a *Staphylococcus* species strain. In an embodiment, the invention is also directed to a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, wherein said protein downmodulates the activity of the Cas9 protein of a class 2 type II-A CRISPR-Cas system of a *Staphylococcus aureus*.

In an embodiment, a protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 encompasses a protein which has a sequence having at least 75%, at least 80%, at least 85%, at least 90%, at least 95%, at least 98% or at least 99% similarity respectively with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86. In an embodiment, a protein which has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 encompasses a protein which has a sequence having at least 91%, at least 92%, at least 93%, at least 94%, at least 95%, at least 96%, at least 97%, at least 98% or at least 99% similarity respectively with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86. In an embodiment, where an anti-CRISPR protein is specified as having an amino acid sequence similar to or identical to a given SEQ ID, it is understood that the anti-CRISPR protein comprises said amino acid sequence. In an embodiment, where an anti-CRISPR protein is specified as having an amino acid sequence similar to or identical to a given SEQ ID, it is understood that the anti-CRISPR protein consists of said amino acid sequence.

A protein which has a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 as defined herein or which has a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 may differ from SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86 by 1 to 15 amino acid residues, 1 to 10, such as 6 to 10, less than or equals to 5, less than or equals to 4, 3, 2, or even 1 amino acid residue.

In an embodiment, the invention is also directed to a protein which has a sequence having at least 70% similarity with or has a sequence having at least 90% identity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein interferes with the interference function of a class 2 type II CRISPR-Cas system. In an embodiment, the invention is also directed to a protein which has a sequence having at least 70% similarity with a SEQ ID NO of a Acr family selected from the group consisting of Acr3 to Acr86 families of Table 1, wherein said protein interferes with the interference function of a class 2 type II CRISPR-Cas system. In an embodiment, the invention is also directed to a protein which has a sequence having at least 70% similarity with or has a sequence having at least 90% identity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein interferes with the interference function of a class 2 type II-A CRISPR-Cas system. In an embodiment, the invention is also directed to a protein which has a sequence having at least 70% similarity with a SEQ ID NO of a Acr family selected from the group consisting of Acr3 to Acr86 families of Table 1, wherein said protein interferes with the interference function of a class 2 type II-A CRISPR-Cas system. In an embodiment, the invention is also directed to a protein which has a sequence having at least 70% similarity with or has a sequence having at least 90% identity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, wherein said protein downmodulates the activity of the Cas9 protein of a class 2 type II-A CRISPR-Cas system, in particular of the Cas9 protein of a class 2 type II-A CRISPR-Cas system of a *Streptococcus* strain, more particularly of a *Streptococcus thermophilus* strain or of a *Streptococcus pyogenes* strain.

In an embodiment, a protein which has a sequence having at least 70% similarity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 encompasses a protein which has a sequence having at least 75%, at least 80%, at least 85%, at least 90%, at least 95%, at least 98% or at least 99% similarity respectively with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, a protein which has a sequence having at least 90% identity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 encompasses a protein which has a sequence having at least 91%, at least 92%, at least 93%, at least 94%, at least 95%, at least 96%, at least 97%, at least 98% or at least 99% similarity respectively with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, where an anti-CRISPR protein is specified as having an amino acid sequence similar to or identical to a given SEQ ID, it is understood that the anti-CRISPR protein comprises said amino acid sequence. In an embodiment, where an anti-CRISPR protein is specified as having an amino acid sequence similar to or identical to a given SEQ ID, it is understood that the anti-CRISPR protein consists of said amino acid sequence.

A protein which has a sequence having at least 70% similarity with 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 as defined herein or which has a sequence having at least 90% identity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 may differ from SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 by 1 to 15 amino acid residues, 1 to 10, such as 6 to 10, less than or equals to 5, less than or equals to 4, 3, 2, or even 1 amino acid residue.

Preferably, reference to a sequence which has a percentage identity or similarity to any one of the SEQ ID NOs detailed herein refers to a sequence which has the stated percent identity or similarity with the SEQ ID NO referred to, over the entire length of the two sequences. Percentage (%) sequence identity is defined as the percentage of amino acids or nucleotides in a candidate sequence that are identical to the amino acids or nucleotides in a reference sequence, after aligning the sequences and introducing gaps, if necessary, to achieve the maximum percent sequence identity. Percentage (%) sequence similarity is defined as the percentage of amino acids in a candidate sequence that are similar to the amino acids in a reference sequence, after aligning the sequences and introducing gaps, if necessary, to achieve the maximum percent sequence similarity. Similarity between amino acids is based on established amino acid substitution matrices such as the PAM series (Point Accepted Mutation; e.g. PAM30, PAM70, and PAM250) or the BLOSUM series (BLOck SUbstitution Matrix; e.g. BLOSUM45, BLOSUM50, BLOSUM62, BLOSUM80, and BLOSUM90). Alignment for purposes of determining percent sequence identity or similarity can be achieved in various ways that are within the skill in the art, for instance, using publicly available computer software such as CLUSTALW, CLUSTALX, CLUSTAL Omega, BLAST, BLAST-2, ALIGN, ALIGN-2 or Megalign (DNASTAR) software. In an embodiment, similarity between amino acids is determined using the BLASTp software with the BLOSUM62 matrix. Appropriate parameters for measuring alignment, including any algorithms needed to achieve maximal alignment over the full-length of the sequences being compared, or gap penalties to be introduced, can be determined by known methods.

Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.). Conservative substitutions, such as exchanging one amino acid with another having similar properties, may be optimal.

Anti-CRISPR Genes, Constructs and Vectors

Any gene encoding a protein, which interferes with a function of a CRISPR-Cas system (herein defined as an anti-CRISPR protein) can be obtained and used in the methods of the invention. These genes are called anti-CRISPR genes.

Some anti-CRISPR genes are described herein and are as such part of the invention, and can be used in the methods of the invention. In an embodiment, the invention is directed to a gene coding for an anti-CRISPR protein as defined herein (under the anti-CRISPR proteins paragraph). In an embodiment, the invention is directed to a gene coding for a protein having the sequence as defined in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or for a protein having a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or for a protein having a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552.

In an embodiment, said anti-CRISPR gene has the sequence as defined in a SEQ ID NO of a Acr family selected from the group consisting of Acr1, Acr2, Acr3, Acr4, Acr5, Acr6, Acr7, Acr8, Acr9, Acr10, Acr11, Acr12, Acr13, Acr14, Acr15, Acr16, Acr17, Acr18, Acr19, Acr20, Acr21, Acr22, Acr23, Acr24, Acr25, Acr26, Acr27, Acr28, Acr29, Acr30, Acr31, Acr32, Acr33, Acr34, Acr35, Acr36, Acr37, Acr38, Acr39, Acr40, Acr41, Acr42, Acr43, Acr44, Acr45, Acr46, Acr47, Acr48, Acr49, Acr50, Acr51, Acr52, Acr53, Acr54, Acr55, Acr56, Acr57, Acr58, Acr59, Acr60, Acr61, Acr62, Acr63, Acr64, Acr65, Acr66, Acr67, Acr68, Acr69, Acr70, Acr71, Acr72, Acr73, Acr74, Acr75, Acr76, Acr77, Acr78, Acr79, Acr80, Acr81, Acr82, Acr83, Acr84, Acr85 and Acr86 families of Table 1 (i.e., selected from the group consisting of Acr1 to Acr86 families). In an embodiment, said anti-CRISPR gene has the sequence as defined in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551. The invention is also directed to conservative variants of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551, because of the degeneracy of the genetic code. Thus, the invention is also directed to any conservative variants of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551, as long as said variants encode respectively an anti-CRISPR protein as defined in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552.

In an embodiment, the invention is directed to a gene coding for an anti-CRISPR protein as defined herein, i.e., a gene encoding a protein having the sequence as defined in SEQ ID NO: 2, 4, 6, 8, 10, 12, 14, 16, 18, 20, 22, 24 or 26, or for a protein having a sequence having at least 70% similarity with SEQ ID NO: 2, 4, 6, 8, 10, 12, 14, 16, 18, 20, 22, 24 or 26, or for a protein having a sequence having at least 90% identity with SEQ ID NO: 2, 4, 6, 8, 10, 12, 14, 16, 18, 20, 22, 24 or 26. In an embodiment, said anti-CRISPR gene has the sequence as defined in SEQ ID NO: 1, 3, 5, 7, 9, 11, 13, 15, 17, 19, 21, 23 or 25. The invention is also directed to conservative variants of SEQ ID NO: 1, 3, 5, 7, 9, 11, 13, 15, 17, 19, 21, 23 or 25, because of the degeneracy of the genetic code. Thus, the invention is also directed to any conservative variants of SEQ ID NO: 1, 3, 5, 7, 9, 11, 13, 15, 17, 19, 21, 23 or 25, as long as said variants encode respectively an anti-CRISPR protein as defined in SEQ ID NO: 2, 4, 6, 8, 10, 12, 14, 16, 18, 20, 22, 24 or 26. In an embodiment, the invention is directed to a gene coding for an anti-CRISPR protein as defined herein, i.e., a gene encoding a protein having the sequence as defined in SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or for a protein having a sequence having at least 70% similarity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86, or for a protein having a sequence having at least 90% identity with SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86. In an embodiment, said anti-CRISPR gene has the sequence as defined in SEQ ID NO: 27, 29, 31, 33, 35, 37, 39, 41, 43, 45, 47, 49, 51, 53, 55, 57, 59, 61, 63, 65, 67, 69, 71, 73, 75, 77, 79, 81, 83 or 85. The invention is also directed to conservative variants of SEQ ID NO: 27, 29, 31, 33, 35, 37, 39, 41, 43, 45, 47, 49, 51, 53, 55, 57, 59, 61, 63, 65, 67, 69, 71, 73, 75, 77, 79, 81, 83 or 85, because of the degeneracy of the genetic code. Thus, the invention is also directed to any conservative variants of SEQ ID NO: 27, 29, 31, 33, 35, 37, 39, 41, 43, 45, 47, 49, 51, 53, 55, 57, 59, 61, 63, 65, 67, 69, 71, 73, 75, 77, 79, 81, 83 or 85, as long as said variants encode respectively an anti-CRISPR protein as defined in SEQ ID NO: 28, 30, 32, 34, 36, 38, 40, 42, 44, 46, 48, 50, 52, 54, 56, 58, 60, 62, 64, 66, 68, 70, 72, 74, 76, 78, 80, 82, 84 or 86. In an embodiment, the invention is directed to a gene coding for an anti-CRISPR protein as defined herein, i.e., a gene encoding a protein having the sequence as defined in SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or for a protein having a sequence having at least 70% similarity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or for a protein having a sequence having at least 90% identity with SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552.

In an embodiment, said anti-CRISPR gene has the sequence as defined in a SEQ ID NO of a Acr family selected from the group consisting of Acr3 to Acr86 families of Table 1. In an embodiment, said anti-CRISPR gene has the sequence as defined in SEQ ID NO: 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551. The invention is also directed to conservative variants of SEQ ID NO: 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551 as defined herein. Thus, the invention is also directed to any conservative variants of SEQ ID NO: 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551, as long as said variants encode respectively an anti-CRISPR protein as defined in SEQ ID NO: 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552.

In an embodiment, the invention is directed to a gene coding for an anti-CRISPR protein as defined herein, i.e., a gene encoding a protein having the sequence as defined in SEQ ID NO: 10 or 28, or for a protein having a sequence having at least 70% similarity with SEQ ID NO: 10 or 28, or for a protein having a sequence having at least 90% identity with SEQ ID NO: 10 or 28. In an embodiment, said anti-CRISPR gene has the sequence as defined in SEQ ID NO: 9 or 27. The invention is also directed to conservative variants of SEQ ID NO: 9 or 27 as long as said variants encode respectively an anti-CRISPR protein as defined in SEQ ID NO: 10 or 28. In an embodiment, the invention is directed to a gene coding for an anti-CRISPR protein as defined herein, i.e., a gene encoding a protein having the sequence as defined in SEQ ID NO: 10, or for a protein having a sequence having at least 70% similarity with SEQ ID NO: 10, or for a protein having a sequence having at least 90% identity with SEQ ID NO: 10. In an embodiment, said anti-CRISPR gene has the sequence as defined in SEQ ID NO: 9. The invention is also directed to conservative variants of SEQ ID NO:9 as long as said variants encode respectively an anti-CRISPR protein as defined in SEQ ID NO: 10. In an embodiment, the invention is directed to a gene coding for an anti-CRISPR protein as defined herein, i.e., a gene encoding a protein having the sequence as defined in SEQ ID NO: 28, or for a protein having a sequence having at least 70% similarity with SEQ ID NO: 28, or for a protein having a sequence having at least 90% identity with SEQ ID NO: 28. In an embodiment, said anti-CRISPR gene has the sequence as defined in SEQ ID NO: 27. The invention is also directed to conservative variants of SEQ ID NO: 27 as long as said variants encode respectively an anti-CRISPR protein as defined in SEQ ID NO: 28.

When an anti-CRISPR gene is specified as having a given nucleotide sequence, it is understood that the gene comprises said nucleotide sequence. In an embodiment, where an anti-CRISPR gene is specified as having a given nucleotide sequence, it is understood that the gene consists of said nucleotide sequence.

In an embodiment, the anti-CRISPR gene as defined herein is provided under an isolated or substantially purified form. An "isolated" or "purified" anti-CRISPR gene, is substantially or essentially free from components that normally accompany or interact with the gene as found in its naturally occurring environment. Thus, an isolated or purified anti-CRISPR gene is substantially free of other cellular material, or culture medium when produced by recombinant techniques, or substantially free of chemical precursors or other chemicals when chemically synthesized. Optimally, an "isolated" anti-CRISPR gene is free of sequences (optimally protein encoding sequences) that naturally flank the anti-CRISPR gene (i.e., sequences located at the 5' and 3' ends of the anti-CRISPR gene) in the DNA of the organism from which the anti-CRISPR gene is derived. In an embodiment, the anti-CRISPR gene contain less than about 5 kb, 4 kb, 3 kb, 2 kb, 1 kb or 0.5 kb of nucleotide sequence that naturally flank the anti-CRISPR gene in the DNA of the organism from which the polynucleotide is derived.

The invention is also directed to a construct comprising an anti-CRISPR gene as defined herein. In an embodiment, the present invention covers a construct comprising an anti-CRISPR gene operably linked to a regulatory sequence. The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences. The term "regulatory sequences" includes promoters and/or enhancers and other expression regulation signals. The term "promoter" is used in the normal sense of the art, e.g. an RNA polymerase binding site.

The construct may even contain or express another gene, such as a marker allowing for the selection of the construct. Various markers exist which may be used, for example those markers that provide for antibiotic resistance—e.g. resistance to bacterial antibiotics—such as Erythromycin, Ampicillin, Streptomycin and Tetracycline.

Thus, in a further aspect, there is provided a vector comprising an anti-CRISPR gene or a construct as defined herein. As used herein, the term "vector" refers to any nucleic acid molecule into which another nucleic acid (e.g., an anti-CRISPR gene) can be inserted and which can be introduced into and replicate within bacterial strain. Thus, the term refers to any nucleic acid construct (and, if necessary, any associated delivery system) capable of use for introducing genetic material into a bacterial strain. Selection of appropriate vectors is within the knowledge of those having skill in the art. In an embodiment, the vector is a plasmid. As used herein, the term "plasmid" refers to a circular double-stranded (ds) DNA construct that can be used as a vector for introducing DNA into a bacterial strain. The constructs or the vectors may be introduced into a bacterial strain as described herein.

Bacterial Strains and Phages Comprising Anti-CRISPR Genes

In the methods of the invention, the anti-CRISPR gene as defined herein, as such, as a construct or contained in a vector is introduced into a bacterial cell in order to be expressed. Thus, the invention is directed to a bacterial strain comprising—in a vector or integrated into its chromosome—an anti-CRISPR gene or a construct as defined herein. The term "expression" or "expressed" as used herein has its normal meaning in the art, i.e., the anti-CRISPR gene is transcribed and translated to produce a functional anti-CRISPR protein.

In an embodiment, the anti-CRISPR gene is expressed from a vector (such as a plasmid), i.e., that the anti-CRISPR gene is kept on the vector once introduced into the bacterial strain. In another embodiment, the anti-CRISPR gene is expressed from the chromosome of said bacteria strain, i.e., the anti-CRISPR gene is found integrated into the chromosome of said bacterial strain. As used herein, the term "integrated" used in reference to a nucleic acid (e.g., an anti-CRISPR gene) means incorporated into the chromosomal DNA of a bacterial strain. In an embodiment, an anti-CRISPR gene is inserted in a plasmid, which is used to transform a bacterial strain, and said anti-CRISPR gene is integrated into the transformed bacterial strain's chromosomal DNA.

In an embodiment, the bacterial strain comprises integrated in its chromosome an anti-CRISPR gene as defined herein (encoding a protein interfering with a function of a given CRISPR-Cas system), and at least one self-targeting spacer(s) inserted in the CRISPR array of said given CRISPR-Cas. "Self-targeting spacer" is as defined elsewhere in this application. In an embodiment, said anti-CRISPR gene encoding a protein interfering with the interference function of said given CRISPR-Cas system. In an embodiment, said given CRISPR-Cas system is a class 2 CRISPR-Cas system, a class 2 type II CRISPR-Cas system, a class 2 type II-A CRISPR-Cas system.

Either as a gene, as part of a construct or part of a vector, integrated or not, in an embodiment, the expression of the anti-CRISPR gene as defined herein is constitutive. In another embodiment, either as a gene, as part of a construct or part of a vector, integrated or not, the expression of the anti-CRISPR gene as defined herein is inducible (i.e., the anti-CRISPR gene is found under an inducible promoter). The term "inducible promoter" refers to a promoter that selectively express a coding sequence or functional RNA in response to the presence of an endogenous or exogenous stimulus, for example by chemical compounds (chemical inducers) or in response to environmental and/or chemical signals. Inducible or regulated promoters include, for example, promoters induced or regulated by light, heat, stresses, sugars, peptides and metal ions.

In an embodiment, the bacterial strain of the invention or used in the methods of the invention as defined herein is a Gram-positive bacterial strain. In an embodiment, the bacterial strain is a lactic acid bacterium. In an embodiment, said bacterial strain is selected from a *Bifidobacterium* species, a *Brevibacterium* species, a *Propionibacterium* species, a *Lactococcus* species, a *Streptococcus* species, a *Lactobacillus* species, an *Enterococcus* species, a *Pediococcus* species, a *Leuconostoc* species and an *Oenococcus* species. In an embodiment, said bacterial strain is a *Streptococcus* species. Suitable species include, but are not limited to *Lactococcus lactis*, including *Lactococcus lactis* subsp. *lactis* and *Lactococcus lactis* subsp. *cremoris*, *Leuconostoc* sp., *Lactococcus lactis* subsp. *lactis biovar*, *Streptococcus thermophilus*, *Lactobacillus delbrueckii* subsp. *bulgaricus*, *Lactobacillus helveticus*, *Bifidobacterium lactis*, *Lactobacillus acidophilus*, and *Lactobacillus casei*. In an embodiment, said bacterial strain is selected from a *Streptococcus thermophilus* strain and a *Streptococcus pyogenes* strain. In an embodiment, said bacterial strain is a *Streptococcus thermophilus* strain. In an embodiment, said bacterial strain is a *Streptococcus pyogenes* strain.

In an embodiment, independently of or in combination with the above paragraph, a bacterial strain is characterized by the presence in its genome of a given CRISPR-Cas system as defined herein. Thus, in an embodiment, the bacterial strain of the invention or used in the methods of the invention comprises in its genome a class 2 CRISPR-Cas system as defined herein. In an embodiment, the bacterial strain comprises in its genome a class 2 type II CRISPR-Cas system as defined herein. In an embodiment, the bacterial strain comprises in its genome a class 2 type II-A CRISPR-Cas system as defined herein.

In an embodiment, when the bacterial strain is a *Streptococcus thermophilus* strain, said strain of the invention or used in the methods of the invention comprises in its genome a CRISPR1-Cas system. In an embodiment, when the bacterial strain is a *Streptococcus thermophilus* strain, said strain of the invention or used in the methods of the invention comprises in its genome a CRISPR3-Cas system. In an embodiment, when the bacterial strain is a *Streptococcus thermophilus* strain, said strain of the invention or used in the methods of the invention comprises in its genome a CRISPR1-Cas system and a CRISPR3-Cas system.

The invention is also directed to recombinant phages, the genome of which comprises an anti-CRISPR gene or a construct as defined herein. As used herein, the term "phage" or "bacteriophage" has its conventional meaning as understood in the art—i.e., a virus that selectively infects one or more bacterial strains or species.

Introduction of Nucleic Acids (Including Anti-CRISPR Genes), Anti-CRISPR Proteins, Constructs and Vectors, into Bacterial Strains The nucleic acids (including anti-CRISPR genes as defined herein), anti-CRISPR proteins as defined herein, constructs and vectors disclosed herein can be introduced into a host cell, in particular a bacterial strain, using any method available.

"Introducing" (and "introduced") is intended to mean presenting to the host cell, the nucleic acid (including an anti-CRISPR gene) or protein (including an anti-CRISPR protein) or construct or vector as defined herein, in such a manner that the component(s) gains access to the interior of the host cell. The methods and compositions do not depend on a particular method for introducing a sequence into a host cell, only that the nucleic acid or protein gains access to the interior of the host cell. Introducing includes the incorporation of a nucleic acid into the host cell where the nucleic acid may be incorporated into the genome of the host cell, and includes the transient (direct) provision of a nucleic acid or protein to the host cell.

Introducing a nucleic acid (in particular an anti-CRISPR gene), construct or vector into a strain can be carried out by several methods, including transformation, conjugation, transduction or protoplast fusion. Methods for introducing polynucleotides or polypeptides by transformation into a host cell, include, but are not limited to, microinjection, electroporation, stable transformation methods, transient transformation methods [such as induced competence using chemical (e.g. divalent cations such as $CaCl_2$) or mechanical (electroporation) means], ballistic particle acceleration (particle bombardment), direct gene transfer, viral-mediated introduction, cell-penetrating peptides or mesoporous silica nanoparticle (MSN)-mediated direct protein delivery. Introducing a nucleic acid, construct or vector into a strain can be carried out by conjugation, which is a specific method of natural DNA exchange requiring physical cell-to-cell contact. Introducing a nucleic acid, construct or vector into a strain can be carried out by transduction, which is the introduction of DNA via a virus (e.g. phage) infection which is also a natural method of DNA exchange. Generally, such methods involve incorporating a polynucleotide within a viral DNA or RNA molecule.

A protein (in particular an anti-CRISPR protein) can be introduced into a host cell by directly introducing the protein itself or an mRNA encoding the anti-CRISPR protein. The protein can be introduced into a host cell transiently. Uptake of the protein into the host cell can be facilitated with a Cell Penetrating Peptide (CPP).

In an embodiment, the introduction can be stable, i.e., that the nucleic acid (construct or vector) introduced into host cell integrates into a genome of the host cell and is capable of being inherited by the progeny thereof. In another embodiment, the introduction can be temporary, i.e., that a nucleic acid (construct or vector) is introduced into the host cell and does not integrate into a genome of the host cell or a polypeptide is introduced into a host cell. Transient transformation indicates that the introduced nucleic acid or protein is only temporarily expressed or present in the host cell.

In an embodiment, whatever the method used for the nucleic acid or protein introduction, the host cell is a bacterial strain, in particular a bacterial strain as defined herein.

Uses of Anti-CRISPR Genes and Anti-CRISPR Proteins

The anti-CRISPR genes and the anti-CRISPR proteins as defined herein [in the anti-CRISPR genes and anti-CRISPR proteins paragraphs] find use in a wide variety of applications in bacterial strains, in particular in the methods described herein or below.

In the methods described herein, when a bacterial strain comprises in its genome a CRISPR-Cas system to be targeted, it is required that this CRISPR-Cas system is functional, i.e., has been shown to be active against a given target nucleic acid or is known to be active against target nucleic acids (able to acquire spacer(s) against target nucleic acids and able to interfere with said target nucleic acids).

In the method described herein, the expression "target nucleic acid" refers to any nucleic acid—which once introduced into a bacterial strain—is able to generate a response, from this bacterial strain. In an embodiment, said target nucleic acid is a DNA, in particular a double-stranded DNA or a single-stranded DNA. In an embodiment, said target nucleic acid is a RNA. In an embodiment, said target nucleic acid is a chromosomal DNA sequence (i.e., a sequence present in the chromosome of the bacterial cell). In an embodiment, said target nucleic acid is a transcript (i.e., a transcript expressed by the bacterial cell). The response can be generated against the target nucleic acid sequence per se. In another embodiment, the response can be generated against a transcription product of the target nucleic acid sequence—such as a transcript of the target nucleic acid sequence [e.g. an RNA (e.g. mRNA)]. Examples of target nucleic acid include, but are not limited to, a bacteriophage genome, the transcription product of a bacteriophage genome, a plasmid, a chromosomal sequence comprising at least one self-targeting spacer, a mobile genetic element, a transposable element and an insertion sequence. In an embodiment, said target nucleic acid is selected from a bacteriophage genome, the transcription product of a bacteriophage genome, a plasmid, chromosomal sequence comprising at least one self-targeting spacer, a mobile genetic element, a transposable element and an insertion sequence. In an embodiment, said target nucleic acid is a bacteriophage genome or the transcription product of a bacteriophage genome. In an embodiment, said target nucleic acid is a plasmid. In an embodiment, said target nucleic acid is a chromosomal sequence comprising at least one self-targeting spacer.

In an embodiment, said target nucleic acid is a mobile genetic element. In an embodiment, the target nucleic as defined herein is able to generate a CRISPR-Cas system-mediated response. In a particular embodiment, the target nucleic as defined herein is able to generate a class 2 CRISPR-Cas system-mediated response. In a particular embodiment, the target nucleic as defined herein is able to generate a class 2 type II CRISPR-Cas system-mediated response. In a particular embodiment, the target nucleic as defined herein is able to generate a class 2 type II-A CRISPR-Cas system-mediated response.

In an aspect, the invention is directed to a method to downmodulate, in a bacterial strain, the activity of a class 2 type II CRISPR-Cas system against target nucleic acids, said method comprising either a) expressing in said bacterial strain a gene encoding a protein which interferes with a function of said class 2 type II CRISPR-Cas system or b) introducing in said bacterial strain a protein which interferes with a function of said class 2 type II CRISPR-Cas system. The expression of said gene encoding a protein which interferes with a function of said class 2 type II CRISPR-Cas system or introduction of said protein which interferes with a function of said class 2 type II CRISPR-Cas system downmodulates the activity of a class 2 type II CRISPR-Cas system. In a particular embodiment, the invention is directed to a method to downmodulate, in a bacterial strain, the activity of a class 2 type II CRISPR-Cas system against target nucleic acids, comprising expressing in said bacterial strain a gene encoding a protein which interferes with a function of said class 2 type II CRISPR-Cas system, wherein said bacterial strain is not of the *Listeria* genus when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26. In a particular embodiment, the invention is directed to a method to downmodulate, in a bacterial strain, the activity of a class 2 type II CRISPR-Cas system against target nucleic acids, comprising expressing in said bacterial strain a gene encoding a protein which interferes with a function of said class 2 type II CRISPR-Cas system, wherein said bacterial strain is not of *Neisseria* genus, when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26. In a particular embodiment, the invention is directed to a method to downmodulate, in a bacterial strain, the activity of a class 2 type II CRISPR-Cas system against target nucleic acids, comprising expressing in said bacterial strain a gene encoding a protein which interferes with a function of said class 2 type II CRISPR-Cas system, wherein said bacterial strain is neither of *Listeria* genus nor *Neisseria* genus, when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26. In a particular embodiment, the invention is directed to a method to downmodulate, in a bacterial strain, the activity of a class 2 type II CRISPR-Cas system against target nucleic acids, comprising expressing in said bacterial strain a gene encoding a protein which interferes with a function of said class 2 type II CRISPR-Cas system, wherein said bacterial strain is a gram-positive strain which is not of *Listeria* genus, when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26.

In the same aspect, the invention is also directed to a method to downmodulate, in a bacterial strain, the activity of a class 2 type II CRISPR-Cas system against target nucleic acids, comprising:
1) providing a bacterial strain, the genome of which contains a class 2 type II CRISPR-Cas system, wherein said class 2 type II CRISPR-Cas system is known to be active against target nucleic acids; and
2) either a) expressing in said bacterial strain a gene encoding a protein which interferes with a function of said class 2 type II CRISPR-Cas system or b) introducing in said bacterial strain a protein which interferes with a function of said class 2 type II CRISPR-Cas system.

In the same aspect, the invention is also directed to the use of a gene encoding a protein which interferes with a function of a class 2 type II CRISPR-Cas system or of a protein which interferes with a function of said class 2 type II CRISPR-Cas system, to downmodulate, in a bacterial strain, the activity of a class 2 type II CRISPR CRISPR-Cas system against target nucleic acids.

As used herein "downmodulating the activity", means decreasing, from partially to completely inhibiting, the activity of said class 2 type II CRISPR-Cas system against target nucleic acids.

Such downmodulation can be checked by providing a bacterial strain which is resistant to a given virulent phage, said resistance being mediated by a given CRISPR-Cas system (i.e., the CRISPR array of said given CRISPR-Cas system comprises a spacer corresponding to a protospacer found in the genome of the virulent phage); producing in said bacterial strain said anti-CRISPR protein (interfering with a function of said class 2 type II CRISPR-Cas system); and exposing said bacterial strain to said given virulent phage. The use of an anti-CRISPR protein as defined herein leads to an increase of the titer of said virulent phage by more than 1 Log (i.e., more than 90%) as compared to a control [where the control is the same bacterial strain—but not producing said anti-CRISPR protein—and exposed to the same virulent phage in the same conditions]. In an embodiment, the increase in the titer of said virulent phage is more than 95% as compared to a control. In an embodiment, the increase in the titer of said virulent phage is more than 98% as compared to a control. In an embodiment, the increase in the titer of said virulent phage is more than 2 Log (more than 99%) as compared to a control. In an embodiment, the increase in the titer of said virulent phage is more than 3 Log as compared to a control. In an embodiment, the increase in the titer of said virulent phage is more than 4 Log as compared to a control.

In an embodiment, the protein interferes with the adaptation function of said class 2 type II CRISPR-Cas system. Thus, the invention is directed to a method to downmodulate, in a bacterial strain, the activity of a class 2 type II CRISPR-Cas system against target nucleic acids, comprising:
1) providing a bacterial strain, the genome of which contains a class 2 type II CRISPR-Cas system, wherein said class 2 type II CRISPR-Cas system is known to be active against target nucleic acids; and
2) either expressing in said bacterial strain a gene encoding a protein which interferes with the adaptation function of said class 2 type II CRISPR-Cas system or introducing in said bacterial strain a protein which interferes with a function of said class 2 type II CRISPR-Cas system.

In another embodiment, the protein interferes with the interference function of said class 2 type II CRISPR-Cas system. Thus, the invention is directed to a method to downmodulate, in a bacterial strain, the activity of a class 2 type II CRISPR-Cas system against a given target nucleic acid, comprising:
1) providing a bacterial strain, the genome of which contains a class 2 type II CRISPR-Cas system, wherein said class 2 type II CRISPR-Cas system has an activity against a given target nucleic acid; and
2) either expressing in said bacterial strain a gene encoding a protein which interferes with the interference function of said class 2 type II CRISPR-Cas system or introducing in said bacterial strain a protein which interferes with a function of said class 2 type II CRISPR-Cas system.

In the method described in the paragraphs immediately above, two techniques have been proposed to provide an anti-CRISPR protein into the bacterial strain: either the expression in said bacterial strain of an anti-CRISPR gene (i.e., a gene encoding a protein which interferes with a function of a CRISPR-Cas system) or by the introduction into said bacterial strain of an anti-CRISPR protein (i.e., a protein which interferes with a function of a CRISPR-Cas system). One technique can be used as an alternative to the other and the person skilled in the art can select which one is the most suitable for a given method described herein. Thus, for any of the methods described herein, and when applicable, the expression in said bacterial strain of an anti-CRISPR gene may be replaced by the introduction into said bacterial strain of an anti-CRISPR protein. Such methods—when the introduction into said bacterial strain of an anti-CRISPR protein replaces the expression in said bacterial strain of an anti-CRISPR gene should be considered described as such and are part of the present invention.

In another aspect, the invention is directed to a method to downmodulate, in a bacterial strain, the CRISPR-Cas-mediated immunity against a given target nucleic acid, comprising:
1) providing a bacterial strain, the genome of which contains a class 2 type II CRISPR-Cas system, wherein said CRISPR-Cas system provides immunity against a given target nucleic acid (i.e., the CRISPR array of said given CRISPR-Cas system comprises a spacer corresponding to a protospacer found in said target nucleic acid); and
2) expressing in said bacterial strain a gene encoding a protein which interferes with the interference function of said CRISPR-Cas system against said given target nucleic acid.

The expression of said gene encoding a protein which interferes with a function of said class 2 type II CRISPR-Cas system downmodulates the CRISPR-Cas-mediated immunity against a given target nucleic acid.

As used herein the term "immunity" or "immunized" refers to the response generated by a bacterial cell into which a target nucleic acid has been introduced, preventing thus said target nucleic acid to be maintained in said bacterial cell. Thus, a bacterial cell is said "immunized" (or has "immunity") against a target nucleic acid, when—after the response generated as a consequence of the introduction of the target nucleic acid—said target nucleic acid is not maintained in said bacterial cell. Thus, immunity against a target nucleic acid can be measured in terms of the maintenance of the target nucleic acid in said bacterial cell (e.g., target nucleic acid replication and/or transcription and/or expression) or in terms of survival of the bacterial cell in response to said target nucleic acid (when the target nucleic acid is detrimental to said bacterial cell), for example survival of the bacterial cell in response to a phage.

In an embodiment, the immunity as defined herein is mediated by a CRISPR-Cas system (CRISPR-Cas system-mediated immunity), i.e., that the maintenance of said target nucleic acid is prevented by a CRISPR-Cas system present in the bacterial strain. In an embodiment, the immunity as defined herein is mediated by a class 2 CRISPR-Cas system. In an embodiment, the immunity as defined herein is mediated by a class 2 type II CRISPR-Cas system. In an embodiment, the immunity as defined herein is mediated by a class 2 type II-A CRISPR-Cas system.

The method as defined herein further comprises: 3) contacting said bacterial strain of step 2) with the given target nucleic acid and checking that the immunity against this given target nucleic acid is downmodulated.

As used herein, "immunity downmodulation" means from decrease to suppression of the immunity of a bacterial strain against a target nucleic acid. Such downmodulation can be checked by exposing the bacterial strain obtained in step 2) to said target nucleic acid; the use of an anti-CRISPR protein as defined herein leads to an increase of the proportion of bacterial cells into which the target nucleic acid is maintained, by more than 1 Log (i.e., more than 90%) as compared to a control [where the control is the same bacterial strain—but not producing said anti-CRISPR protein—and exposed to the target nucleic acid in the same conditions]. In an embodiment, the increase in the proportion of bacterial cells into which the target nucleic acid is maintained is more than 95% as compared to a control. In an embodiment, the increase in the proportion of bacterial cells into which the target nucleic acid is maintained is more than 98% as compared to a control. In an embodiment, the increase in the proportion of bacterial cells into which the target nucleic acid is maintained is more than 2 Log (more than 99%) as compared to a control. In an embodiment, the increase in the proportion of bacterial cells into which the target nucleic acid is maintained is more than 3 Log as compared to a control. In an embodiment, the increase in the proportion of bacterial cells into which the target nucleic acid is maintained is more than 4 Log as compared to a control.

As used herein, "exposing a bacterial strain to a (target) nucleic acid" or "contacting a bacteria strain to a (target) nucleic acid" means that the bacterial cells and a given or given nucleic acid(s) are physically mixed together (e.g., in the same medium), such that said nucleic acid(s) is introduced into the bacterial cells.

In the same aspect, the invention is also directed to the use of a gene encoding a protein which interferes with the interference function of a CRISPR-Cas system to downmodulate the CRISPR-Cas-mediated immunity against a given target nucleic acid in a bacterial strain, wherein said bacterial strain expresses said gene.

In another aspect, the invention is directed to a method to decrease the CRISPR-mediated instability of a plasmid in a bacterial strain, comprising:
1) expressing, in a bacterial strain, the genome of which comprise a CRISPR-Cas system known to be active against target nucleic acids, a gene encoding a protein which interferes with a function of said CRISPR-Cas system, and
2) transforming said bacterial strain with a plasmid;
wherein the expression of said gene encoding a protein which interferes with a function of a CRISPR-Cas system decreases the CRISPR-mediated instability of said plasmid in said bacterial strain.

The decrease of the CRISPR-mediated instability of a plasmid can be checked by determining the proportion of bacterial cells obtained after transformation in step 2) into which the plasmid is maintained; the use of an anti-CRISPR protein as defined herein leads to an increase of the proportion of bacterial cells into which the plasmid is maintained, by more than 1 Log (i.e., more than 90%) as compared to a control population [where the control is the same bacterial strain—but not producing said anti-CRISPR protein—and exposed to the plasmid in the same conditions]. In an embodiment, the increase in the proportion of bacterial cells into which the plasmid is maintained is more than 95% as compared to a control population. In an embodiment, the increase in the proportion of bacterial cells into which the plasmid is maintained is more than 98% as compared to a control population. In an embodiment, the increase in the proportion of bacterial cells into which the plasmid is maintained is more than 2 Log (more than 99%) as compared to a control population. In an embodiment, the increase in the proportion of bacterial cells into which the plasmid is maintained is more than 3 Log as compared to a control population. In an embodiment, the increase in the proportion of bacterial cells into which the plasmid is maintained is more than 4 Log as compared to a control population.

The proportion of bacterial cells into which the plasmid is maintained can be calculated by determining any phenotype linked to the presence of the plasmid, such as a marker (e.g., an antibiotic resistance gene).

In the same aspect, the invention is also directed to the use of a gene encoding a protein which interferes with the interference function of a CRISPR-Cas system to decrease the CRISPR-mediated instability of a plasmid in a bacterial strain, wherein said bacterial strain expresses said gene.

In another aspect, the invention is also directed to a method to increase the efficiency of gene transfer methods in a bacterial strain, said method comprising:
  either: A1) expressing, in a bacterial strain, the genome of which comprise a CRISPR-Cas system which is known to be active against target nucleic acids, a gene encoding a protein which interferes with a function of said CRISPR-Cas system; and A2) introducing a nucleic acid into said bacterial strain; or
  B1) introducing a nucleic acid into a bacterial strain, the genome of which comprise a CRISPR-Cas system which is known to be active against target nucleic acids, said nucleic acid comprising a gene encoding a protein which interferes with a function of said CRISPR-Cas system,
wherein the expression of the gene encoding a protein which interferes with a function of a CRISPR-Cas system decreases the CRISPR-mediated targeting of said introduced nucleic acid.

The decrease of the CRISPR-mediated targetting of said introduced nucleic acid can be checked by determining the proportion of bacterial cells (obtained after the introduction of said nucleic acid) into which the introduced nucleic acid is maintained; the use of an anti-CRISPR protein as defined herein leads to an increase of the proportion of bacterial cells into which the introduced nucleic acid is maintained, by more than 1 Log (i.e., more than 90%) as compared to a control population [where the control is the same bacterial strain—but not producing said anti-CRISPR protein—and exposed to the nucleic acid to be introduced in the same conditions]. In an embodiment, the increase in the proportion of bacterial cells into which the introduced nucleic acid is maintained is more than 95% as compared to a control population. In an embodiment, the increase in the proportion of bacterial cells into which the introduced nucleic acid is maintained is more than 98% as compared to a control population. In an embodiment, the increase in the proportion of bacterial cells into which the introduced nucleic acid is maintained is more than 2 Log (more than 99%) as compared to a control population. In an embodiment, the increase in the proportion of bacterial cells into which the introduced nucleic acid is maintained is more than 3 Log as compared to a control population. In an embodiment, the increase in the proportion of bacterial cells into which the introduced nucleic acid is maintained is more than 4 Log as compared to a control population.

In an embodiment, said nucleic acid is introduced through transformation, transduction or conjugation.

In an embodiment, said nucleic acid to be introduced is a DNA. In an embodiment, said nucleic acid to be introduced is a plasmid.

In the same aspect, the invention is also directed to the use of a gene encoding a protein which interferes with the interference function of a CRISPR-Cas system to decrease the CRISPR-mediated instability of a nucleic acid to be introduced in a bacterial strain, wherein said bacterial strain expresses said gene.

In an aspect, the invention is also directed to a method to favor the screening of a bacterial mechanism providing resistance against a virulent phage other than a given CRISPR-Cas-mediated resistance, comprising:
  1) providing a bacterial strain, the genome of which contains a given CRISPR-Cas system which is known to be active against target nucleic acids;
  2) expressing in said bacterial strain a gene encoding a protein which interferes with a function of said given CRISPR-Cas system;
  3) exposing said bacterial strain obtained by step 2) with a virulent phage; and
  4) selecting bacteriophage-insensitive mutants (BIMs),
wherein the resistance in said selected BIMs is provided by a bacterial mechanism other than the given CRISPR-Cas-mediated resistance.

The term "resistance" or "resistant" refers to the status of a bacterial cell with respect to a phage infection. Thus, a bacterial cell is considered "resistant" (or to have "resistance") against a phage, when the phage is not able to replicate in said bacterial cell (because the phage genetic material is not able to enter into said bacterial cell or is not able to be maintained in the bacterial cell). As used herein, a phage resistance is "CRISPR-Cas-mediated", when the maintenance of said phage (i.e., its genetic material) into said bacterial cell is prevented by a CRISPR-Cas system present in the bacterial cell. In an embodiment, the resistance as defined herein is mediated by a class 2 CRISPR-Cas system. In an embodiment, the resistance as defined herein is mediated by a class 2 type II CRISPR-Cas system. In an embodiment, the resistance as defined herein is mediated by a class 2 type II-A CRISPR-Cas system.

Methods to expose a bacterial strain to a phage (challenge) and to select a bacterial strain resistance to a phage (also called bacteriophage-insensitive mutants or BIMs) are known from the person skilled in the art.

In an embodiment, the bacterial mechanism providing phage resistance to the bacterial strain of step 4) is not mediated by a CRISPR-Cas system. In an embodiment, the bacterial mechanism providing phage resistance to the bacterial strain of step 4) is selected from the group consisting of a mechanism of blocking phage adsorption, a mechanism of blocking genome injection, a mechanism of restriction-modification and a mechanism of abortive infection. In another embodiment, the bacterial mechanism providing phage resistance to the bacterial strain of step 4) is mediated by a CRISPR-Cas system other than the given (interfered) CRISPR-Cas system.

In a further aspect, the invention is directed to a method to enrich a bacterial population in bacteriophage-insensitive mutants (BIMs), other than BIMs due to a given CRISPR-Cas system:
  1) providing a bacterial strain, the genome of which contains a given CRISPR-Cas system which is known to be active against target nucleic acids;
  2) expressing in said bacterial strain a gene encoding a protein which interferes with a function of said given CRISPR-Cas system;
  3) exposing said bacterial strain obtained by step 2) to a virulent phage; and
  4) selecting BIMs,
wherein the selected BIMs have acquired resistance to said virulent phage by a mechanism other than the given CRISPR-Cas system.

In an embodiment, the mechanism providing phage resistance to the selected BIMs of step 4) is not mediated by a CRISPR-Cas system. In an embodiment, the mechanism providing phage resistance to the selected BIMs of step 4) is selected from the group consisting of a mechanism of blocking of injection, a mechanism of restriction-modification and a mechanism of abortive infection. In another embodiment, the mechanism providing phage resistance to the selected BIMs of step 4) is mediated by a CRISPR-Cas system other than the given (interfered) CRISPR-Cas system.

In another aspect, the invention concerns a method to identify a gene encoding a protein which interferes with the interference function of a given CRISPR-Cas system, comprising:

1) identifying a protospacer in a virulent phage which is virulent against a bacterial strain, the genome of which comprises a given CRISPR-Cas system known to be active against target nucleic acids;
2) inserting a spacer corresponding to said protospacer into the CRISPR array of said CRISPR-Cas system of said bacterial strain;
3) exposing said bacterial strain obtained by step 2) to a set of virulent phages comprising said protospacer, wherein each phage of the set is exposed to said bacterial strain independently;
4) identifying among said set of phages, the ones which are still virulent against said bacterial strain of step 2) and selecting these phages;
5) identifying within the genome of the selected phages in step 4) the gene or the genes interfering with the interference function of said given CRISPR-Cas system.

Figure 2:
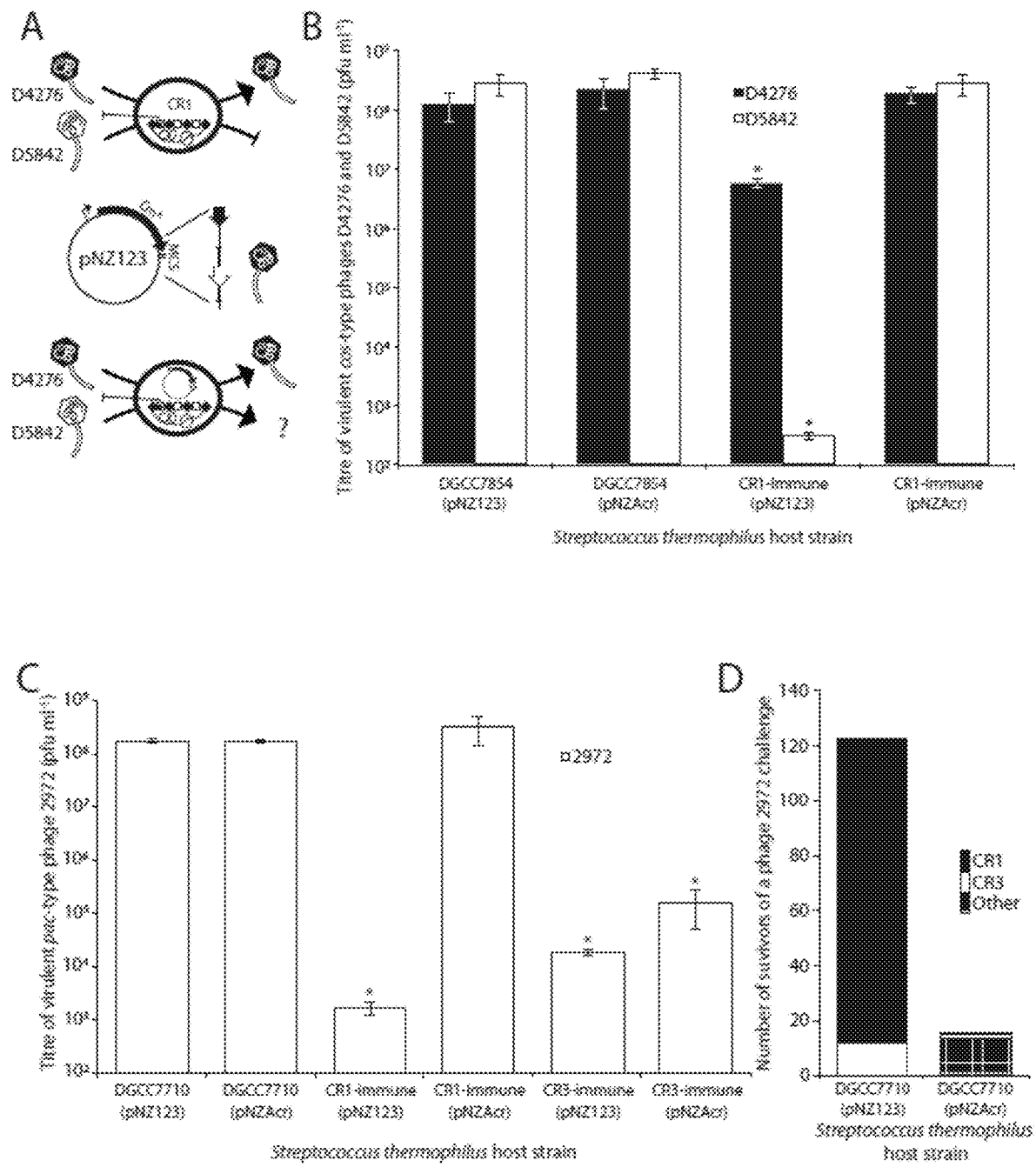
FIG. 2 provides a representative anti-CRISPR activity of the Acr protein (SEQ ID NO:10) in Streptococcus thermophilus. (A) Genes cloned from the CRISPR restrictive (black capsid) phage D4276 were expressed in the DGCC7854-derived immunized strain, and the resulting transformants were assayed for increased sensitivity to the permissive (white capsid) phage D5842. (B) Titer of the restrictive (black) cos-type phage D4276 and permissive (white) cos-type phage D5842 on the naïve DGCC7854 or its CR1-immune derivative, carrying either the empty vector pNZ123 or the vector expressing the acr gene (SEQ ID NO:9) (pNZAcr). Each column depicts the average of three biological replicates, each of three technical replicates. (C) Titer of the permissive (white) pac-type phage 2972 on the naïve DGCC7710, a CRISPR1-immune mutant or a CRISPR3-immune mutant carrying either the empty vector pNZ123 or the vector expressing the acr gene (pNZAcr). Each column depicts the average of three biological replicates, each of three technical replicates. In (B) and (C), error bars represent the standard deviation, and an asterisk denotes a difference ($p<0.001$) from all other data, while no other strain differed from any other ($p>0.5$) as determined by one-way ANOVA and Tukey HSD test. (D) Number and characterization of survivors following a phage 2972 challenge of DGCC7710, carrying either the empty vector pNZ123 or the vector expressing the acr gene (pNZAcr). The single CRISPR1 acquisition detected in the presence of the anti-CRISPR targeted the plasmid and not the phage. CRISPR3 acquisitions targeted the phage, as expected. All cells maintained an intact acr gene.

The protospacer of step 1) is as defined herein, and can be identified according to the considered CRISPR-Cas system (class, type), taking into consideration, if needed, the presence of a protospacer adjacent motif (PAM). The spacer of step 2) is to be inserted in the CRISPR array of the CRISPR-Cas system considered when identifying the protospacer; the CRISPR spacer is inserted as a repeat-spacer unit, such that the spacer is flanked by two repeats. For the design of the set of virulent phages, the presence of the protospacer in the genome of said phages is determined as for step 1), i.e., taking into consideration, if needed, the presence of said protospacer adjacent motif (PAM). The identification of anti-CRISPR gene(s) in step 5) can be performed for example as detailed in the experimental part, i.e., by a systematic cloning of the genes of said selected phage(s) into a vector to obtain constructs, then introducing independently these constructs into the strain of step 2), expressing the genes borne by these constructs, exposing independently the transformed strains to the virulent phage from which each gene comes from, identifying which construct (and thus gene) enables said phage to still be virulent on the transformed strain, wherein said gene is anti-CRISPR gene (see FIG. 2A).

In another aspect, the invention is directed to methods to trigger the death of a bacterial population. In a first embodiment, the method comprises:

1) providing a bacterial population, wherein the genome of said bacterial strains comprises in the CRISPR array of a given CRISPR-Cas system at least one self-targeting spacer(s) and a gene encoding a protein which interferes with the interference function of said given CRISPR-Cas system (gene encoding an anti-CRISPR protein); and
2) inactivating the expression of said gene encoding a protein which interferes with the interference function of said given CRISPR-Cas system, wherein said inactivation relieves the interference mediated by said anti-CRISPR protein on the interference function of said given CRISPR-Cas system, what results in the cleavage of said at least one self-targeting spacer(s) and the death of said bacterial population.

In said first embodiment, as defined herein "self-targeting spacer" means a spacer sequence corresponding to a protospacer (as defined herein) the sequence of which is present in the genome of said bacteria (associated with a PAM if required) and can therefore be cleaved by the associated CRISPR-Cas system. The inactivation of said anti-CRISPR gene can be performed by any method known from the person skilled in the art. An example, includes but is not limited to, expressing a repressor which prevents the transcription of said anti-CRISPR gene.

In a second embodiment, the method comprises:

1) providing a bacterial population, wherein the genome of said bacterial strains comprises in the CRISPR array of a given CRISPR-Cas system at least one spacer(s) corresponding to the protospacer of a virulent phage and a gene encoding a protein which interferes with the interference function of said given CRISPR-Cas system, wherein said gene is not expressed; and
2) expressing said gene encoding a protein which interferes with the interference function of said given CRISPR-Cas system; and
3) exposing said bacterial population to said virulent phage, wherein the expression of said gene is performed before or simultaneously to the exposure to said virulent phage, and wherein said expression downmodulates the interference function of said given CRISPR-Cas system on said phage, what results in the cleavage of said at least one spacer(s) and the death of said bacterial population.

In said second embodiment, the protospacer of step 1) is as defined herein, and can be identified according to the considered CRISPR-Cas system (class, type), taking into consideration, if needed, the presence of a protospacer adjacent motif (PAM). The spacer is to be inserted in the CRISPR array of the CRISPR-Cas system considered when identifying the protospacer. The anti-CRISPR gene is functional when expressed. Expression of said anti-CRISPR gene in step 2) can be performed by any method known from the person skilled in the art. Example includes, but is not limited to, expressing a protein, which activates the transcription of said anti-CRISPR gene (by for example an inducible promoter). Said activator can for example be produced from a plasmid introduced into said bacterial strain in step 2). Said activator can also be for example be produced from a gene previously inserted into the genome of the virulent phage exposed in step 3).

In an embodiment, when a method as described above referred to a CRISPR-Cas system, said system is a class 2 CRISPR-Cas system. In an embodiment, said system is a class 2 type II CRISPR-Cas system. In an embodiment, said system is a class 2 type II-A CRISPR-Cas system.

In an embodiment, taken alone or in combination with the previous paragraph, when a method as described above referred to a protein which interferes with a function of a CRISPR-Cas system, said protein interferes with the interference function of said CRISPR-Cas system. In an embodiment, said protein interferes with the interference function of a class 2 CRISPR-Cas system. In an embodiment, said protein interferes with the interference function of a class 2 type II CRISPR-Cas system. In an embodiment, said protein interferes with the interference function of a class 2 type II-A CRISPR-Cas system.

In an embodiment, when a method as described above referred to a protein which interferes with a function of a CRISPR-Cas system, said protein interferes with the interference function of a CRISPR1-Cas system of a *Streptococcus thermophilus*. In an embodiment, when a method as described above referred to a protein which interferes with a function of a CRISPR-Cas system, said protein interferes with the interference function of a CRISPR3-Cas system of a *Streptococcus thermophilus* strain.

In an embodiment, said protein which interferes with a function of a class 2 type II CRISPR-Cas system downmodulates the activity of a Cas9 protein, component of said class 2 type II CRISPR-Cas system, and in particular at least one its activities as defined herein. In an embodiment, said protein downmodulates the activity of a Cas9 protein of a *Staphylococcus* genus strain, such as a Cas9 protein of a *Staphylococcus aureus* strain. In another embodiment, said protein downmodulates the activity of a Cas9 protein of a *Streptococcus* genus strain, such as a Cas9 protein of a *Streptococcus thermophilus* strain or a *Streptococcus pyogenes* strain. In an embodiment, said protein downmodulates the activity of the Cas9 protein of a CRISPR1-Cas system of a *Streptococcus thermophilus*. In an embodiment, said protein downmodulates the activity of the Cas9 protein of a CRISPR3-Cas system of a *Streptococcus thermophilus*. In an embodiment, said protein downmodulates the activity of the Cas9 protein of a CRISPR1-Cas system and CRISPR3-Cas system of a *Streptococcus thermophilus*.

In an embodiment, when a method as described above referred to a protein which interferes with a function of a CRISPR-Cas system, in particular a protein which interferes with a function of a class 2 type II CRISPR-Cas system, in particular a protein which interferes with the interference function of a class 2 type II CRISPR-Cas system, said protein is an anti-CRISPR protein having a sequence as disclosed herein [in the anti-CRISPR proteins paragraph]. In particular, said protein has the sequence as defined in a SEQ ID NO of a Acr family selected from the group consisting of Acr1 to Acr86 families of Table 1, or has the sequence as defined in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552. In an embodiment, said protein has a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 as defined herein, or has a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 as defined herein.

In an embodiment, when a method as described above referred to a protein which interferes with the interference function of a class 2 type II CRISPR-Cas system, said protein has a sequence as defined in SEQ ID NO: 2, 4, 6, 8, 10, 12, 14, 16, 18, 20, 22, 24 or 26. In an embodiment, said protein has a sequence having at least 70% similarity with SEQ ID NO: 2, 4, 6, 8, 10, 12, 14, 16, 18, 20, 22, 24 or 26, or has a sequence having at least 90% identity with SEQ ID NO: 2, 4, 6, 8, 10, 12, 14, 16, 18, 20, 22, 24 or 26, and is an anti-CRISPR protein as defined herein.

In an embodiment, when a method as described above referred to a gene encoding a protein which interferes with a function of a CRISPR-Cas system, in particular a protein which interferes with a function of a class 2 type II CRISPR-Cas system, in particular a protein which interferes with the interference function of a class 2 type II CRISPR-Cas system, said gene has a sequence as defined above [anti-CRISPR genes paragraph] or has a sequence encoding an anti-CRISPR protein as defined herein [anti-CRISPR proteins paragraph]. In particular, said gene has a sequence encoding an anti-CRISPR protein having a sequence as defined in a SEQ ID NO of a Acr family selected from the group consisting of Acr1 to Acr86 families of Table 1, or an anti-CRISPR protein having the sequence as defined in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552, or having a sequence having at least 70% similarity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 as defined herein, or having a sequence having at least 90% identity with SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550 or 552 as defined herein. In an embodiment, said anti-CRISPR gene has a sequence as defined herein, and in particular has the sequence as defined in a SEQ ID NO of a Acr family selected from the group consisting of Acr1 to Acr86 families of Table 1, or has the sequence as defined in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551, or is a conservative variant of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549 or 551 as defined herein. In an embodiment, when a method as described above referred to a gene encoding a protein which interferes with the interference function of a class 2 type II CRISPR-Cas system, said gene has a sequence encoding an anti-CRISPR protein as defined herein, in particular has a sequence encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26. In an embodiment, said anti-CRISPR gene has a sequence as defined in SEQ ID NO: 1, 3, 5, 7, 9, 11, 13, 15, 17, 19, 21, 23 or 25 or is a conservative variant of SEQ ID NO: 1, 3, 5, 7, 9, 11, 13, 15, 17, 19, 21, 23 or 25 as defined herein.

In an embodiment, when a method as described above referred to the expression of an anti-CRISPR gene in a bacterial strain, said expression is constitutive as defined herein. In another embodiment, the expression of said anti-CRISPR gene in a bacterial strain is inducible.

In an embodiment, when a method as described above referred to a bacterial strain, said strain is not of *Listeria* genus. In a particular embodiment, said strain is not of *Listeria* genus, when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26.

In an embodiment, when a method as described above referred to a bacterial strain, said strain is not of *Neisseria* genus. In a particular embodiment, said strain is not of *Neisseria* genus, when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26.

In an embodiment, when a method as described above referred to a bacterial strain, said strain is neither of *Listeria* genus nor *Neisseria* genus. In a particular embodiment, said strain is neither of *Listeria* genus nor *Neisseria* genus, when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26.

In an embodiment, when a method as described above referred to a bacterial strain, said strain is a Gram-positive bacterial strain which is not of *Listeria* genus. In a particular embodiment, said strain is a gram-positive strain which is not of *Listeria* genus, when said gene is not a gene encoding an anti-CRISPR protein having a sequence as defined in SEQ ID NO: 2, 4, 6, 8, 10, 12, 14, 16, 18, 20, 22, 24 or 26, having a sequence having at least 70% similarity with SEQ ID NO: 2, 4, 6, 8, 10, 12, 14, 16, 18, 20, 22, 24 or 26, or having a sequence having at least 90% identity with SEQ ID NO: 2, 4, 6, 8, 10, 12, 14, 16, 18, 20, 22, 24 or 26.

In an embodiment, when a method as described above referred to a bacterial strain, said strain is a Gram-positive bacterial strain. In an embodiment, the bacterial strain is a lactic acid bacterium. In an embodiment, said bacterial strain is selected from a *Bifidobacterium* species, a *Brevibacterium* species, a *Propionibacterium* species, a *Lactococcus* species, a *Streptococcus* species, a *Lactobacillus* species, an *Enterococcus* species, a *Pediococcus* species, a *Leuconostoc* species and an *Oenococcus* species. In an embodiment, said bacterial strain is a *Streptococcus* species. Suitable species include, but are not limited to *Lactococcus lactis*, including *Lactococcus lactis* subsp. *lactis* and *Lactococcus lactis* subsp. *cremoris*, *Leuconostoc* sp., *Lactococcus lactis* subsp. *lactis* biovar, *Streptococcus thermophilus*, *Lactobacillus delbrueckii* subsp. *bulgaricus*, *Lactobacillus helveticus*, *Bifidobacterium lactis*, *Lactobacillus acidophilus*, *Lactobacillus casei*. In an embodiment, said bacterial strain is selected from a *Streptococcus thermophilus* strain and a *Streptococcus pyogenes* strain. In an embodiment, said bacterial strain is a *Streptococcus thermophilus* strain. In an embodiment, said bacterial strain is a *Streptococcus pyogenes* strain.

All publications and patent applications mentioned in the specification are indicative of the level of those skilled in the art to which this disclosure pertains, and all such publications and patent applications are herein incorporated by reference to the same extent as if each individual publication or patent application was specifically and individually indicated to be incorporated by reference.

EXAMPLES

Example 1

Materials and Methods

As *Streptococcus thermophilus* is a model for the study of CRISPR adaptation, a detailed step-by-step protocol for many of the methods used here is available elsewhere.

Strain Culturing

*S. thermophilus* cultures were grown in M17 medium (Oxoid, Ontario, Canada) supplemented with 0.5% w/v lactose (LM17). Chloramphenicol, when necessary, was added at 5 µg/ml. When used to generate an overnight culture for use the following day, cultures were grown at 37° C. without shaking. In all other cases, they were grown at 42° C. without shaking. If phages were to be added, the media was further supplemented with 10 mM $CaCl_2$.

*Lactococcus lactis* cultures were grown in M17 medium (Oxoid, Ontario, Canada) supplemented with 0.5% w/v glucose monohydrate (GM17). Chloramphenicol or erythromycin, when necessary, were added at 5 µg/ml. Cultures were grown at 30° C. without shaking, except when the activity of an SpCas9-containing construct was assayed, in which case incubations took place at 33° C. If phages were to be added, the media was further supplemented with 10 mM $CaCl_2$.

*Escherichia coli* cultures were grown in LB medium. Chloramphenicol, when necessary, was provided at 20 µg/ml. Cultures were grown at 37° C. with shaking.

Phage Amplification

A scraping from a phage lysate preserved at −80° C. with 15% glycerol was co-inoculated with its host strain, in media supplemented with 10 mM $CaCl_2$, and grown until complete lysis was observed. This first amplification lysate was then filtered through a 0.45 µm PES filter, and 100 µl used to inoculate its host strain grown to an $OD_{600}$ of 0.1 in media supplemented with 10 mM $CaCl_2$. This second amplification lysate was also filtered through a 0.45 µm PES filter, then stored at 4° C.

Phage Titreing

1) Spot test (FIG. 1): Phages were serially diluted in phage buffer (50 mM Tris-HCl, pH 7.5, 100 mM NaCl, 8 mM $MgSO_4$). Three ml of molten 0.75% agar medium at 55° C., supplemented with 10 mM $CaCl_2$, was inoculated with 300 µl of an overnight culture of the host strain, then rapidly poured over a pre-set plate of the same medium with 1% agar. The plate was allowed to set and dry. Phage dilutions, 3 ul from each, were spotted onto the dry overlay and allowed to dry for 20 min. The plates were then incubated overnight, and plaques counted at the lowest dilution at which they were visible.

2) Full, (FIG. 2): Phages were serially diluted in phage buffer. Three ml of molten 0.75% agar medium at 55° C., supplemented with 10 mM $CaCl_2$, is co-inoculated with 300 µl of an $OD_{600}$ 0.6 culture of the host strain and 100 µl of diluted phage. The plates were then incubated overnight, and plaques counted from plates with between 30-300 plaques.

Immunizing Assays

These are also referred to as "BIM assays" (Bacteriophage Insensitive Mutants). Phages were diluted in phage buffer in order to obtain a final multiplicity of infection (MOI) of 0.1 plaque forming units per colony forming units (pfu/cfu). Three ml of molten 0.75% agar medium at 55° C., supplemented with 10 mM $CaCl_2$) was co-inoculated with 300 μl of a culture at an $OD_{600}$ of 0.6 (~$1.2×10^8$ cfu/ml) of the host strain and 100 μl of the appropriate phage dilution. The plates were then incubated overnight, and surviving colonies counted.

Characterization of Surviving Colonies

Random surviving bacterial colonies were screened by PCR for acquisition of new spacers at the CRISPR1 & CRISPR3 loci (S. thermophilus strain DGCC7710) or CRISPR1 locus (S. thermophilus strain DGCC7854). An increase in the size of the PCR product relative to the wild type was indicative of CRISPR immunization. The resulting PCR products were sequenced to confirm the identity of the newly acquired spacer. For assays in FIG. 2, presence of the insert in pNZAcr was confirmed by sequencing in cells that had acquired spacers.

Transformation

Commercial NEB5α E. coli cells were transformed according to the manufacturer's recommendations (New England Biolabs, Ontario, Canada). S. thermophilus strains were transformed by growing them to an $OD_{600}$ of 0.4, subjecting them to a glycine shock for 1 h, repeated washes and then electroporation. L. lactis strains were transformed using a similar glycine-based protocol.

Plasmid Programming

A plasmid was designed to contain a protospacer (CRISPR-acquirable sequence) targeting the five phages used in the challenges. Two oligos consisting of a conserved protospacer in the gene encoding the tape measure protein, as well as overhangs suited for cloning, were annealed together by mixing them in equal parts, heating them to 98° C., then cooling them slowly to 50° C. This annealed construct was then ligated directly into an EcoRI/XhoI double-digested pNZ123, transformed into commercial NEB5α, and selected for with chloramphenicol. The constructed plasmid was then isolated using Qiaprep Spin Miniprep kit (Qiagen, Ontario, Canada) according to the manufacturer's recommendations. S. thermophilus DGCC7854 was transformed with this plasmid, pNZ5phage, then grown in the absence of selection for 7 generations and subjected to an immunizing assay (see above) with virulent phage D5842. The surviving colonies had naturally acquired the desired spacer from the plasmid, immunizing them to the phages. The spacer sequence was confirmed as described in "characterization of surviving colonies" above.

Phage Genome Sequencing & Annotation

DNA from the phage D4276 was purified using a PureLink Viral RNA/DNA kit (Invitrogen, MA, USA). The purified DNA was sequenced on a MiSeq system using a MiSeq reagent kit v2 after preparation using the Nextera XT DNA library preparation kit (Illumina, British Columbia, Canada). The resulting reads assembled using Ray version 2.2.0 (32). The genome was annotated using NCBI ORF finder and GeneMark.hmm prokaryotic, and those annotations then manually curated based on comparisons to related phages.

Phage Gene Cloning and pNZAcr Construction

Primers were designed to systematically clone all of phage D4276 into pNZ123 oriented so as to drive transcription from the promoter upstream of the chloramphenicol resistance gene, cat. Initially, inserts were designed to contain several genes, but if cloning failed the inserts were redesigned as smaller, single-gene constructs. The gene of greatest interest, D4276_028, exemplifies this cloning technique. Primers were designed to amplify the gene and append 30 nt extensions overlapping the pNZ123 MCS (5'-ATTACAGCTCCAGATCCAGTACTGAATTCTCGCT-GATGGTGATAGCATTGG-3' and 5'-GAAAATATGCACTCGAGAAGCTT-GAGCTCTTGCTTTCGCAGTCTCGAATT-3'). The amplified gene was then cloned by Gibson reaction into XhoI digested pNZ123. The resulting plasmid, pNZAcr, was transformed into commercial NEB5α, isolated using a Qiaprep Spin Miniprep kit, and then transformed into the relevant S. thermophilus and L. lactis strains. The sequence of the insert was confirmed by sequencing using primers (5'-AATGTCACTAACCTGCCCCG and CATTGAA-CATGCTGAAGAGC-3').

Plasmid Loss Assays

Cultures carrying pNZAcr were serially grown in the absence of selection, inoculating fresh 10 ml of LM17 broth media with 100 μl of a culture grown to saturation. This was repeated 5 times. Dilutions of the resulting culture were spread upon plates in order to obtain isolated colonies, and 120 such colonies were then patch-plated on LM17 with and without chloramphenicol. Colonies, which grew on LM17 (all 120) but failed to grow on LM17 Cm (two), were screened by PCR to confirm plasmid loss using pNZinsF and pNZinsR, and their CRISPR1 locus was amplified to confirm the presence of the immunizing spacer. Colonies were then used to titer the phages D4276 and D5842, and confirm that they had regained resistance to the phages from losing the plasmid.

pL2Cas9-44 Construction pL2Cas9 (Lemay et al. 2017) is a derivative of the lactococcal vector pTRKL2 (O' Sullivan et al. 1993) with the SpCas9 module of pCas9 (Jiang et al. 2013). A pair of oligos consisting of a spacer sequence targeting orf44 of phage p2 and overhangs for ligation into pL2cas9 were designed (5'-AAACTCCGTTACAATTAGAACAAAAT-TCTTGTTTG-3' and 5'-AAAACAAACAAGAAT-TTTGTTCTAATTGTAACGGA-3'). They were annealed together by mixing them in equal parts, heating them to 98° C., then cooling them slowly to 50° C. This annealed construct was then ligated directly into digested pL2Cas9 and transformed directly into L. lactis. The resulting transformants were screened by PCR amplification and sequencing to confirm the presence of the desired spacer, using primers (5'-GTTCTTAGTGCATATAACAAACATAGA-GAC-3' and 5'-CCAAGTAGCGAAGCGAGC-3').

Efficiency of Centres of Infection (ECOI)

Figure 3:
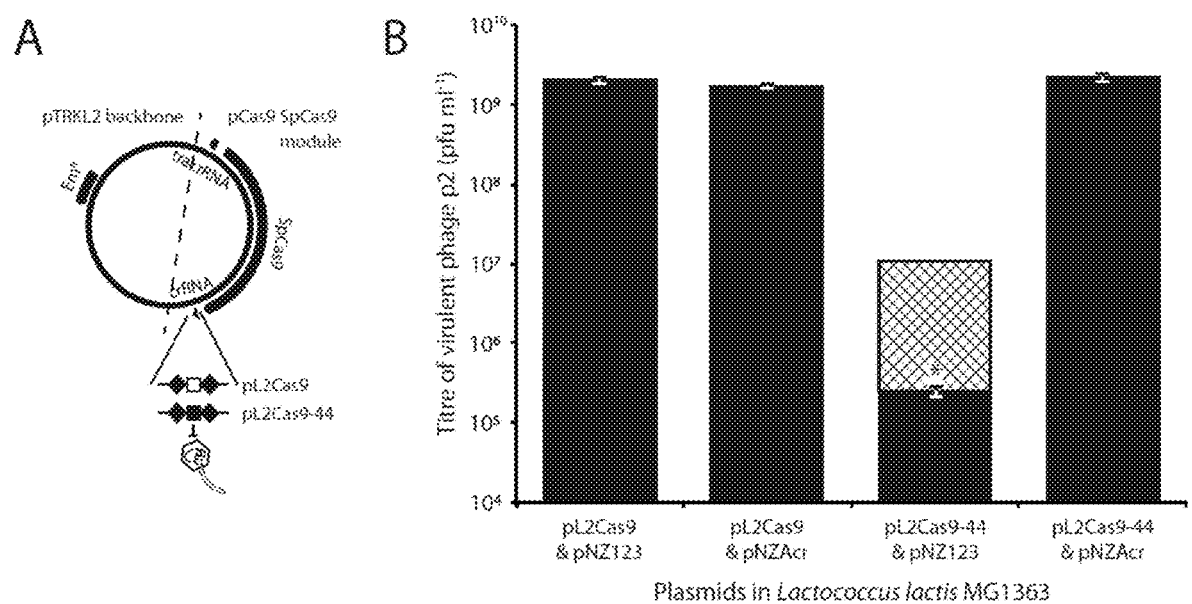
FIG. 3 provides schematic representation of one example of anti-CRISPR activity against SpCas9 (A) Generating an immunized Lactococcus lactis MG1363 strain. pL2Cas9 (24) contains the SpCas9 module from pCas9 (23) on a pTRKL2 (30) vector backbone. A spacer targeting orf44 of L. lactis virulent phage p2 was cloned-in to create a phage-targeting SpCas9. (B) The titer of virulent phage p2 on its host L. lactis MG1363 carrying either pL2Cas9 or pL2Cas9 targeting the phage (pL2Cas9-44), and either the empty vector pNZ123 or the vector expressing the acr gene (pNZAcr). The titer was assayed by spot test, and each bar represents an average of three biological replicates, each of three technical replicates. Only plaques with typical morphology were counted, although a secondary morphology of tiny plaques occasionally appeared when plated on pL2Cas9-44 with pNZ123. While these plaques were not reliably countable, the maximum threshold at which they appeared is depicted by a patterned box. Error bars represent the standard deviation, and an asterisk denotes a difference ($p<0.001$) from all other data, while no other strain differed from any other ($p>0.5$) as determined by one-way ANOVA and Tukey HSD test.

Cultures of all four strains depicted in FIG. 3B were grown at 33° C. to an $OD_{600}$ of 0.8 (~$1.9*10^8$ cfu/ml), 2 ml spun down and resuspended 1 ml in fresh GM17 media with 10 mM $CaCl_2$. Then, phage p2 was added to an MOI of 0.2, mixed by inversion, and given 5 min to allow adsorption to the cells at 33° C. The phage-cell mix was then spun down and resuspended in fresh media thrice in order to wash away unbound phages, then serially diluted. 100 μl of the resulting dilutions were then added to 300 μl of indicator strain (MG1363 pNZ123 pL2Cas9), embedded in a soft agar overlay (see phage titreing), and incubated at 33° C. overnight.

Results

Streptococcus thermophilus has become a model for acquisition of new CRISPR immunities, shares its genus with the source of SpCas9, and its active CRISPR-Cas systems are also of type II-A. A set of five virulent phages infecting *S. thermophilus* strain DGCC7854 proved ideal for identifying phages that were less likely to lead to the acquisition of new spacers (phage-derived sequences in the CRISPR array, conferring immunity); while two of the phages readily gave rise to CRISPR-immune colonies, three did not (FIG. 1, Top). The dearth of spacer acquisition from these three phages did not necessarily confirm the presence of anti-CRISPRs. Those phages could simply be more sensitive to non-CRISPR forms of resistance, be quicker to take over the host cell, or produce fewer immunogenic defective particles. It was necessary to establish whether the CRISPR-Cas system was impeded during the adaptation ('memorization' of new targets) or interference (cleavage of that target) process. Using plasmid-programming, a strain targeting a protospacer conserved in all five phage genomes was generated. Then, in plaquing each phage upon this strain, it was observed that four of the five phages suffered a drastic reduction (~6 Log) in titer, consistent with CRISPR interference, but one phage, D4276, did not (FIG. 1, bottom). These phages were categorized according to these CRISPR-interacting phenotypes; permissive (white) phages D5842 and D5843, impeded adaptation (fractal pattern) phages D1024 and D5891, and restrictive (black) phage D4276—a candidate to harbor an anti-CRISPR.

We set about systematically cloning genes from the restrictive phage D4276 into a vector where they could be expressed in the immunized strain (FIG. 2A). A phage gene encoding an anti-CRISPR protein should inactivate the pre-existing immunity and thereby restore the titer of a sensitive (permissive) phage plated upon the strain. In this manner, we found a new anti-CRISPR gene (acr gene, defined herein as SEQ ID NO:9 encoding an anti-CRISPR protein as defined in SEQ ID NO:10), which completely restored the immunized strain's sensitivity to the permissive phage D5842 (~6 Log increase), as well as increased sensitivity to the restrictive phage D4276 back to wild-type levels (FIG. 2B). We attribute this increase in titer for even the anti-CRISPR-containing phage D4276 to high anti-CRISPR production before phage exposure, which would otherwise be a time-sensitive process whereby production must outrace CRISPR activity. In order to ensure the gain-of-sensitivity phenotypes were due only to this anti-CRISPR, we allowed loss of the anti-CRISPR-bearing plasmid and confirmed a return-of-resistance phenotype (data not shown).

As all five phages infecting *S. thermophilus* DGCC7854 are related cos-type phages, we could not rule out that the anti-CRISPR might be dependent upon interaction with partner proteins present in these phages. Furthermore, strain DGCC7854 contains only a single active CRISPR-Cas system (CRISPR1), as opposed to the two systems (CRISPR1 & CRISPR3) commonly active in *S. thermophilus* strains. We ported our anti-CRISPR vector over to the well-characterized model strain, *S. thermophilus* DGCC7710, which is sensitive to an unrelated virulent pac-type phage, 2972—and for which we have strains immunized at either the CRISPR1 or CRISPR3 locus (FIG. 2C). In this system, the anti-CRISPR activity was maintained, completely restoring phage sensitivity to a CRISPR1-immunized strain, and partially restoring sensitivity for a CRISPR3-immunized strain. When we attempted immunizing assays on DGCC7710 bearing the acr gene, the number of surviving colonies fell sharply (FIG. 2D). Moreover, the nature of those survivors changed drastically. The number of CRISPR3-immune colonies dropped, a number of previously undetectable non-CRISPR mutants were observed, and whereas CRISPR1 immunizations normally compose upwards of 90% of surviving colonies, only a single colony with a CRISPR1 spacer acquisition was recovered (FIG. 2D). Of note, the CRISPR1 spacer in question targeted the plasmid (still present and carrying an intact acr gene), rather than the phage genome. This indicates that the Acr protein likely impedes Cas9-mediated cleavage, but not Cas9's role in spacer acquisition.

The Acr protein (SEQ ID NO:10) is 140 amino acids long and is predicted to contain a distinctive coiled-coil motif, which might act in a nucleic acid binding role, similar to HTH and AP2 motifs associated with other anti-CRISPR proteins. We have found several new anti-CRISPR genes both in phage genome (SEQ ID NO: 1, 3, 5, 11, 13, 15 and 17 encoding respectively anti-CRISPR protein as defined in SEQ ID NO: 2, 4, 6, 12, 14, 16 and 18) as well as in the genome of *Streptococcus* strains (SEQ ID NO:5, 7, 19, 21, 23 and 25 encoding respectively anti-CRISPR protein as defined in SEQ ID NO: 6, 8, 20, 22, 24 and 26).

Finally, despite the fact that the genome-editing tool SpCas9 (Cas9 from *S. pyogenes*) is more closely related to the Cas9 of the CRISPR3 system of *S. thermophilus*, we were keen to determine whether the Acr protein would have any effectiveness against SpCas9. We initially attempted to assay the effectiveness of Acr (pNZAcr) on SpCas9 (pCas9) in *Escherichia coli*, but despite the ability to clone each separately, the two systems were not able to co-exist. We suspect some aspect of the ACR-Cas9 interaction is pernicious to *E. coli*. Instead, we used a pCas9 derivative adjusted for use in *Lactococcus lactis*, with demonstrated efficacy in the genome-editing of virulent phages (FIG. 3A). The pL2Cas9-44 construct, targeting orf44 of the virulent phage p2, resulted in a 4 Log decrease in measurable phage titer (FIG. 3B), which was completely restored by the presence of the acr gene. This is the strongest reported anti-CRISPR activity against SpCas9 to date.

The 4 Log reduction associated with pL2Cas9-44 was also accompanied by a 'tiny plaque' phenotype that proved difficult to quantify, as they were only observable on some technical replicates. The maximum number of tiny plaques observed is displayed in pale orange (FIG. 3B). We characterized the phenotype and genotype of these smaller plaques, establishing that they were CRISPR-bypassing mutants genetically indistinguishable from those in the larger plaques, but arising only after several rounds of replication on the 'leaky' targeting strain. Notably, however, the expression of the ACR completely rescued both the titer and the tiny-plaque phenotype.

The Acr protein (SEQ ID NO:10) is the first anti-CRISPR protein with demonstrated activity from a virulent phage, is structurally distinct from previously characterized anti-CRISPRs, and displays the strongest in vivo activity against SpCas9 to date.

Example 2

Materials and Methods

Strain culturing, phage amplification, phage titreing, immunizing assays, characterization of surviving colonies and transformation were done the same way as in example 1.

Phage Genome Sequencing & Annotation

DNA from the phage D1811 was purified using a PureLink Viral RNA/DNA kit (Invitrogen, MA, USA). The purified DNA was sequenced on a MiSeq system using a MiSeq reagent kit v2 after preparation using the Nextera XT DNA library preparation kit (Illumina, British Columbia, Canada). The resulting reads assembled using Ray version 2.2.0 (32). The genome was annotated using NCBI ORF finder and GeneMark.hmm prokaryotic, and those annotations then manually curated based on comparisons to related phages.

Phage Gene Cloning and pNZAcr Construction

Primers were designed to amplify a gene of interest, D1811_026, and append 30 nt extensions overlapping the pNZ123 MCS (5'-ATTACAGCTCCAGATCCAGTACT-GAATTCTTCGCTGAAAAAGTTTGGGAAGT-3' and 5'-GAAAATATGCACTCGAGAAGCTT-GAGCTCTCCTCTCTCTTATGATAGTCTGCCA-3'). The amplified gene was then cloned by Gibson reaction into XhoI digested pNZ123. The resulting plasmid, pNZAcr-1811, was transformed into commercial NEB5α, isolated using a Qiaprep Spin Miniprep kit, and then transformed into the relevant S. thermophilus. The sequence of the insert was confirmed by sequencing using primers (5'-AATGT-CACTAACCTGCCCCG and CATTGAACATGCT-GAAGAGC-3').

Plasmid Loss Assays

Cultures carrying pNZAcr were serially grown in the absence of selection, inoculating fresh 10 ml of LM17 broth media with 100 μl of a culture grown to saturation. This was repeated 14 times. Dilutions of the resulting culture were spread upon plates in order to obtain isolated colonies, and 160 such colonies were then patch-plated on LM17 with and without chloramphenicol. Colonies, which grew on LM17 (all 120) but failed to grow on LM17 Cm (two), were screened by PCR to confirm plasmid loss using pNZinsF and pNZinsR, and their CRISPR1 locus was amplified to confirm the presence of the immunizing spacer. Colonies were then used to titer the phages D1811 and D5842, and confirm that they had regained resistance to the phages from losing the plasmid.

Results

In plaquing an additional phage (D1811) upon the DGCC7854 strain, it was observed that this phage suffered a much smaller reduction in titer than 4 other related phages (FIG. 1, bottom). This phage was categorized as restrictive (black) phage.

Figure 4:
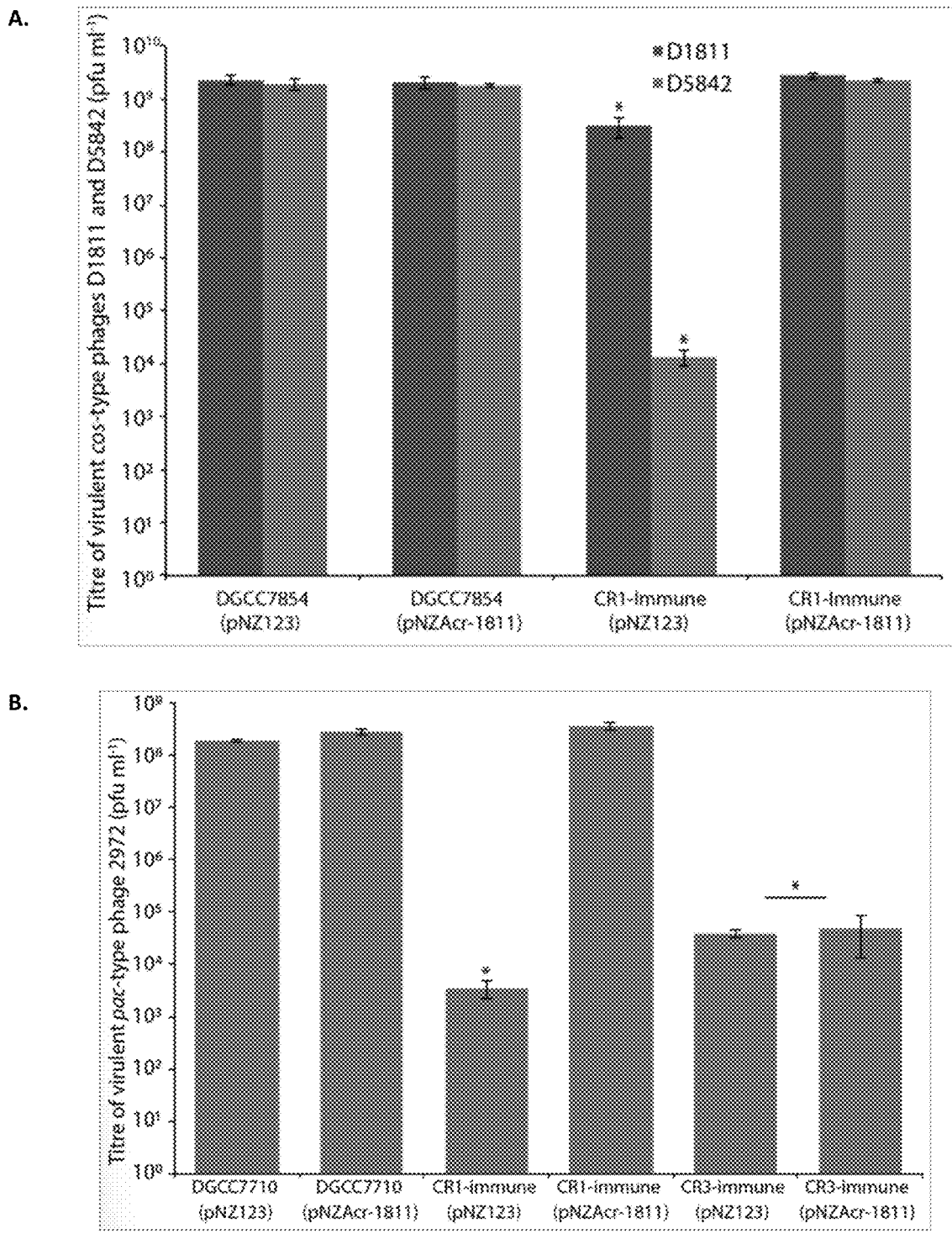
FIG. 4 provides a representative anti-CRISPR activity of the Acr2 protein (SEQ ID NO:28) in Streptococcus thermophilus. (A) Titer of the restrictive (black) cos-type phage D1811 and permissive (white) cos-type phage D5842 on the naïve DGCC7854 or its CR1-immune derivative, carrying either the empty vector pNZ123 or the vector expressing the acr2 gene (SEQ ID NO:27) (pNZAcr). Each column depicts the average of three biological replicates, each of three technical replicates. (B) Titer of the permissive (white) pac-type phage 2972 on the naïve DGCC7710, a CRISPR1-immune mutant or a CRISPR3-immune mutant carrying either the empty vector pNZ123 or the vector expressing the acr2 gene (pNZAcr). Each column depicts the average of three biological replicates, each of three technical replicates. In (A) and (B), error bars represent the standard deviation, and an asterisk denotes a difference ($p<0.001$) from all other data, while no other strain differed from any other ($p>0.5$) as determined by one-way ANOVA and Tukey HSD test.

We found a second new anti-CRISPR gene (acr2 gene, defined herein as SEQ ID NO:27 encoding an anti-CRISPR protein as defined in SEQ ID NO:28), which completely restored the immunized strain's sensitivity to the permissive phage D5842 (~5 Log increase), as well as increased sensitivity to the restrictive phage D1811 back to wild-type levels (FIG. 4A). We attribute this increase in titer for even the anti-CRISPR-containing phage D1811 to high anti-CRISPR production before phage exposure, which would otherwise be a time-sensitive process whereby production must outrace CRISPR activity. In order to ensure the gain-of-sensitivity phenotypes were due only to this anti-CRISPR, we allowed loss of the anti-CRISPR-bearing plasmid and confirmed a return-of-resistance phenotype (data not shown).

Since D1811 is related to the five other phages disclosed in example 1, we could not rule out that the anti-CRISPR might be dependent upon interaction with partner proteins present in these phages. We ported our anti-CRISPR vector over to the well-characterized model strain, S. thermophilus DGCC7710, which is sensitive to an unrelated virulent pac-type phage, 2972—and for which we have strains immunized at either the CRISPR1 or CRISPR3 locus (FIG. 4B). In this system, the anti-CRISPR activity was maintained, completely restoring phage sensitivity to a CRISPR1-immunized strain.

The Acr2 protein (SEQ ID NO:28) is 183 amino acids long. We have found several new anti-CRISPR genes both in phage genome (SEQ ID NO: 29, 31, 33, 35, 37, 39, 41, 43, 45, 47, 49, 51, 53, 55, 57, 59, 61, 63, 65, 67, 69, 71, 73, 75, 77, 79 and 81 encoding respectively anti-CRISPR protein as defined in SEQ ID NO: 30, 32, 34, 36, 38, 40, 42, 44, 46, 48, 50, 52, 54, 56, 58, 60, 62, 64, 66, 68, 70, 80 and 82) as well as in the genome of Streptococcus strains (SEQ ID NO: 83 and 85 encoding respectively anti-CRISPR protein as defined in SEQ ID NO: 84 and 86).

Example 3

Based on the location of the genes encoding the Acr1 and Acr2 proteins in phage genomes (examples 1 and 2), the corresponding region [immediately downstream of the lysin gene] was analyzed in silico in more than 250 phage genomes, considering more than 3,000 coding sequences (CDS). After clustering of these CDS based on blastn and a manual screening step (taking into account the genetic environment, predicted protein size, and elimination of genes with known function), 233 potential ACR genes (SEQ ID NOs 87 to 551) grouped into 84 families (Acr3 to Acr86 families) were identified.

These 84 families, and the corresponding SEQ ID NOs of the ACR genes and SEQ ID NOs of the ACR proteins encoded by these ACR genes are detailed in Table 1 above.

REFERENCES

Barrangou, R. et al. CRISPR provides acquired resistance against viruses in prokaryotes. Science 315, 1709-1712 (2007).

Bondy-Denomy, J., Pawluk, A., Maxwell, K. L. & Davidson, A. R. Bacteriophage genes that inactivate the CRISPR/Cas bacterial immune system. Nature 493, 429-32 (2013).

Bondy-Denomy, J. et al. Multiple mechanisms for CRISPR-Cas inhibition by anti-CRISPR proteins. Nature 526, 136-139 (2015).

Chylinski K. et al. Classification and evolution of type II CRISPR-Cas systems. Nucleic Acid Research 42(10): 6091_6105 (2014).

Chowdhury, S. et al. Structure reveals mechanisms of viral suppressors that intercept a CRISPR RNA-guided surveillance complex. Cell 169, 47-57.e11 (2017).

Jiang, W., Bikard, D., Cox, D., Zhang, F. & Marraffini, L. A. RNA-guided editing of bacterial genomes using CRISPR-Cas systems. Nat Biotechnol 31, 233-239 (2013)

Jinek, M. et al. A programmable dual-RNA-guided DNA endonuclease in adaptive bacterial immunity. Science 337, 816-821 (2012).

Labrie, S. J., Samson, J. E. & Moineau, S. Bacteriophage resistance mechanisms. Nat Rev Micro 8, 317-327 (2010).

Lemay, M.-L., Tremblay, D. M. & Moineau, S. Genome engineering of virulent lactococcal phages using CRISPR-Cas9. ACS Synth Biol (2017).

Makarova, K. S. et al. An updated evolutionary classification of CRISPR-Cas systems. Nat Rev Microbiol 13, 722-736 (2015).

Makarova, K. S., Zhang, F. & Koonin, E. V. SnapShot: class 2 CRISPR-Cas systems. Cell 168, 328-328.e1 (2017).

Maxwell, K. L. et al. The solution structure of an anti-CRISPR protein. Nat Commun 7, 13134 (2016).

O'Sullivan, D. J. & Klaenhammer, T. R. High- and low-copy-number *Lactococcus* shuttle cloning vectors with features for clone screening. Gene 137, 227-231 (1993)

Pawluk, A., Bondy-Denomy, J., Cheung, V. H. W., Maxwell, K. L. & Davidson, A. R. A new group of phage anti-CRISPR genes inhibits the type I-E CRISPR-Cas system of *Pseudomonas aeruginosa*. MBio 5, e00896-14 (2014).

Pawluk, A. et al. Inactivation of CRISPR-Cas systems by anti-CRISPR proteins in diverse bacterial species. Nat Microbiol 1, 16085 (2016a).

Pawluk, A. et al. Naturally occurring off-switches for CRISPR-Cas9. Cell 167, 1-10 (2016b).

Rauch, B. J. et al. Inhibition of CRISPR-Cas9 with bacteriophage proteins. Cell 168, 150-158.e10 (2017).

Samson, J. E., Magadán, A. H., Sabri, M. & Moineau, S. Revenge of the phages: defeating bacterial defences. Nat Rev Microbiol 11, 675-87 (2013).

Schmakov et al. Diversity and evolution of class 2 CRISPR-Cas systems. Nat Rev Microbiol 15, 169-182 (2017)

---

The invention claimed is:

1. A method to favor the screening of a bacterial mechanism providing resistance against a virulent phage other than a given class 2 type II CRISPR-Cas mediated resistance, comprising:
   1) providing a bacterial strain, the genome of which contains a given class 2 type II CRISPR-Cas system, which is known to be active against target nucleic acids;
   2) expressing in said bacterial strain a gene encoding a protein which interferes with a function of said given class 2 type II CRISPR-Cas system;
   3) exposing said bacterial strain of step 2) to a virulent phage; and
   4) selecting bacteriophage-insensitive mutants (BIMs), wherein the resistance in said selected BIMs is provided by a bacterial mechanism other than the given class 2 type II CRISPR-Cas-mediated resistance.

2. The method of claim 1, wherein said bacterial mechanism providing phage resistance to said BIMs selected in step 4) is a mechanism mediated by another CRISPR-Cas system.

3. A method to enrich a bacterial population in bacteriophage-insensitive mutants (BIMs) other than BIMs due to a given CRISPR-Cas system, comprising:
   1) providing a bacterial population comprising a bacterial strain, the genome of which contains a given class 2 type II CRISPR-Cas system, which is known to be active against target nucleic acids;
   2) expressing in said bacterial strain a gene encoding a protein which interferes with a function of said given class 2 type II CRISPR-Cas system;
   3) exposing said bacterial strain of step 2) to a virulent phage; and
   4) selecting BIMs,
   wherein the selected BIMs have acquired resistance to said phage by a mechanism other than the given class 2 type II CRISPR-Cas system.

4. The method according to claim 1, wherein said protein which interferes with a function of a given class 2 type II CRISPR-Cas system is a protein which interferes with the interference function of a class 2 type II CRISPR-Cas system and downmodulates the activity of a Cas9 protein component of said class 2 type II CRISPR-Cas system.

5. The method according to claim 4, wherein said protein downmodulates the activity of a Cas9 protein of a Gram-positive bacterium.

6. The method according to claim 5, wherein said protein downmodulates the activity of a Cas9 protein of a *Streptococcus* genus strain or a *Streptococcus pyogenes* strain.

7. The method according to claim 1, wherein said protein which interferes with a function of said given class 2 type II CRISPR-Cas system is a protein, which has the sequence as defined in SEQ ID NO: 10 or has a sequence having at least 70% similarity with SEQ ID NO: 10 or has a sequence having at least 90% identity with SEQ ID NO: 10.

8. The method according to claim 1, wherein said bacterial strain is a Gram-positive bacterial strain.

9. A method to downmodulate, in a bacterial strain, the activity of a class 2 type II CRISPR-Cas system against target nucleic acids, comprising expressing in said bacterial strain a gene encoding a protein which interferes with a function of said class 2 type II CRISPR-Cas system, wherein said gene encodes a protein having at least 70% similarity or at least 90% identity to the sequence defined in SEQ ID NO: 10.

10. The method according to claim 3, wherein said protein which interferes with a function of a given class 2 type II CRISPR-Cas system is a protein which interferes with the interference function of a class 2 type II CRISPR-Cas system and downmodulates the activity of a Cas9 protein component of said class 2 type II CRISPR-Cas system.

11. The method according to claim 10, wherein said protein downmodulates the activity of a Cas9 protein of a Gram-positive bacterium.

12. The method according to claim 11, wherein said protein downmodulates the activity of a Cas9 protein of a *Streptococcus* genus strain or a *Streptococcus pyogenes* strain.

13. The method according to claim 3, wherein said protein which interferes with a function of said given class 2 type II CRISPR-Cas system is a protein, which has the sequence as defined in SEQ ID NO: 10 or has a sequence having at least 70% similarity with SEQ ID NO: 10 or has a sequence having at least 90% identity with SEQ ID NO: 10.

14. The method according to claim 3, wherein said bacterial strain is a Gram-positive bacterial strain.

* * * * *